United States Patent
Vogelstein et al.

(10) Patent No.: US 9,982,304 B2
(45) Date of Patent: May 29, 2018

(54) ARID1A AND PPP2R1A MUTATIONS IN CANCER

(75) Inventors: Bert Vogelstein, Baltimore, MD (US); Kenneth W. Kinzler, Bel Air, MD (US); Victor Velculescu, Dayton, MD (US); Nickolas Papadopoulos, Towson, MD (US); Sian Jones, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 219 days.

(21) Appl. No.: 13/819,933

(22) PCT Filed: Sep. 6, 2011

(86) PCT No.: PCT/US2011/050487
§ 371 (c)(1),
(2), (4) Date: Apr. 19, 2013

(87) PCT Pub. No.: WO2012/071096
PCT Pub. Date: May 31, 2012

(65) Prior Publication Data
US 2013/0210900 A1    Aug. 15, 2013

Related U.S. Application Data

(60) Provisional application No. 61/379,875, filed on Sep. 3, 2010.

(51) Int. Cl.
*C12Q 1/68* (2018.01)
*A61K 31/7088* (2006.01)
*G01N 33/50* (2006.01)
*A61K 31/711* (2006.01)

(52) U.S. Cl.
CPC ........ *C12Q 1/6886* (2013.01); *A61K 31/7088* (2013.01); *A61K 31/711* (2013.01); *G01N 33/5011* (2013.01); *C12Q 2600/156* (2013.01)

(58) Field of Classification Search
None
See application file for complete search history.

(56) References Cited

U.S. PATENT DOCUMENTS

| 4,376,110 | A | 3/1983 | Gary et al. |
| 4,486,530 | A | 12/1984 | David et al. |
| 4,683,195 | A | 7/1987 | Mullis et al. |
| 4,800,159 | A | 1/1989 | Mullis et al. |
| 5,965,377 | A | 10/1999 | Adams |
| 2010/0196426 | A1* | 8/2010 | Skog et al. .......... 424/400 |

FOREIGN PATENT DOCUMENTS

EP    0332435 B1    4/1992

OTHER PUBLICATIONS

Huang et al; Genes Chromosomes and Cancer, vol. 46, pp. 745-750, 2007.*

Wang et al; Biochem. J. vol. 383, pp. 319-325, 2004.*
Jones et al; Science vol. 321, pp. 1801-1806, 2008.*
International Preliminary Report on Patentability for PCT/US2011/050487 dated Mar. 5, 2013.
Ahmadian et al., "Single Nucleotide Polymorphism Analysis by Prosequencing," Anal. Biochem., Apr. 2000 280:103-110.
Arguello et al., "Mutation detection and typing of polymorphic loci through double-strand conformation analysis," Nat. Genet., Feb. 1998 18:192-194.
Brownie et al, "The elimination of primer-dimer accumulation in PCR." Nucleic Acids Res., Aug. 1997, 25(16):3235-3241.
Calin et al., "Low frequency of alterations of the alpha (PPP2R1A) and beta (PPP2R1B) isoforms of the subunit A of the serine-threonine phosphatase 2A in human neoplasms." Oncogene. Feb. 2000, 19(9):1191-5.
Cao et al. "The prevalence of PALB2 germline mutations in BRCA1/BRCA2 negative Chinese women with early onset breast cancer or affected relatives," Breast Cancer Res Treat, 114(3):457-62 (2009).
Cariello, "Resolution of a Missense Mutant in Human Genomic DNA by Denaturing Gradient Gel Electrophoresis and Direct Sequencing Using In Vitro DNA Amplification: HPRT Munich" Am. J. Human Genetics, May 1988, 42:726.
Castro et al., "Single-Molecule Electrophoresis" Sep. 1995, Anal. Chem., 67:3181-3186.
Chen et al, "A Homogeneous; Ligase-Mediated DNA Diagnostic Test", Genome Res., May 1998 , 8(5):549-556.
Chen et al., "A microsphere-based assay for multiplexed single nucleotide polymorphism analysis using single base chain extension", Genome Res., Apr. 2000, 10:549-557.
Cho et al., "Ovarian cancer." 2009 Annu Rev Pathol 4:287-313.
Collins et al., "A branched DNA signal amplification assay for quantification of nucleic acid targets below 100 molecules/ml," Nucleic Acids Res., Aug. 1997, 25(1):2979-2984.
Conner et al., "Detection of sickle cell BS-globin allele by hybridization with synthetic oligonucleotides" Proc. Natl. Acad. Sci. USA, Jan. 1983, 80:278-282.
Cooksey et al., "Evaluation of the invader assay, a linear signal amplification method, for identification of mutations associated with resistance to rifanipin and isoniazid in Mycobacterium tuberculosis." Antimicrobial Agents and Chemotherapy May 2000 44(5): 1296-1301.
Dalgliesh et al., "Systematic sequencing of renal carcinoma reveals inactivation of historic modifying genes" Nature. Jan. 21, 2010, 463(7279):360-63.
Detmer et al., "Accurate quantification of hepatitis C virus (HCV) RNA from all HCV genotypes by using branched-DNA technology." J. Clin. Microbiol, Apr. 1996. 34(4):901-907.

(Continued)

Primary Examiner — Jehanne S Sitton
(74) Attorney, Agent, or Firm — Fish & Richardson P.C.

(57) ABSTRACT

Two genes, ARID1A (AT-rich interactive domain-containing protein 1A) and PPP2R1A (protein-phosphatase 2, regulatory subunit 1, alpha), can be used in methods which are useful for detecting cancer, diagnosing cancer, contributing to a diagnosis of cancer, confirming a diagnosis of cancer, identifying appropriate treatments for cancer, monitoring treatment of cancer, and evaluating treatment protocols for cancer, including ovarian clear cell carcinoma, breast cancer, colon cancer, gastric cancer, lung cancer, medulloblastoma, pancreatic cancer, and prostate cancer.

19 Claims, 3 Drawing Sheets

(56) References Cited

OTHER PUBLICATIONS

Eigen et al., "Sorting single molecules: application to diagnostics and evolutionary biotechnology." Proc. Natl. Acad. Sci. USA, Jun. 1994, 91(13):5740-5747.
Erzen et al., "Endometriosis-associated ovarian carcinoma (EAOC): an entity distinct from other ovarian carcinomas as suggested by a nested case-control study." Gynecol Oncol., Oct. 2001. 83(1):100-8.
Eshleman et al., "Diverse hypermutability of multiple expressed sequence motifs present in a cancer with microsatellite instability." Oncogene, Apr. 4, 1996, 12(7):1425-32 (abstract only).
Finkelstein et al., "Use of denaturing gradient gel electrophoresis for detection of mutation and prospective diagnosis in late onset ornithine transcarbamylase deficiency," Genomics, 7: 167-172 (1990).
Fox et al., "The detection of K-ras mutations in colorectal cancer using the amplification-refractory mutation system." Br. J. Cancer, Apr. 1998, 77(8):1267-1274.
Fukunaga et al., "Ovarian atypical endometriosis: its close association with malignant epithelial tumours." Histopathology, Mar. 1997 30(3):249-55.
Gatlin et al., "Automated identification of amino acid sequence variations in proteins by HPLC/microspray tandem mass spectrometry." Anal. Chem., Feb. 2000, 72(4):757-763 (2000).
Gibson et al.,"A homogeneous method for genotyping with fluorescence polarization" Clin. Chem., Aug. 1997, 43(8 Pt 1):1336-1341.
Giunta et al., Dec. 1996, Diagn. Mol. Path, 5:265-270.
Graber et al., "Advances in DNA diagnostics." Feb. 1998. Curr. Opin. Biotechnol., 9(1):14-18.
Graham et al., "Selective Detection of Deoxyribonucleic Acid at Ultralow Concentrations by SERRS." Anal. Chem., Nov. 1997, 69(22):4703-4707.
Greenman et al., "Patterns of somatic mutation in human cancer genomes." Nature. Mar. 2007, 446(7132):153-8.
Hawkins et al., "Rapid DNA mutation identification and fingerprinting using base excision sequence scanning," Electrophoresis, 20: 1171-1176 (1999).
Holland et al., "Detection of specific polymerase chain reaction product by utilizing the 5'-3' exonuclease activity of Thermns aquaticus DNA polymerase." Proc. Natl. Acad. Sci. USA, Aug. 1991, 88(16):7276-7280.
Horn et al., "An improved divergent synthesis of comb-type branched oligodeoxyribonucleotides (bDNA) containing multiple secondary sequences" Nucleic Acids Res., Dec. 1997 25(23):4835-4841.
Horn et al., "Chemical synthesis and characterization of branched oligodeoxyribonucleotides (bDNA) for use as signal amplifiers in nucleic acid quantification assays." Nucleic Acids Res., Dec. 1997 25(23):4842-4849.
Huang et al., "Genomic and functional evidence for an ARID1A tumor suppressor role." Genes Chromosomes Cancer, Aug. 2007, 46(8):745-50.
Iannone et al.,"Multiplexed Single Nucleotide Polymorphism Genotyping by Oligonucleotide Ligation and Flow Cytometry", Cytometry, Feb. 1, 2000, 39:131-140.
Jimenez et al., Clin Biochem., 42(15): 1572-6 (2009).
Kalnina et al., "Nanoliter scale PCR with TaqMan detection" Nucleic Acids Res., May 1997, 25(10):1999-2004.
Kern, "Quantitative selection constants" Mar. 2002, Cancer Biol Ther.1(2):189-94.
Kinzler et al., "Identification of a Gene Located at Chromosome 5q21 That is Mutated in Colorectal Cancers" Science, Mar. 15, 1991, 251:1366-1370 (1991 ).
Kuo et al., "DNA Copy Number Profiles in Affinity-Purified Ovarian Clear Cell Carcinoma." Clin Cancer Res. Apr. 1,2010, 16(7):1997-2008.
Kuo et al., "Frequent activating mutations of PIK3CA in ovarian clear cell carcinoma." Am J Pathol. May 2009, 174(5):1597-601.
Landergren et al., Science, 241: 1077-1080 (1988).
Lizardi et al., Nature Genetics, 19:225-23 2 (1998).

Luo et al. Proc Natl Sci USA 105, 20380 (2010).
Lyamichev et al.,"Polymorphism identification and quantitative detection of genomic DNA by invasive cleavage of oligonucleotide probes." Nat. Biotechnol., 17 :292-296 (1999).
M. D. Fallin et al., "Genomewide linkage scan for schizophrenia susceptibility loci among Ashkenazi Jewish families shows evidence of linkage on chromosome 10q22." Am J Hum Genet., Sep. 2003, 73(3):601-11.
M.D. Fallin et al., "Bipolar I disorder and schizophrenia: a 440-single-nucleotide polymorphism screen of 64 candidate genes among Ashkenazi Jewish case-parent trios." Am J Hum Genet. Dec. 2005, 77(6):918-36.
Markowitz et al., "Inactivation of the type II TGF-beta receptor in colon cancer cells with microsatellite instability." Science, Jun. 1995, 268: 1336-38.
Marquez et al., "Patterns of Gene Expression in Different Histotypes of Epithelial Ovarian Cancer Correlate with Those in Normal Fallopian Tube, Endometrium, and Colon." Clin Cancer Res., Sep. 2005, 11(17):6116-26.
Medina et al., Hurn Mutat 29:617-22 (2010).
Meyerson et al., "Advances in understanding cancer genomes through second-generation sequencing." Nat Rev Genet. Oct. 2010 (10):685-96.
Monforte et al., "High-throughput DNA analysis by time-of-flight mass spectrometry." Nat. Med, Mar. 1997, 3(3):360-362.
Morin et at., "Frequent mutation of histone modifying genes in non-Hodgkin lymphoma" Nature. Jul. 27, 2011, 476(7360):298-303. doi: 10.1038/nature10351.
Nagl et al., "Distinct mammalian SWI/SNF chromatin remodeling complexes with opposing roles in cell-cycle contral" EMBO J. Feb. 7, 2007;26(3):752-63.
Nazarenko et al., "A closed tube format for amplification and detection of DNA based on energy transfer." Nucleic Acids Res., Jun. 1997, 25(12):2516-2521.
Nelson et al., "Detection of all single-base mismatches in solution by chemiluminescence" Nucleic Acids Res., Dec. 1996 24(24):4998-5003.
Newton et al., "Analysis of any point mutation in DNA. The amplification refractory mutation system (ARMS)" Nucleic Acids Res., Apr. 1989, 17(7):2503-2515.
Nilsen et al., "Dendritic Nucleic Acid Structures," J.Theor. Biol., 187:273-284 (1997).
Nordstrom et al., "Direct analysis of single-nucleotide polymorphism on double-stranded DNA by pyrosequencing.," Biotechnol. Appl. Biochem., 31(2): 107-112 (2000).
Orita et al., "Detection of polymorphisms of human DNA by gel electrophoresis as single-strant conformation polymorphisms" Proc. Natl. Acad. Sci. USA, Apr. 1989, 86:2776-2770.
Parsons et al., "An integrated genomic analysis of human glioblastoma multiforme." Science. Sep. 26, 2008, 321(5897):1807-12.
Parsons et at, "The genetic landscape of the childhood cancer medulloblastoma." Science., Jan. 28, 2011, 331(6016):435-9.
Rampino et al., "Somatic frameshift mutations in the BAX gene in colon cancers of the microsatellite phenotype." Science., Feb. 14, 1997, 275(5302):967-9.
Roberts et al., "Potassium permanganate arid tetraethylammonium chloride are a safe and effective substitute for osmium tetroxide in solid-phase fluorescent chemical cleavage of mismatch" Nucleic Acids Res., Aug. 1997, 25(16)3377-3378.
Robertson et al., "Development and validation of a screening test for 12 common mutations of the cystic fibrosis CFTR gene.", Eur. Respir. J., Aug. 1998. 12(2):477-482.
Rychlik et al., "A computer program for choosing optimal oligo-nucleotides for filter hybridization, sequencing and in vitro amplification of DNA," Nucleic Acids Res., Nov. 1989, 17(21):8543-8551.
Saiki et al., "Genetic analysis of amplified DNA with immobilized sequence-specific oligonucleotide probes", Proc. Natl. Acad. Sci. Aug. 1989, USA 86:6230-6234.
Sato et al., "Loss of heterozygosity on 10q23.3 and mutation of the tumor suppressor gene PTEN in benign endometrial cyst of the ovary: possible sequence progression from benign endometrial cyst

(56) References Cited

OTHER PUBLICATIONS to endometrioid carcinoma and clear cell carcinoma of the ovary." Cancer Resm Dec. 2000, 60(24):7052-6.
Sharkey et al., "Antibodies as Thermolabile Switches: High Temperature Triggering for the Polymerase Chain Reaction," Nature Biotechnology 12(5):506-509 (1994).
Sheffield et al., "Attachment of a 40-base-pair G+C-rich sequence (GC-clamp) to genomic DNA fragments by the polymerase chain reaction results in improved detection of single-base changes." Proc. Natl. Acad. Sci. USA, Jan. 1989, 86:232-236.
Sheffield et al., "Identification of Novel Rhodopsin Mutations Associated with Retinitis Pigmentosa by GC-clamped Denaturing Gradient Gel Electrophoresis" Am. J. Hum, Genet., Oct. 1991, 49:699-706.
Shumaker et al., "Mutation Detection by Solid Phase Primer Extension," Hum. Mutat., 7:346-354 (1996).
Syvanen et al. "A primer-guided nucleotide incorporation assay in the genotyping of apolipoprotein E." Genomics, 8:684-692 (1990).
T. Sjoblom et al., "The consensus coding sequences of human breast and colorectal cancers." Science. Oct. 13, 2006, 314(5797):268-74.
Tang et al., "PP2A is required for centrometric localization of Sgo1 and proper chromosome segregation." Dev Cell, May 2006, 10(5):575-85.
The 1000 Genomes Project Consortium. "A map of human genome variation from population-scale sequencing." Nature. Oct. 28, 2010, 467(7319): 1061-1073.
Tyagi et al., "Molecular Beacons: Probes that Fluoresce upon Hybridization" Nat Biotechnol., Mar. 1996, 14:303-308.
Tyagi et al., "Multicolor molecular beacons for allele discrimination", Jan. 1998, Nat Biotechnol 16:49-53.
Van Raamsdonk et at, "Frequent somatic mutations of GNAQ in uveal melanoma and blue naevi" Nature. Jan. 29, 2009, 457(7229):599-602.
Varela et al., "Exome sequencing identifies frequent mutation of the SWI/SNF complex gene PBRM1 in renal carcinoma" Nature., Jan. 27, 2011, 469(7331):539-42.
Veras et al, "Cystic and adenofibromatous clear cell carcinomas of the ovary: distinctive tumors that differ in their pathogenesis and behavior: a clinicopathologic analysis of 122 cases." Am J Slug Pathol.., Jun. 2009, 33(6):844-53.
Vogelstein, K.W. Kinzer, "Cancer genes and the pathways they control." Nat Med, Aug. 2004, 10(8):789-99.
Wang et al, "Two related ARID family proteins are alternative subunits of human SWI/SNF complexes." Biochem J., Oct. 15, 2004 383(Pt 2):319-25.
Wartell et al., "Detecting base pair substitutions in DNA fragments by temperature-gradient gel electrophoresis" Nucleic Acids Res., May 1990, 18:2699-2705.
Weissman & Knudsen, "Hijacking the chromatin remodeling machinery: impact of SWI/SNF perturbations in cancer." Cancer Res., Nov. 1, 2009 69(21)8223-30.
Whitcombe et al., "A homogeneous fluorescence assay for PCR amplicons: its application to real-time, single-tube genotyping." Clin. Chem., May 1998 44(5):918-923.
Wiegand et al, "ARID1A mutations in endometriosis-associated ovarian carcinomas." N Engl J Med., Oct. 14, 2010, 363(16):1532-43.
Wolf et al., "Detection of nucleic acid hybridization by nonradiative fluorescence resonance energy transfer." Proc. Nat. Acad. Sci. USA, Dec. 1988. 85(23):8790-8794.
Wood et al., "The genomic landscapes of human breast and colorectal cancers." Science. Nov. 6, 2007, 318(5853):1108-13.
Wu et al, "Understanding the words of chromatin regulation." Jan. 23, 2009, Cell 136(2):200-06.
Yan et al., "IDH1 and IDH2 mutations in gliomas." N Engl J Med. Feb. 19, 2009, 360(8):765-73.
International Search Report and Written Opinion dated Jun. 26, 2012 (PCT/US2011/050487); ISA/KR.
Hung, J. et al, 'Genomic and functional evidence for an ARID1A tumor suppressor role' Genes, Chromosomes & Cancer, May 10 2007, vol. 46, pp. 745-750.
Calin, G. A. et al, 'Low frequency of alterations of the a(PPP2R1A) and b(PPP2R1B) isoforms of the subunit A of the serine-threonine phosphatase 2A in human neoplasms' Oncogene, Feb. 24 2000, vol. 19, pp. 1191-1195.
Jones, S. et al, 'Frequent mutations of chromatin remodeling gene ARID1A in ovarian clear cell carcinoma' Science, Oct. 8 2010, vol. 330, No. 6001, pp. 228-231.
Maeda, D. et al, 'Clinicopathological significance of loss of ARID1A immunoreactivity in ovarian clear cell carcinoma' International Journal of Molecular Science, Dec. 13, 2010, vol. 11, pp. 5120-5128. .
McConechy, M.K. et al, 'Subtype-specific mutation of PPP2R1A in endometrial and ovarian carcinomas' Journal of Pathology, Apr. 2011, vol. 223, pp. 567-573.
Wiegand, K.C. et al, 'ARID1A mutations in endometriosis associated ovarian carcinomas' New England Journal of Medicine, Oct. 14, 2010, vol. 363, No. 16, pp. 1532-1543.

* cited by examiner

SEQUENCE LISTING

<160> NUMBER OF SEQ ID NOS: 158

<210> SEQ ID NO 1
<211> LENGTH: 84353
<212> TYPE: DNA
<213> ORGANISM: Homo sapiens

<400> SEQUENCE: 1

```
atggccgcgc aggtcgcccc cgccgccgcc agcagcctgg gcaacccgcc gccgccgccg      60
ccctcggagc tgaagaaagc cgagcagcag cagcgggagg aggcgggggg cgaggcggcg     120
gcggcggcag cggccgagcg cggggaaatg aaggcagccg ccgggcagga aagcgagggc     180
cccgccgtgg ggccgccgca gccgctggga aaggagctgc aggacgggc  cgagagcaat     240 gggggtggcg gcggcggcgg agccggcagc ggcggcgggc ccggcgcgga gccggacctg     300
aagaactcga acgggaacgc gggccctagg cccgccctga caataaacct cacggagccg     360
cccggcggcg gcggtggcgg cagcagcgat ggggtggggg cgcctcctca ctcagccgcg     420
gccgccttgc cgcccccagc ctacggcttc gggcaaccct acggccggag cccgtctgcc     480
gtcgccgccg ccgcggccgc cgtcttccac caacaacatg gcggacaaca aagccctggc     540
ctggcagcgc tgcagagcgg cggcggcggg ggcctggagc cctacgcggg gccccagcag     600
aactctcacg accacggctt ccccaaccac cagtacaact cctactaccc caaccgcagc     660
gcctaccccc cgcccgcccc ggcctacgcg ctgagctccc cgagaggtgg cactccgggc     720
tccggcgcgg cggcggctgc cggctccaag ccgcctcccct cctccagcgc ctccgcctcc     780
tcgtcgtctt cgtccttcgc tcagcagcgc ttcgggggcca tggggggagg cggcccctcc     840
gcggccggcg gggaactcc  ccagcccacc gccacccca  ccctcaacca actgctcacg     900
tcgcccagct cggccggggg ctaccagggc taccccgggg gcgactacag tggcgggccc     960
caggacgggg gcgccggcaa gggcccggcg gacatggcct cgcagtgttg gggggctgcg    1020
```

```
gcggcggcag ctgcggcggc ggccgcctcg ggaggggccc aacaaaggag ccaccacgcg   1080
cccatgagcc ccgggagcag cggcggcggg gggcagccgc tcgcccggac ccctcaggta   1140
cacagctgag tggggagggg gctggggcga gcgtggtcct gggggtgggt ggcggctgcg   1200
gtgagcgggc cacagccttg ggctcccctc agtcccgggc ccccactgct ggggagctgc   1260
cattgtctgg ctcttctctc ttaaaatggc tgcctgtctg ccttcctctc cttccctcct   1320
tcagcctttg tgttgggttt ttccagaggt gtctgctcct cttttcctc tccctggtc     1380 ccttcgaact ccaggggtct tgatgggggt gcggggcaga gtgtgcgggg aagggcctgg   1440 ccggggtga gggggtgagg gggcgctggg ggctcaggtt aggagtgtag gcagtggtag     1500
gagcccagga gttgaatgaa cgtttctttg ctcacctgcc gctcctctcc gtccccggc     1560 cttcctctgg gccgcccccc atctgtgctt caaagagggg ccctagagc tcgaggggac     1620 ctcgagggga gggcagggga ctgcttggga gctgctagag gccggctgcg gttcacctag   1680
ggcagcccgg tccatctcct gtcttaggct ccgccggccc agtggcctgg gcttctccct   1740
ggaagtgctg gtaaacagct gagtgattgg agtagtaagt gcagattgct ttggtttggg   1800
atttgaatta tggaggtaaa atccttctgt caaagccagg agacagttgg tcttaggttg   1860
acatcctatc tgtgatctga ttggctcccc atctcctgct cttggccatt tataattgcc   1920
tctgatgtaa tggtacaaca atcctgatga gctcataaac ttttacactc tgcttttctg   1980
ccagtgataa cccaaactat cgctgccact atctgccttt tattccagag ctgaaattgg   2040
ctgtgacctt gaggagggag gtttaagtag caatactgta tcagcaagag caaagcctca   2100
gacagcctgc ccttgttaca ttgtgcccaa acaaaagagg aggcaatggc attttgcttg   2160
taccttggat ttattttgct tgttatgttt tatgcagcct gaaatgaatt ctgtgttgtc   2220
agaacagtag ctgagttttt tctctacaat gggtttgctg tttgttttgg ttttgtgact   2280
ttcctgatgg tataaatgac ttctttgatg gctctgaaga tgcatttatc ttgagtaatt   2340
ttgacactgt ttgcttttgca gaattgaaat gattttactg ggcttttat tgagtggcaa    2400 atgtgggatc tttatggggg gccagaaaac agttttttgtt atttttttta gaactgggag    2460 cttttctgagg aatttttatat taggttcaag cggtctgttt taaggaagac tggcctcatt   2520
ctttgtttac atgttgaatc ttgttaacac tttcttttgt taattgaact ttggaatagc    2580
agcttaattt aaagggaagc tggtgtcttt catgatcttg agggactttc tcctaaaggc    2640
ttggtttggt gaaattgttt ttttcctgga ataacaaaaa gtctagtttt ctgttttgtc    2700
atcagtcatt ttagagcttt gaaatagaga ctggccagtt tattccttttg cattttaatg   2760 tatgttccac ttttttttctt gtcttccaag atatgaagat acgacctaga atgacactta   2820
agatttgctt agaaattgca acttctgagt accttgttac actattctat cttgttttat    2880
tttgttgctt ttcttccatc ttcatcatgc tctgtcagca gtgcttttgg tcagggatat   2940
tgagtattct gtggagtcat acatgttttc aaagaggggg aagctccatt catcccctcc   3000
caaacccctt gcgcttttgt gctaggagga aattttgttc acttactagc tgtattccca    3060
gcccatccta gagctacttt actactcttt tgagctgggg attttgaaat tagctgtgtt    3120
agatggtggg cttggagctc tgtgccttga ttctacatct tccatgatgt tctgcatctg   3180
gacaagaaat agggaaatgt tacattgttt ttctagtgtc tggaggaaaa gttttgtctt    3240
aaaagacagc atcctcttgt ctctgggtca tcctatagtc tgaacctctt tcctctcatt   3300 cccccttgttt tgtttggttt tggctgaaaa ttttactttt cttgaaaact attagaataa   3360
gtcatttggg gtagtaagtc agggttcatt taaaagcaaa attgattgga attctgctgg   3420
```

-continued

```
tttggaaata tttagtcaaa ggttttaaag aaaaagccaa ctcttttggt ataatgattt    3480 ttgttttca gtcagtaaat tatggaacac tttctgtgta gatgatagga gaatagatac    3540
agtccctgtt tggatgcctg tctgtgctgc ctttggatga attttctgat ctctttatt    3600 atcactagac ccacacaaca tagattccta attaatttca gctcagttgt ctactcccca    3660
gagacccagg gaatgggctg gtgagcattc agttgtgtaa gagacagtgc agcttccact    3720
tctgtggact gcttcaggtg tgtggtagta gtctaggtga gggttgtagg ttcagacttt    3780
gttctgaatt tctctttgct acttgataaa cctcttttca gaccatgatg ctctactctt    3840
caacattctt aaattaaaaa gtcttgctct gtctccatct tttcctggcg cagtcttaga    3900
ttaagaatat tttgcagaga cttaattaac acagctaagg tgataacgtt ttcatttgac    3960
tctgcgctta tgaaataaag tttaggtaag tgtgtgtatt gtggctatgt cttttcaca    4020 ggacctggga agatcttaga caaactttta ctttattcct tttcataagt agtgtatctc    4080
aagtgttgaa tcccggtact gatgaaatag ttttagatta cttacacaca tgaagttgat    4140
ttaaggcttt ttattgggac gcttttttagc aataatactt tgagagtaat accagtttac    4200
caaggtaaaa aataaaatac aataaatagt ccaggaacaa gttggatttt attgtagaag    4260
tttggttgtt agtttctact acggaaacat caaatgatat ttctgactcc tgggaaacag    4320
atacaggaat cctagattta ttatgggaat gcctactggc agaaattcta ggctggctga    4380
aatacaggac tcttggagct ctctcaagta ggagggacca ggaaaaccac actgagatgg    4440
cactttagtt gtgggggttt catgtttctc tactgttcat gagagagctg gggtgatgag    4500
gattgagatg gtggtgtgag aacagagaaa gcagccagga ccaggtttgg cttcttgtgt    4560
attgggccct gtgaggactt tttaggttcc tttctttgtg tgtgacatga gtaaccatga    4620
caagcagcac ctgctgaaac aggatgtctt ggattgcatt aaacattaat atgttggatt    4680
gactcctgta ggtgtaatgt ctacagtaga ccttttgcaa agaggttagt gaacttttt    4740 agaatgaggg aataggctaa caaagtaata ggcagggctc tttcctgttc ccatccctca    4800
aaaggttgta ttgattggct tcaactctca aaattctaga agcaactgaa gcttgtaaat    4860
atggtaaaaa tgtggtattc aaatatattg gcaccgagta gttcttttct gccagtgagc    4920
tgtaatacct ggggcttgaa tggagtcctg attcctgtgg cttttatctc tgggtttttc    4980
cttgtttaga ttggtcatta tcattactga cgcacactta cgttgttatt actgatgcat    5040
acttgagttg tgtgttgcgt tagtggtaaa gagcacagga ctcacaacag gaggaggaag    5100
gaggaggctt aggttccaca tacagctcca gattaagctg tgtgaccctg gcaggtcat    5160 ttgctttctc tattttcat tttctccctc atcaataaaa tgaagttggt ctgcatggcc    5220
ttctcactct aagatgctac atatctgtgc ttccatagct ggcttgttat gaaggcagct    5280
ttctgtacat aaatcagggg tcttgagacc atctttcttc ccctggactg aaggaactca    5340
aagctatttt ctcctgggat tcacaggaac aagctctgaa cagttgggtg ccattgtggt    5400
ctgtagactt ttacagaaaa agctctacca gactgttgcc ttgaaactgt taatctgttt    5460
gtcattagtc attccacctg gctggtggtt ttaaaacact aaatagtcgt tggaaagtta    5520
ggtagatttc attaaagcaa gacttgaaaa atagttgctt caggatcccc aggaggcttt    5580
tgcacttggg gttggggtga ggaatggata ttcataagtt cagtgttgat attctgctgc    5640
ttttggggag gggtagggag agagagggag cattaagctc tccagactcc tggtgtttgg    5700
gcaggtctag gtctggtttg ggcagttggt tgtaatctga gtgcctggac ttgccctgta    5760
```

```
agttttgctg agagagaagc aaatgttcct gagactggaa gaggaaaagc tgcgtttcag      5820
ggtcaatttc ataggtgcat ttgttgtttc tcatcgctat ggtttaaaaa actacatggt      5880
gtgctttgca cgtggtcctg gaaatgctat tctttctctt ctccagcaca cctgaatttc      5940
cattctttct cttcctggct tagtagttta gaagtgtaat ttaggtatat tagaggaagg      6000
aagcttccct ttataaagga gggaaaaggg tagagggaac agtgtttgat aattctgtgc      6060
ttgacacagc atcttctatc gtctctgaag gaaccaaatg tttcagagct ttgtgtaaat      6120
acttgctgag ctgtcaatat gtacccagga ggtttctgta gtaagatgta aactgttcta      6180
tagaatgttt gacaggcaaa ttaataaaca gttttcaagc aaagataatg ctagcctcct      6240
catgtggtgg agtaaaataa cattggggaa aaagacttgg ggataggaaa agggtagtgc      6300 tgggggggcag tgagtgtgga gataagaagt gatctaaaaa aaaattgaaa tggaaagatg      6360
ctgccctggt agtgaaacct ctgtggccct ggctgcgtgc taagttcagg gcatgtggta      6420
tcctgttaaa gtcaattgca gtttcatagt gaaatagaa gtttggaaag aagatcctga      6480
ctgtcaatag taaggtaagt attaccccag acacttggct tatgagactt tgaggtttaa      6540
agggtagctt ggtgagatta ttttttggctt gggtttgcat ttctggaata ttagaaagga      6600
gaaaaaagat actgcaactt gagtgtgatc tttatcctca attttgctgt tgtgctgggg      6660
attataagtc cactacccaa tggcctgggt ttatttatac agtttttact ggacttctgt      6720
gtatcactta tgataaaatt aatatgcctt tacactctgt tcctgggtca gtacaaagtc      6780
caaatatttg gggactcact acatcttact tgaaggatta tgtgagtaga tacagtcttt      6840 gttttgaaa ttgccatttt aggattaaaa acatatctgg gttccttcag tgacacattc      6900
tttttatgga agaagaagaa gaatctatga atattttagc tgtctgtctg tggtcctctt      6960
ctttggtagc cttgtgagat gaccagattt gccttctcag aatgtctttt ttaactagat      7020
tcattgattc tgacaccagt tttctttata agaagtgttt tttacaccag agtcctggaa      7080
gtgccctttt gacttagctg tttatatagt agcagggaat atgaatgtaa ttatggtcct      7140
gactatgatt tttaggttca gctaacttac taccaaaggc tatcagcttg ttttaataca      7200
aaacacaaaa acttggattg gcactgacat aggttgctta atattgcatg gtccttttccc      7260 agtatgttgg tagtgagggt attaggaact tcagacttat tgctgagagc atagtttcta      7320
agtcagagag atcaggaaat tccaatgggg atgggaaata gccctatgtg attacaccag      7380
ctaggtacta ggaagagatt taaaaggtag aaacaatatc tccttcagag gcatttagtt      7440
ttcttaggaa agcatgctta tgtgcacaca tctggaaaac ttgaaaagca aggttttcata      7500 aatggatgta gaccacacta attatgtgag ctgaaggaat tagaggaaaa ggttcaatca      7560
gtttggcagg gttaacctgg gacagctttt cagaggcttt ttttgtgaag ctaaatgttc      7620
aagaaactta gaatactaat ttgccttttc ataatgctat tcttaagttc catgggcttg      7680
atagaatcca cattgcacat ccatctccag accagtagct gtctcagtgt tccaatgact      7740
ttgagaattt ggactctaac cataaaactc cctgaaagag tggttccagg gtcttagtgg      7800
ttcttgtggt caggtagagc ctttggtaca gactgttaag ttcttggcta gttcaggggc      7860
acttttctag taaatttgga tttggaaggt catgtcacct tcagagttgt gtgccctgga      7920
cagctctgta gtaatggtgg ttcaactttg ttggtgagtc tgtcttggca gagttagttg      7980
acctttctta aaacaagagc cacgaagtaa gtatctgttg ggactcttag gctgctattt      8040
ctgaggagct gggagctgtg ttcaagtcaa gttgcttgtg ttagacctta tattgaggtt      8100
gatgggttag gtaagcctgc acatatgcag tctgcccatt tattcataga aatggccttt      8160
```

```
aatactgttt ttggccgggc gcggtagctc acacctataa tcccagcact ttgggaggcc    8220
aaggtgggag gattgcccaa gcccaggacc agccttggga ccaggctatt aacataggga    8280
gaccccatct ttacaagaca caaaaattgc tggatgtggt ggtacgtgcc tgtagtcgca    8340
gtttacttag aaagctgagg caggaggatt gcttgagccc aggaggttga ggctgttgta    8400
agccatgatt acgccagtgc actccagcct gggcaatgga gccaagacct tgtctcaaaa    8460
aaaaaaaaaa aatttgtttt ttattaggtt actatggcca agcagctaac aaatgctgct    8520
caccaatgct taatccttgt ggagcctctg aatatagtg attttggttt ctttacctgc     8580
tggtcgatct gtggttgggc cttggcactt caccggtcaa ggatcatcag tggatgctta    8640
acagctgaag atgcatggca tgtccagtgc caggccactg taatgcttct acctggagaa    8700
ggattggtta cactgctcca gtacagaagt actgcagacc tttttttttt tttgagatgg    8760
agtcttactt tgtcacccag actggagtac agtggtgcaa tctggctcat tgcaacctct    8820
gcctcccagg ttcaagcgat tctcatgcct cagcctcctg agtagctggg attataggct    8880
tccaccacca tgcccggcta attttttgtat ttttagtaga ggtgggtttt catcatgttg   8940
gccaggctgg tcttgaactc ccaacctcgg gtgtgatcca cccaccttgg ccttccaaag    9000
tgctggaatt acaggtgtga gccaccacgc ccagcctttt ttttttttcc cccccctca    9060 agtaatggtc catgacctgc tgaaagtact ggagtcttgg ataaacattc tggtttagaa    9120
ataccttttc cactttttt gccttgccat tttggcattt tgcaaaagtg ggttttcagt     9180
tactcagaat tgggcaccat agttaacctc ctatggatta caggtgttta ggggcttgaa    9240
ctctgatcat tcccaggttt tagaggaatc caagttcggg tgaatattga cttagtagcc    9300
ttgagtattc ttcctgaaat taccccctcct ctccatttaa atggatgaaa ttagtttttt   9360
actgaatgtg aagggacatc tgaatgaact tctgtttgtt tttgttagtc acttgtgcat    9420
agctggaata ttatcttggg acaggttgag tctatttccc agtggcttct gcattttcta    9480
agggtggact ggaatgggaa gaagtctaat gccaagaatg cattccaaca tgctgcagag    9540
taggaaattt gatccctaaa atgttgactt agtgttggtc atggtacata ttagaaatca    9600
cccagtaatc caggacagat ttttgtcacc ctccaggaag ttatgttgat ataaatacta    9660 agggctttg ggtactgagc taagtgctct gcaggcccaa agcgctgctt gaattgctac     9720
ccatatgaag aggaaatgtg ccatgtgcct ttttttctct cttttgcatt tgggcttcct    9780
tatggctttg ttgcttttat gttcccaagt ctgcaaagtt agatattaga cttcctcctc    9840
ccttggcact ggcagattca tgattttcca tggctcatca ctagcagcca agattttgt    9900 atgcttttct ctcttaaact tgttcgtttt cagcttgctt gtttataggc atctctgtta    9960
aaaggaaccc ttcttttccc cttaagatct agcaccaggg gtgcttgggg gttgttgtga   10020
tatcagtcaa ttaaaagccc atttggtgtg tgcttggtgt tttatttttg ctcatgtttt   10080
ctttgaggtc acaacgtgct tgccgggcat gagtgccttt gggcccagct gtttactctc   10140
aactgccgtg tactttgact ttaagaaaag tgcaaattca gccacgtggt agagggatta   10200
aaggccacat agtgttggat gcttcctttt ggaagaaaca gatatatctt tgggctcttc   10260
ttgcccagtg atttctcctg tctggggtag acattgttgc tttctgttgt ccttagaaa    10320 cagggcagaa atgctgggaa ttggtttatt actgtgtctc tttggcaaat atgtatgtct   10380
ttttctcttg cccttttggac aacattctgt tctggtccta aggtgttgga gttcacaggt  10440
tgatctagcg ttatgtgaaa ctcttggtaa tttaggtttg gataaccggc ttttagtctc   10500
```

```
cagatttcta acattgtgct tgtttaggaa tttaggcttc taaagagaac catattacaa    10560
agcttttggg gaacaattct gtaggtagtt tatctgttct tgggtcacag atcctcacca    10620
ggatcctgac ttttttttt ttttagacgg agtcttgctc tgtcacccag gctggagtgc    10680
agtgcagtgg ggcaatttca gctcactgca gtctccgcct cctgggttca aggggttctc    10740
ctgcctcagt ctcctgagta gctgggacta caggcatgcg ccaccgcggc tggctaattt    10800 ttttttttt ttttttttt tttgagatgg agtcttgttc tatcgcccag gctgagtcc      10860 agtggtgtga tctcggctca ctgcaacctc cgtctcccag gttcaagtga ttctcctgcc    10920
acagcctccc gagtagctgg gactacaggc gccttccacc acgccctgct aattttgta    10980 ttttagtag agatggggtt tcatcatgct ggccaggctg gtctgaaact cctgagctcg     11040
tgatctaccc gtctcggcct cccaaagtgc tgggattaca ggcataagcc accacgcccg    11100
gcctaatgtt tgtatttta gtagagatgg ggtttcacca tgttggctag gctagtctcg    11160
aactcctgac ctcaggtgat ccgccggctt tgacctccca aagtgctggg attacaggcg    11220
tgagccactg tgcctggcaa ggatcctgac tttcaaatga tggccaccat gcatttgagt    11280
acttattatg tgctaagcat tatgcttagt cctcttgatg aatttcctaa tttaatcttc    11340
aaaactgtat aggaggtggg ttctattatt aatcttcctc ttttacaaat gaggaaatag    11400
agtaagataa gaaatttgcc ctagggaaaa tagctggtaa aaggtagagt tgggtttgtc    11460
tgacaaggta gacaaggttt gtctgactct tcaaaggtat tacaatctaa aatactaact    11520
ttgcttctcc aaaataaatt actcaggcac caagattgtt taggacatta tttttacaat    11580
agcctgaaac tcttaaatgg ggtgaaagac tgaaaagcca ttagttaaca atttgacatc    11640
gtgcctagag ctctgtcctg tcattccctt ccatcccttc cacttagggt tttgttgttt    11700
tggatttccg atgaatggcc atggcacttg gtttatagct gccttgtgat tccattggtg    11760
agaactggca gcatctggtc ctctggtccc cggtcctctc tttctcaaga gggatcttt     11820 ggggttgaga gtgagattca gccttttaaga tacagtcctt cacttttttt ttttttttt    11880 ttttttttt ttttttttg agacggagtc ttgcactgtc gcccaggctg gattgcagtg     11940
gcgtgatctc ggctcactgt aacctctgcc tcctgggttc aagtgattct tctgcctcag    12000
cctcctgagt agctgggatt acaggtgccc accaccacgc ccaggtaatt ttttgtattt    12060
ttagtagaga tggggtttca ctgtgttggt caggctggtc ctgaactcct gaccttgtga    12120
tccacctgcc tcggcctccc aaagtgctgg gattacaggt gcgagccacc gcacccagcc    12180
agagtctttc actttgatct gagtgaaagt gacttgaatt atgaaagtat atgcagagtg    12240
atattacttt tccagaaact tggagcactt gctgaagagg cagggattat tgtctttttt    12300
tttcttttga gatggagtct ttgctctgtc gcccaggctg gagtgcagtg gcgcgatctt    12360
ggcccactgc aagctccgtc tcctgggttc acgccattct cctgcctcag cctcccgagt    12420
agctgggact acaggtgccc gccaccacgc ccggctaatt ttttgtatt tttagtagag     12480 atggggcttc accatgttag ccaggatggt ctcggtctgc tgatctcgtg atccgcccgc    12540
ttcggcctcc caaagtgctg ggattacagg tgtgagccac cgcgcccagc ggattattgt    12600
cttaatttgc cacttggggg aaatgaacac ataaagttga gtgccacata caaagtttca    12660
tagcagagtc atctctaaaa cctaggttta aagttctctt agggcagtat gactttaggt    12720
aagtcacttc tctgaatctg tattctcaac tatataatga ggaaaaatat ctaccttgaa    12780
gctatggtaa atattagata tgtgaaagta ctattcgttt atcaaataca attctaacat    12840
gactcctgat tggtcaatcc cacaactatc tctcccactc tccagccgtc cttttcagaa    12900
```

```
gcaagcctcc aggagagttg ataccactat tcccaccttc ctcctgtgca tccaccaatc   12960
tacctcacat tctcctcccc tgcacccagc acccctggaa tgctaccacc ctgctccagc   13020
caggaggcca aagggtgat gtaggaagat tgcagcacta ccatggaagt tctcaacagc   13080
acccccgacc caggacccca ggttccact ggccctgctt ctcaattcag gagagataga   13140
attgagtggt taaagctagt attggtcttt accgaattca aaattttccc tagttttag   13200 ctacatctga gttactgtaa tgctttttt tttttttttt tttaaacta aaatttgttt   13260 agagacaggg tctttctctg tttcccaggc tggagtgcag tggctatcca caggcacaat   13320
catagcccac tctcaaactc ctgacctcaa gcaatcttcc ttcctcagcc tcccaagtag   13380
ctgagctaca agcacatgtc actatgccag ctatcagggc tagcttgctt actttttt   13440 ttttttggag acagaatctc gctctgtcgg ccaggctgaa gtgcagtggc atgatctagc   13500
tcactgcaac ctccgcctcc tgggctcaag caattctcct gcctcagcct cccgagtagc   13560
tgggattaca ggcgtgtgcc accacgcctg gctaatttt gtattttag tagagacggg   13620 gtttcaccac gttggccagg ctggtctgga actcctgacc tcaggtaatc cacccacctg   13680
ggcctcccaa agtgctggga tgacagatgt gagccaccgc acccggccta tcagtgcatt   13740
aaaacacaca ggccgggtgc ggtggctcat gcctgccatc ccagcacttt gggaggccaa   13800
ggcgggtgga tcacaaggtc aagagatcga ccatcctg ccaacatgg tgaaccccg   13860 tctctattaa agtacaaaa attagctagg cgtggtggcg gatgcctgta gtcccagcta   13920
cttgggaggt tgaggcagga aatcgcttg aacctgggag gcagaggttg cagtgagccg   13980
agatcacgct tgaacctggg aggcagaggt tgcagtgagc cgagatcaca ccattgcact   14040
ccagcctggg cgacagagcg agatgccatc tcaaaaata aataataca tacacacaca   14100 cacacacaca cacacacaca cacaccactt gttgttccag cttgagaagt ggattagtgc   14160
agtggttctc agtgtggtcc ctagccacca gcatcagcat tactaggtcc tgttaagaag   14220
cacagaccct tggccagtcc tatcgaatcc aaaactctgt caatatgttc taacaagtcc   14280
tctaggccat tctgatgaac actgaagttt gagaactact agatttatac atttacactc   14340
aactgggctg cagagtatat ccagattacc tgaggggctg cttctaaatt ataccataga   14400
ttgatgtttt atgtctatgt gccctcctat gaaaaagta ttaatgaatg gagaaaaggt   14460
taaaatgctt gaggctaggg gagtgtgtta gtttgcttgg actgctgtca caaaatacca   14520
tagacgaggt ggcttaaaca acaaacattt actacttgaa gtcctggagg gtgagaagtc   14580
caagatcaaa atgctggcag atcgggttct tggtgacagt cattttcctg gcatgtaggc   14640
aactgtcttc tgtcttcttg ccggtctacc accccaatta atgccctctt agcctcttat   14700
gtctcttgct ctttttttt tttgagacag agtctcgctt tgtcacccag gctggagtgc   14760
agtggtgcaa tctcagctca ttgcaacctc cgcctcctgg gttcaagcaa ttttcctgcc   14820
tcagcctctc gtagctggga ttacaggtcc acgccaccac gcccggctaa ttttattat   14880 ttatttatat atattttta gtagagacga gatttcacca tgttggccat gcaagtctca   14940
aactcctgac ctcaagccat tgtccacct cagcctccca agtgttggg attacagacg   15000 tgagccagcg ccccggctc ttgctcttat aagggcacta agcccatcat gggggcacac   15060
cctcatgact taatctaacc ctaattacct cccaaaggcc ccacctccta ttaataatac   15120
cgtaacgttg gaggttaggg cttcaacatt aatttcaggg tttcataaac attcagccag   15180
taacaggaga agaaagaaaa tacttttgag atggaccttt actagtgcag tgataagttc   15240
```

```
tagtcacaaa acacgtctgc ttgtttatag gacttggggg ctccctgcct tccatttctc   15300
tttctcttag ttcttcggca atatggcatg aagataatct ggacctgtgg tcctgggatt   15360
ttgatgaagg tgggaaaggt attttaagat cttgactggc agggcatggt ggctcatgcc   15420
tgtaatccaa gcactttggg atgctgagct gggcggattg cttgagccca ggagttcgag   15480
accagcctga gcaacatggc aaaaccctat ctctacaaaa acaaaaaaat cagccaggca   15540
tggtgatgcg cgcctgtagt ctcagctacg tgggggctga gatgggagga tcacttgagc   15600
aaggaaggct gaggctgcag tgagccatga tggcaccact gcactccagc ctaggtgaca   15660
cagcaagacc ctgtctatat acagaaaaaa aataggatc ttgactgtgg tggtctccaa   15720
gtatggccaa tacagtacac ttttccaaga aagtgattct tgaaaatgcc acttaaaggt   15780
cagtgttgga gcactaatta aatgccatga tgtccctttt gcctgtgatg ctgtctgat   15840 ctgagaacag ggcgttgggt gatttggtgt tctcacagta agcctttatt gacctctctc   15900 cctcacccc tacttcttag tggccagtct gagttttgct gtgaattcct ttccttgtgt   15960
ctcttcttgt gaagttttag taaataaacc ctgtaagtag gccgagagca gtggctcaca   16020
cttgtaatcc ccgtgcttta tgaggctgag atgagaagat tgcttgagcc caggagttcg   16080
agaccagcct tggcaacata gcaagacctt gtctctctta aaaaaattt tttttaaatt   16140 agctgggcct ggtggcatgc acctattgtc ccagttactt gagaggctga ggcaggagga   16200
tcacttgagc ccaggagttt attggaggct gcagtgagac ctgattgtgc tattggacta   16260
catacagcct gggcaacaga gcaagaccct gtctcaaata aaaataaacc ctctaagtag   16320
attcctgaac aagccacctc atctctgcag tgaatgagga ctctctgagg ggtggacatt   16380
tgagccaaga cctgtctcca gttgtataac ttaatgaata aggattgtgc ttggcacaga   16440
tgtgggagtt acagaagtgg tcaggtgata aatattaaca gtttgaagac caagtgaaga   16500
accagtgttc taattcattt ggactttctg aacaccttat gtggtttctc tgtccttccc   16560
attaaaaaca agtattctgc taccaggcct ctttttcctc ctgcctgaga agcgtagctg   16620
tgatcactgg gacctagctg caatgaaggc agtggtttcc aggaggagac tacagtttga   16680
tctgtgattt catatttgta tgtacagatg aatactttag taaggaatct tatgtttgtg   16740
tgtgcatgtg tgttttaaac tctatcactt ttaagcttta ttttctctgt tcttggcttt   16800
ttcttttttc cttttcatt ttctccttg atgtctaact ctgcattagt agaatgcaga   16860
gcacatggaa actccagtaa ctttaccaca ccagagctgg taaaatggag atacaacata   16920
caccagtttc agactaacat cattttggtg aagattgatt tttttttttt tttttggcag   16980
agtcttgctt tgttgcgcag gctggagtgc aatggcgtga tcttggcttt ctgcaacttc   17040
tacttcctgg gttcaagcaa ttctcttgcc tcagcctccc gagtagctgg gactacaggc   17100
gcccaccacc acacctggct atttttttgt attttagta gagacagggt ttcaccatgt   17160
tggtcaggct ggtcttgaac tcctgacctc aagtaatctg cctgcctcgg cctcccagag   17220
tgctgggatt acaggcgtgc gcccagcctg tgaagatttt tagtatctgc tttcctttct   17280
tggaaaagcc tggctaacta gaggcaggaa atgtctatgt ctgattaaca agttcctaaa   17340
tggtctctac ctcttctcat ttcccacttt attgtctttg gtctgagac agattccttc   17400 atctgttttt ggggttctgt tgacccagta cagatttgta acattgtttt tctttacagt   17460
ttgtgatttc aatcctctgc tttcccaatg ccactttgaa ttggcttctt taaaactcca   17520
acataaaacc tcagtgacc aatatgtggt ctcattatgg tatttggggt taaaatgaaa   17580
ttaagatagc tgggctcacc cagccaaaca catttaccaa agggaaattt tgaggcatca   17640
```

```
tagactgtga agtggttagg gaaaaagaga gttaaatgtt ggctagttta gaatgccaag    17700
tgtccatccc aacttggtta tactggccag agatggcaaa gaatagagac aataaggttc    17760
tgaaaagaca gctggtgact ggtatggccc tgtatactcc tgggataaat catgaagtga    17820
gggtctcctg tacatacttg tatagttttgt atagacagtg gtgtagatga ggttggtatg    17880
taccagcata cttttggaac tttgagaaga actgtagaat tgtagtact  ctggttttcc    17940 atccagggaa ttgctgacct taaaacctga ggatttggat gcatctataa tcttttttgt    18000
ttgtttgttt gtttgtttgt ttgttttttga dacggaatct cgttcggttg cccaggctgg    18060
agtgtagtgg cgcaatctcg gctcactgca gtctccgcct cctgggttca agtgattttt    18120
ctgcctcagc ccagcctcct gagtagctga gactacaggt gtgtcaccat gccgggctaa    18180 ttttttgtatt tttagtagag atggggtttc actatgtcag ccaggctggt ctcgaactcc    18240
tgacctcatg atccacctgc ctctgcctcc caaagtgctg ggatgacagg catgagccac    18300
cgcgccgcat atataatctt aataaggttg actattccct gggccgttct ttaacttatt    18360
taattgtgcc tgctatagtt cagagtggac ttaggggggac ctagtgaaag actggtatttt   18420 tgggaagta gtccaaggca gccctaggaa ttaatgaaat aaacagtggc attgctgctg      18480
cttcttggtg ttttttatcaa catacagtac ttgattggat tgatgtacaa gcatgatgac    18540
aaacagaatc ccagactgca tgtaacttca gttcctacag ctcagtgatc tgtcacagat     18600
accttctttg gcgggatata gaactatgta ttagagaaat ttagcgtctt ttttgtataa     18660
ctgaaagacc agcccaagtt tgcagttgta gataaaataa aaagaatggg agaagttaga    18720
gaaagaaaac gaggctttga agttttgtgg ctaggggcag tttttatctt tatttacttt    18780
gtttatttgt ttgtttgttt ttagcactta tctgcaaatt agtttaacat ggaagaggga    18840
ggagtatttt agaaactaga tcagaagatg catttagaac aaaagttgga atgtgcacac    18900
ctgggtaaag ctctgtaagg ttactcttgc ccctccatgt attccttaag tgtaccatat    18960
cacttaatgg taggtaatga taagtagggc agaaaacatc aaaaggacag caatattcag    19020
ttgggcatgt ggtccatcca taccaaggac cttttcctag tagaagcacc agaggatggt    19080
ctgtgggagg aagtaccttt ttctgatttc aatctatatc acctcacatg gggacaaatt    19140
ttctaatttt tgagcatata ttgggatgca gtataccagt gtgtctttgc gtaccatcag    19200
gatttcctag actttgatga tattttccat ttctcaggaa ttttttaggat aagaactttt    19260 taaagttcac ttaattgccc agtcctgttg ttgaaatgtt gtttaattta aagcataaaa    19320
tatgctgggg agagtggcac acgcctataa tctcagctac tgcagaggct gaggcaggaa    19380
gatcacatga gcctggagt  tccaggccag cctgggcaat gtaggagac ccgtcttaaa     19440 aaaaaaaaca taaatagtt gggccttgcc aatgtaagaa gtcatatggc agaatctttt    19500
ttgaaaaacc tgtgagtatc aggctgggcg cggtggctca cgcctgtaat cccagtactt    19560
ggggagactg aggtgggcgg atcatgaggt caggagtttg agaccagcct tatcaacatg    19620
gtgaaacccc atctctacta aaaataacaa aaattagcca ggagtggtgg tgcatgcccg    19680
taatcccagc tactcaggag gctgaggcag gagaatcact tgaacccggg aggcagaggt    19740
tgcagtgagc caagatcgcg ccactgcact ccaacctggg taacagcgag attccgtctc    19800
aaaaaaaaaa aaaaaaagaa aaagaaaaaa acctgtgagt atctgccaca tgctagttgc    19860
ttacattaat gcaaaaacac ttactgagct tctacagtga atcagatagt atgttatgaa    19920
cataggattc ataattcctg cctccatgga gtactttcta gtggggaaaa atatgtaagc    19980
```

```
agataagcac aaataactgt agttacagtt gtaataaatg cattggagaa caacacaact    20040 gttttttaa attttattt atgcttacct tgtctgatgg gtggctttgt agtcttgaga      20100
tcttaggatg ggtgctggtc agttctgagt cccttccct ctagggtcaa gttttatagg    20160
aagttatcca ttgaggcatg ctgggctaga gttcattgtt cctcagcaag gctcttctgt   20220 tttgttttg ttttgtttt acggggagat ggagtcttac tctgtcactc agggtgaggt    20280
gcagtggtct cagctcactg cagccactgc ctcccaggtt caaaccattc tcctgcctca   20340
gcctcccgag tagctgagat tacaggcatg caccaccaca cccaactaat ttttgtattt   20400
ttagtagaga cagggttttc ccatgttggc caggctggtc ttgaactcct gatctcaggt   20460
gatctgcctg cctcgccctc ccaaagtgct gagattacag ggtgagccaa ctgtgcctgg   20520
ccaggaaggc tcttctttt gtggtgctat attgcaggac attggcatct tgctccccgg   20580
gtaataaatg ccagtagcac tatagagttg ctgtgacaac caaaaaggc gctttcatac    20640 attatttcc aaacacttct cagtggttgg tattgccccg gttgaatact actggctgta    20700
ctgtcaggat tcttggaagg agctttgaac aaaatcctct gggagaacag actgaaagta   20760
ggtggtgctt gagacttgga ctggccaacc cttttggtgt ctgacttgtg tgttcatgtt   20820
ttttaagtag gtattttgaa actgctctca accccatttt gccatttctc ctattgaggg   20880
tgcagagaga gaagtattgt gtgtgtgctt tatgaactgg cactgtaaca agcatttcac   20940
atacttacca tttgaactgt tttgtatctt tgttaaacag ttttaaatcc ctgtttacag   21000
atggttctgg tgctaagaga taaagtgact tgctcaaagt ggtgtgaaac tatacttttt   21060
tttctttctc aaaagtaca gcctaaattt atttgattgt cagttaacct ctagttgatg   21120
actttggact tctggtctta agtgtatggg acagacatta attgttctac aaatttccaa   21180
gctctactgc cagaaactta gcacttgtgt aggatgatga tagctgccat tctggatgct   21240
agaggataca gcagtgaatt aaacatacac aggacatata gattgaacaa gataaataag   21300
tgaatcatat atatagtatg ctagtgatac atgcttggga gaaaaagtta atcaggaacc   21360
aagtatagga gtgtgcaggg ttaaaatctt agaggagttc accagggaag gccacactga   21420
agtgatattt gacatgaaag tgagctatac taatatctgg gtgaagaaag tattccaggt   21480
agaaggatct atgaatacaa aggctctgag gctagaggat gcccagctga tttgaggaac   21540
agtttttttg tttgttttg ttgttattta ttttgttgt tgttgtttct gagatgaagt    21600
ttgctctgtt gctcaggctg gagtgcaaag gtgcaatctt ggctcaacgc aacctccgct   21660
tcccaggttc aagcagttct cctgcctcag cctcctgagt agctgggatt acaggcatgc   21720
accaccacgc ccagctaatt tttgtatttt tagtagagac gcggtttctc catgttggcc   21780
aggctggtct cgaactcccg acctcaggtg atccacctgc ctcgcctcc caaagtgctg    21840 ggattacagg cgtgagccac cgcacccagc cgttgttttg ttctttattt actttattcg   21900
accctgaagt gtggtactac tatctgttct gttgataagg aaacagagac aaaagttgaa   21960
ggcactgcag gggcagagct cttaagccac tgcctagaac tggccatgta caatagtcct   22020
cccttatctg tgcggcgata tcttccaaga cccccagtgg gtgcctgaaa gtaccagacc   22080
ctatatgtac aaatgcccct cggtatccgt aggggtgg ttccaggact ccctgaggat    22140
actgaaattt gtggaatata taaaattgca tggtatttgc atataaacca ttaatacgta   22200
cattctcctg tatacgttaa atcatctcta gattacttat aatacctcat acaacgtaga   22260
tattatgtaa gtagttgtta tgctatattg tttagggaat aatgacaaga aaaaagtgt    22320 acacattcag tacaggcaca accatcgtag gcctactaac tacattttg atctgaggct    22380
```

```
ggctgaatct gtggatgcag aacccatgga tacaaaggtt tgactgtact ttgtttttcc   22440
tatacatgca tacctatgat aaagtttaat ttattaggca tagtaagaga ttaacaataa   22500
ctaatgataa aatacaacag ttatgtgatt gtggtctctc tctttcaaaa tatcttattg   22560
tatgtaatgt tttcagattg tggttgaccg tgggtaactg aaaccttgga aagcaaaatc   22620
aaggataatg gggggtactc ctgtagatcc aaagcatttc agttcagcat taatagggac   22680
aggaattgcc aggccactag agtttcactt tctcttctac attccccttt cctttcctgc   22740
ttttgggcat aggggagcat tgtttgttt tgtatacata tctcttatct ctgcctacct    22800
gaaatttata ttctagtcaa ggatacagat agcaaacaag ataaataagt aaagcattag   22860
tatgttacga tacttgccca ggtgaaccag aaaaatctga gactgagtat aggaatttgg   22920
ggaagcttga ttttggctga aagtgctgct catttgggaa tctgaggtgc atttctagct   22980
tttctttact ggccaggcac tgccctcttc agaccattgt ttggctaagg aaaacgaatg   23040
tacatctgaa ttctagagac actctgtgct ggagatggat tgcactata acaggcatt    23100 cacatactta tcgtttgaac tgtctcatat ttttgttaaa cagtttttaa tccctgttta   23160
aagatgattc tggtgccaag ggatgaagtg acttgcttaa agtggtgtga aactctatac   23220
tttttttttt tttcttttta aaaggtaca actgaggccg gcacagtgg ctcacgcctg     23280 taatcccagc actttgggag gctgaggcgg gcagatcacc tgaggtcagg agttggagac   23340
cagcctgacc aatgtgatga aaacccgtct ctactaaaaa tacaaaaatt agccgggcat   23400
ggtgacatgc gcctgtaatc ccagctactc gggaggctga gacaggagaa ttgcttgaac   23460
ccgggaggca gaagttgcaa tgagccgaga tcgcgccatt acactctagc ctgggcaaca   23520
aaagtgaaag tccgtctcaa aaaaaaaaaa aaaaaaaggt acaactgggc tgggcgtggt   23580
ggctcacacc tgtaatccca gcactttggg aggctgaggc aggtggatca cgaggtcagg   23640
tgtttgagac cagcctgacc aacatggtga accccgttg ctactaaaaa tacaaaaatt    23700
agccgggcat ggtggcatgc acctgtaatc tcagctactc aggaggttga ggtaggagaa   23760
ttgcttgaac ccgagaggca taagttggag tcagccgagg tcacgcactg cactccagcc   23820
tggtgacaga gcgaggctct gtctcgaaaa aaaaaaaaa ggtacaacct tccagattgg    23880
ccaacatgat gaaatcctgt ctttaccaaa aataaaaaaa ttagcaggcc ctggtggcac   23940
aggtctgtaa tcccaactgc tagggtgact gtggcaggag aatcacatga aaccgggagg   24000
tggaggttgc agtgagctga gatggcgtca ttgcactcca gcatgggcga cagagcaaac   24060
aagactccat ctcaaaaaaa aaaaaaaggt acaaccttaa tttatttgat tgtcagttaa   24120
cctttgggca tgtagcccaa atgctcccag actggatacg agactctctt aagattaaaa   24180
atacagattc ctggctgggc gcagtggctc atgcctataa tcccagcact ttgggaggct   24240
gaagctggca gatcacttga gcttaggagt tgaagaacag cctgggaaca tggtgaaacc   24300
ccatctctac aaaaactggc tatgatggca tgtgcttata gtcccagcta tcaggaggc    24360 tgaggtggga ggatcacctg agcccaggat aggaggttga ggctgcagtg ggccatgatt   24420
gcaccactgc actccagccg gggtgacaga ttgagacacc ctgtctcaaa agaaaaaaaa   24480
aaaaagattc ctggcccggc ccccatccca gacctgctaa ttaagaatct ggagggtaga   24540
attggattga gtagctgagg aggttgaggt tcaacctggt tgattgtctt gaccactccc   24600
tcaggaagtt ggtctgagaa ctgggattgg accccagatg tacttactgc ctctcagttt   24660
actgctcttt gcacctggtt gtactgctgc cttttgagat aaaaagttgt aaagaagggg   24720
```

```
acgtttaatt ttatgagatg acatttttggt tcttgtttca tagttttctt ggggtcttac   24780
tattgttttg gtcaccctgg tttgtttttg ttttttgtttt tgttttgaga ccgagtctca   24840
ctctgtcacc caggctggag tgcagtggtg cgatctcggc tcactgtgac ctccacctcc   24900
caggttcaag tgattctcct gcctcagcct cccaagtagc tgggactaca ggcgcgtgcc   24960
atcacacccg gctaatattt gtattttcag tagagaccag gtttcaccat attggccagg   25020
ctggtctcga actcatgatc cgccctcctc ggcctcccaa agtgctggga ttacaggcgt   25080
gagccaccgc gcctggcaac ccttggtttt aagcagtacc tgaaaggatt ttttccagag   25140
aagttacttg gtttccttag tggcttttgt aatttgtttg aaatagggag aaattggtta   25200
agtttagtct taggaaaaag tgatcttcat cattttagga agagcatttt ctctggaaat   25260
gatgatagcc acctgttatg gaaaatgtgg ctaatgaaag tgccctggat gaagagagaa   25320
ggacttatca tttgttggga ttcattagtt tgatgctgta gctgctttat ttgaagggcc   25380
ctttctggtg ccaaagaagt gaagaagcat cagtcacttg gttgtggttt ttctggcatg   25440
cctctttttg gtagacagct gtgaggtggt tattatggtt gtttctcata atctgattga   25500
gttttgctac atgattcaat gactcttccc cttttggtct ccttcttcta accttagtga   25560
gttttctctt atcttctggt ctggaaggat agagatatgg tagtctatat atctctaagc   25620
ccagaagaga atgaggcctt tgtcttgttt tacatcactt tctagatgtt cttggtttga   25680
catctggttg caagcgcctt cctggaggtt tgatcaggct agtgcttcag gggatatcat   25740
tggaatgggc taagtctgca aaggggaatg tgtctgatct tctagaatgg tttctgtaag   25800
cagaatgggg tagatagaac ttttcactga tttttgtggt ggtttttttt gtttgttttc   25860
aagatagagc cttgctctgt cacccaggct ggagtgcagt ggtgtgatct ctgctcacta   25920
caacctctgc ctcccaggtt caagcgattc tcctgcctca gcctcccgag tagctgggat   25980
tacaggcacg tgccaccatg ccaggctaat tttggtattt ttagtagaga cggggtttca   26040
ccatgttggc cagcctggtc tcaagctcct gacctcaggc gatctgccgc cttggccacc   26100
caacgtgttg ggattacatg cgtgagtcac tgcgtctggc caattttat tccacttgga   26160 aatttatgga agtttgaaag aattttaaa aaacaaaact tttttgggga gtggtagttg   26220
caaactagtt gttgattcct ctctcaccaa aggcagatgg tcagtttgtt tagaacttga   26280
atgaactaga atgaaggaat tgtgaagtag aaaactgagt tatggttcct aggttatgaa   26340
tgaagagaat cataggctga gtgggtttga ttccctgtga caggtgttgg tataatctaa   26400
tgagattttt ttatttttcct gtcatcagct tggcttcagg aaatctttag tgttgtctct   26460
gttgaggcca aataggaggt tagaaatctc ttattgtcct aggtcatata aaaagtcatg   26520 tttcccact atttaaaaca agatgaaggt agtctcctta ttttaggagg cggggtctag   26580
gagtaaaact aagacaaaca tgtttctgga caatttctcc tcaattgggg ctagggggtt   26640
cttgactagt cttcaaagaa ggtctgaaat actaggggat atagaaaaga caggataagg   26700
ggcgttagat acagttgtct ggctggggag agaagggaca atgagaatga tttatgctgg   26760
tcattttatg taccagggta cataggggtga ttttttttggt ggaagcctag tctgtcctaa   26820
gatattactc ctgagatcta agtgagccac gtgcagctgg caggaagctg aaagctgttg   26880
gttgggagag gccttaattt ttacacttgc ccctgcctgg aatgccctat cacaggggag   26940
ggtcccatac tggaactgga tcaacagctg tcgcctgtcc ctggaatcac aggaagcgga   27000
ggacggggtg cctttgtata gggagctctg aagccagaca atagtttgtg ctggcggggc   27060
catgtggcga gtcatgtgac ctggggctgt tttctgctgg ggtccttacc catctgttct   27120
```

```
ctcggctctt tctgggttat caggcgccag tccaagtcct cccaggcagc cagcttcatg   27180
gccagagatt acgagcacta accttcctgg cagggqcggt gtggcttcga gtttatgcag   27240
attagccatg tgtttctcac ttcaaggcgt tccacaggaa aagccttttc ctgtgtttgg   27300
ctctcagtgg gcggttccca gcttactgta ctgggactca gcaagcagca ggcatgcacc   27360
agagggatca cagtacactg gccccctct ccattccacc tccaatgcta cgtcaccaca    27420
acacaaccac tcgcgctctc atactgttgg tgtcattcat tcggtgccaa gattgcttta   27480
aaaaattccc ttggccccag ttcaaacagg agtacagctg ggatgtgtta gattttaggc   27540
agtctgccct caatttgaga tgagttataa atagcagtgc cgacttcctt aactaccgct   27600
ctctgaggta aaatgcaggt taattactgt gggaatcaat taggggggtt cttttggtta   27660
aagagccagg gatgcatttt tttaattatt attattaaaa gtcatataac aaatctagcc   27720
aggaataaat tgaaagcaca aggagtaata atacttaaat gtccaaaagc caaggttata   27780
gctctaggtt tacactagcc ccaactagtt agcatttagg atgataaaat gagtagtggt   27840
caagacttct cctctctgat ggacaccttt ttggcagctc ctggcccaac cctctctgtt   27900
cttattcttg ctggcccttg gcactgttga gtactaaatt tagctcctta gggttgccgc   27960
ctggtcactt cttctatttt ccttggattg gaactggagc tttcctcagt tggactttta   28020
tttaaataaa attatgaagt ttctctttcc tggtgccact gccacgggtg gtacattttt   28080
gtgaatggta tatctctgct tagaagtttt gagttcttgg ctctgtcttc tctgctctct   28140
cctcggtcat ggtcagatgg agaatttgca gctatttaa tctgtgagtt tcacaaagtg    28200
gttactttgg gttataagac attcagccca ggtctaccttt aaaagtctag tctgttattt   28260
cagccgtttt tggggqtcat tttggttttc cttgatgcaa taagaagttg taagaggttc   28320
cagtagccag ctagtctgga gggtcttgta attctattgg cttggagcag gggaactccc   28380
tatgcaaggg gtctgtctgc tagctgtttg ttctgaatat attcggaagg acaagctgct   28440
aggcatcctt gcctttgatg cccctaaact gcatcttttg atacatttca tttggcaggc   28500
agtttataac atggccagtg atctggaagg aggtggtaag tggtagatgg agatgaggag   28560
ttttcttatg gctctttccc cctttttat ttttattttt tatgaatgca ggagagtata    28620 tagcagggg cccgactttg ctgatcaagg ggcagcattt tcctctcaat tatgtgtctc   28680
tgtggcagag cctttgcttt tgaagtgtaa tcacagtaat ctactcctgt ggtttcccat   28740
tgaaaggatt tcctctgtct ttcccagagt ggaatctctg gcttttgca gctagggttt    28800 ggagtttcca tccctgcct tgtgcctgca gactgctgat actggctttt gtatcttgca    28860
tgtagggatt tttctggtct gaaattgcta cttttccaata aaactgatta gtgaatattt   28920
aaggcccctt ctctgttacg agagattggg agatggcatt tcatctgtaa ctgcaaatca   28980
caaatatttc acgatggttt taaatgtcat aagtgtgagt tatgtccctg ctcacctccc   29040
cttctgattt gagcagatgt ctaacttta catgagatca gaataatctg attgtttgaa    29100
ctgaatatat atttagtttg ccaaataagc tgcatattct gttgatcata agccttttgt   29160
gatgggaggg agtcaaaaat ctgacgacca gaaaaagaaa gcatattaat tttattttta   29220
gaataaaaat ttctttgatg tacatttatt tttggtctac aaagatttcc taaagttgag   29280
gtgggacatt ccttgaaccc tttatagccc ccatgtaagt agctgtactc aattgggagc   29340
gcaggcctcc gtgtgagaga ggaaaaggtg acttgtcctt agccttttgt ttttaagcag   29400
tgtatatgag gatgcccctg cagttctgaa attctctctg gtataaacct ttttttttt    29460
```

```
ttttttttttg agacagagtc ccactctgtt gcccaggctg gagtgcggtg cacaatctc   29520 cgctcgctgc agcttctgcc ttctgggttt aagtggttca cctgcctcag cctgctgagt   29580
agctgggatt aacaggcgtg cgccaccacg tccggctaat ttttgtattt tagtagagac   29640
ggggtttcac catattggcc aggctggtct ggaactcctg acctcaagtg attcacctgc   29700
ctcagtcttc caaaatgttg ggatttacag gcatgagtca ctgcgcccag ccttgggttt   29760 gtttttttttt gttttttttt ttttttttgag acagactctt gctctgctgc ccaggatgga   29820
gtgcagtggc tcgatctcgg ctcgcttcag tcttcgcctc ccaggttcaa gtgattctca   29880
tacctcagcc tcccgagtag ctgggactta taggcatgtg ccgccacacc cagctaattt   29940
ttgtgttttt agtagagatg aggttttgct atgttaggca ggcttgtctc ccaactcctg   30000
gcctcaagtg atccacctgc cttggcctcc caaagtgctg ggattacagg cgtgagacac   30060
tgcgcccagc caggttattc ttaaagtgtg cttgttctcc cttgaatatt ctcatccttc   30120
tttctcatct ttcacttcag tccaacttttt tttctacctt caaagtcata acccctgtgt   30180
tagggttaga tttaggctat gaccctggct ttatggctag atagtttgat ttgggcttttg   30240 tccccatagt gtctcctacc cttttttgga ataggacagc attgcacatt gaacagtcac   30300
tgagcccaag ctctgtactt tggtatttgg gagagctttg aagataaaac acctgatctc   30360
tggcttccca gaagttagtc ttgagaaatg caatcagtta gttggaatag ttagctgcaa   30420
ctaagtgtta aatcttagga tgctaactgg atttacaata gggcatttag aaatgttaga   30480
gatcaaagtg tactgaagat atgggaagtg gcttcatttt gaaaggtcaa gtttctgtta   30540
ctagaagcca ctgtggacag gagggcaggg caggatgcca ttgcatagag ctgggcatgt   30600
acagtatgtg gggaatcttg gagtgagact gaaaaaatgt ggaaactgg ttcacattgt   30660 agagggcttt agagccaggt aaaagcactg ttttatcatt actgataatc gctaccattt   30720
attggacatt taaataccag gcactgtgtg aagtgtgtta tgtgcattta aagaactgat   30780
gtgttcaagg taggatggtg agagaggtag gatttggacc caagtctatc aaattactac   30840
actaccctct atgtaataat actgtgcagg atttagtagt taggaagttt ggaactatta   30900
ttgaccaggt agtggtggaa gtgatttggg aacagcattg tcctagaact gctctaacat   30960
aataagccac tagccacatg tagttatgtg aatttaaatt aattaaatgt aaataaaaat   31020
aaaaatttag ttcctttgtc atatttcaag tgttgaatag ttacccatca cagaaaatgt   31080
tattggccag tgcttctcta gatcactggt tcttagctaa tagtatacac cagactcatt   31140
caaagatctt aaggaggttg gagaagagca caagcccttc cagacccagt aaattggaat   31200
ctctagggag aggcctagcc atttgtgaag cttcacagaa aattctaatc tgcagccctg   31260
gttaatagct actgctctag aagctctata gtaaccatgg taatgactgc ccctcatgtt   31320
gtggggagac ctagactgac agagataccc agagcaggct gatctctttg ttcaacaaaa   31380
tagtctctcc agttggaggc cacatggaca gcagctgcag tctgtgatga gatgaggacc   31440
tcagtgtgat atgtggcatg atatggccat gtaagccccc aagctctttta caggggagaa   31500 tggtgatgtt ttggctccat tgccaggtgt attggggagg accgtatgct atttattaat   31560
tgttgttaaa ttcgaacttc ctaagtaacc ctaaaatcta tgtagctcta aaattatgat   31620
agggaacatt attggagctt ctgatatgga tgaaagactt gggcaaaaat tgtttagtta   31680
ggattgttgg caacagtact ttaataatat tgacatgtag tagtgatttg ggacacagtt   31740
ttactatgac tttgtacagt ttagaaacat ggggaggag tattcccatc atcactcacc   31800
aatttagctg agatttcaga tatagcctaa gaaataactc tgcttctctt ttttccctttt  31860
```

```
gatattaaga agaacagcct ctgtggctta ttgtcttacc tgttttcttt catgaaagct   31920
ctacttcctc tactataaaa cacttaatag cattattaaa aaacaaacac gtacagagaa   31980
cgaattgttt ggatctcccc ttcctttatt ttggaggttt tgttgttgtt taaggtctta   32040
acagcttaaa ttatagaata gcttattaat tattgaataa tagaactgga aggaaccta    32100
gggataacct agaccagtcc tgggaggtgg gttctagcag tctgttttaa caagcctttc   32160
aagtgattct gatgcatgct aaaatcaatg aaccactgaa ctccttcatg tgacggttaa   32220
tgataggcct agagtatcag tatctatttc accccccaatg taagagctag ttttttaagtt  32280
ttatatcaga cccatgccta ctctccatct tgtgtgtgtc ttaaaggtgc ttagagaaac   32340
ttccccctcc ccgcacacca ccaatagata taggtagata tttctggcag gggaaagtgt   32400
gctctggagt gccagtagga taaaggcata tcaaaaagtg aatgagctgg ttgaacctgt   32460
tgctccacaa agagctggaa agaaagctgt tgcatcaaat acctgtgaat tgaattttga   32520
gctttcatta ttggtgctag ctgtacctct ctgtcttctt gctctttttt ttttaacttc   32580
catgacagcc taccattgaa tcttcttgtc tctcaaagag ataaaagttc tgttcttctt   32640
atatcttcaa actcttgaat attaaaggaa atgagctttt cagttgagat gcacaagact   32700
cttaattcag agttcccatt ccctcaactg tcacttagct gctttgctta tttggaagaa   32760
agcataaatt taactgtgcc atagtgcaaa caggctatag atgtgtaagg ggagtttcca   32820
ctattggaag aatagaaaca tctagatgtt tgtgtatttg aattccccgt catggtattg   32880
aagcatcaat tttggtgtgt aacaaggtga tggcagtgca tagcagcacc gtcctctacc   32940
aactgaaggg cctttgttta tacccggcct gtcccttgga tctcaagcag taccacagtt   33000
acaaagtagt ttttagctta caaggtgttt tcacaaatag gtggtatttt cattttttcaa  33060
atgacaaaat tagggttctg aggcgggtca gttgacttaa aggttactag gttggtctca   33120
ttgctctttc aaagtaactg tatttcttta tagcatacag actaaaaaaa cctgtgtact   33180
tgggttatat attcagtggc cagaggccat caaagctcag gttaatgaaa tgctctttat   33240
tttgtagcca tccagtccaa tggatcagat gggcaagatg agacctcagc catatggcgg   33300
gactaaccca tactcgcagc aacagggacc tccgtcagga ccgcagcaag gacatgggta   33360
cccagggcag ccatacgggt cccagacccc gcagcggtac ccgatgacca tgcagggccg   33420
ggcgcagagt gccatgggcg gcctctctta tacacagcag gtagatggtg attgtgatta   33480
ccttgaccct tgttgctgtc caaaatctga tctgtgagct atagaatcag aatgtatcct   33540
tggcttccaa gcctcttgac aggaatgtag acctgttggc tcagttaatt acagagtgct   33600
actaacaaag ccaaagctat aggcaccgtt ccatgtgtgc tccaaggaaa actacttact   33660
ccctggtcac agtacgtat  ctcttttct cttgacctga ctggccagct tatacctagt    33720
gagtggtcat ctctgaatga gatgggatga aaggcagtgg ctgaacatgt aggcactgct   33780
actattagga aaaccattca tatcatgtgc cctggtgacg gaagaggccc tttatgcttc   33840
tgaatacctt taacatatct gccttctggt tcaaaatgaa tgtgactggg agtagaagaa   33900
aaggggaaga ttaaacagaa aagatgttaa cagcattgat acaaatgtta agatttcccc   33960
ttatccatct cttttgtcg aaccattcac atcattatct ctttattgtc attttttgtat  34020
tgacaaagtt ttctatcatt tatctttgag tgatactcat actgaaaata gggagagaat   34080
ataaaacaaa tttacttct aagactttaa agcaaagtac gcctttaata tagaaaattg    34140
tctcttttttt ccaatagagg agagatgagg taattttatt tattttttt  atttttttgc   34200
```

```
ctgcttacta aatatatccc cagtgcctaa aatagtgcct ggtacaagta attgagtagg    34260
ctgtcaaata ttttttttga atgaaaacta aatgaaagag agaaccaaag tagcttagtg    34320
attttcacac tgtctgaatt actaaacctt aggttttcag ttggttgagc caggctgcta    34380
ttgactattc attgtggtta gggtacagat tcctaacact tataaaaaca gtctaggccg    34440
tgataaaaag agttaggctc actggtagaa acagctgctc tcaaacttat gttgcccaaa    34500
tagtaaaatg tgtaaatttt cagtggataa atgtagtcca cttgtaaaca aaccacctaa    34560
aaacccagct tggccgtcct tcctggctca gtttaggcag ggtgagagaa aaaccctggg    34620
cctcctaagt atgaggcctt gcatgcttgc tttctatact catcatcagt gcatagcttc    34680
tcacaaaaca cttcatcttt cctcatgcag agagtcagt gctaaaagta tattttcctt    34740
tcctacagat tcctccttat ggacaacaag gccccagcgg gtatggtcaa cagggccaga    34800
ctccatatta caaccagcaa agtcctcacc ctcagcagca gcagccaccc tactcccagc    34860
aaccaccgtc ccagacccct catgcccaac cttcgtatca gcagcagcca cagtctcaac    34920
caccacagct ccagtcctct cagcctccat actcccagca gccatcccag cctccacatc    34980
agcagtcccc ggctccatac ccctcccagc agtcgacgac acagcagcac ccccagagcc    35040 agcccccta ctcacagcca caggctcagt ctccttacca gcagcagcaa cctcagcagc    35100 cagcacccctc gacgctctcc cagcaggctg cgtatcctca gccccagtct cagcagtccc    35160
agcaaactgc ctattcccag cagcgcttcc ctccaccgca ggtaagatat ccctgcctcc    35220
tgcccttccc tgtgtgtgac tacagacagc ttgggggtta gtgtcatgag aactttgctg    35280
tacagagtgg ttctctaacg tgcacttaaa gaccaattaa actctgggta acatgataa    35340 ctggattgat tgaactaata aaggcataac ctccttaact gcataaagac ctgtagctct    35400
ccttaatgat gaagaaatag ggcaatggaa agttgcatag atggataaga aattaaagat    35460
aatgggactg gttttttttat tttattttat tttattttat tttgtaaatc aacatcagaa    35520
cttcagcatc taagtgagtt ggtcttttt caaaacagtc actttgagag gcagtactgt    35580
acattcactc caactgccat tccattctgc tatcgctcaa aatacttgga tcccttcatt    35640
tggaattgcc accagagctg ataccacatt ctttagaata ctctcagtgg tgcaaatct    35700 tatttttgt gggtggattt tgtttgggga aatagcaaaa attcatttgg agttatgtct    35760
ggtgaacaag atgtaggtaa tagagcctaa aatagcattt ggggctttat ttttgtagag    35820
cccaaagaaa agagatgact gagtgatgac aggtccacta aaaagtttat gtattggtgg    35880
cactgttgga ataaatatct catcccaagg tgatgtcttt gaatgaagca gtactcattt    35940
taatgcagag gttctagcat gatttttttg tggtttcatt ggtctcattc cttgatagat    36000
ttaacttgaa gttggccaga cattagcatt taaccccaag aaacagccct ctgtaggcag    36060
caataaatgg gtgacaattc tgtcagaaag agtccactgt tgacattctt accagtcaca    36120 gcttggatttt ttctggcctt cacataatac ttttcgcaac tggactttct ctcacactca    36180
tgagagacag tcccataacc cttttcacagt gaagtaagcc tgcctggttt atcaatacca    36240
ggccatcaca gcttttgttt ttcttgttgt aggagctatc tcaagattca tttgggtctc    36300
aggcatcctc agcccctca atgacctcca gtaaggagg gcaagaagat atgaacctga    36360
gccttcagtc aagaccctcc agcttgcctg tgagtatttc tgcaccttct gaaaggtgat    36420
aggggcagag aggaaaccaa tgcaaactag ttagtttctg gttggaagtt tagctaattt    36480
tgacctaaat gaataagtta tttcttgaat tcaaggaact taaaggctga cttgtagatg    36540
tctgttctgt ctccctgccc agggaatagg tttgtgatct gtttagtttg ttttttgtctt    36600
```

```
tttaagtctt gtgcttttag acatggaccc acatgagggg cagagaagat ggagatatca    36660
gaagcactgt ctgctctcca tcaaagttga gaaaaatatc agtttcttga ctttactctt    36720
acaggcttaa ttttaggtt tttggcttaa tgtttagcta caaggtagga tcctggagca     36780
attcagcatg cattgtcaca ttgagcgtgg ctggagcaaa agcagttttt ctggtggtga    36840
ttttgtgtga atactttttt tttttatttt tggtagagta cttgatgccc aggtgcttaa    36900
gttatggaat caggtactta tttatgggat ggactgacca tatcctgaga caggcagtat    36960
agtctagtga ttaagaactt gggctctaga gccagagttc ctggctctag cttctgccac    37020
caactctgtt tcataggggt ggtggtgaac attaaatagg ttactagaga gtgcacacga    37080
gcactgcaca ttgtaggcac tccataaatg tcagcctttg taatcatcgc ctcagagggc    37140
attgggactg tgctttatac ctgaaaggca gttaacacca tactaggtgg ttgtaggaac    37200
ctttactgtt agtcttagct ctgtgggcaa gttactcagc ctctgaaagt taatctgctg    37260
ggcacagaaa taaataggc tactctgaaa tctagtcatc tagtaagatg gtgggtagca     37320
aacccaccat gacaaatcct gcttcagtta ggaaatggaa attcagccac atacccagat    37380
aagaatcttt tggaattttg actctacttg gatgtaaagc ctgtgtcttc atttattctg    37440
acctgagaga aatggtttca ggatctctaa gaaataggca gaaggcggga actctcttca    37500
tcatgaagcc tcccatggat tccctgaag gtctctgaga cacctcaata gggcaaggtc     37560
tgcagagtcc cttagtacct ggtgttcagg cttctgaggc cagaatgcag ataggacgtc    37620
tgagattgtt gactttctca actgaggaat tgggggaagg aagtgcctta ataaagtgat    37680
cactctttgt tcccttctca ttagtgtctg ttgcaatcct tttctgcatc ctgaacttca    37740
ttggaatgtg cttttaacc tgattcagtc agaatgtgta accactccct catcatctgt     37800
ggtctgtggc taaatctggg tgaggtgcta ttgtgtcaag acccaaatc ggtggatttc     37860 tgtcagtgct gtaagttgct tcattccaaa aagttttttgc ttgcttctgg tgaccttttg   37920
atagatctgt atttggcttc tttttttttt tttttttttg gtcctgagaa ggcttgtatc    37980
cagagatgct acatgccttg taagggttgg gaatcttaag aacttcttat ctgacccact    38040
gaagtgaagg tgaaggtgtt ggcagccttt taggcccagg ggatggttgt tcctgggaag    38100
gctatcacaa ggaacattcc cacgtttggg cttttttctaa agattcatcc aaatgggtca   38160
tttgctcagt ggtagaagct ccatgtggga ggtaagctgg ctgggttatt ggcatcttgt    38220
tttttgaatt gcttttttatc cctttgctac ttgggcaggc atcaaaaagt ggttattctt   38280
tgaaattttg gttgatgcc agatttgcct acgcaggcta ggaagcagcc ccatctgaag     38340
aaatgacaag ttggattccc tacaagagcc ctctcctttc ttaaccagtc gtgttaaagg    38400
atccctaggt ttgccagtgc attgcttcac taaacaaatg tttatgaggt acctattggc    38460
accagagcag attccaggct ggctggagag cagcccctca gatttcacat tgctctcctt    38520
actcattcac gttaccttcc tggccctaaa ggcattatga ttgtgaccct tgaatattac    38580
aaaaattaaa ttttgaggag tctgtgctca gttattgatg ccaagccatt tgggtgctat    38640
tatcctgatc atgttatccc tatatttaaa cctctcaatt atttttttgt taatcttaga    38700
ataaaatcca gaattttttt tttttttttt ttgggggag agagagtttc acactcttgt     38760
tgcccaggct ggagtgcaat ggcacgatct tggttcactg cagcctccac ctcctgggtt    38820
caagtgattc ttctgcctca gtctcccgag tagctgggtt tacaggtgct cgccactacg    38880
cccaactaat ttatttattt attttggat actgagtctc actctgttgc ccaggctgga    38940
```

```
gtgcaatggc acgatctcag ctcactgcaa cctcagcctc ccaggttgaa gtgattctcc    39000
tgcctcagcc tcccgagtag ctgggattac aggcgccctc taccacgccc acgtaatttt    39060
tgtattttta gtagagacgg gtttcaccag gttggccagg ctgatctcaa actcctgatc    39120
tcaggtgatc cacctgcctt ggcctcccaa ggtgctggga ttataggcgt gagccacctc    39180
acccggcctg aaatccagaa tctttaatgt tagacatcag aaacacagat tgctgttccc    39240
tctcagctcc catccctgt gtctttctca ttcagtaggt ctggagtggg cccaagaat     39300
gtgcatttct aacaagttcc tctgtgattc tgttgctgct agaccaggga tggcactttg    39360
agaacctcta ctttattctt ttttctctgc cttgctcttg gctttctttc agtttctcta    39420
aggcaccata tgctattttt tgctttcaga cctttgcaca cacccttccc tttgcctcat    39480
acttttcccc tcaactcctc ctgttcatct ttcagactat atcttaaaga ttgttccttc    39540
agaaaactac tacctaatca agcttcaaga cgcaccttaa ataacttcta tgatgacttc    39600
attgactaaa ggccattgtt attttacctt taaaaaaaag gccgggcgtg gtggctcacg    39660
cctgtaatcc cagcactttg ggaggccaag gcgggcagat cacgaggtca ggagatcgag    39720
accatcctgg caaccatggt gaaaccccgt ctctactaaa aatataaaaa attagccagg    39780
catggcagtg ggtacctgta gtcccagcta tttgggaggc agaggcaaga gaatcacttt    39840
agaacctggg aggcagaggt tgcattgagc cgagatcaca ccactgcact ccagcctagt    39900
tgacagtgaa ctccatctca aaaaaaaaaa aaaaaaaaa gtatagctgg gcgcggtggc    39960
tcacacctgt aatcccagca ctttgggagg ccgaggctgg cggatcacaa ggtcaggagt    40020
tcgagaccag cctggccaat atggtgaaac cctgtctcta ctaaaaaata caaaattag    40080
ctgggcgtgg tggcgggcac ctgtagtccc agctactcag gaggctgagg caggagaatt    40140
gcttgaaccc gggaggcgga gattgcagtg agccaagatt gtgccactgc attcagcct    40200
gagtgacaga gagagactct gtctcaaaaa aaaaaaaaa aaagggcaca gtggctcagg    40260
aggccgaggc gggcaaatcg cctgaggtct ggagtttgag accagcctga ccaacacgga    40320
gaaaccccgt ctctactaaa aatacaaaat tagccaggcg tggtggtgca tacctgtaat    40380
cccatctact cgggaggctg aggcaggaga attgcttcaa tccaggaggc agaggttgca    40440
gtgagccaag atcacgccat tgcactccag cctgggcaac aagagtgaaa ttctgtctca    40500
aaaaaaaaaa aaaaaaaaac cctgcacaat atataaggcc tacaaaaact ataagaaca    40560
gttcagtacc tgagtaccca tctgtagaaa tcaagccttg ctaacacagg taaaacttta    40620
tatagctctc tgggatcact tatccctctt ggtaagcacc atcctgtatt tgacagagca    40680
ttttgccaat gccctctacc tgtgcttgct ttttttttgt ttgtttgttt tgagatgggg    40740
gtctctctgt cacccaggct ggagtgtagt ggtttattct cggctcactg cagtctccac    40800
ctccccaggt tcaggtgatc ctcccacctc agcctcctga gtagctggga ctacaggtgt    40860
gagtcaacat gcccagctaa ttttggact ttttagtaga gatggggttt cacgatgttg    40920
cccaggctgg tctcgaattc ctgagctcaa gcagtctgcc cgccttggct tcccaaagtg    40980
gtgggattat aggcatgcac caccttgcct ggcctgactc tacttactta aatggtaagt    41040
tcctggaagg caggcactgt gttattgacc tctgtgcccc cagtacctat catgtgatgc    41100
ccaagaccag tggttctcta ctgtgtctgc atgttagaat tacccagggg agtgtattat    41160
ctttaaaaat taatgcccag gcccgagcac ggtgcctcac gcttgtaatc ccggcacttt    41220
gggaggctga ggtgggcgga tcacctgagg tcgagagttt gagaccagcc tgaccaacat    41280
gaagaaacac catctctact aaaaatacaa aattagctgg gcatggtggc acacgcctgt    41340
```

```
aatcccagct actagggagg ctgaggcagg agaatcgctt gaacctggga ggcagaggtt   41400
gcggtgagcc aagatggtgc cattacactc cagcctgggc tacaagagcg aaactccgtc   41460
tcaaaaaaaa aaaagaaaa aattaatgcc cagagttcac agagttctga tttgtttcat    41520
gtggggtttg ggcattggtg tggttagcag ctgtcccagg tgaatcccga tttgcaggta   41580
gagatctatt ccagactgta tgaggttcct ttgctatagt aaactctttt ttttttttga   41640
gatggagtct cactctgtca cccaggctgg agtgcagtgg cacaatcgca gttcacaaca   41700
acttccgcct cccgggttca aacgattctc ctgcctcagc ctcccaggta gctggaatta   41760
cagacgcccg ctaccacacc cggctaattt ttgtattttt aatagagacg aggtttcact   41820
atgttggcca gactggtctc gaactcctga cctgggtgat ccacccgcct cggcctccca   41880
aggtgctggg attacagcca tgagccacg tgcccagcct atagtaaatt cttagcaccc    41940
atacttcttg ttagtactta tctcaagtgt aatttaaatt acttatttaa tgcaagttca   42000
ttgaggactg acttgctgtc ttgcttattg ccatagtgcc tggcatctgg ttgcttattg   42060
ccatagtgcc tggcatatag taggctccaa cttactgaat agatgaacct gagcagcatc   42120
cattatagtc ctcattcagg aagtatacat ctgacaggag cagcttgact gtattaccag   42180
agtcttgctc tgtcacccag gctggagtgc agtggcacga tcttggctca ctgcagcctc   42240
cgcctcccgg gttccagcga ttctcctacc tcagcctctt gagtagctgg gattacaggt   42300
gtgcgccacc actcccggct agttttgta tttttagtag agacagggtt tcaccacgtt    42360
ggccaggctg gtttcgaact cctgacctca agtgatccac ccacctcagc ctcccaaagt   42420
gctgggatta taggcgtcag ccactgcgcc cagcttctgt aacttttctt ttgtttttt    42480 ttttttttt gagacagagt ctctgttgcc caggctggag ggctgagtg ctggagtaca     42540 gtggtgccat ctgggctcac tgcaagctcc gcctcccggg ttcaagcaat tctctgcctc   42600
agcctcccta gtagctggga ttacgggcac ccaccaccac gcctggctaa ttttttttgta  42660 ttttagtag agatggggtt tcaccatctt ggccaggctg gtcttgaact cctgaccttg    42720
tgatccaccc accttggcct cccaaagtgc tgggattaca ggcatgagcc actgcgcccg   42780
gcccagcttc tgtaactttt cttactgaga cacatttgta aatttacatt ttggtcttga   42840
aagtgtacct aggatagagt aatggaaaat ggatacagga ttgaaagctg tgatctgaag   42900
aggttagcta gtgcttcaca aactttagcg tgtgttaaga atcacctgaa ttactgcctc   42960
tacctgagaa attctgattc agtaggtgtg ggctgggacc taagaatttg catttctaac   43020
aagctctgaa gtggtacaga tgctgccagt tcagaagacc acaattggaa tgagactgaa   43080
gtaggtagtc acctttaagg gaaggaaaaa aaattactag actaggaagc cacagcggta   43140
actagaataa tagtggtgat ttacactgta gtttgactct tgattatttg gaaggcacac   43200
tgtgggttaa gaatggtaga aagaaaagag acttgaaaga aactagactt cctgtagctg   43260
tggcctcagt gcagtttatt cctgggtaac ggagcccttg ccctgccagt accaccctgg   43320
gagctcctct gctctatggt gctcatcact ggatcccttc ctttagtggg gccaaactta   43380
gttggtcacc aaatcttagt ctaccacaga aatggtttt gcttttgaat ctggtttccc    43440
ctctctttct ccactgcctt ttgttttttc gggtccctgt tatctctcac ctggtgtctt   43500
gccacaaact tctgactgtt ctgtttcttt tcttcctctt ttccttccaa gtctgtcctc   43560
agcataatca ccagagtgat catcttaaaa aaaaaaaaa agaaaaaaaa aacctggcca   43620
agttatgtta atgctttaaa acctggctac gtgttgtctg tagatttaag tccaagtgtg   43680
```

```
acatacaagt aagttttttt gggatctgga ggatgaggag agatgtaggt aagtttcctg    43740
tccctggagt aaaacctggc acacttttg ctatgggtgt tatgtagaag acaaacagac    43800
atttgacaag ggttgaactt gtgtgacttc tgaggtcatt tgaactcttg ggtccatgat    43860
tccgaatatg atacgatgat tcctaaagga tcctcctgtg tttcattagt aaaatagaca    43920
taaaacagaa gaccatgtgc ctgtatgtta taatgagtgc tgtcagagtt tggtgaagtc    43980
actgatccat ttatgtctca atagttgaag gaagaagtca tgttgaagtt cagtcagtat    44040
gagctagatg tggatgtatt taagtggtta gttacaaagg gaaagtccag cttgaacaga    44100
ggccatgcag ggatggggat gaggtgcagt atagatactt gggggctggt cagcttccag    44160
gggtgggaag taacaggaag gaaagctaga tcacagggat cctgctgagc ttaagccatt    44220
tagatctgat cttatgggct tgcagatagg taactgggc aatcatgtga taaaactaat    44280
gttttacaaa aatgatccat tagtttgtag tatgctttga aaacgggaga gtcttaaagc    44340
agtggaataa gttaaaccgt agaactactt ctggcaagag gtatgagtt ctggtccttc    44400 tgtctcattt gcatagccac ctgctcccac atgtggaaca tgcaggaaag aatacaggac    44460
tgagaataag tgggttctgt gtggtggaat atttaaagat tttgattgac tggtgggcag    44520
ggggagtctc atttttgagg aaaagttaaa ttccatattt attttgtgga ataataata    44580 gtaagatttc tgaaaacaaa tgtccagttt ctagttggag ataagaaact gaaacttggg    44640
taagacctga gtctggatac aagtttgcga gttacctgtg tggtagttaa tagttaaacc    44700
atagaatgaa acaggcctcc taaactggag tttagagata gaagccagat ggagctctgg    44760
acgatgccgg aggccatcag gtagaagcag ccaacagaga gttggagaga tcggagaagg    44820
accaggattg tgtaatattt ctggaagcca agggaggagg gacgaagtca aatttatat    44880 tcaaagaaaa taggtagttg ggtttgtcat aaagcatttt attgggatcc ttttagata    44940 aggaaaaggc cttatttctg agggcttgag aaaaggaaat gagcaaggga aagggaaaga    45000
gcactcttga aatgcactga gaaaaaggag agtctggctg aatcagtcca attcctccgc    45060
ttcatcccaa agacccgcat gtgtataagg cagatggaag agggaaaagt gaaggtgctg    45120
gcagaatatt aggagggtat aaacaggcac atctttctgg agttgtgaga aaaaggaatc    45180
aaaggcatcc actggattaa tttctaaggg acgctatacc cttggctgaa aaaaaggtaa    45240
tcttaaagac tgttgttgaa gattggatca tactcatttc ctcaggttag gtaggagtga    45300
atgttatcga tatcaggagg gaggtggaga acagaattag gatctgtaat gtctatcaaa    45360
ttatcccttg agtttctgag ccattctta gatttcactt aacatcttag ctattaccct    45420
tcgtattttt acttctgtaa tgctctcaga cgctgagatc ttggaattac attggtctag    45480
aaagaggaaa tgcagggag ctatgctgtc cctgtagaat ccagatttta gagggcagga    45540
gtaaggccag gcaaggagct acagtcaaca tcagttattc tgaaaagata ggaattggaa    45600
ggtacagaat acccactcct gttttacata tgaaaaacca agggtcagaa tcaagatttg    45660
aatctagctc tgatatttca ggtgaaatat ttcctccagc atcccaccca gtagaggaaa    45720
gacatggaca atctgatcct ctcttcattt ttaggcaaaa aactcaactc tttgccattt    45780
agcatttgct agacttgtcc taaaaggaat gtcaatggat ttccatttta cttctgttttt    45840 cccagacatc cctgtgatgg aggcacagat gagctgtgga aagagcgagt ggtaggaaag    45900
atagccaaac ctataggacc tgcttggagg aactagccaa ctaggaatc gcctcaaaca    45960 gtgaaccgtt gactagagtt tggttatttg gttcctgtgt gggatgagag caagccctgt    46020
tctgtgtctg tcttcttaga acatactgtc ctggtcagtg ctaactttaa tcagttagat    46080
```

```
ccttgctact cagtgtggtc cattgtctag aagcaccaac atcaccggga agcttgctag    46140
aaatgtagat tttcaggccc catcctagat ttattggatc taactgttaa taagatctct    46200
aagtgattca tgtgtctaat ggtttagaag cacagagacc ctgagagctg agagtaaaat    46260
tttcaaatga aatatcaagc tggtaggcca ggcacggtgg ctcacacctg taatcccagc    46320
actgtgggag gctgaggcgg gtggatcatg aggtcgggag ttcgagagca gcctgaccaa    46380
tatggtgaaa ctccatctct actaaaaata taaaaattta gctgggcgtg gtggcatgca    46440
cctgtgatcc cagctactca ggaagctgag gcaggagaat cccttgaacc cgagaggcgg    46500
aggttgcagt gggctgaggt cgcgccactg cactccagcc tatgtgacag agcgagactg    46560
tctcaaaaaa agaaatataa aaaatatcaa gctgggcgtt tggaacgtca taaattttac    46620
agattgtatc cagtaatatt taagtaatct ctgagtgtgg gagaccacca ccagttgttt    46680
cgtgcgtgtt ttggggaccc tggctcccag tgccttaccc agttcagaac ccatagtgga    46740
gccatccaca gctcccagca tacctctgca acttcatctc cagccactca tttgtacctt    46800
aagctcctca caattcctgg tcctcttgat taggatgtat acctgtttct ctctctttct    46860
gtcatgctca gcaaacttct actttggctt caaaacctag ctggaatact ctctctgaga    46920
cttcttcccc attttcatat tggcatagcc ttatgctggt acctctgctt gaactgtatc    46980
tgacatctgt catgttgtgc ccagaacagg cagatatttg taaacctttg ttgaatacct    47040
cctagattct tgctacctag ttgagctttg ggagctgacg ttttgttgtt taggtttatt    47100
gagaggagtg acaaatcctc tcaataaatg ctttaaaaat tagaacattt ggctgggcac    47160
ggtggctcac acctatagtc ccagcacttt gggaggctga ggcgggtcat catgaggtca    47220
agagttcaag accagcctgg acaacatggc gaaaccctgt ctctactaaa aatacaaaaa    47280
taggcaggtg tggtggcagg ggcctgtagt cccagctact cgggaggctg aggcaagaga    47340
atcgcttgaa cccgggaggc agaggatgca gtactccatc tcaaaaaaaa aaaaaaaaa    47400 ttaaaacatt tgaaggattt taattttaca cagtttctgt tcccttttgt tcatttcatg    47460
atagaaggag agagggccca cagtccttat ctaggttttt gatggttgat tttcaaaaag    47520
ataacagaaa tgtcactagc gattttggta accagagaag cagggtcttt ctgaggttgg    47580
tgacctgttt tctttatagc tgaccatgta tctgtgcctg ctccccttga attatagccc    47640
aggtgctctc tcagagtctc gaaaaggaaa tccccacccc ctctgtcata tctgcccaga    47700
ctgctaagag cagcatgtac cctgtgcatg tagccatccc ttctctagaa cgctggttct    47760
ctgggctgga ctggccaatc cgcttctcca tcttagtcac actgttccaa ccctgatact    47820
gcctgctgac tgcctgagcc tgtgctgctt gcagcagatt actgtatgct tgttcctggg    47880
cccatttcct gtttctattc tagtcgctgg tggctcagct ctgcttcctg cctgtgtgtc    47940
tcacacagat tcctcttgct ggaaccttt  gtttccttcg gaacagcctc aatctttgaa    48000
aagcaactga gccttaactc tagtatgatg gctcttgagt cacttagtcc tacagaggtc    48060
tggctggaag tacctcttcc ccattaagca caccgtttga attttacctt gttttttcagt   48120 ttgtcgtcag ccctgctgta ggaagttaag ttgggccaaa cttgtcctca cttattagta    48180
cacagagcta tcgggactgg tatgtcctga ttcttttgta cctggagctt ttaaatgtat    48240
ttcctactac tcaagaagac acttggtatc ctctctggcc caagcttccc tgaagcccag    48300
gtgatactta ttttgagttg ggcaggttat gccatcctca gcagaataac aggctgcaga    48360
aaacataggg atggaaaaga aagcgtgtgc tgactcaacc ctccatcctg tgtgagcaat    48420
```

```
tcaaaccccc cacccacccc ctcagagctt agggtgagag agagaaagta cagtgaggtt    48480
gtaaaaaggg aagaagtgaa ggaggttgtc ctggacaaat gtatttaaag gcctaaggct    48540
cccccctctt gcccatttcc tacaaaaaat atgcttcgtg aataaatctt ttttctcttc    48600
ctttacagcc actcttttgg gatcatttga taatactgag tcagaggatt tctgtactgg    48660
accctaggtc tagctatgtt taaaagagag agatttaata tagggaattt gggcttacaa    48720
ctggaaggag tgagggagct tgctctaggc ttggcctcca agaaaccaga cccagattta    48780
acctagattt gacctaccag gggaacgtct atctcggagc tactattaga ttgattgctc    48840
ttgaatcata cccctaaacc tgtggtccag aatcagtaaa ctggaatcaa gaagcagtag    48900
ctgctgccgc cagaaccagc acccagttaa gtggaggatg gaaccaaaat gctcctgcag    48960
aaacaagtaa aggagacaga aatatggtct ctgcttactt tgatctaatc tcatgagtca    49020
gcttctcatt agcagaagct gaattgtatc caaaaccaag ggattcttgg aaatttcgtt    49080
tttaagcttt ttaacctcta caattagaga aagaatagaa tggaggctgc atgaactagc    49140
ccaacagaat atttacaata ctgacacccc attcccgtct cccctcccac cccaactttt    49200
acatatgacg aacctaaggc ccagaaaggg caagagactt gtccagggtc attcagtaaa    49260
tgagaacatt ggattctctg actgctagtc cagtggttct actgttgctt ttactgttag    49320
gaccaactcc tgtacaagac cagcaaaaag atcctttaag aaaaggccgc aggcacggta    49380
gctcacacct gtaatcccag cactttggga ggttgaggcg tgagatcac  ctgaggttgg    49440 gagttcaaga ccagcctgac caacattaag aaactccgtc tctactaaaa atacaaaatt    49500
agccgggcgt ggtggcatgt gcttgtaatc ccagctactt gggaggctga ggcaggagaa    49560
tcgcttgaac ctgggaggcg gaggttgcgg tgagtcaaga ttgtgccact gcactccagt    49620
ctgggcaaca agagcaaaac tctgtctcaa aaaatagaa  aaggaaaaat gccatattca    49680
gaaaatggac tttgccttcc gtattctctt tggagaaagg gaaggagtta tgaacagata    49740
tgaggttgag atttctagat ttctaggcaa agttaatgat actacagctt ctggatttag    49800
ttctgttctc cagaaggata taagaagcat ttactctgaa aggaagaatt ctcaaaaact    49860
agaatgtcct gatattcctt agtcatcatg gatgaactca gttgttgtag tgacagtggc    49920
tcaccttcac ctattccccc ttgccttttc ttttgctgtt ggtgcttttc tgtccaaaaa    49980
gatcaaccaa aatccagaaa accagccccc agatgtttgg ttgcttagct gtttcatgtc    50040
tgcccttggg gagacttggg tcttttgaac agaaaatgag ccaagtccac ccagaaatac    50100
tatctttgta gaaaccacta gggtcccttta agccaaggtg agaatctgtt tcttcaaact    50160
tggcccagag gggaggacct gtaggtgtgg agctatgtta acatatctgg ccaggcgcag    50220
tggctcacgc ctgtaatccc agcactttgg gaggccgagg taggtggatc acaaggtgag    50280
gagattaaga ccatcctgga caacatggtg aaaccctgtt ttagtaaaat acaaaaaatt    50340
agctgggtgt gggctgggtg cggtggctca cgcctgtaat cccagcagtt gggaggcca    50400 aggcgggcaa atcacctgag gtcaggagtt caaggctggc caatatggta aaaccctatc    50460
tctactaaat aatataaaaa taagctgggt gtggtggcag gcacctgtaa taccagctac    50520
ttgggaggct gaggctgagg caggagaga  attgcttgaa cccgggaggc agaggttgca    50580
gtaagccaag atcgcgccac tgcactccag cctggtgaca gagtaagact ccgtgtcaaa    50640
aaaacaaaac aaacaaacaa aaaaacaac accatacctg ataaatcaag cgtagaatta    50700
gccctattgt ttttttcttt gtgtctacga catactagaa agctgtgatg aaatcgtatat   50760 gtattctgtt gccatccctc tggggaccag tgcttggtct cctaatcccc ctactcgatg    50820
```

```
gcctgaaagt gtttcatctt ccctgcctgt tatcagcata gaattggttg gtattgtgac    50880
ataatctgat tgccttgagg cagagcttac ctccaagctg ctagcttcct tcccatttga    50940
cctttcccaa agaagctaag aatccatgcc ttgttgaagg tgggaactag gggttgaagg    51000
cttaatcttg agagtcagcg aacctgtccc ttaaggccag ctttgatgtg ggaagaatat    51060
tgaatattgt ttactgagat ggagatgggt ggaggtaatt tttcctgaca ttttggggaa    51120
ggtaagagaa accaaattta gactgaaagg gatcagtggc caggtgtggt ggcttacacc    51180
tgtaatccca gcagtgtggg aggctgaggc agtaggattg cttgaggcca ggagctggag    51240
accaccaccc tgggcaacac agcaagatcc ccatctctac caaaaaaaaa aaaaaaaata    51300
gttggccatg gtggtgcatg cctgtagtcc tggctacttg ggaggctgag gcaggaggat    51360
cgcttgagcc caggagtttg aggctgcatt gagctatgct tgcacgactg cactccagcc    51420
tgggtgacag agcaagaccc tatctgaaaa acaaacaaat aatataggtc aatgttcaga    51480
ggaaccatta tcaagaatat ttggattttt atccctctta ttttctagaa cttgattata    51540
gctcccttgt gttcagagtt gttcttttca aagtcctttg aggttgtatt ctggtttaag    51600
attctatcca tttctcactc tcagatctgt ttgttccacc ctctcccct aaatatttgg     51660 attttatata gaccagtagg ctaaggtagg gaagaccact gacaagtata aatttaagag    51720
tttacaaaac caaggaggcc atccagcccc tagttctaag ccatgttcag cacagtgcca    51780
actttgcctt ccctggctgt ccttgcttgc tttctggttg ctgtaattct gaggggcaac    51840
caggcttgct gtagagagga gagccagatg atgtggaagc ctaaggcaac accccctcct    51900
tattacactt ctcatacca gaactctgct tgctttctgt gttcctttcc tctcactccc     51960
ctttcctgcc ctctttactc aagttctaag attatagctg atgatcttca taatagaaca    52020
aactctgttt ggttgacctt cctaacaggg aatgcttggc tttgagaaag taggggttc     52080 ctaacttctt tgccttctct agctttacag tgctcttact tcctgctggg attagaacag    52140
ccctattcca taaatatgca ctgctcttgg ctgctgtaac tcaggcccag ctctgaccca    52200
gattcttttt ttttttttt tttttgtcag atttgagtct attaactagt gaccctcaaa     52260
acacttcata catttttggc caaaaagtgg ttactgactg gataagacag aagcctttgg    52320
ggggcagggt gactggtcgg gcaggtaaca tggtattata caggcctgat ggggactgtg    52380
acaaactgaa aagcagggtt tcaaccagtt agcggcctat gggagttcca gaatcatcat    52440
catcatcttt ttttttattt ttattttgg aaaactctcg gccaggcgca gtggctcacg     52500
cctgtaatcc cagcactttg ggaggccgag gcaggcagat cacgaggtca ggagatggag    52560
accatcctgg ctaacacggt gaaaccccat ctctactaaa aaatacaaaa aattagctgg    52620
gcatggtggc gggcacctgt agtcccagct actcgggagg ctgaggcagg agaatggtgt    52680
gaacccggga ggcagagctt gcagtgagcc aagatcgcgc cactgcactc cagcctcggt    52740
gacagagcga gactccgtct caaaaaataa taataataat aattctctgg ggtctgtggg    52800
tctgtccctg cagtgtcttg tggactgccc cgtgtagctt tggctctctc ttggatttac    52860 tcccttgag ctggtgccta gaatttctcc gggggtaggg gacagctgtg aggagcacct     52920
tctcatctat cctttgccag ttctcattgt gtttggtgtt tgtttatttt gtttgttggg    52980
gggcggcggg gagcgacagg ggaaatgttg agcagaagca ctcgatgtga ttaaacctcc    53040
ggctgagcag atctgtagga gtagaatatc gaccccctgga aaatcaatgg ctgctgcagt   53100
gacccagccg ctgtttgcag gggctaccac cacaggaatg caagcagccc agcagtcttt    53160
```

```
cttctccccca cctttttacc tcagcagtgc cctcagcctc cacccagagg gtcagacctg   53220
cctcaagaga ttttgcagag gtgggttaga acagcacgtt ctcgtatttt cacaattaga   53280
ttgaaatttc tccagtgaca cagagccctg cctctggcag cctcctttcc agacattcct   53340
tttctgcact gctgcagttc tagcaacagc tcttaccaag ttgccaaaac ccattcgggg   53400
ttgtacttct gagttttaaa caggagaatc aattctcttg ataccagcac ccaagagccc   53460
ctcccttgtg gaggtctaga attcaggtac tggggtatag gatgggggaa tagagattaa   53520
gggaaagaaa gaggactaat agaggttgtg tctaaagagg atgcttttga gtagataatt   53580
cattgagcaa catttatcaa gcatcttgtc gtttgtgtgt ctggcatctt tctggtcact   53640
aatagcctga tcttgctctg gtcccacagg ctagtggaga aaaagggcgg atagaacaca   53700
gtgccatcag tcctgtaaca ctgcttctag aggagcctca gaggaactct gtgccctgcc   53760
tatagggtga gagtagggaa ctagtcctgt gacttgggtc aaaatagatg gtttaataga   53820
atggctagca gatctctgct tggagcatgg aggcttctga ttcctcactg cctccacaaa   53880
actgttttca tcttggaagt tcccaaggct aaaaaacaat tttagccttt agttgttgta   53940
cctataatgc caattctact ctggtggttg ggaaaccagc cagcctgatg tgtgtgaaag   54000
gagagctcag ttgccctatt gttggagcac ctctgtggcc agagggttga agcttgcttg   54060
gcttttaaag cctctagaaa ggagccttcc cgtcttgtag cttggagagt ggggtcccta   54120
aacaaaaccc aaacatcctg cagtttggaa gggtggctgc agtgctgggt gaggaggaaa   54180
gtgtgagggt ttgaagtggc ctaagaggag gccatctaga ggccaggaat atcttgattt   54240 ttttttttctc tgtgagccac acccttgtga ttgataaaag gcttagaaca tattcagttt   54300
gaatacccag cagagaccag gctcctacct tcatgggact tctaccttca tgggacttct   54360
gcttgtttcc ctacattcaa agtcaccctc cccacagccc tctgtcctct tacacattaa   54420
gtaccctaca gaaacccag gggtgagaaa aagtactgta cccttttaatt tagcatagaa   54480 aaattaggtt gaagttgaag gttatcagtg aaagggctga tttgaaataa aggctgaaag   54540
ttatagcaag agtaattagg aaagaggggg gccgggcatg gtggctcaca cctgtaatcc   54600
cagcactttg ggaggccgag gcgggtggat cacttgaggt caggagttcg agaccaacct   54660
gatcaacatg gtgaaacccc gtctctacta aaaatacaaa aattagccgg gcgtggtggc   54720
gagggtctgt aatcccagct actcgggagg ctgaggcagg agaatcacta gaacctggga   54780
ggcggagatt gcagtgagct gagattgcac cactgcactc cagcctggag gacagggcaa   54840
aactccgtct aaaaaaaaaa ggacagggga acacatagca tcacagattt gtagagtttg   54900
attatctagt gtaagtcttt ccttcaataa aggagttaag tgagcctcgt gaggttagcc   54960
agttgagtca gtagctaat cacgcagcat gtctggtgat ataggttgtt ggccttacct   55020
ctattggagc atggaaccca gcctttgatc atgtcaagct tctattaata ccttatggaa   55080
agagtgtaaa gtaataatgg atttgaacct caggtctatt taatagctgt ctgtccttgg   55140
gcaagtcact tctgaacctg cttctttgtt aaaatggggg taatacctat atcagaagat   55200
gattgtgaaa attaaatgag agtcaaccac tcaccttagg gttgaatatg tgatagtcac   55260
atattcatgt caattctgct tcctttcaaa aggaatatat aaaggaactt tattaacttt   55320
atctaacatc ctttgtattt ggagatttgg tctccagagc tttctttatg aattctgatg   55380
tgtatatagg gagtttcctc ttggagacgg gcccctgaaa agcattctgg agacaagaag   55440
agtcttaacc cctctctcct gtgtcttccc cgtcaggtgg ccaaaaggta tcaggaagaa   55500
tgaatcatta tcttcagaac aatagcctat gtagaaaaag agaagaggga gtttggtggg   55560
```

```
ggatttcatc ctatgcaatg gttttctaaga tacaaaccaa gttttggaa acttgacggg   55620 ggcaagtagg aaacacattt ttctaaacct ttcctggagt agtttctgct gttccaaacc   55680
atggaggtag tccatgtagg tgatagggct tggtcctaca ctaaaagggt agtgtcaacc   55740
tctgcatctt ttcttcccgt tccttagtac ctgcttaatt aacttctgac ctggaattac   55800
caccgggtgt gaaaggcagc ctattctgtg tgttgattct ttcttggcat ttcagttaac   55860
atcagcaagc ctgctctcta tgcataggtg gcagttaatc tgttggattg agaccactcc   55920
gtggaataat gtcacagcag ttctgtaact tttggagtcc ctaccagtct ggggtgggtc   55980
aaatttctct ttcttacatt tatagcaaag actaaggaga aaaaagaac ttatgactga    56040 aactttattg tacaagtgtt cagtagaggt agtcccttct cctctgctac cctcaacaag   56100
ttgttgctta aggaaggttt tatgaaaagc caagtctccc aaaaacttat ttgccttaag   56160
taattaattt tgtctcagtt tttcttcctt agagtttaag gctattgcct cctctcctac   56220
cttttccttt tcttcatggg ttatgttttcc cagtctcttc tgtgttcttc aggatttcct   56280
cccattcttc agcatgagag cagcctaggg gcggggcggg gataagggac tgacaaatta   56340
ctagtgtaga tttggtcatt atggaatttt ttattcaagt attgtcattt aagtgggggat  56400 ggctgagctg caaggttccc agtgcacaca cttactacag gcatgtgcgt aggatttacc   56460
tggttctcat gacgggtggt ttacctgcca gtatcagcac aactcagcaa agcttttcc    56520 caactaaatg ggtacaagaa ctccatctgg gattccccaa ggatttagcc agatttatgg   56580 gaaaaccta atctgagca ttgccatgag cctattcttt atacttaacc tgttgccatt     56640
taacctgctc agcaaaatga actgatgtca tcctcatgtg gctctattgg gagataattt   56700
aaacttccct cctctaaccc tgatctggtg tcttcctgct taaaaatatt cttcagtggg   56760
cagccaattc atcttagaac ttgcagttct tcctgtgaga gtaccagcac ccccaccgtc   56820
cctaccccac aaaataaggt atggactgtg tgatttcagg catggttttg ttgtggtgtg   56880
aagagaaggt gtttagctgc tgagttctgt ttgttagcag agcctgacaa actcatgctg   56940
gcactcacta gggctgggca accaatcaca gctgggacgg ttatcgtcat ggagtcccta   57000
tgggcttcct ctatcaggtc acatcccaaa ataacattgg gcagtatttc aactgaagaa   57060
atgaaggctt tcagggctgt agccagcctg gagtgtgaga ttctgtgtga aatagttgga   57120
tctgctccag cgcttttgat ctgcatggta gatgagcaat aaaatgcaca aaacacattg   57180
gaaacacgtg aggaaattct cctggccctg ctgcttcctt ggaactggta gggcactgag   57240
tgggctgatc ctcacctccc atctctcagc aggattatac ttggaggaga acaaacccgg   57300
gaaaagaaat cttcccatta aaggggcatt gctacagtta tttccgcagt ccttccagaa   57360
gatgcctgtt aggtgtgctc ttttgggaga attgagaacc tgagagtcct gagatgccaa   57420
gggcatccct caccagggag aataggggct tggattgcag tggcgtgatc tcggctcatt   57480
gcaagctccg cctcctggat tcatgccatt ctcctgcctc agcctcccga gtagctggga   57540
ctacaggcac acgccaccac gcctggctaa ttttttgtat tttttagtag atgggggtt    57600 tcactgtgtt agtcaggatg gtctcagtct cctgaccttg tgatctgcct gcctcggcct   57660
cccaaagtgc tgggattaca ggcatgagcc accacacctg gcccgactga acttttatt    57720 aatgataaat gtgttgtaga aaactgaact gttaggaaca ttgaggtctg actcaacaat   57780
cagacatctg gcttttgtg gaacaaaaga cctgaaaaac tggctttttg tagagtagaa    57840
agcagaggtg tgtcctgtgt aataaaagga tgtggagctg agagcaatat ctgttcatgt   57900
```

| | |
|---|---|
| agatagaggg gcaggacatc tttttggagac ttctgcccctt accactccct cccatttccc | 57960 |
| aataaaaata tttactatga ctagccactg ggactggtgg gtatgtctta gaacttatat | 58020 |
| tgctggtatg ttgttatatc tctcattcca gaatattgct gctggtcgtt tgaccctgac | 58080 |
| catatggtgc tagggggggat tcatgcatat gccccagggg tgtcatagac ttagatttat | 58140 |
| ccagccccct ctgattgtat atgtgagaaa actgaagcct gacttgttgc cagtttgcct | 58200 |
| aaggtcacaa ctgataagta ccaaaagctg ggccttggtt tcctaactca gaggcgtgac | 58260 |
| cttctcctc agttcatata gtgtcacaac ataatggaga gagaaagcca gcatggccta | 58320 |
| tggggttcag cagtcccggg tttaaaatct ggcttccacc acttgccaga tgacctaagc | 58380 |
| atgtaatcca atctctttag gcatcagctt cctcatcttc aaattggtaa tgtggctggg | 58440 |
| tacagtggct cacgcctgtg atcccagcac tttgggaggc caaggtagga ggattgcttg | 58500 |
| agctcaggaa tttgagacca gcctgggcaa catggtgaaa ccccaccact acaaaaatac | 58560 |
| aaaaaaaatt aaccaggtgt ctgtagtcgc agctactctg gaggttgagg tgggaggatg | 58620 |
| gcttgaaccc aggagacaga ggttgcagtg agccaagatt gtgccactgc actccagcct | 58680 |
| gggtaacagc cagaccctga ctcaaaaaaa accaaaccaa aaccaaaatg gtaatggtag | 58740 |
| tagtatctat aaccaagact tgtagaaaat tgggtaactt tgctaagtgt ctggcatata | 58800 |
| gtagatgctt aaatggtagc tgtagttaat cgtaaatgat ttaccccttt ctatgctaac | 58860 |
| attttggctc ttaaaattat ttgaaaccaa ctatctgatg ctgaccagtt gccatctaat | 58920 |
| gaaaatgaca gtttgagagg ttggcctcaa gccaaccaaa tcagagagat aagaagatta | 58980 |
| atgctcttcc ttccctagta ttttttctata cccaggcatc ccagccaggt gggactactg | 59040 |
| ttgacagtgg tttatttagc acttttttctc caagaagctc agggcacttt accaaaagtg | 59100 |
| acagctctcc tgaagaaggg gaagccacct ctttgccagc cacagatgcc tccagagttc | 59160 |
| tgagacccca gccccaagag ctacagaggt tttcttttagg ctcctaggat ccctcaggtg | 59220 |
| gaccaggggc attctccttt tggatctatg gtgagcctgg tttttttaact gaaagtgtgg | 59280 |
| ctgaaaggac ctcctcagtt cttgccctga gctgatagga gtggttggtg ggttttggtt | 59340 |
| ttttggtttt tttttttttga gatggagtct cgctctgttg cccaggctgg agtgcagtgg | 59400 |
| tgcgatctcg gctcactgca acctccgcct cccgggttca cgccattctc ctgcctcagc | 59460 |
| ctcccgagta actgggactg caggcacctg ccaccacacc tggctatttt tttgtgtttt | 59520 |
| tagtagagac agggtttcac tatgttagcc aggatggtct cgatctcctg acctcgtgat | 59580 |
| cctcctgcct cggcctccca aagtgctggg attacagacg tgagccaccg cgcctggcca | 59640 |
| agttttggtt ttttgttttg tttcttgttg tttgtttttg ttttttttc ttagcgcttc | 59700 |
| agtcacatgtc caaagataca caccaaggcc aggggcagtg gctcatgcct gtaatcccag | 59760 |
| aacgttagga ggctgaggag ggcagatcgc ttgagcccag gagttcgaga caagcctgag | 59820 |
| caacatggca aggccccatc tctacaaaaa aatttaaaaa ttagccgggg ggccaggcgt | 59880 |
| ggtggctcat gcctgtaata ccggcatttt gggaggccaa ggtgggcgga tcacctgagg | 59940 |
| tcaggagttc gagaccagcc tggccaacat gttgaaaccc cgtctctact aaaaatacaa | 60000 |
| aaattaactg ggtgtggtgg tgcacgcctg taatcccagc tactcaggag gctgaggcag | 60060 |
| gagaattact tgaaccaagg aggtggaagt tgcagtgagc caagattata ccactgccct | 60120 |
| ccagcctggg tgacagaccc agaccgagac cctgtctctt taaaaaaaaa aaaaacaaaa | 60180 |
| aaacacacac aaaaaaaaac ccacaaagat acacaccaaa ttgaacagcg gtttctctat | 60240 |
| tgagggcaac agaaagacag ccatggggca ctttggcttc acctataata gctgaaatgt | 60300 |

```
tttttttttt cttttttgag acggagtctc gctctgtcgc ccaggctgga gtgcagtggc    60360
acaatctcgg ctcactgcaa gctgcgcctt ccagattcac gccattctcc tgcctcagcc    60420
tcccgagtag ctgggaccat gggtgcccgt caccacgtct ggctaatttt ttgtattttt    60480
agtaaagacg gggtttcacc gtgttagcca gtatggtctc gatttgctga ccttgtgatc    60540
cgcccgcctc agcctcccaa agtgctggga ttacaggtgt gagccactgc gcccggccca    60600
atatctgaaa tgttttatc atgagaatgt ttatgtttta cttgtataac aagacacaaa    60660
aatgatcaaa acaaaacatt taattttct aatcccagct actcaggagg ctgaggcagg    60720
agaatcactt gaacctggga ggtggaggtt gcagtgagct gagatcatgc cactgcactc    60780
cagcctaggc gacagacgga gaccctgtct cttaaaaaaa aaaaaaatg ctgaggcgag    60840 cggatggagg tcaggagatc cagaccatcc tggctaacat ggtgaaaccc cgtctctact    60900
aaaaatacaa aaaaaatta gccgggcatg gtggcgggtg cctgtagtcc cagctactca    60960
ggaggctgag gcaggagaat ggcgtgaacc caggaggcgg aagtcacagt gagccgcgat    61020
agcgccactg cactccagcc tgggcaacag agtgagactc cgtctcaaaa aaaaaaaaa    61080 aaggaaataa aaacgcacaa agatacgcac caaataattg aacagtggtt tctctgttga    61140
gggcaacaga aggacagctg tggggaactt tggtgtcgga gactttggct tcacctgtaa    61200
tatctgaaat gttttatca tgagaatgtt catgttttac ttgtataaag acaaaaataa    61260
tcaaactttt ttttttttc ttgagacgga gtctcactct gtcacccagg ctggaatgca    61320
gtggtgctat cttggcacac tgtaacctcc acctcccggg ttcaaggaat tctccctgcc    61380
tcagcctcct gagtacctgg gattacaggt gcccaccacc acgcccgggt tttgccatgt    61440
tggccaggct ggtcttgaac tcctgacctc gtaatccgcc tacctcggcc tcctaaagtg    61500
ctgggattac ggacatgagc tactgcgcct ggccaacata taattttca aagcgatttg    61560 aactgaacca agttcgtc tgatggatgg atccctgatt cctattctgt tctgaaatac    61620
acttcttttt cctgtaagca ggaaagttct tattaccaga agctggcagt ttgataagga    61680
atggagactg taggaaggag tgggtgaggg aaccttctgg tccctaaaac agcattgagc    61740
tgtggaattt gctatataga ctgtagggcc taacgagtgc ttcttgagac cctttctact    61800
tacagtggct ctccttgtca tcttgctgcc tcttttagtt tgttcttggc tcagaggcta    61860
gatgtccatg gtataactta gccatcaaaa cagggatggg gctgggcaca gtgactcatg    61920
cttatcatat caggagtttg ggaggccaat gtgggaggat tgagcccaag agtttgagac    61980
caccctgggc aacatggcag aatcccttct ctacacacac acaaacacag ccagacatgg    62040
tggcgcctgc ctgtacacac acatacagag ccagatgtgg tggtgcgtgc ctgtagtccc    62100
agctactcag gaggctgagg taagaggatc acttgagttg gcaggttga ggctgtaggg    62160 agctggcatc atgccaatgt actgcagcct ggggtaacag agtgagaccc tgtctcaaaa    62220 aaaaaaaaa aagaagaaga agaaccaagg atgtaatccc tctatcttgg gattaacatg    62280
gggctcttca tagctccagg tactttagtc cttcgagaaa ggaggatgtc ctttgctgtt    62340
accttgtggt tggcctcttg aaatcattct atgctggaac gaattctcat tgcatttta    62400 aagtatgcta tggcatacct ggcctacttc ttaccaacaa gaaagctagc attttctgac    62460
ttctcagcta acatggaaag ctggacacag gcacaaatgc acacctacct acctgccttc    62520
agagcaaact ttgtctccaa gagctcagca gaaatgctcc cagcctaatg aggtacccaa    62580
gtggtttgtg gaaggtccac ccagcttgga tacttgaagg agagcctaaa agctgccctc    62640
```

```
tgacctccag tgttaactgt cagatcttag ggtcaaagtc actttcagcc gatctttccc   62700
gggtgagctt gtttgtgtga gcaggaatag actcaaatca aaccaacttg gatctcctcc   62760
tccttgagat gtgtggtgtt ttcggttttg tttttgtgtg tttgtttgtt tgttttgag    62820 atggtgtttt gctccgttac ctatgctgga gtgcagtggt acaatctcgg ctcactacag   62880
cctcctcctc ctgggcttaa gtgattctcc cacctcagcc tcccaagtag ctgggactac   62940
agctgcacac caccacacct ggcttatttt tgggggtatt tttagtagag acagggtttt   63000
tgccacgttg cccaggctgg tctcgaactc ctgggctcaa gtgatctgcc cgcctcggcc   63060
tcccaaaagg ctgggactac aggcatgagc cactgcgcgt ggcccagtgt gtttctttaa   63120
gagaactctt tatttaccat ttaagtatca gggttttcat cctttcttca attacagtta   63180
gttcccagcc tgaagtaatg ttgctagaga atgaacatgg ggcaggggat ggagttaggg   63240
tacattttct ggggtgaata ttttcatat tgagctcctg tttgctaata ctggagtttg    63300
ttgacctaga gtgaactctt tattgattaa ctgaagacaa gcaaagccta caaacaaata   63360
ccaagttctc actgaaaaac ataaaagctg gaaaaaaac agaatttgtt caattggcaa     63420
acatttgttg attactgtta tagaccaggt gttaggagtg tagtcccaga ccttcttggc   63480
agttaagaaa ttgtctttct catccaatgt ctctctttct tacctcctac cccttatgtt   63540
gcaaagtatg gtgacttgga gtgagtcctt ggcaaatgga ggctgtgata atctatagta   63600
ataatcatca ttgtaatata aatagaagg agagggatc tataaatgtt tcccaaactt      63660
gttaacattc tcttgtagct cctggtgcca tcctggcagc attttgtaaa gttttgctat   63720
tagaaaagaa ctaaagcctc actgaaatag ttgctttctt atgactgtag aagttatgac   63780
tgggaaagaa gacaaaagtg ctagatctgc ttctgagggg atagaatagg agtcagcaaa   63840
actcagtcac accattgttt gtatattgtc tgactactgt tgcactatag tgtcagagtt   63900
gagtagtttt gaaggaggct ttatggccca caaaggtcta atatatattc cacctggtcc   63960
ttaacagagt ttgccatatg taagttatag tatgatgact agggccgggc gcggtggctc   64020
acgcctataa tcccagcact ttgggaggcc aaggagggtg gatcacctga ggtcgggagt   64080
tcaagaccag cctgaccaac atggagaaaa cccgtctcta ctaaaaatac aaaaatttag   64140
ccgggcgtgg tggtgcttgc ctgtaatccc agccactcgg gaggctgagg caggagaatt   64200
gcttgaaccc aggagtcaga ggttgcgatg agccagacg tgccattgca ctccagcctg    64260
ggcaacgagt gaaacactgt ctcaaaaaaa aaaattttt ttttaataa aatagtatc       64320 atgactaaag aacgtgtgtg atgtatttgc tcttggttgt ttaaggaaaa tgctaagcaa   64380
gtagtaggat tattgaaagt agaatctttc tgcctaatat tactaatcca tgttcttata   64440
tatatgttct aggatctatc tggttcaata gatgacctcc ccatggggac agaaggagct   64500
ctgagtcctg gagtgagcac atcagggatt tccagcagcc aaggagagca gagtaatcca   64560
gctcagtctc ctttctctcc tcatacctcc cctcacctgc ctggcatccg aggcccttcc   64620
ccgtcccctg ttggctctcc cgccagtgtt gctcagtctc gctcaggacc actctcgcct   64680
gctgcagtgc caggtaccct caagtgctgg gctttaggga gagggaaagg tgactgcccc   64740
cagtaatatt aaggagccct agtcttccac tggcagagaa agcatctctg gctcatgcct   64800
gcatagtttc cccttagcat ttggagaagg agattggaac ctgttggctg gatctctttg   64860
tgtgtgatac tgggaggtac ttggcctctt catgagccat ttctagctct gaattaactt   64920
cctagttaga attcccaggc ttagcccatga tatgcttatg ttgttctttg tctggagcag   64980
gcaaccagat gccacctcgg ccacccagtg gccagtcgga cagcatcatg catccttcca   65040
```

```
tgaaccaatc aagcattgcc caagatcgag gtgagagcct gggtgttggg gaggggcagg   65100
gagctagggc agacatttga gtgccctatg cagtagcttt tggagagctg tttgaccatg   65160
aagcttagga caatccctgc agcaaattgt ttttatattc tttaaaagtt gacgtaataa   65220
ttgtactcat ttatgggta cataatgatg tttcaataga agtaacgtat agtgatcaga    65280
tcagggtaat tagcagatat ataatctcaa acacttatta cttctttgtg ctgagaccca   65340
gcagcaaatt gtgaagttag agtgggcttg gccgtgttaa tgtctccatt tcacagtact   65400
tgtctgtgtt ttgatggttg cccccttaca ttttgcctca tttggtcggc agttgctgaa   65460
gactcaatgt tcggtcttca ctcatcaagt cattcatttt ggttttgtc attgttcttt    65520 gtcttttcaa acctccattt agtagaaaca gctggcatgc cctggttaat ggttcatgtc   65580
actctgaagg tgcctaaaat gacacaccac tatatagaaa atcagataga gactccatgc   65640
aagtggctgc taaagaaaat gtagatggta aagtcccagg ataaggatgg agagcatttg   65700
ttcgcattgt ataaagctaa taactatatg gatgctaccc acaaataggt tatatgcaga   65760
ggaaccccca gatgccccag tacagttccc cccagcccgg ctcagcctta tctccgcgtc   65820
agccttccgg aggacagata cacacaggca tgggctccta ccagcagaac tccatgggga   65880
gctatggtcc caggggggt cagtatggcc cacaaggtca gtatactacc cagttaggag    65940
tagatacggg tgagaggaga aaacagttcc ttgtctgata tgttgccatc tagcttgtaa   66000
ccttgtgaga gaagggctgt cctttgcctt taatccaccc agcccaggcc ctgaagtagg   66060
gcaaggcaag attccatttg tctccactta ttctgtcacc atgagaaagt ctttcaattt   66120
cactgagcct ctgtttcatt tataaaaatg gagattaggt gtttactcca ccattgagca   66180
cagacaattt atacatggta gctcttggtt attatttttt tattaattat ttttagtgaa   66240
taagtcataa tggaatagat ctttgctcaa aattgcagcc ctaggctgat caaaagttga   66300
gaatcttaca cagagcatgg aaatagaaag gaagttatct tcttctggaa gttgaaatgc   66360
ctgtgtggca gcaaagccag ccttgctctg acctgccttt acatgcttct ggaatccccc   66420 ccttttctc atggcgataa aggctaccat gaagttgatc tctttcctaa ccaaaatatt    66480
gaatgacatt gtttggtgtt ctagagttga gagatattag tgagttgcta gtgagtgact   66540
aaccaagtct tgtcttcctc ccctcccagg tggctacccc aggcagccaa actataatgc   66600
cttgcccaat gccaactacc ccagtgcagg catggctgga ggcataaacc ccatgggtgc   66660
cggaggtcaa atgcatggac agcctggcat cccaccttat ggcacactcc ctccagggag   66720
gatgagtcac gcctccatgg gcaaccggcc ttatggccct aacatggcca atatgccacc   66780
tcaggttggg tcaggatgt gtcccccacc aggggcatg aaccggaaaa cccaagaaac     66840
tgctgtcgcc atgcatgttg ctgccaactc tatccaaaac aggtaaggcc tgggaagcag   66900
agagggtgtc agtgcaagaa aatgtattat agacccactc agattattga gatgcttctg   66960
gacctaaacc aggggggaa aatgggtgtg tgtgtatgaa gtgttaattc ttacatacct    67020
tagatgggtc tgaaatttca cgtgactaaa catcatatgt aatgagcttt ataaaagaca   67080 ggttttggc cgggcgtggc ggctcatgcc tgtaatccta gcactttggg aggccaaggc    67140
gggcagatca tgaggtcaga aatcaagacc agcctgatca acatggtgaa accccgtctg   67200
tactaaaaat acaaaaatta gctgggtgtg gtggcgcacg cctgtaatcc ggctatcgg    67260 gaggctgagg caggagaatc acttgaaccc aggaggaaga ggttgcagtg agccaagact   67320
gcgccaccac actccagcct gggcgacaga gcgagactgt cgaaaaaagg ggttttgtgg   67380
```

```
ggtgttttat tttggggtct tttgagacag gaccctgctc tgttcccag gctgaattgc    67440 agtggcatga ccacagttca ctgcagcctc gacctcccag gctcaagtga tcctcccacc    67500
tcagccttct gagtagttgg gactacaggc acacaccacc acacccagct aattttttt     67560 attttttata tttatttatt tatttagaga ctgtctcact ctgttgccca agctggagtg    67620
taatggcaca ctttcagctc actgccacct ctgctttcca ggttcaacca attgtcctgc    67680
ctcagcctcc caagtagctg tgttacagg cacccgccac catgcccgc taattttttat    67740 attttagac tgggtttcac catgttagcc aggctggtct caaaatcctg acctccagtg     67800
agctgcctgc cttggcctct gaaagtgctg ggattacagg catgatccac catgcccggc    67860
cttttttttt ttttttaaa tagagatggg gtctcagtgt gttgccaggg ctaaagactg     67920
cttattttga tgtgcaaaat aagtgttcag agtaggtggt ttaacttcta tcagtcaact    67980
ttttggtttc caaaaggatt cttaatgata catatgtctt ggatctttgg tgttagaaat    68040
agcaaatggt aagcttgtgg tttgccattt ctcctactgt tttatgtggt cctacgtgtt    68100
gactctggtg ctagagtaca aaggctcat gtgattaggt ttaacaactt ctttagccac     68160
taaatcttac tgagttgttg ttgatgaacc aaggtagaat agggcgattg actataaaga    68220
ggtggatttg gtagaacttc agaatgatgg aagtgcaaag tttgcattgg gcccctcaag    68280
aaataatgca aagccacctc tgggtgctat gctgagggtt ccagtctggt tgggatttag    68340
catgacaaaa agtggtacag ttcagcattt catctatgcc ttttgccaca gacagggccc    68400
ttaaatggaa atacaacttg actttggagg tggctttgag gaaggcagta cttaaaggac    68460
acagcagggc tctgcttcaa agaattacac cctttgaaat tgagctattg tggccgggtg    68520
cggtggctca ctcctgtaat cctagcactt tgggaggctg aggcaggtgg atcacctgag    68580
gtcagaagtt caagaccagc ctgcccagca tggcaaaacc ccatctctac taaaaataca    68640
aaaaaatagc caggcatggt ggtgggcgcc tgtaatccca gctactcacg aggctgaggc    68700
agaatggctt gaacctggga ggcggaggtt gcagtgagcc gagatcatgc cattgcactc    68760
cagcctggga gatgagtgaa actccatctc aaaaaaaaat tggccgggca tggtggctca    68820
cccctgtaat cccagcattt tgggaggctg aggcaggcgg ataacgaggt caggacatcg    68880
agaccatcct ggctaatacg gtgaaaccct gtctctacta ataaagtaca aaaaattagc    68940
cgggcgtggt ggcaggtgcc tgtagtccca gctacttggg aggctgaggc aggagaatgg    69000
cgtgaacccg ggaggcggag cttgcagtga gctgagatcg cgccactgct ctccagcctg    69060
ggcaacagag cgagactcca tctcaaaaaa aaaaaaaatt gaactattgt ttgctatcta    69120
gagcttgaac tctcttagta tctttcgtgg gaggtagaag ataagaaaat ctgggtgttg    69180
gccgggctcg gtggctcatg cctgtaattc cagcattttg ggaagccgag gcaggtggat    69240
cacctgaagt caggagttcg agaccagcct gaccaacatg gagaaagccc atctctacta    69300
aaaatacaac attagccggg tgtggtggta catgcctgta atcccagcta tttgggaggc    69360
tgagaaagga gaattgcttg aacctgggag gctgagattg cagtgagccg agatttcacc    69420
attgcactcc agcctgggca acaagagtga aactctgtct caaaaaaaaa aaaagaaaaa    69480
tctgggtgtt agctggacat ggtggtgcat gcctcatagt cttaggcact caggaggctg    69540
aggaaggcag attgtttgag ctcaggagat taaggctgca gtaagctatg atcacaccac    69600
tgcattccag ccagggtgcc agagcaatac cctgtctcaa gaaataaat taagaaaaa     69660 taatatctgg atgttgcata gttctagttt tggggaccca taaatgtttt ccttttaatc    69720
cttactagat gatcacacag cactatttgg ctccagttca aatctaaaag ctcagagtct    69780
```

```
aacctttgtc tctctcactt tccatcttct tccttaggcc gccaggctac cccaatatga    69840
atcaaggggg catgatggga actggacctc cttatggaca agggattaat agtatggctg    69900
gcatgatcaa ccctcaggga cccccatatt ccatgggtgg aaccatggcc aacaattctg    69960
caggtaagtg ctagtcattc tcactaggga tttcttcaag agtcacatca cagctaaact    70020
tactggactt gagaattttt ttctctttta cagggatggc agccagccca gagatgatgg    70080
gccttgggga tgtaaagtta actccagcca ccaaaatgaa caacaaggca gatgggacac    70140
ccaagacaga atccaaatcc aaggtagtga tttttgtctt gactcctttc aactttgtgt    70200
cctatctttt tcagtgatag gaaggaaaaa gaaaagagag tgacaagatc ccagcctttt    70260
atgacaccgg actagatagt ctctgaaaaa gctgctgttg cctcctctta tcatgaaagg    70320
tcccagaata atagctcagt gagttgggtc tgggttggtc taagggatcc tggtaaataa    70380
cataatattc tcacagctgt ttgttatggg ggaaatgcca gacactgcag catcaaactc    70440
tctgtactgt ttggctggtg ccctctgtga aaccgtgcct cctatactca agcattgata    70500 gatgggtgt gccatgggca actagttgct cttctcttcc tgaaccttac tcatagcagc    70560
aggaatggta ccctgtgttc tgtaaagaag gagataaggc agatgaggct tgagtccttg    70620
gcttccctta ggttggtcct gggtgtactg ttaggctgtg cggtagtaaa gggtcctact    70680
cagcatttgg gtcatttgta atatttctgt ccttggccat acctcacttt ccctatctgt    70740
atacataggg aaaataaaaa tcatagctgt taattcctgt gagtcttcac ctctggctcc    70800
cagccctttt gaccacgttc ctgtcttgta caggataata tccaaagccc ttcaaccagg    70860
tgggaaacct ttcctttgtt tagaagaggc aaagagtttc ttttcatttt agtccatccc    70920
attgcctcaa gatcatgttg tgagtttttc gatttctcta aaacatagta cctaagtatg    70980
ttcaggctcc tgggtagtag tgtgggagca gtagtggctt tgatgtcagg tggacaagga    71040
tttgatactc agcctgccac ttaaaagctg tgagatctta ggctttgcct cctggtgcct    71100
gcttccttat ctttacaaat ggggataatt ttataatacc taatatataa aggcatctag    71160
cacagcaccc agtacataac atatatttag tgttagcttc cttcctttat aggaaaaaaa    71220
aatttggttc tcttttggcc cttcaacctt atgaaggtag gacaggtgtt agtaaccacc    71280
ccagagtaag aagctttaac actgctccag tcaagagact tctgagaccc ttagcacagg    71340
ctttgaatct gacccattcc tatgaatttt gacctgaacc ttccagaaat ccagttcttc    71400
tactacaacc aatgagaaga tcaccaagtt gtatgagctg ggtggtgagc ctgagaggaa    71460
gatgtgggtg gaccgttatc tggccttcac tgaggagaag gccatgggca tgacaaatct    71520
gcctgctgtg ggtaggaaac ctctggacct ctatcgcctc tatgtgtctg tgaaggagat    71580
tggtggattg actcaggtga gtgggcgcct gacacttgac tgcccctgtg gtttccacaa    71640
accccttcct aggtactcac tggcttcatg tggtaccatg catcccacag ggacatcatc    71700
ccctctcccg ctttctgagt ctaatattga tagaccgggg agcacaggtt cccagaaga    71760 taaggcagga agcagagacc tccctggtag tatgaggtat tagcagtaag tttaccgtgt    71820
atctatggtc ccactgaggt gtaaagctag ggaaagtctg tggcattct gattccatgg     71880 gaggcaattt ggcatagtag caaagacagg atttggagag atggacctgg ttttgaatcc    71940
cttcttggcc acttataaca tatatgacct taaggtgtgt aaccactctg aaccttaatt    72000
tcattatttg taaatacaa acagtatgta acagtatata acccactaga ctgtcaaaag    72060
ttagaaataa cttttggcttt cagcaaggtt tctgccacat aaatcggcct gcaagatggt    72120
```

| | |
|---|---|
| acagaggcag ccagagtaga agtagatctt cccattcctg gaagcttccc agtagagata | 72180 |
| ggatttcagg aactgcttag tagaaatagt ttataataaa ggaagaagta gtaggaaatt | 72240 |
| atgtgtttag ttattctgta tgggaaactt aaatgaaaac ctgaattgga caccacccag | 72300 |
| agcttgtgcc tactctgata ccttacaatt ttgtagactc agcccaggaa gcaaacaggt | 72360 |
| gaggcagcac agacagacag cagactgtgc cttgcagact tccctcctgt gtatgttctg | 72420 |
| tagtcaccag accagaagcc tgctgttgga tcagtttgtg gctgagctcg ggaggtgtg | 72480 |
| gcagggaggg atttattcca aaccttctaa atcagaagag gaaaacagct gtcaccagca | 72540 |
| gaaaagaaag tggttggaat gaagccagcc aacagtcagt tatgaattcc ttctcccttc | 72600 |
| aggctttatt cccctccccc acaaaggaaa acaaaacaaa ataagacacg tgcatactgc | 72660 |
| cacataactg gcatgagaag caaagccacg gaaggctttt gaggtgactc catgcatatt | 72720 |
| cctgccattc tccctgatac tcagatctca tagtcaagcc ttccctgtct atagggaaag | 72780 |
| ggagcattgg gttaggtttc gctcacttct gattgggtgg gcttcagggt tcactgaacc | 72840 |
| taggatgagg tacagagaga attctaatgc ctgagcctgt cttccagatt ggaaaaggat | 72900 |
| gcaaaccttt aaaatgccgt gattgtaact gaacttttat aaaggcagtg ataattcagg | 72960 |
| ggcaaaagag tgctatttat aagttagttt gtgaaggctc caagaaagca aagctgaatc | 73020 |
| ttgagcttat ctaaaggatt agtagggttt aggtggaaga gtggccaatc cagtagactg | 73080 |
| gcctagatgc cacggagatg ggagagagtc tagatatttc ccaccaaggc catctccaac | 73140 |
| catgaagact tagctcaggt gttacccact ctaagaagta ttcctagtca cctctgcccc | 73200 |
| tctaggttgt ccccctctgt gcctctttaa actcttcttt ctagtatcat aggtatcata | 73260 |
| tcagcagaca ttacaaccta ttgaacttcc tttgtgtata gggacttgaa aacccttgtt | 73320 |
| cccaggcctt gggggaacag gcttaccata tggtagatga ataagcataa gaatacatga | 73380 |
| agaaggagac ctgtccagct agagcagaaa gactaattgt agggagcatc tggggaatgg | 73440 |
| gcttggtcag tgtgccctga agctgaggga aggaggcaga actgtaggtt ggctgctcgg | 73500 |
| gaggtacaaa agtcataata aggccccggg ccaggcgcag tggctcacac ctgtaatccc | 73560 |
| agcactttgg gaggccgaga cgggcggatc atctgaggtc aggagtttga gaccagcctg | 73620 |
| gccaacatgg ccaaaccttg tctctactaa aaatataaaa atcagtgggg tgtggtgaca | 73680 |
| ggcacctgtg gtcccactac ttgggaggct aaggcaggag aatcacttga cacgggagg | 73740 |
| cggaggttgc agtgagccga aatggcgtca ctacactcga gcctgggtga cagagtgaga | 73800 |
| ctctgtctct aaataaataa gaccctgaac acccggacca tcaggacagt gactggtaag | 73860 |
| ggaaagggac ctgtggttat ttgtcaatga gatatgtagg ggagcagtgg cacaagaatg | 73920 |
| tcaaatttgc agggagccac cacccccaaga aaaaaatatg agtaaatccc aagtttgaca | 73980 |
| aagcaagtca agcagggtgg tcactgatat tatcatgagt ctccatttta taaaatgtta | 74040 |
| gttttttatta gtgcatctaa aataggattt agggccaggc gcggtggctc acgcctgtaa | 74100 |
| tcccaacact ttgggaggct gaggcgggta gatgacttga cgccaggagt ttgagaccag | 74160 |
| cctgatcaac atggtgaaac cccgtctcta ctaaaaatac aaaaattagc caggcgtggt | 74220 |
| ggtgcacacc tgtaatccca gctactcggg aggctgagat aagagaatcg cttgagcccg | 74280 |
| ggaggcagag gttacagcga gccaagatca cgccactgca ctccagccta ggcgacagag | 74340 |
| cgagatttat ttttctgtc tcaaaaataa ataaataaaa taggatttag atatccagat | 74400 |
| gatttgtaca ccactttta gcagcgtact aaaaaaccgg actctgaatt ctgttccagt | 74460 |
| agtaatgtga aatttgccct gttgtgaata agcacagtct gatagttgca gtggaacatc | 74520 |

```
ctgagggtaa aatgaagcca gctgcagatt taacacttct tgtggactat ccaccaagca    74580
agattaactt tttcaattac ctaagaactg tggttctaca aagatgaata ccttacagcc    74640
tgatggggct tggggcttat gggcaggaaa accaggcggg agatatacct cgactccttt    74700
ggtttggtta tacaggtcaa caagaacaaa aaatggcggg aacttgcaac caacctcaat    74760
gtgggcacat caagcagtgc tgccagctcc ttgaaaaagc agtatatcca gtgtctctat    74820
gcctttgaat gcaagattga acggggagaa gaccctcccc cagacatctt tgcagctgct    74880
gattccaaga agtcccagcc caagatccag cctccctctc ctggtaagga tggggtcagc    74940 ggcccccacca aggctgagag ggcctgttgc cctggcctct tattcaggat atgaataaga    75000
ggcttatcca acaggatatg ccaaggatct gtgctctgcc ttgccctacc acagggctta    75060
acaggttggc tgactagaga gtgggcagtg gaaactccct tggaggtac tctacggcag    75120 ctcttaagtt ttaatttttg ttgtgcagct gacaacttgc caaatgtttg taaactggtg    75180
aatgggaggg gcacaagagg agtcggtgga acttataaat ggcagcaagg cagggccatc    75240
tgggagcttt ggcctattga tgtcagcacc ttagaatgca gctcagacta gagccctgaa    75300
ttccccaggg agctgagatg gtaatgaatg ggaaggaggg agtggggaag ggttatgaat    75360
ggaactccct gatgggagtg gctctgctca ccctcctttc tgagaggagg ctgaggccta    75420
gggtgagcct agagagggaa gaaggccagg gtgcctggaa ggtgggtgta acacatgtg    75480 ccctggtgtt gacctctgag ggtgtaatga gtgcctgaga tgactcatca gctggggagg    75540
cctcagcagt gggatatcta ctgctgggaa tggtaactat tggaaacatt aattactagt    75600
agttttgtac tcatcagctt agaagaacat ttgaagttga ggagtgacac catgctggat    75660
gctttagaac aggagctcct agactcctaa aatgcatccc agatttggga cccccttccc    75720
acccaggact tgggaggctc tgactggagc tcatgcacca gcattacagg gtttagtagg    75780
ttagacaagg tcctttggcg gagtgaagag aaatagccag ggaagctggc aatgactcag    75840
ggaatcacca gcatggtgat gtcatggcca catcactcct cttttctaca cgtaaaacaa    75900
aaacaaagag ctacaaaacc ctcagattcc cgtctttatg acctggcctt gtagatcctc    75960
tgctaagaag ggtgatcagg cttaaaggc cttaggaaga actttcccaa agagattctg    76020
ggtcgttcgt gtgtttgtgt gagagttaaa cactgtcatg ccaagcaaac tactcaactt    76080
gtatctctgt ccacagcggg atcaggatct atgcaggggc cccagactcc ccagtcaacc    76140
agcagttcca tggcagaagg aggagactta aagccaccaa ctccagcatc cacaccacac    76200
agtcagatcc ccccattgcc aggcatgagg taaggccaag agcaggggca gatggttggg    76260
aggatggctg aagataagtg catgggaact ccttgcagcc caaggtggtc cttgcctctg    76320
ccttcccagc cagtgactcc tgcgtgtcct ttgttatatt ggaggaattg gtttatttgt    76380
ggtttacttg gttttcctca ctctggagca ggagcaattc agttgggatc caggatgcct    76440
ttaatgatgg aagtgactcc acattccaga agcggaattc catgactcca aaccctgggt    76500
atcagcccag tatgaatacc tctgacatga tggggcgcat gtcctatgag ccaaataagg    76560
atccttatgg cagcatgagg aaaggtgact gatctgattg ctatttgaac ttgtgctcgt    76620
aaagacaggg ccagtgaaat ggggggaaat cttgagaatg gctcagggtt cttgtggagc    76680
catcctctga gataatgcat ttcctgccct aactacccct cttcatcctt acctcctttc    76740
ttgtcttctc cttggcttca ccttgtcatc ccttaataag tacatgcttt tcgctggttg    76800
gggcctcttt agatctctgt tttgaacttg tctggaaaac aatgagatca aacctgaact    76860
```

```
ctgaagaggg cctgggtcaa agggtagatt accaggcttg tcaacttacc agtttgttca     76920
ccgcttgcct ttctacgctc agctccaggg agtgatccct tcatgtcctc agggcagggc     76980
cccaacggcg ggatgggtga cccctacagt cgtgctgccg gccctgggct aggaaatgtg     77040
gcgatgggac cacgcacagca ctatccctat ggaggtcctt atgacagagt gaggtaagca    77100 tgacccccagc tcctgtccac tcccccagca ccctgaagct atagtgggct caatctgcct    77160
ctccaatttt gtttaggacg gagcctggaa tagggcctga gggaaacatg agcactgggg     77220
ccccacagcc gaatctcatg ccttccaacc cagactcggg gatgtattct cctagccgct     77280
accccccgca gcagcagcag cagcagcagc aacggtgagt aaagcctggt ctcggtgctg     77340
ctatggatca ggcttcgcca ctgcccaccc taatcctgtg tttctttgcc tcctatagac     77400
atgattccta tggcaatcag ttctccaccc aaggcacccc ttctggcagc cccttcccca     77460
gccagcagac tacaatgtat caacagcaac agcaggtgag gagggtagct gggaatggac     77520
tggcatgcag gttcgccttg aaaactagtt agtaaactaa tctaacgtgt tgaagtctaa     77580
gaagctcact ttagatattt tggcattctt ctctcacctg actggccagt cctgcctgaa     77640
gagccacgtc ctcaatctct tctctatttg gagttggaag gggctagaaa tagaccttat     77700
tttgattttt aggttttgta tattttttcta cttaagcaag ggaagggaag aaagagtggt    77760
ggttgctttt ggaaacaact tcaaaagaca atttgttaag gtgattccca tgttttcttg     77820
gagtctgtgt ccaccaagca tctggttgta gccatcttgg catctgtggg ctttatgtcc     77880
ctgagtgcag agtattaact tcccctctgc ttgtctctgc cttagaatta caagcggcca     77940
atggatggca catatggccc tcctgccaag cggcacgaag gggagatgta cagcgtgcca     78000
tacagcactg ggcaggggca gcctcagcag cagcagttgc ccccagccca gccccagcct     78060
gccagccagc aacaagctgc ccagccttcc cctcagcaag atgtatacaa ccagtatggc     78120
aatgcctatc ctgccactgc cacagctgct actgagcgcc gaccagcagg cggcccccag     78180
aaccaatttc cattccagtt tggccgagac cgtgtctctg cacccctgg caccaatgcc      78240 cagcaaaaca tgccaccaca aatgatgggc ggccccatac aggcatcagc tgaggttgct     78300
cagcaaggca ccatgtggca ggggcgtaat gacatgacct ataattatgc caacaggcag     78360
agcacgggct ctgcccccca gggccccgcc tatcatggcg tgaaccgaac agatgaaatg     78420
ctgcacacag atcagagggc caaccacgaa ggctcgtggc cttcccatgg cacacgccag     78480
cccccatatg gtccctctgc ccctgtgccc ccatgacaa ggccccctcc atctaactac       78540
cagcccccac caagcatgca gaatcacatt cctcaggtat ccagccctgc tcccctgccc     78600
cggccaatgg agaaccgcac ctctcctagc aagtctccat tcctgcactc tgggatgaaa     78660
atgcagaagg caggtccccc agtacctgcc tcgcacatag cacctgcccc tgtgcagccc     78720
cccatgattc ggcgggatat caccttccca cctggctctg ttgaagccac acagcctgtg     78780
ttgaagcaga ggaggcggct cacaatgaaa gacattggta aggagatctt cctcattcgg     78840
ttgcctaatc tgccccttc catcttgtcc attgttccct ccaccttact attctggatg       78900
aggttgaatc tggtccagtg ttgactaaaa tagaaccaaa gaactttgga aaaggaagaa     78960
ataagctaac taaaggttct ccttcattgc catgcaatga agtcctagac agacagctta     79020
gaagccatga ggggctggtg tgtttcatct cccagacaga aactgccttc caccttgtgt     79080
tatcttcaga gtagcttcac tgatggggca gccctagggg tgcctccagc caacctgggc    79140
ttggtggata gacgacatgg aggttttatt caggaacccc ggaggcatgg cgggtaatga    79200
tgtccctcaa gtctggtctc ctggcagaga gcacatgggc attagatacc atcaacatcc    79260
```

```
tgctgtatga tgacaacagc atcatgacct tcaacctcag tcaggtgagt atcagtgcct   79320
ggggaagatt gagagggttt gggatcttct tagtgtagac aatgggaatg tctcatcttt   79380
agccaccttg gtctttctct ttctctcttg tagatatctt ccatgccagt actttgcttc   79440
ctttgcctct gggcacgggc ccaggatttt gacagcaata ataatttgtt tacatgataa   79500
ccttaacaca ggattgactt caaaaggaat tgggagaca ctttgtggta ttagtaagaa    79560
ttcagattca atcgatgcca gtggggacac cacattttct agaagaatct gtgttttttt   79620 gttttttaa tagagacgag gtctcactat gttgccgagg ttcatgaact cctgagttca    79680
agtgatcctc ccaaagtgct aggattacag gcatgagcca ccaggcccag cctgaatctg   79740
tggtcaaatt tttatcagtg agcagagtat gttttttcca ttttttccctt tcttctctga  79800 acagtagggg cctttgttga tcccagtttt ccttagatgt agagtggatg ggggatttga   79860
ttgtttaaca atattctttt tttttttttt ttgactgagt ctctctgtcg cccaggctgg   79920
agtgcagtgg cgctatcaca gctcactgca acttccgcct cctgggtaca tgccattctc   79980
ctgcctcagc ctcccaagta gctgggacta caggcgcccg ccaccacgct cggctaattt   80040
tttgtatttt tagtagagac ggggtttcac cgtgttagcc aggatggtct cgatctcctg   80100
acctcgtgat ccagccgcct cagcctccca aagtgctggg attacaggcg tgagcaaccg   80160 cgccggccc tacaatattc ttacaaagct gattcttcag acccacectc cataggatgt    80220 gcacactagt ggaggtgctg gaaagagttt gtgctgcatc atcctactct ttttctttg    80280 atcatcttta gtacctacca acctgtatat caaggagctg acttattaat agttaccatt   80340
tatcgtgctc ttatttttgtg ccaggtcctt aatatttgt ttcatgtcat cctagcaaca   80400
gccctcagag gtaggaggta tggccattta gggatgagta aataggctca gtcttatcct   80460
tgttgaggtt cacatagctg tcagtagaat ctatctgatt cctaagcctg atttttattc   80520
cattgcataa tattgcctac catgagaaag gaaaaatttt gatagagcaa ttttcatatg   80580
ccaggtattt gacatctccc atttacacct cagaacaacc ctgtaaagtt taggaatttt   80640
tatcatttta tacagctact tcctggaaaa gccagaattt tttttttaag agactctggc   80700
acctaggctg gagtgtagta gtgccctcat ggctcactgc agcctcaaac tcctgggctc   80760
aagcgatcct cttgcctcag tctcctgagt agctgggact acaggcaaat gccaccatgt   80820
ccagctattt atttattttg agacagggtc tccattactc aagctagagt gcagtggtgc   80880
aatcacagct cactgcagtc tcaacttccg aggctcaggt gatcctccca cctcagcttc   80940
ccaagtggct gggactacag gtgcgtgcaa acatgctcat gctcagctaa ttttttttt    81000 tttttttt gagagatgag gcttcaccat gttgcccagg ctgatttcaa actcctgggc     81060
tcaagtgatt gacctacctc agcctctcaa agtactagga ttacaggtgt gagccaccgt   81120
tccaggcccc ggataacttc tttattttt tatagaggca gggtctcact gtgttgccca   81180
ggctggtctc aaactcctag gctcaagtga ttctcccact tcaaccttcc aaagtgttgg   81240
gattactggc tgggtgcagt ggctcacgcc tgtaatccca gcacttcagg aggccgaggc   81300
aggaggatca tttgaggtca ggagtttgag gccagctggc caacatggtg aaactccatc   81360
tctactaaaa ctataaaaat taggctgggc gcagtggctc acgccagtaa tcctagcact   81420
ttgggaggcc aaggtgggtg gatcacttga ggttaggagt tcaagaccat cctggccaat   81480
atggtgaaac tccatctcca ccaaaaatat aaaaattagc cgggcctggt ggcacacacc   81540
tctaatccca gctacttggg aggcagaggc agaagaatca ctttgaaccc aggaggcaga   81600
```

```
ggttgcagtg agctgagatc gtgccactgc actccagcct gggcaacaga gcgggactct    81660
gtctcaaaaa aaaaaaaaaa aaaatacaca cacacacact ctcacacact agcccgatgt    81720
ggtggcaggc gcctgtaatc ccagctactt gggaggctaa ggcaggagaa aaatcgcttg    81780
aacccaggag gcggaggctg cagccaactg agatcacacc actgtactcc agcctggatg    81840
acagagtgag acttcatctc aaaaaaaaaa aaaagtgttg ggattacagg tgtgagccac    81900
tgcttccagc ccctagatct aattcgaaag cccttatttt tttttccatc tgctctactg    81960
ttcagccaaa gattgtgact ggagaggagt gttttcttct agaggtaaat aaatggccta    82020
tatattatcc aaggtggaat ttgggtctct gtagcaccag cttggaccag tgtttggaga    82080
gctgaagcct cgtcccactc cttatgctgc aagatccatg gagttccagc ccctggact    82140 tgtgggagc ttggagaaga gagccatgaa catctgccca catggcattc tcttctctta    82200
gcttaagtca ccatgcctaa gcttgggttc cacttggcag tgagatggag agagtgtcct    82260
aaaagagata atggcaatga ccaccaggtt gaaaactggc ctggtgaaga aaagcagaag    82320
attaattggg aaagagaag gctaagagat gattggccct ggtgggtgag gtgcaaagct    82380
gttggctagt gttcctggag ataggcttac gtgaaggtag gttgggcaga agaaagaact    82440
ttgtgttggg catagaagag attaagatga acaatttgct ctgtggagaa cctttgggaa    82500
aggagcaact ctgcctctcc caactgatac agaagacttg gggaggtctc tcaagtcaat    82560
aattctgttc ttaggccact tttctccctt aattattttc ctgttctttc tcttttagc    82620 tcccagggtt gctagagctc cttgtagaat atttccgacg atgcctgatt gagatctttg    82680
gcattttaaa ggagtatgag gtgggtgacc caggacagag aacgctactg atcctggga    82740 ggttcagcaa ggtgtctagt ccagctccca tggagggtgg ggaagaagaa gaagaacttc    82800
taggtcctaa actagaagag gaagaagaag aggaagtagt tgaaaatgat gaggagatag    82860 cctttcagg caaggacaag ccagcttcag agaatagtga ggagaagctg atcagtaagt    82920
ttgacaagct tccagtaaag atcgtacaga agaatgatcc atttgtggtg gactgctcag    82980
ataagcttgg gcgtgtgcag gagtttgaca gtggcctgct gcactggcgg attggtgggg    83040
gggacaccac tgagcatatc cagacccact tcgagagcaa gacagagctg ctgccttccc    83100
ggcctcacgc accctgccca ccagcccctc ggaagcatgt gacaacagca gagggtacac    83160
cagggacaac agaccaggag gggccccac ctgatggacc tccagaaaaa cggatcacag    83220
ccactatgga tgacatgttg tctactcggt ctagcacctt gaccgaggat ggagctaaga    83280
gttcagaggc catcaaggag agcagcaagt ttccatttgg cattagccca gcacagagcc    83340
accggaacat caagatccta gaggacgaac cccacagtaa ggatgagacc ccactgtgta    83400
cccttctgga ctgcaggat tctcttgcca agcgctgcgt ctgtgtgtcc aataccattc    83460
gaagcctgtc atttgtgcca ggcaatgact ttgagatgtc caaacaccca gggctgctgc    83520
tcatcctggg caagctgatc ctgctgcacc acaagcaccc agaacggaag caggcaccac    83580
taacttatga aaaggaggag gaacaggacc aaggggtgag ctgcaacaaa gtggagtggt    83640
ggtgggactg cttggagatg ctccgggaaa acaccttggt tacactcgcc aacatctcgg    83700
ggcagttgga cctatctcca taccccgaga gcatttgcct gctgtcctg gacgggactcc    83760 tacactgggc agtttgccct tcagctgaag cccaggaccc cttttccacc ctgggcccca    83820
atgccgtcct ttccccgcag agactggtct tggaaaccct cagcaaactc agcatccagg    83880
acaacaatgt ggacctgatt ctggccacac cccccttcag ccgcctggag aagttgtata    83940
gcactatggt gcgcttcctc agtgaccgaa agaacccggt gtgccgggag atggctgtgg    84000
```

| | |
|---|---|
| tactgctggc caacctggct caggggggaca gcctggcagc tcgtgccatt gcagtgcaga | 84060 |
| agggcagtat cggcaacctc ctgggcttcc tagaggacag ccttgccgcc acacagttcc | 84120 |
| agcagagcca ggccagcctc ctccacatgc agaacccacc ctttgagcca actagtgtgg | 84180 |
| acatgatgcg gcgggctgcc cgcgcgctgc ttgccttggc caaggtggac gagaaccact | 84240 |
| cagagtttac tctgtacgaa tcacggctgt tggacatctc ggtatcaccg ttgatgaact | 84300 |
| cattggtttc acaagtcatt tgtgatgtac tgtttttgat tggccagtca tga | 84353 |

<210> SEQ ID NO 2
<211> LENGTH: 6858
<212> TYPE: DNA
<213> ORGANISM: Homo sapiens

<400> SEQUENCE: 2

| | |
|---|---|
| atggccgcgc aggtcgcccc cgccgccgcc agcagcctgg caacccgcc gccgccgccg | 60 |
| ccctcggagc tgaagaaagc cgagcagcag cagcgggagg aggcgggggg cgaggcggcg | 120 |
| gcggcggcag cggccgagcg cggggaaatg aaggcagccg ccgggcagga aagcgagggc | 180 |
| cccgccgtgg ggccgccgca gccgctggga aaggagctgc aggacgggc cgagagcaat | 240 |
| gggggtggcg gcggcggcgg agccggcagc ggcggcgggc ccggcgcgga gccggacctg | 300 |
| aagaactcga cgggaacgc gggccctagg cccgccctga caataaccct cacggagccg | 360 |
| cccggcggcg gcggtggcgg cagcagcgat ggggtgggg cgcctcctca ctcagccgcg | 420 |
| gccgccttgc cgccccagc ctacggcttc gggcaaccct acggccggag cccgtctgcc | 480 |
| gtcgccgccg ccgcggccgc cgtcttccac caacaacatg gcggacaaca aagccctggc | 540 |
| ctggcagcgc tgcagagcgg cggcggcggg ggcctggagc cctacgcggg gccccagcag | 600 |
| aactctcacg accacggctt ccccaaccac cagtacaact cctactaccc caaccgcagc | 660 |
| gcctaccccc cgcccgcccc ggcctacgcg ctgagctccc cgagaggtgg cactccgggc | 720 |
| tccggcgcgg cggcggctgc cggctccaag ccgcctccct cctccagcgc ctccgcctcc | 780 |
| tcgtcgtctt cgtccttcgc tcagcagcgc ttcggggcca tggggggagg cggcccctcc | 840 |
| gcggccggcg ggggaactcc ccagcccacc gccaccccca ccctcaacca actgctcacg | 900 |
| tcgcccagct cggccggggg ctaccagggc taccccgggg gcgactacag tggcgggccc | 960 |
| caggacgggg gcgccggcaa gggcccggcg acatggccct cgcagtgttg gggggctgcg | 1020 |
| gcggcggcag ctgcggcggc ggccgcctcg ggaggggccc aacaaaggag ccaccacgcg | 1080 |
| cccatgagcc ccgggagcag cggcggcggg ggcagccgc tcgcccggac ccctcagcca | 1140 |
| tccagtccaa tggatcagat gggcaagatg agacctcagc catatggcgg gactaaccca | 1200 |
| tactcgcagc aacagggacc tccgtcagga ccgcagcaag acatgggta cccagggcag | 1260 |
| ccatacgggt cccagacccc gcagcggtac ccgatgacca tgcagggccg ggcgcagagt | 1320 |
| gccatgggcg gcctctctta tacacagcag attcctcctt atggacaaca aggcccagc | 1380 |
| gggtatggtc aacagggcca gactccatat acaaccagc aaagtcctca ccctcagcag | 1440 |
| cagcagccac cctactccca gcaaccaccg tcccagaccc ctcatgccca accttcgtat | 1500 |
| cagcagcagc cacagtctca accaccacag ctccagtcct ctcagcctcc atactcccag | 1560 |
| cagccatccc agcctccaca tcagcagtcc ccggctccat acccctccca gcagtcgacg | 1620 |
| acacagcagc cccccagag ccagcccccc tactcacagc cacaggctca gtctccttac | 1680 |
| cagcagcagc aaccctcagca gccagcaccc tcgacgctct cccagcaggc tgcgtatcct | 1740 |

```
cagccccagt ctcagcagtc ccagcaaact gcctattccc agcagcgctt ccctccaccg   1800
caggagctat ctcaagattc atttgggtct caggcatcct cagcccctc aatgacctcc    1860 agtaagggag ggcaagaaga tatgaacctg agccttcagt caagaccctc cagcttgcct   1920
gatctatctg gttcaataga tgacctcccc atggggacag aaggagctct gagtcctgga   1980
gtgagcacat cagggatttc cagcagccaa ggagagcaga gtaatccagc tcagtctcct   2040
ttctctcctc atacctcccc tcacctgcct ggcatccgag gcccttcccc gtccctgtt    2100 ggctctcccg ccagtgttgc tcagtctcgc tcaggaccac tctcgcctgc tgcagtgcca   2160
ggcaaccaga tgccacctcg gccacccagt ggccagtcgg acagcatcat gcatccttcc   2220
atgaaccaat caagcattgc ccaagatcga ggttatatgc agaggaaccc ccagatgccc   2280
cagtacagtt ccccccagcc cggctcagcc ttatctccgc gtcagccttc cggaggacag   2340
atacacacag gcatgggctc ctaccagcag aactccatgg ggagctatgg tccccagggg   2400
ggtcagtatg gcccacaagg tggctacccc aggcagccaa actataatgc cttgcccaat   2460
gccaactacc ccagtgcagg catggctgga ggcataaacc ccatgggtgc cggaggtcaa   2520
atgcatggac agcctggcat cccacccttat ggcacactcc ctccagggag gatgagtcac   2580
gcctccatgg gcaaccggcc ttatggccct aacatggcca atatgccacc tcaggttggg   2640
tcagggatgt gtcccccacc aggggggcatg aaccggaaaa cccaagaaac tgctgtcgcc   2700
atgcatgttg ctgccaactc tatccaaaac aggccgccag gctaccccaa tatgaatcaa   2760 ggggcatga tgggaactgg acctccttat ggacaaggga ttaatagtat ggctggcatg   2820
atcaaccctc agggacccc atattccatg ggtggaacca tggccaacaa ttctgcaggg   2880
atggcagcca gcccagagat gatgggcctt ggggatgtaa agttaactcc agccaccaaa   2940
atgaacaaca aggcagatgg gacacccaag acagaatcca atccaagaa atccagttct   3000 tctactacaa ccaatgagaa gatcaccaag ttgtatgagc tgggtggtga gcctgagagg   3060
aagatgtggg tggaccgtta tctggccttc actgaggaga aggccatggg catgacaaat   3120
ctgcctgctg tgggtaggaa acctctggac ctctatcgcc tctatgtgtc tgtgaaggag   3180
attggtggat tgactcaggt caacaagaac aaaaaatggc gggaacttgc aaccaacctc   3240
aatgtgggca catcaagcag tgctgccagc tccttgaaaa agcagtatat ccagtgtctc   3300
tatgcctttg aatgcaagat tgaacgggga aagaccctc ccccagacat ctttgcagct   3360
gctgattcca agaagtccca gcccaagatc cagcctccct ctcctgcggg atcaggatct   3420
atgcaggggc cccagactcc ccagtcaacc agcagttcca tggcagaagg aggagactta   3480
aagccaccaa ctccagcatc cacaccacac agtcagatcc ccccattgcc aggcatgagc   3540
aggagcaatt cagttgggat ccaggatgcc tttaatgatg aagtgactc cacattccag   3600 aagcggaatt ccatgactcc aaaccctggg tatcagccca gtatgaatac ctctgacatg   3660
atggggcgca tgtcctatga gccaaataag gatccttatg gcagcatgag gaaagctcca   3720
gggagtgatc ccttcatgtc ctcagggcag ggccccaacg gcgggatggg tgacccctac   3780
agtcgtgctg ccggccctgg gctaggaaat gtggcgatgg gaccacgaca gcactatccc   3840
tatggaggtc cttatgacag agtgaggacg gagcctggaa tagggcctga gggaaacatg   3900
agcactgggg ccccacagcc gaatctcatg ccttccaacc cagactcggg gatgtattct   3960
cctagccgct acccccgca gcagcagcag cagcagcagc aacgacatga ttcctatggc   4020
aatcagttct ccacccaagg cacccccttct ggcagcccct tccccagcca gcagactaca   4080
atgtatcaac agcaacagca gaattacaag cggccaatgg atggcacata tggccctcct   4140
```

```
gccaagcggc acgaagggga gatgtacagc gtgccataca gcactgggca ggggcagcct    4200
cagcagcagc agttgccccc agcccagccc cagcctgcca gccagcaaca agctgcccag    4260
ccttcccctc agcaagatgt atacaaccag tatggcaatg cctatcctgc cactgccaca    4320
gctgctactg agcgccgacc agcaggcggc ccccagaacc aatttccatt ccagtttggc    4380
cgagaccgtg tctctgcacc ccctggcacc aatgcccagc aaaacatgcc accacaaatg    4440
atgggcggcc ccatacaggc atcagctgag gttgctcagc aaggcaccat gtggcagggg    4500
cgtaatgaca tgacctataa ttatgccaac aggcagagca cgggctctgc cccccagggc    4560
cccgcctatc atggcgtgaa ccgaacagat gaaatgctgc acacagatca gagggccaac    4620
cacgaaggct cgtggccttc ccatggcaca cgccagcccc catatggtcc ctctgcccct    4680
gtgcccccca tgacaaggcc ccctccatct aactaccagc ccccaccaag catgcagaat    4740
cacattcctc aggtatccag ccctgctccc ctgccccggc caatggagaa ccgcacctct    4800
cctagcaagt ctccattcct gcactctggg atgaaaatgc agaaggcagg tcccccagta    4860
cctgcctcgc acatagcacc tgcccctgtg cagccccca tgattcggcg ggatatcacc    4920
ttcccacctg gctctgttga agccacacag cctgtgttga agcagaggag gcggctcaca    4980
atgaaagaca ttggaacccc ggaggcatgg cgggtaatga tgtccctcaa gtctggtctc    5040
ctggcagaga gcacatgggc attagatacc atcaacatcc tgctgtatga tgacaacagc    5100
atcatgacct tcaacctcag tcagctccca gggttgctag agctccttgt agaatatttc    5160
cgacgatgcc tgattgagat ctttggcatt ttaaaggagt atgaggtggg tgacccagga    5220
cagagaacgc tactggatcc tgggaggttc agcaaggtgt ctagtccagc tcccatggag    5280 ggtgggaag aagaagaaga acttctaggt cctaaactag aagaggaaga agaaggaa    5340 gtagttgaaa atgatgagga gatagccttt tcaggcaagg acaagccagc ttcagagaat    5400
agtgaggaga agctgatcag taagtttgac aagcttccag taaagatcgt acagaagaat    5460
gatccatttg tggtggactg ctcagataag cttgggcgtg tgcaggagtt tgacagtggc    5520
ctgctgcact ggcggattgg tggggggac accactgagc atatccagac ccacttcgag    5580
agcaagacag agctgctgcc ttcccggcct cacgcaccct gcccaccagc ccctcggaag    5640
catgtgacaa cagcagaggg tacaccaggg acaacagacc aggaggggcc cccacctgat    5700
ggacctccag aaaaacggat cacagccact atggatgaca tgttgtctac tcggtctagc    5760
accttgaccg aggatggagc taagagttca gaggccatca aggagagcag caagtttcca    5820
tttggcatta gcccagcaca gagccaccgg aacatcaaga tcctagagga cgaaccccac    5880
agtaaggatg agaccccact gtgtacccct ctggactggc aggattctct tgccaagcgc    5940
tgcgtctgtg tgtccaatac cattcgaagc ctgtcatttg tgccaggcaa tgactttgag    6000
atgtccaaac cccagggct gctgctcatc ctgggcaagc tgatcctgct gcaccacaag    6060
cacccagaac ggaagcaggc accactaact tatgaaaagg aggaggaaca ggaccaaggg    6120
gtgagctgca acaaagtgga gtggtggtgg gactgcttgg agatgctccg ggaaaacacc    6180
ttggttacac tcgccaacat ctcggggcag ttggacctat ctccataccc cgagagcatt    6240
tgcctgcctg tcctggacgg actcctacac tgggcagttt gccccttcagc tgaagcccag    6300 gaccccttt ccaccctggg ccccaatgcc gtcctttccc cgcagagact ggtcttggaa    6360
accctcagca aactcagcat ccaggacaac aatgtggacc tgattctggc cacacccccc    6420
ttcagccgcc tggagaagtt gtatagcact atggtgcgct tcctcagtga ccgaaagaac    6480
```

| | | |
|---|---|---|
| ccggtgtgcc gggagatggc tgtggtactg ctggccaacc tggctcaggg ggacagcctg | 6540 | |
| gcagctcgtg ccattgcagt gcagaagggc agtatcggca acctcctggg cttcctagag | 6600 | |
| gacagccttg ccgccacaca gttccagcag agccaggcca gcctcctcca catgcagaac | 6660 | |
| ccacccttg agccaactag tgtggacatg atgcggcggg ctgcccgcgc gctgcttgcc | 6720 | |
| ttggccaagg tggacgagaa ccactcagag tttactctgt acgaatcacg gctgttggac | 6780 | |
| atctcggtat caccgttgat gaactcattg gtttcacaag tcatttgtga tgtactgttt | 6840 | |
| ttgattggcc agtcatga | 6858 | |

<210> SEQ ID NO 3
<211> LENGTH: 2285
<212> TYPE: PRT
<213> ORGANISM: Homo sapiens

<400> SEQUENCE: 3

```
Met Ala Ala Gln Val Ala Pro Ala Ala Ser Ser Leu Gly Asn Pro
 1               5                  10                  15

Pro Pro Pro Pro Pro Ser Glu Leu Lys Lys Ala Glu Gln Gln Arg
                20                  25                  30

Glu Glu Ala Gly Gly Glu Ala Ala Ala Ala Ala Glu Arg Gly
                35                  40                  45

Glu Met Lys Ala Ala Ala Gly Gln Glu Ser Glu Gly Pro Ala Val Gly
 50                  55                          60

Pro Pro Gln Pro Leu Gly Lys Glu Leu Gln Asp Gly Ala Glu Ser Asn
65                  70                  75                  80

Gly Gly Gly Gly Gly Gly Ala Gly Ser Gly Gly Pro Gly Ala
                85                  90                  95

Glu Pro Asp Leu Lys Asn Ser Asn Gly Asn Ala Gly Pro Arg Pro Ala
                100                 105                 110

Leu Asn Asn Asn Leu Thr Glu Pro Pro Gly Gly Gly Gly Gly Ser
                115                 120                 125

Ser Asp Gly Val Gly Ala Pro Pro His Ser Ala Ala Ala Ala Leu Pro
130                 135                 140

Pro Pro Ala Tyr Gly Phe Gly Gln Pro Tyr Gly Arg Ser Pro Ser Ala
145                 150                 155                 160

Val Ala Ala Ala Ala Ala Val Phe His Gln Gln His Gly Gly Gln
                165                 170                 175

Gln Ser Pro Gly Leu Ala Ala Leu Gln Ser Gly Gly Gly Gly Leu
                180                 185                 190

Glu Pro Tyr Ala Gly Pro Gln Asn Ser His Asp His Gly Phe Pro
                195                 200                 205

Asn His Gln Tyr Asn Ser Tyr Tyr Pro Asn Arg Ser Ala Tyr Pro Pro
                210                 215                 220

Pro Ala Pro Ala Tyr Ala Leu Ser Ser Pro Arg Gly Gly Thr Pro Gly
225                 230                 235                 240

Ser Gly Ala Ala Ala Ala Ala Gly Ser Lys Pro Pro Ser Ser Ser
                245                 250                 255

Ala Ser Ala Ser Ser Ser Ser Ser Phe Ala Gln Gln Arg Phe Gly
                260                 265                 270

Ala Met Gly Gly Gly Pro Ser Ala Ala Gly Gly Thr Pro Gln
                275                 280                 285

Pro Thr Ala Thr Pro Thr Leu Asn Gln Leu Leu Thr Ser Pro Ser Ser
                290                 295                 300
```

```
Ala Arg Gly Tyr Gln Gly Tyr Pro Gly Gly Asp Tyr Ser Gly Gly Pro
305                 310                 315                 320

Gln Asp Gly Gly Ala Gly Lys Gly Pro Ala Asp Met Ala Ser Gln Cys
            325                 330                 335

Trp Gly Ala Ala Ala Ala Ala Ala Ala Ala Ala Ala Ala Ser Gly Gly
            340                 345                 350

Ala Gln Gln Arg Ser His His Ala Pro Met Ser Pro Gly Ser Ser Gly
            355                 360                 365

Gly Gly Gly Gln Pro Leu Ala Arg Thr Pro Gln Pro Ser Ser Pro Met
370                 375                 380

Asp Gln Met Gly Lys Met Arg Pro Gln Pro Tyr Gly Gly Thr Asn Pro
385                 390                 395                 400

Tyr Ser Gln Gln Gln Gly Pro Pro Ser Gly Pro Gln Gln Gly His Gly
                405                 410                 415

Tyr Pro Gly Gln Pro Tyr Gly Ser Gln Thr Pro Gln Arg Tyr Pro Met
            420                 425                 430

Thr Met Gln Gly Arg Ala Gln Ser Ala Met Gly Gly Leu Ser Tyr Thr
            435                 440                 445

Gln Gln Ile Pro Pro Tyr Gly Gln Gly Pro Ser Gly Tyr Gly Gln
450                 455                 460

Gln Gly Gln Thr Pro Tyr Tyr Asn Gln Ser Pro His Pro Gln Gln
465                 470                 475                 480

Gln Gln Pro Pro Tyr Ser Gln Pro Pro Ser Gln Thr Pro His Ala
                485                 490                 495

Gln Pro Ser Tyr Gln Gln Pro Gln Ser Gln Pro Gln Leu Gln
            500                 505                 510

Ser Ser Gln Pro Pro Tyr Ser Gln Gln Pro Ser Gln Pro Pro His Gln
            515                 520                 525

Gln Ser Pro Ala Pro Tyr Pro Ser Gln Gln Ser Thr Thr Gln Gln His
530                 535                 540

Pro Gln Ser Gln Pro Pro Tyr Ser Gln Pro Gln Ala Gln Ser Pro Tyr
545                 550                 555                 560

Gln Gln Gln Gln Pro Gln Gln Pro Ala Pro Ser Thr Leu Ser Gln Gln
                565                 570                 575

Ala Ala Tyr Pro Gln Pro Gln Ser Gln Gln Ser Gln Thr Ala Tyr
            580                 585                 590

Ser Gln Gln Arg Phe Pro Pro Gln Glu Leu Ser Gln Asp Ser Phe
            595                 600                 605

Gly Ser Gln Ala Ser Ser Ala Pro Ser Met Thr Ser Ser Lys Gly Gly
610                 615                 620

Gln Glu Asp Met Asn Leu Ser Leu Gln Ser Arg Pro Ser Ser Leu Pro
625                 630                 635                 640

Asp Leu Ser Gly Ser Ile Asp Asp Leu Pro Met Gly Thr Glu Gly Ala
                645                 650                 655

Leu Ser Pro Gly Val Ser Thr Ser Gly Ile Ser Ser Ser Gln Gly Glu
            660                 665                 670

Gln Ser Asn Pro Ala Gln Ser Pro Phe Ser Pro His Thr Ser Pro His
            675                 680                 685

Leu Pro Gly Ile Arg Gly Pro Ser Pro Val Gly Ser Pro Ala
            690                 695                 700

Ser Val Ala Gln Ser Arg Ser Gly Pro Leu Ser Pro Ala Ala Val Pro
705                 710                 715                 720

Gly Asn Gln Met Pro Pro Arg Pro Pro Ser Gly Gln Ser Asp Ser Ile
```

```
                    725                 730                 735
Met His Pro Ser Met Asn Gln Ser Ser Ile Ala Gln Asp Arg Gly Tyr
                740                 745                 750
Met Gln Arg Asn Pro Gln Met Pro Gln Tyr Ser Ser Pro Gln Pro Gly
            755                 760                 765
Ser Ala Leu Ser Pro Arg Gln Pro Ser Gly Gly Gln Ile His Thr Gly
        770                 775                 780
Met Gly Ser Tyr Gln Gln Asn Ser Met Gly Ser Tyr Gly Pro Gln Gly
785                 790                 795                 800
Gly Gln Tyr Gly Pro Gln Gly Gly Tyr Pro Arg Gln Pro Asn Tyr Asn
                805                 810                 815
Ala Leu Pro Asn Ala Asn Tyr Pro Ser Ala Gly Met Ala Gly Gly Ile
                820                 825                 830
Asn Pro Met Gly Ala Gly Gly Gln Met His Gly Gln Pro Gly Ile Pro
                835                 840                 845
Pro Tyr Gly Thr Leu Pro Pro Gly Arg Met Ser His Ala Ser Met Gly
            850                 855                 860
Asn Arg Pro Tyr Gly Pro Asn Met Ala Asn Met Pro Pro Gln Val Gly
865                 870                 875                 880
Ser Gly Met Cys Pro Pro Gly Gly Met Asn Arg Lys Thr Gln Glu
                885                 890                 895
Thr Ala Val Ala Met His Val Ala Ala Asn Ser Ile Gln Asn Arg Pro
                900                 905                 910
Pro Gly Tyr Pro Asn Met Asn Gln Gly Gly Met Met Gly Thr Gly Pro
            915                 920                 925
Pro Tyr Gly Gln Gly Ile Asn Ser Met Ala Gly Met Ile Asn Pro Gln
        930                 935                 940
Gly Pro Pro Tyr Ser Met Gly Gly Thr Met Ala Asn Asn Ser Ala Gly
945                 950                 955                 960
Met Ala Ala Ser Pro Glu Met Met Gly Leu Gly Asp Val Lys Leu Thr
                965                 970                 975
Pro Ala Thr Lys Met Asn Asn Lys Ala Asp Gly Thr Pro Lys Thr Glu
            980                 985                 990
Ser Lys Ser Lys Lys Ser Ser Ser Thr Thr Thr Asn Glu Lys Ile
        995                 1000                1005
Thr Lys Leu Tyr Glu Leu Gly Gly Glu Pro Arg Lys Met Trp Val
    1010                1015                1020
Asp Arg Tyr Leu Ala Phe Thr Glu Glu Lys Ala Met Gly Met Thr Asn
1025                1030                1035                1040
Leu Pro Ala Val Gly Arg Lys Pro Leu Asp Leu Tyr Arg Leu Tyr Val
                1045                1050                1055
Ser Val Lys Glu Ile Gly Gly Leu Thr Gln Val Asn Lys Asn Lys Lys
            1060                1065                1070
Trp Arg Glu Leu Ala Thr Asn Leu Asn Val Gly Thr Ser Ser Ser Ala
        1075                1080                1085
Ala Ser Ser Leu Lys Lys Gln Tyr Ile Gln Cys Leu Tyr Ala Phe Glu
    1090                1095                1100
Cys Lys Ile Glu Arg Gly Glu Asp Pro Pro Asp Ile Phe Ala Ala
1105                1110                1115                1120
Ala Asp Ser Lys Lys Ser Gln Pro Lys Ile Gln Pro Pro Ser Pro Ala
                1125                1130                1135
Gly Ser Gly Ser Met Gln Gly Pro Gln Thr Pro Gln Ser Thr Ser Ser
            1140                1145                1150
```

-continued

Ser Met Ala Glu Gly Gly Asp Leu Lys Pro Pro Thr Pro Ala Ser Thr
            1155                1160                1165
Pro His Ser Gln Ile Pro Pro Leu Pro Gly Met Ser Arg Ser Asn Ser
        1170                1175                1180
Val Gly Ile Gln Asp Ala Phe Asn Asp Gly Ser Asp Ser Thr Phe Gln
1185                1190                1195                1200
Lys Arg Asn Ser Met Thr Pro Asn Pro Gly Tyr Gln Pro Ser Met Asn
            1205                1210                1215
Thr Ser Asp Met Met Gly Arg Met Ser Tyr Glu Pro Asn Lys Asp Pro
        1220                1225                1230
Tyr Gly Ser Met Arg Lys Ala Pro Gly Ser Asp Pro Phe Met Ser Ser
    1235                1240                1245
Gly Gln Gly Pro Asn Gly Gly Met Gly Asp Pro Tyr Ser Arg Ala Ala
        1250                1255                1260
Gly Pro Gly Leu Gly Asn Val Ala Met Gly Pro Arg Gln His Tyr Pro
1265                1270                1275                1280
Tyr Gly Gly Pro Tyr Asp Arg Val Arg Thr Glu Pro Gly Ile Gly Pro
            1285                1290                1295
Glu Gly Asn Met Ser Thr Gly Ala Pro Gln Pro Asn Leu Met Pro Ser
        1300                1305                1310
Asn Pro Asp Ser Gly Met Tyr Ser Pro Ser Arg Tyr Pro Pro Gln Gln
            1315                1320                1325
Gln Gln Gln Gln Gln Gln Arg His Asp Ser Tyr Gly Asn Gln Phe Ser
        1330                1335                1340
Thr Gln Gly Thr Pro Ser Gly Ser Pro Phe Pro Ser Gln Gln Thr Thr
1345                1350                1355                1360
Met Tyr Gln Gln Gln Gln Asn Tyr Lys Arg Pro Met Asp Gly Thr
            1365                1370                1375
Tyr Gly Pro Pro Ala Lys Arg His Glu Gly Glu Met Tyr Ser Val Pro
        1380                1385                1390
Tyr Ser Thr Gly Gln Gly Gln Pro Gln Gln Gln Gln Leu Pro Pro Ala
    1395                1400                1405
Gln Pro Gln Pro Ala Ser Gln Gln Ala Ala Gln Pro Ser Pro Gln
        1410                1415                1420
Gln Asp Val Tyr Asn Gln Tyr Gly Asn Ala Tyr Pro Ala Thr Ala Thr
1425                1430                1435                1440
Ala Ala Thr Glu Arg Arg Pro Ala Gly Gly Pro Gln Asn Gln Phe Pro
            1445                1450                1455
Phe Gln Phe Gly Arg Asp Arg Val Ser Ala Pro Pro Gly Thr Asn Ala
        1460                1465                1470
Gln Gln Asn Met Pro Pro Gln Met Met Gly Gly Pro Ile Gln Ala Ser
            1475                1480                1485
Ala Glu Val Ala Gln Gln Gly Thr Met Trp Gln Gly Arg Asn Asp Met
    1490                1495                1500
Thr Tyr Asn Tyr Ala Asn Arg Gln Ser Thr Gly Ser Ala Pro Gln Gly
1505                1510                1515                1520
Pro Ala Tyr His Gly Val Asn Arg Thr Asp Glu Met Leu His Thr Asp
            1525                1530                1535
Gln Arg Ala Asn His Glu Gly Ser Trp Pro Ser His Gly Thr Arg Gln
        1540                1545                1550
Pro Pro Tyr Gly Pro Ser Ala Pro Val Pro Met Thr Arg Pro Pro
    1555                1560                1565

```
Pro Ser Asn Tyr Gln Pro Pro Ser Met Gln Asn His Ile Pro Gln
    1570                1575                1580

Val Ser Ser Pro Ala Pro Leu Pro Arg Pro Met Glu Asn Arg Thr Ser
1585                1590                1595                1600

Pro Ser Lys Ser Pro Phe Leu His Ser Gly Met Lys Met Gln Lys Ala
                1605                1610                1615

Gly Pro Pro Val Pro Ala Ser His Ile Ala Pro Ala Pro Val Gln Pro
            1620                1625                1630

Pro Met Ile Arg Arg Asp Ile Thr Phe Pro Pro Gly Ser Val Glu Ala
        1635                1640                1645

Thr Gln Pro Val Leu Lys Gln Arg Arg Arg Leu Thr Met Lys Asp Ile
    1650                1655                1660

Gly Thr Pro Glu Ala Trp Arg Val Met Met Ser Leu Lys Ser Gly Leu
1665                1670                1675                1680

Leu Ala Glu Ser Thr Trp Ala Leu Asp Thr Ile Asn Ile Leu Leu Tyr
                1685                1690                1695

Asp Asp Asn Ser Ile Met Thr Phe Asn Leu Ser Gln Leu Pro Gly Leu
            1700                1705                1710

Leu Glu Leu Leu Val Glu Tyr Phe Arg Arg Cys Leu Ile Glu Ile Phe
        1715                1720                1725

Gly Ile Leu Lys Glu Tyr Glu Val Gly Asp Pro Gly Gln Arg Thr Leu
    1730                1735                1740

Leu Asp Pro Gly Arg Phe Ser Lys Val Ser Ser Pro Ala Pro Met Glu
1745                1750                1755                1760

Gly Gly Glu Glu Glu Glu Leu Leu Gly Pro Lys Leu Glu Glu Glu
                1765                1770                1775

Glu Glu Glu Glu Val Val Glu Asn Asp Glu Glu Ile Ala Phe Ser Gly
            1780                1785                1790

Lys Asp Lys Pro Ala Ser Glu Asn Ser Glu Glu Lys Leu Ile Ser Lys
        1795                1800                1805

Phe Asp Lys Leu Pro Val Lys Ile Val Gln Lys Asn Asp Pro Phe Val
    1810                1815                1820

Val Asp Cys Ser Asp Lys Leu Gly Arg Val Gln Glu Phe Asp Ser Gly
1825                1830                1835                1840

Leu Leu His Trp Arg Ile Gly Gly Gly Asp Thr Thr Glu His Ile Gln
                1845                1850                1855

Thr His Phe Glu Ser Lys Thr Glu Leu Leu Pro Ser Arg Pro His Ala
            1860                1865                1870

Pro Cys Pro Pro Ala Pro Arg Lys His Val Thr Thr Ala Glu Gly Thr
        1875                1880                1885

Pro Gly Thr Thr Asp Gln Glu Gly Pro Pro Asp Gly Pro Pro Glu
    1890                1895                1900

Lys Arg Ile Thr Ala Thr Met Asp Asp Met Leu Ser Thr Arg Ser Ser
1905                1910                1915                1920

Thr Leu Thr Glu Asp Gly Ala Lys Ser Ser Glu Ala Ile Lys Glu Ser
                1925                1930                1935

Ser Lys Phe Pro Phe Gly Ile Ser Pro Ala Gln Ser His Arg Asn Ile
            1940                1945                1950

Lys Ile Leu Glu Asp Glu Pro His Ser Lys Asp Glu Thr Pro Leu Cys
        1955                1960                1965

Thr Leu Leu Asp Trp Gln Asp Ser Leu Ala Lys Arg Cys Val Cys Val
    1970                1975                1980

Ser Asn Thr Ile Arg Ser Leu Ser Phe Val Pro Gly Asn Asp Phe Glu
```

Met Ser Lys His Pro Gly Leu Leu Ile Leu Gly Lys Leu Ile Leu
1985                1990                1995                2000
                                2005                2010                2015

Leu His His Lys His Pro Glu Arg Lys Gln Ala Pro Leu Thr Tyr Glu
                2020                2025                2030

Lys Glu Glu Glu Gln Asp Gln Gly Val Ser Cys Asn Lys Val Glu Trp
                2035                2040                2045

Trp Trp Asp Cys Leu Glu Met Leu Arg Glu Asn Thr Leu Val Thr Leu
                2050                2055                2060

Ala Asn Ile Ser Gly Gln Leu Asp Leu Ser Pro Tyr Pro Glu Ser Ile
2065                2070                2075                2080

Cys Leu Pro Val Leu Asp Gly Leu Leu His Trp Ala Val Cys Pro Ser
                2085                2090                2095

Ala Glu Ala Gln Asp Pro Phe Ser Thr Leu Gly Pro Asn Ala Val Leu
                2100                2105                2110

Ser Pro Gln Arg Leu Val Leu Glu Thr Leu Ser Lys Leu Ser Ile Gln
                2115                2120                2125

Asp Asn Asn Val Asp Leu Ile Leu Ala Thr Pro Pro Phe Ser Arg Leu
                2130                2135                2140

Glu Lys Leu Tyr Ser Thr Met Val Arg Phe Leu Ser Asp Arg Lys Asn
2145                2150                2155                2160

Pro Val Cys Arg Glu Met Ala Val Val Leu Leu Ala Asn Leu Ala Gln
                2165                2170                2175

Gly Asp Ser Leu Ala Ala Arg Ala Ile Ala Val Gln Lys Gly Ser Ile
                2180                2185                2190

Gly Asn Leu Leu Gly Phe Leu Glu Asp Ser Leu Ala Ala Thr Gln Phe
                2195                2200                2205

Gln Gln Ser Gln Ala Ser Leu Leu His Met Gln Asn Pro Pro Phe Glu
                2210                2215                2220

Pro Thr Ser Val Asp Met Met Arg Arg Ala Ala Arg Ala Leu Leu Ala
2225                2230                2235                2240

Leu Ala Lys Val Asp Glu Asn His Ser Glu Phe Thr Leu Tyr Glu Ser
                2245                2250                2255

Arg Leu Leu Asp Ile Ser Val Ser Pro Leu Met Asn Ser Leu Val Ser
                2260                2265                2270

Gln Val Ile Cys Asp Val Leu Phe Leu Ile Gly Gln Ser
                2275                2280                2285

<210> SEQ ID NO 4
<211> LENGTH: 35885
<212> TYPE: DNA
<213> ORGANISM: Homo sapiens

<400> SEQUENCE: 4
atggcggcgg ccgacggcga cgactcgctg tacccccatcg cggtgctcat agacgaactc      60
cgcaatgagg acgttcaggt ccggaggcta cgggggactt gggaagacg cggagggta      120 cctgggggca cgggcggccc tcgcggagaa gactcagcgt tcgctgggag tggcggaagg      180
gggcgacggc caatcagcgt gcgtctctta tctccccggt tgcccggact ccttgagacg      240
gcgctcccga ttgggtgtcg gcccagtgga gggcgggggc cagcgctagc ctcgagggtc      300
ccgggcctgc cctgtgcgcg cggcggtccg cggtcctggg aggttgtggc cagggctggg      360
gtctgcggac tgggtctggg agagaggagg actccgtgat tggcggcggc ctctgaatgg      420
cctcttgggg atgtggggcg cgcatgactt gctccaagta ggggagggcc gccgggtggg      480

```
tcgggacctg ggaaggtttt tttgttttct gggtttcgac tgctgggcca agtggggacc      540
gagaggcgaa ggcctgccat cctaattcct gctcttcctc cgcctctcat tttggtttag      600
gtgtcctaag aggacgggga cgcaaaaaca ccccccacc aaaggtgggg actagccaag       660
tttaggagcg aattaggttg tagaaacccg cctccccatc tccccggatc ctcccattga      720
ccaggatagg ggttgaggga tttgctaagc agatgaacat ttatttattt ctttttttg      780 agacagtctc tgtgtcgccc aggctgggc tggggagcag tggcgcgatc tcggctcagt      840
gcaacctctg cataccgggt tcaaaccatc ctcgcccctc agctccctaa ttagctgcga      900
ttaccggcgc gagccaccac gcccgactaa tttttgtatt tttagcagag acggggtttc      960
accatgttgg ccaggcttgg tcgggaactc ttgacctcaa gcgatccacc cgcctcggcc     1020
tcccaaagtg ttggaattac aggcgtgagc caccgcgccc agcccggatg aacattcctg     1080
gttatgggat gaggtgaccc aaggctctga gccgggctgg tgtgggattg agaacagtta     1140
gaactgcaag tccacctccc acctgctgtg tgaccttgtg caaattactt caccgctttg     1200
ggtctctgtg ttccataaaa tatgggctaa ttgtagtcct ggtcttgctg gagggacttg     1260
tgagggactg aacgaattat gacacaaata aaagtagaa tggtgtcagg cctgttgtaa      1320
gggctcgata atattagct gtaattattg ggagtggtga ttaaagaggt cccatcctcc      1380
ctttaggtct gttttcccat ttataaaatt ggacaaggtg cactgggtaa cctgccaaac     1440
gtgggtctcg cctcctaggt tcctggtata tcactgtttc tggtggcata caggttgtgg     1500
ttgtattccc ggcccttcca cttgttactg attgacaagg gcaagttagt taatctctct     1560
aggcctgttt cctcttctct ttaatggggt taattaccta gttcataggg cggttgtatg     1620
aattcttttg ttcagtaaat atatgccatg tatgagatat gatgctgggg atatagtgga     1680
gacaccagtt gctatacagg atccagatgt gaaacaggtc agcagagctg aatagatgag     1740
tgtttgaaaa gtgatgggaa ggaaacaaat aggatgtagt ggtagcgaat ccatattgaa      1800
ttgggcctct attctgtgca gggcgctgtt ctaagcactg gtatatagca ggaacaagac     1860
agaaaaaact ctaggccttg gggagtttat tttgtagtga ggagagacag acaataaaca     1920
gagtatactg gggataagca ttaggagac aaataaaaat aagagagatg gggtatatat      1980
agggcatgca gttttaaagt gtggtcaggg gaggccttgt tgagatcctg tttgagaaca     2040
cgcctgaaag cagagggcac agcaagtaca agtgggggtg gggcagatcc attttaagaa     2100
ggccaatcag gcaaggcccc tctgaggatg cagagtttga aagagattg aaagaaggtg      2160 ggggagagcc tcccaggaag agggaacaga tatgtaatgg ccttttttt tttttcttct     2220 ttttttgaga cggagtcttg ttgctctgtt cccaggctg gagtgcactg acgcgatctt      2280
tgctcactgc aacctccacc tcccgggttc aagcaattct cctgcctcag cctcttgagt     2340
agctgggact acagacgcag gccaccacgc ctggctgatt tttgtgtgtg tgttttaga     2400 agagactggg tttccggtg ttggccaggc tggtctcaga ctcctgatct caggtgatcc      2460
tcctgcctcg gcctccgaaa gtgctggaat tacaggcgtg agccactatg cccggccagt     2520
tttttgtttt tttttaactcc aggatcactt ccttcagcta tctatcctcc catctttca     2580 ttcatccatc catccactaa ccagcagaca tttgtaggga gatgtctttg tgccaggatc     2640
agagctaggc agcttaccgg tttattctaa agaatattgc aaaggataca gatgaagaca     2700
catgcagggt gaggtgtggg ggaagttgtg tggagcttcc atgccctccc taggcattcc     2760
accccccagg aaccgcgagg tgttcatctg tctggaagct cctatggctg cttttgtgct     2820
```

```
acagcccaga gttgcatggt tgtaacagag atggccgcaa agcttcaaat atttgctgtc    2880 taacccttg  cagggaaaaa attgctgacc tctgacttaa accatctgcg taacaaatta    2940
ttgggtgctt gctctatgtt aggtacagta cagaggaata tcactgacga tcttactgaa    3000
ttctcacaat cactctttga agtaggtcct gtccttgtcc acattttcca gatgaggaaa    3060
ctgaagcacc ataaataaca tggccaaagc tgtgcagctg agaaatgaag gagccaggaa    3120
aggaagtagg acctaagggt ggaatagaat ctggggtggg acacacggtt gctgattata    3180
ttcatatgcc agacattta  attgtgtctg agacagttca ggatactaga aggaacatgg    3240
gacatgaaat cctgtagtct tgatttattt gttcagcaaa tatttatcag cacctcctgt    3300
gtgccagact ctgttttaga tactagacat acagtaggga acaaacagc  aaagctgccc    3360 ttgtggggtt tacattctgg tttgggagac agatagtaga tctgtagtgg gatgtcagtg    3420
gcagtaattg ctaagaagaa aaattgctgg acgtggtggc tcaagcctaa ttgtaacact    3480
ttggttttat tttattttat ttttttgag  acagagtctc actctgtcgt ccaggccgtc    3540
tctgctcatt gcaacctccg cctcccgggt tcaagtgatt ctcctgcctc agcctcctga    3600
gtggctagga ttagaggcgc ccaccaccac atccagctaa ttttgtatt  tttagtagag    3660 agtgggtttc accatgttgg ccaggctggt ctcaaactcc ctgcccgcct ctgcctccca    3720
aagtgctggg attacaggca tgagccacca cccctggcca attctagcac tttggaaggc    3780
caaggtgaaa ggatcgcttg agcccaggag tttaagacca gctgggcaa  caaagtgaga    3840 ccctgtctct accaaaaaaa aaaaaaaat  tagctggtgt gatgacacag gccttggtcc    3900
cagctgctca ggagactgag gtcggaggat tgcttgaacc agggagatcg aggctgcggt    3960
gagagcctgg gcgacagcaa gaccctgtct ccaaaaaaaa aaaaaaaaa  aaaaagaac     4020 aaaataagac aggtacaggg aatagagcaa gcacctgggg ctgctttgtt agatagggag    4080
gttagagaaa gctgctctga ggaagtgatg ttgaacaagg atttgaatga aatgaacagg    4140
tcgtggaaga gcagtctggg cagagggaat agttggtaca aaggccagga gtgggaggat    4200
gcttgatgcg ttcaaagcac agcaaaaagg ccagtgtgac tgaggcagag agaatggcaa    4260
agtggtggga ggtgaggact agaccaggac tagatcaagt gaggcctgtg ggccaaggtg    4320
aaggccttga agatgggagg gaggaggagg aattgcaagg ctttcagtag taattatggg    4380
ttctggtata attttaaagg atccttcctc tggctgtcat aggggttggg ccctgttgag    4440
gtgccattac aaagcaccca ggaccagtgt tagcatgcag gggggaagta tggttacagt    4500
caggacatgt tgagggggc  tgatgggatt tgctggtggg taatgtagag ggaagagttg    4560
agggtgactg aagtttgaac ccccgctctg ccagttgtgc tctctgtgtg ccctggagc     4620 agtacttcc  cctctttgga cccagattcc tcatctgcaa aatggggata atgatgaaga    4680
atcagcgtgt gcctggttgt gaagatgcag tgaaattggc ttgctcattg ttctgcggta    4740
gtcatatggt ggggattgag cagacctgag gaaatggggc atctggggaa ccgtgtggga    4800
ccaagtcagc aagtgctaaa gcctggttg  ggaatacact gggctgtttg tttttttggt    4860
tactatcaag gaagcagttg tgacaagcca ggcccagtga aatggatca  gtagactagg    4920 gtcagattgt gttgggccctt gtaggccaga gtaaggcctt agcttttatt ctgaatgtgc    4980
agggaaaaca tactacatgt gggattatac catatacatt catattatgg aaggctccat    5040
gggttgaatg cagggtggat cttcaaaagt gggtcccctt tccacaggtg catatagtgg    5100
gaaggcggat tttattttatt aactcaccac agagcaggct ctgtgccgag gcctgctggg    5160
acacagagag tcccagtcta gggtggtaag tgctgtcatg gaaccatatg ggtggactct    5220
```

```
ttggaaaatc ccaattccta ttctctcact taacacaaca atcaacaaca cagaagaaga      5280
cttccgtgac taaatgtgtg ttggggtggg gagggattct tcaccaccac taagcaagca      5340
ttcagttctg cagcacacgc caactggatg tcctccaatt cagttcagac acgacctgga      5400
gacagtgttg gatccaacag gttgagggct caggcctcaa aactgccct tggccctcgc       5460 cttcagttgc cattctgggt cgtcagaact tctgatctac ctgcttcaag ttggagttcc      5520
catgaccacc ctgcctttgg gtttgattaa tatgctagag cagctctcag aactcaggga     5580
aacatgtaag tttatcagtt cattataaag gatagtataa agaatacaga tgaagagagg     5640
cataggtgga gctatggggg aagggtgtg gagcttccat gcccttcttg ggtgcaccac       5700
cctccaggaa cctctgtgtg ttcggctatg ttgaagttcc caggccctgt ccttttgggt     5760
ttttataaag gcattgttag gtaggcagga ttgattaaac ctggtgatca ccttgacctt     5820
cagcccctct ccgatccctg gaggttgtgg ggtgggactg aaaatcccaa ccctctaatc     5880
atgcctctct gttttccatg actatctttc cagtgaccat ggaccccatc ctgaaggtat     5940
cagtcaacat tagcatacaa aaagcgcctt ggagattcca aagatttgag gagttgtatg     6000
caaggaaatg gggatgaagc ccaaatctgt atctcacagt atcacaactg tagcaggtgc     6060
ttggtgggga cacacttggg agatagtcag tgcacaggga attctcagga tatgacatga     6120
tcaatggcca gtcaaggttt ctgaaatgat attaatagat tttctatcag gaatgtgacg     6180
gagaccccaa cctagagttg tttaaacaag taagagttct ctttatttct catatagcaa     6240
gttcagcagc tcaaagctat cacagaattg ggtcagctca aagatatcac agaaatgcgg     6300
tttttttgac tggcctgttt tggttataag attccagcag catctgctgt cctagtggaa     6360
ctgcactttt tagtgcagtt tagcagaggc cagcttagga cacagaggtt ctttcccctcc    6420 tccctttttat gaaggaggaa aatctctcct gaatctcctc agcagacttg cttgtatatc    6480
tctttgccaa gaactaggtc atatgcagag ttagttgaag ttaagtttgg ctgtaagtag     6540
tagaaaaact ctaaataaca ggggcttaaa tgagcttgaa gtttctatct gactgatgac     6600
caaaatgtct ggtggcaatc caggctgctg tggcacttca tggtgtcagg gtcccaggct    6660
cttaccatta tgcgctggtt gtatcctcca ttctaccctc cgtgtccccc aggttacctc    6720
aggtccccaa gttggctgcc gaagcccaa ccattatagc tccattccag acaggaagga     6780
gggaagataa gtgtgacccc catccctata agttgcacaa acatttcca cttggatttt      6840 attggccaga tgttagtttt atagtcacat tcagatgcaa aggcaattca gaaatgtctt    6900
ttccaggggt catgtgtaca gctgaaaacc aaggattatg aacagcagta tagccccatg     6960
caggagctcc taacttgggg atcatctgca attcccaggc aggtccatga atttggatgg    7020
caaaaataac atctttattt tcattaacct ttaacttaca tttaacttcc cttctgttat     7080
agattataat atcactatag tatatcatag gtagcgttag caaaacctgt gacttaccag    7140
tggaaatcag gagttgtgtt cacatgtcat ttctgctatt atacatatct tctagtgttg     7200
tttatgttca cctctttcaa aattgcgttc attattagac ctgctaaggg gattcatggc     7260
accaccccac ccctctacaa gagaaaaacc aaaaaaagcc gggtgcagtg gctcatgcct    7320
ataatcctag cattttggga ggtcgaggtg ggaggattgc ttgagctcag gagtttgagg    7380
gcagcttggg caacatagtg aggcctcatc cctacaaaaa gttaaaaaac tagctgggct    7440
tggtgacacc tgcctgtaga cccgtctact tgggtagctg aggcgggaga atcacttgag    7500
cccgggaggt caaggctaca gtgagctacg attgtgccac tgcactccag cctgggtaac    7560
```

| | |
|---|---|
| agagtgagac cctgcctcaa acaacaaca agcacaacaa aaaagaaaaa acagagcaaa | 7620 |
| tatgaatcca tagtactggt taagaacctg gtggctggga ttcaaatcct ggctttacta | 7680 |
| ccagtaagct gtatgcagtt aagctccctg tgcctttgtg ttctctgcct caagacgggg | 7740 |
| gattctgtat ttccctcatg ggattgtgag ggtcaaatga attaaaacat taaagcctgg | 7800 |
| ggcatagtag agactaagga aatatttact gttattattc tgtcatggtg aaaaaggga | 7860 |
| aaagaaacat cagtggacca gctgccacga tgtccttctt aataatctga acaaaatcag | 7920 |
| gatgctgtca gtgaggcgtg gttgccacgg ctgccattat taatcttccc ctggtgctag | 7980 |
| ggtgtccctg tagaatgtca ttttgtactc aagacaaccc tctgagggta ggtattctca | 8040 |
| tcatccccac ttcacagatg agaaaattga ggctcagaaa ggtacaagga ttgcccaaga | 8100 |
| ttccacagct aatatgtaag cagtttagcc ttgaacctgg acagtgcagc tctgtagtac | 8160 |
| caccctaggc catctttctc aagcattgat gatgctgtct gcctgaagaa acacttttaa | 8220 |
| tgaaaccaaa agcagaatcc caagaacag cagtggaagg aagggagctc tctggatggg | 8280 |
| aaagcagcct gattgtcatg gcccacctc ttgggcatcc ccagcttcaa gttgggttc | 8340 |
| ccacgacccc ctctttgggt ttgattaatt tgctggagcg gctcacagaa ctccaggaaa | 8400 |
| cacttaggtt taccggttta ttataaagga tattccaaag gatacagatg aagaggtgca | 8460 |
| tagggtgagc tatggaggaa ggggcgggga gctttcgtgc catccctggg gatgccaccc | 8520 |
| tccaagaatg tgcatgttct gctatcagga agctctctga atcctttcct ctttggtttt | 8580 |
| tatggaagct tcatgataca aacattttg cctaaatgac agtatgatat tgaaattgag | 8640 |
| tcaggctgcc tggcttcatt gctttccagt aagtgacagc ctcacctctg tgcatcagtg | 8700 |
| tcctcactcg cctctgtgca tcagtgaagt ggggacgctg ctaacaatac atacctcaga | 8760 |
| gcagttatga ggattcagtg tgttaatcat ccatgtcaat cacttggatt gctgccaagc | 8820 |
| acgtagcaaa caataaatgt ttgttgctat tgttctggca tttatgatta tgattattaa | 8880 |
| ttgtaattat tccctgtacc atctcattgt cctcagggct gttgctcacc tagtatggcc | 8940 |
| ctagcccatg tgtatatttc cccatagctc aggctgagag aagaacacac agatcaactt | 9000 |
| ggagaaaaca aagaggaaag aaataggcaa ctaggtcaat actccccaca gtattttatg | 9060 |
| ttattttatt ttatttattt atttatttga cacagagtct cactctgtca cccaggctgg | 9120 |
| agtgcagtgg caccatctcg gctcactgca agctccacct cccaggttca cgccattctc | 9180 |
| ctgcctcagc ctcccgagta gctgggacta taggcgcccg ccaccacgcc cggctaattt | 9240 |
| cttttttgtat ttatggtaga dacggggttt caccgtgtta gccaggatgg tctcgatctc | 9300 |
| ctaacctcat gatccgcctg cctcggcctc ccaaggtgct gggattacag gcatgagcca | 9360 |
| ctgcgcctgg cctccccaca gtattttatt atgaaagttt tcagacatgc ataactttgg | 9420 |
| aagactaaca caagggtcag cagactacag tccatgggtc caattcagcc cactgtctgc | 9480 |
| ttttgcaagt aaagttattg gaacacagct atgcctgttt gcttctctag ttctggttct | 9540 |
| atggttgttt tcagtgccac gcaagcagag ttcagtagtt aggtttgcaa agctgaaaat | 9600 |
| aattactgtc tggcaatgta tagaataagt tttgctgact tctagcatag tgcagtgagc | 9660 |
| acctctatac ttcaccccca ggtcagtgat tgttagtgtt tgctatatta gttttttatc | 9720 |
| tttctatagg tctgtctcta tatacgtttt attttttagc tgaaaatcag ttgcaggttt | 9780 |
| tgtagtactt tatcctgagg tccgtttaat gccagaatgg tgagttttg gactacctgt | 9840 |
| atgaaagatt tactgtgtgc attttctga ggagagacca tcacaacact tcatcagatg | 9900 |
| ctcatcgtct gtgatcgcag agatattctt caactcctgg accggagaac ccaactcacg | 9960 |

```
caagatctta gtcacttgta gacctcgtct cagttatgta gggcctcaga acagaacagg   10020
ctaagggagc tcctgctcct caacctcgcc ctgtccctac ctgttctgcc tctatccagg   10080
aagaaaggtc ccccgtggga ccattagtca ctctccccct catgaaagca tttcctccca   10140
ctctcacact catgagctca ttccattctt gtgacagtgc tgggagctat taataatagg   10200
agaggcctcg tggtgatgaa gaaatgaggg gagagtttca cagtctgtcc tgccatcaga   10260
gcagctggct ttggatccca cactccctcg gtgcttgctt tggtaggtgt ctttacctct   10320
ctgatcgtca ctttccaaag tggtgaaaag aggatattag ccatgctttt cttttaggat   10380
ctggaggatc aaatgaggtc ccaacatgta aatgcttgtt gtgagatcta ttatgtgtgt   10440
tagccaaata taatagttct ctaggactgc cacagcaaat caccatgaac tgggtagctt   10500
aacacaacga atttattctc tcacagttct ggaggccgga agtctgaaat caaggtctcg   10560
gcagggttgg ttccttttgg aggctctgag ggagacccat tccatgcctc tctggaagtt   10620
aggacttctg gtggctccag caattccttg tgttcctggg cttgtggatg catctcctgg   10680
tctctccacc catcttcaca tgcgtgcctt ccctctgta tctgtcttcc tttctgtctc    10740
ttagaaggac actgtcactg gattcaaggc taaccctccg tttaggatga tattatctgg   10800
acacacttaa ctacgtctgc aaagactgtt ttgacgtgca cgtcactgga ttcaaggcta   10860
accctccgtt tagggtgata ttatctggac acttaact acgtctgcaa agactgtttt    10920
gatgtgcacg tcactggatt caaggctaac cctccgttta ggatgatatt atctggacac   10980
acttaactac gtctgcaaag accgttttga cgtgcacgtc actggattca aggctaaccc   11040
tccgtttagg atgatattat ctggacacac ttaactacgc ctgcaaagac tgttttgacg   11100
tgcacgtcac tgggacataa cttttttgagg ctgctattca gcctcctgta ctggtggtat   11160
tattactact gctaatgcta ctcttgtttt tgtagtcatt ttattacaat aattttttt    11220 tctctttgag acaaagagtc tcactctgtt gcccaggctg gagtgttgtt tgttctttta   11280
caatcactta gccagcaatc ctggctttaa atcctgctcc atgtgatctt agctgtctga   11340
ccctgagagg ggcttttgtt ccccgagcct gtttccctgt ctgtaaaatg ggactccagc   11400
tagtgacatg ggtgcaggtg tgtggatgtg tttagccgag gaccgggcac agaggaagcg   11460
tgttataaac gtggctgctg ctgttaaagt acagtgcatt ggcatgttac atgatactgt   11520
gtataggaga aagtgatgaa gagagaggag gagagggagt acagttttca acagagtggt   11580
cctggaaagt gcaactgagt aggtgtcacc ttcataagac ccaagggatg cttttgcatt   11640
tgttgctgct gccactacta ttgttgttat ttaatgattc cctcgaggtc acagggtctc   11700
ttggtgggtg tttgccaaat tactcttgag catcttcaca tgtaaccaag caaggcttcc   11760
aggggctgac tgggttgaga gctgtcagaa ctcacgcgtg tctgggattt ctaacattct   11820
cccctcctct tcttgttctc tcattagctt cgcctcaaca gcatcaagaa gctgtccacc   11880
atcgccttgg cccttggggt tgaaaggacc cgaagtgagc ttctgccttt ccttacaggt   11940
aacaaagggg accctggg ccagatgtg gggactcttg ggaggtggtt ttcactatat      12000
aagagaagac ttgtggattt aacatattgt ttgtgaatat ctgccctgtg ttagacacta   12060
tggagtggga aaagggattc agagaagtgc agtcttgctc taaaagaatg gtctggaatg   12120
atggagacag atggtgaaag ggatctagaa gcaggtagaa cgaggtttga gttgcagctc   12180
caacagttgg aagctggtga ctttagacaa gttagtttac ctgtttctta tattttcat    12240 ctgtagattg ggataatcat ccatgtgcca aagtgttgat ctgagcattc aatgttaata   12300
```

```
acaattgcta atacttatga tatgcttact gtatgccagg tggtgttcta caccgtatct   12360
tgtgaggatt gagttcatat aaagtgttta gaaagctgcc tgtactcagt aaacatacat   12420
cactatcatt tcacccagtt gatctcacag cagtgcttta agcaggtaat actgctgtcc   12480
ccatgttata gatgaagaaa ccaaggtgta gagaggtgaa gtgattcatt tgcccaaggt   12540
catgcagtga ggaggtaact gagaagggat atttatctag tcattctggc ctttaacttg   12600
acagcattgg ttaatgactg atttcaaatc tgagctctac cactttctag gtgtgtgact   12660
ttgggcaaga tattttacat ctgcctgctt cagattcttc acaggtgaaa tgggcataat   12720
tatgtaacct aacatgaaga ctaaataaga tactgtaaag tgcttataac actgtatagt   12780
acgtgccgcc taagcgatag ctgccaggct gttactaagc actgctgttt gtgaggatgt   12840
aggtaaagca tttaatacac tgtctgacac agactggacc acaattaata gtaaattctc   12900
tgttatcatt attcccatta ctacttcata ttttatactt attaccagct gaaatcacag   12960
ctgaaggttc agagtgcttt gtcactaaac tcttgtgtat gggaacatct tacttggacc   13020
tagtgatgat cctggggagg aaggagcttg agattgttac ccctccccac actgacagag   13080
tggggtattg gagcctaaag aggtgcagtg actcgcctac agtggcacag ctagtgactg   13140
aggggtgcag gtgtgtctga ctggatggtg catgaagagt aggtgtctgc tcgtatgaca   13200
ctgaacaaat ggccccaaac caggtggctt ctattggtga actgttgggg agacttgaaa   13260
gctttagaat gctgaagcat ggcaggataa taaagtggtg aagaagttgt agaggaaaaa   13320
tgttggacct gggtttgcaa taagcagctc tgccactgac ttgctaggaa aacctgagta   13380
ggtcactcca cctctcttag cctcatttcc cttgtctgta aaggagtcta ataagaggag   13440
tacctaacac tcggggtgtg tagggaaaac tctgtgactt tcctctactt tcacaccaca   13500
gcaatcataa cacagaacat gacttctgtg accatatgtc tgggtttttt tccccaaact   13560
aagcagtgga cagcagctgg ttgtcctcta attcagttct gacacgtctg cccagagaca   13620
ggttcagatc ccacagattg atagctcagt ccccaggact gtccccagcc ctgaccacca   13680
gtcgctggtc ctgtggaact tctgattgat cagcttcaag ttgggattcc cacgaccccc   13740
tctttgggtt tgattaggct catagaactc agggaaacac ttatgtttac tggtttatta   13800
taaaggattt tgcaaaggat acagatgaag agatacagag aatgaggtgt gggggaaagg   13860
gcctggagct tccgtgccct ccctgagccc accaccctca agaacctcta tgtgtttcac   13920
catctggaag ctctctgaac cctctgggtt tttatggaag cttaatggca gagggtcctg   13980
agtggaacgg aggcaccagc catgtggaac tctgtgggaa gagcatttca ggctgtgggg   14040
agaggcagat gtaagctcag tgtgttggaa gaatagcagt gaggtagcca tgggttgagc   14100
aagattgtta agggagagtg agactaggac atgaggttgg agaagaacag tgaccacagt   14160
atgtgagatc aggtttcttt gaaactattg gcagattgaa atgaaagagt gtcgggattt   14220
cttttacacc tgaaagagtc actctggggt ctgggagatc agatggtgta ggggcaaagg   14280
tggaagcagg aaaaccaggt aagaagctgt tgcagtctcc caggcgacag ctagtgatga   14340
tcagagtgac cttagtttgg gagggttgac aggcttggct cagaaggagc tgccaaccct   14400
tccaagaagg atagttctct gtggattggt ggaaagacaa ggtgctggca gttcccaggt   14460
gtttggcctt cagcagcatt gcttggctat aaggtctaga ctggagataa agatgaataa   14520
gaattgagtc cgtggatacg cataaggtct tcaggagaca aagaaaacag ggagggtggt   14580
tttaactgtg tgcagaggga gccagggaaa ctgaggctgg gaacgagcct aagaacagtg   14640
tagctggagt cacattggcg agaatttatt tattgaagga agaggcagag atactaaccc   14700
```

```
tcctactggg ccctgtgctg agctcttcaa tgaaagcatt tatttccctt tagtctccga   14760
acaaccctat gaagtgagaa cagccctgtg gtgatttagg ggatgacaaa ggctcagaga   14820
gatgaagtga gctgctgtat aagcagccaa cagtaaagca agatttgaac ctaccataaa   14880
atggagatga tgataatgac tccttaaatg agagggttgt ggtaaggagg tgatgcaaa    14940 gttgaaccca ccacttacac tcacacccct ttggccagag caaggttacg tggccttgcc   15000
aactgcaagg gcgtctggga aatgcagtcg gctgctggat tgccatacac ccaacttaaa   15060
tgcaggaggt ttaagtgcca atagatgcca gggatattag cagcttgtgc tgtgcagaga   15120
tcagcagttc ccactgcctc agggatgaga ggatggagct taagagagag gcctttggat   15180
gtgggcatta gggacagaac ggattttccc ttcacatatt cattctttca gcaaacctga   15240
attgctgtct gtctgtgctc agctctggca ggaactgggg cacagagagg agccagtcct   15300
gggctcgctg attatagcct atgttaagga tgtggtaaag gtggcatgga aggagagaga   15360
gactgagccc agagaaggtg tagcggacat cctagaaatc ttccaagaag gggcggctaa   15420
actgaatctc caaggataaa aataaatttc tggcagaggg aacagtgctg aggggagaag   15480
ctggacccca aaaaagctct cgttgaccat gctctgcgct ttatacacct agtcatattt   15540
gctcctcact gtaaccgttg ctacgaggga gggatggtga acaccatttt acagacgcag   15600
aagctgggac tcagagaggt ggaatcactc agtcagtatt tcacacccgc tagagggcag   15660
aagcaggact tagggctctc ttatcccagc caagcctgta ccttaatatc tgtggcagcc   15720
caggtggaga gtgggggagc aagtgggcgg atggaagaac tgagtgctga cagcctgagg   15780
aagcagaatg gagtccatgt gttctgagct tgggctgggg tcagagttga gatgggatag   15840
tcacgaagtc tgtcttggtt ccacagatac catctatgat gaagatgagg tcctcctggc   15900
cctggcagaa cagctgggaa ccttcactac cctggtggga ggcccagagt acgtgcactg   15960
cctgctggtg agtggaaggc aggaagtcct cttgcccacc ccttagggtc ggcccatggt   16020
cctgccggcc tagggcaggg aggggagcgt gtcagagagc gtggggatca cgtcagaaca   16080
gccgggccat ggacatccgc tttaatccaa caagtcagga gtggctttta atatcgtgaa   16140
ctcagggtgc agttatcatc cttcctgttt agtggtcagg taggtgccca gtgccaggcc   16200
ttacctggga ttctacatag ggctgtgggt ttagagtcag gttgggttct actgcttatt   16260
tgctgtgtga cttgtaagag aattacttac cctctctgtg ctgtaccttt ctcatctgca   16320
caatggggtt atgaaaacct ttttaaatta ccttgaagag ccctagcaca gtacttggca   16380
cttagtaggt actaaccgat gttaactgca attgtcatta ttgttgctgt gacatcatat   16440
ccagcctttg gggtaggagg gattccctgt ttatgggtga gccacctgga gcactgagag   16500
gttaagcgtc tcttcagatt gtatgactag tagatggcag agctgggatt cttggtctgt   16560
ccatttgact gtctgccagg tccccacccc actgcctgcc tgtgtgtccc gtgctaggtg   16620
atggccaagg acacaaagat gggccagatc ccaacaagca gcgttgtttg agagaagatg   16680
atctgggaag gcagaccgta caggttacct agtcccctgg ttttcactgt tctcagagtg   16740
ctgggccact gctgctgcct ctgcctctgc cccactcccc cagtgattgt gtatttcact   16800
gtcgctagag atacaatgtg gcaccggcag ttgatggtgt attagttagc agcagccttt   16860
ctcctagctc tagtggtgta taaagaatgg tgcttatcat tgttgggatc ttgggatttg   16920
agtaaatata acaatttgtt tcttcccaaa tagcattatg taaagaaact tgatagttac   16980
cattaaattc ggatatctca gccttcatct gggcatatgt gtataatttg tgcgtatgga   17040
```

```
cacacagaaa attgtataca aatagatcgt ttcatacatt ttacacaaaa cagggcttaa    17100
catgagcatg atgaggtttg ggggccagcc tagaaggggt tccttgaatt tcacaaaatt    17160
atctgtagcc cctgcctggt atttgtcagg tggaacttct gagcagtgaa ttcatagctt    17220
tcagtagctt ctcagaggac ttaggagcag aagacattat ttttatgaaa ccgcaaggct    17280
tcaacaaggg cccccagggt ctgcaactga ggttgggact caggcttgct gtggagctgg    17340
gctgggaccc agggatcctt ctcctacctg gccagggtct cccaacagaa cattctcagt    17400
gaggaaagtc ccagtcaagc cacgcttcct tttgggaagc agttccctgt gaccgatgtg    17460
cctgacgttc atgtcagcca gcagacacat cctggggctg tctgggccag gcagtgctgg    17520
aaaccagaga agagttagat cagaatagct tgtgcttgct cgttgcctgc agtgcacatc    17580
ccaagagcct tacacagttg tatactgatg ttagctgtat tgcccagatg aggaaactga    17640
ggcacaggca gatttaagtg aattgtccga gctgggaaga ggcagagtcc agattcgatc    17700
ccaggcccct aattcttagc cactcctatg tgctatcctc agagggctcc tggttgcttt    17760
cagagctgta aacaagggag gcaggggggt ccttaaaccc agggaaggcg cctaacctgc    17820
ttaggtggga tgggaagttg tcagggaagg cttcctggag gaggtggctg ttaacctgga    17880
ttttgacagg ttataagaaa tagaaaatgg cttttgtgtag tttcttcatt ccacaaacat    17940
tgagcaaggt ctctaggcta tggaaaccca gagatgtgtc agacccactc ccggcccttg    18000
ctctcagcag tggtgaaatg gaattaatta cagagactcc tgtagctgca gtgtaaggat    18060 tgttttttg tttgttttgt ttttttcccg agatggagtt tcactcttgc tgcacaggct    18120
ggagtgcagt ggcgggatct cggctcactg caacctctgc ctcccaggtt caggtgattc    18180
tcctgcctca gcctcacgag tagctgagat tacaggcgtg tgccaccgca cccagctaat    18240
ttttgcattt ttagtagaga cggggtttca ctttgttggt cagattagtc tcggaatcct    18300
gacctcaggt gatccaccca ccccggcctc ccaaagtgct aggattacag gtgtgagcca    18360
ccgtgcctgg gtgtgagggt tgtttctgtg tcagcagctc tttttatttt tattttttctt    18420 tgagacagag tctcgctctg tcacccaggc tggagtgcag tgttgtaatc tcagctcact    18480
gcagcctctg cctcccgggt tcaagtgatt ctcaagcctc agcctcccaa gtagctggga    18540
ttacaggcac ccatcaccat gcctggctaa ttttttgtatt ttttgtagag acagggtttc    18600
accatgttgg ccaggctggt ctagaactcc tggcctcaaa tgatcacctg ccttggcctc    18660
ccaaagttct gggattacag gcgtgagcca ccgcatccgg ccagcagttc ctaactcttt    18720
tggaattatg gatcccttg agaatctgtt aaattctgga ccctcttctt ataaaagtac    18780
acaggatttt aggcggttca cactcttccc taccctgtgt ggtctccagg tttgagaacc    18840
cttgccccca gacttcacag agaggcttca cagtagtgag tcttcactgt gcaaaggcat    18900
caattgcagt ttcttaaatg tgtaccttcc tgggccctgc ctccagatat tctgattgtt    18960
ttggtccatg ctgggatagg cctccggggtg attctgctgc agggtggtca gggatcatcc    19020
tttgagaact acttcctgca gtaacctaca ggagaagaga accttggctt acataattac    19080
tgctcagcct ctgtcccagg cctccttata acagattgcc gtaagttcca ccggtagtca    19140
cttggcaagt gttgattgag taccttctct gtgccagccc aggtggtggg agaactgagg    19200
tgaacaagag gaactctgtc cctgcagtat cccagtcaca ccgcacctat ggtcacactc    19260
ccatgatact gtcctgaact tgagacgtca cgatagcatg aggacctgtg acagtgacat    19320
tatgctggct tgcttagtat tacatttttc ctttgaatca ttcattgcaa ctatttttaa    19380
atgctatttt taaacatttg ttttttattct tagttttact gtaaaaatat acatagaatg    19440
```

```
tgctatttta attattttaa agtgtgtagc tctgtggcgg taggtttatt cacattgtgc    19500
agccattatc accctccatc tccagaattt ttcacctcct caaactgaaa ttccaaaccc    19560
attggacatg agctccccct tccctctccc ccagcccctg gcagccaccg taggagtttg    19620
actgttctag attcctcata taagtggaat cagaaaatat ttgtctttat gactattagc    19680
taatttccct tggcataaca tcttcaaggt tcatccatgt tgtagcatgt gttacatgag    19740
acttctcaca tacaagattc ttgagttttt ttgagggctg catttggaaa accagatttg    19800
cttattgcca gctgcattct cccatagtga cagtccttgg agctggggag cacctgccct    19860
ccctgggcta catgccctcc agggtgccac agtgcctgcc tcttcctatt catgcctcct    19920
gccacccctg cctgtcacct tggctgatgg catcattctg ttacttgact gagccctgga    19980
ggcatttcca tttatgattt ttttttttcct gctttaaata cctgtcagcc caagttgaat    20040
ttcagatcag agacctccac acctttattt gaacatattg ggataagttg agtctccctt    20100
cagtaggtca ctaattaaga gttcctgtct tgtgctaaga gtgctgctgg gctctgggga    20160
tacagtggag agccagtcgt atgtatctga aggagcacag tcattctagg cccacagtaa    20220
caaccagcga gcagtcccga gccccatagt cccccagaaa catgagatcc caattcagtc    20280
accagagctg tgtgtaactg ttcatgggaa gcttaggtca ggttttcgat cctgacctgt    20340
agctattact agcttgggca agccaggctg tacctcagtt ttctcttctt tttttttttt    20400
ttttttttct ttttgagacg gagtctcgct gtgttgccca ggctggagtg cagtggtgcg    20460
atctcggctt actgcagcct ctgcctcccg ggttcaagga ttcttctgcc tcagcctccc    20520
gagtagctgg gattacaggt gcgcaccacc accccagct aattttttg tattttagt    20580 agaaacgggg tttcaccata ttggccaggc tggtcttgaa ctcctgacct cgtgatccac    20640
ccgcttcagc ctcccatagt gctgggatta caggcgtgag ccactgcgcc cggcccgttt    20700

tctcttcttt aaaatcagga cttgctttat agaattcagt gaggaagaac aagcacccct    20760
ggtacaacac ggaggtcctg cctagtacac acagтgагта gatgttctac acagtgtcag    20820

tgatgatcat tgcactttga gaggctaaga actttctcct cagaaagcaa cgtgtgtaat    20880

tttaaggttt atggacccca gtgaaactcc ttcaaggacc cctaaataag aacctttgtg    20940
gaaggcacgc tgacagagac cttctgctgg ctggcataat atacgttttt тcсттттgагт    21000 caттcатгтgc aaccatttt aaaggctatt ttaatgaagg tcgggatggg taataggaaa    21060 gtttctctg aggagatgag cccatgatgg ggtgcaggat ggggctccag ggctgcggat    21120
ggtggagagg gagctgtcca gtgactttgt gttctcacca cagccaccgc tggagtcgct    21180
ggccacagtg gaggagacag tggtgcggga caaggcagtg gagtccttac gggccatctc    21240
acacgagcac tcgccctctg acctggaggc gcactttgtg ccgctagtga agcggctggc    21300
gggcggcgac tggttcacct cccgcacctc ggcctgcggc ctcttctccg tctgctaccc    21360
ccgagtgtcc agtgctgtga aggcggaact tcgacagtga гтстстgccт ccttggaagc    21420

tccaagctcc catctcagct ccaaccttct ctaaagcctc agactccttt tggtctagct    21480
ggggcccaaa tgcccctgaa ctctctccac tcccactcct gcttaccacc tgataggcca    21540
catcctcgag agttggtctc tggacacggc cacgtgtcag tttacccacc tctgccccct    21600

tgctcactta ggaattgaga tgatgacagg tcctccttcc cactggttaa tgtgaggatt    21660

taaaagaatt atcacacata aagtgcttag agcaaaatct ggaacataaa aactttcagc    21720
aacttacatc tgatggtatc tccagcctgt cccaggtcca gtgcctttgg cagataaacc    21780
```

```
acctcagttt tcagcctcct gctcgtctac tttgcaaacg attgaccgtc aagcccgggt    21840
ttgagcctga ctcactccag aactctggtt tatggctgta cacttgctta gatacttaca    21900
ctggccccca ccgcctttga tcgaagcaat tgctgctgaa aaataaagcc tttctgtggc    21960
tctagacctg cctcttagtt aagcagtttt ttgtttgttt gttttttgag ataggatctc    22020
gctctgtcat ccaggctgaa gtgcactggt gcagtcatag cccactgcag cctcaacctc    22080
ctgggctcaa gcattcctcc tgccttagcc tctcaaatag ctgggaccac aggtgtgcaa    22140
caccacgctg ggctcatttt ttattttggg cagagatggg gtctcactat gttgctcagg    22200
ctggtcttga actcctgggc tcaagcaatc ctcctgcctt ggtcttccaa agtgttcaga    22260
ttacaggtat gagccactgt gcctggctcg ttggttaagc aattttttatg ggaatgatgt    22320 aatcgtcagc acttagcatt gactagattt attatgcgca atctgcgaag tgtctcacac    22380
acactatttt catttaaacc tcatgcggac ctgtggggta ggtactgtta ctatcagctc    22440
cgtttcatag gctgggaag acagagaggg ggtcatcact tgcccaaggt cattcagcta    22500
aaacctggac ccacacaact gcagagtctg tgcttgctcc tctctgccat actgcctgct    22560
gcctcaggat cccgtcccc gactcccagg tacttccgga acctgtgctc agatgacacc    22620
cccatggtgc ggcgggccgc agcctccaag ctggggagt tgccaaggt gctggagctg    22680 gacaacgtca agagtgagat catccccatg ttctccaacc tggcctctga cgagcaggtg    22740
agttttgctt cctggccctc tgctctcccg tccttctggt ggttcctgcc catgaaagag    22800
aatcccagag ctcagcaagg cctctgctgc cctcccactg ttcctctcct ctccctagga    22860 ctcggtgcg ctgctggcgg tggaggcgtg cgtgaacatc gcccagcttc tgccccagga    22920
ggatctggag gcctggtga tgcccactct gcgccaggcc gctgaagaca gtcctggcg    22980 cgtccgctac atggtggctg acaagttcac agaggtagat gagcgaccgt tgacattgtc    23040
ccactggtgg ggacactgac actctcagaa gggaagcata taggagctga ggtttccatt    23100
aggccgatgg aaccattggg cgtttgagca ataagatctc tatgatcatc taactgcgtc    23160
tcgcttcgtg tgccaatcct ggttgattga catggcatct taaagtgctg ccttgagaaa    23220
gattctgagg caaagttaag gctacgtgga ggaaagtgcc acaggagcag agaagggtag    23280
cacatgtggg gtgttcctga cataatcaag ctgtcctttc acaaggggga agacagccca    23340
aaaaggtggg gttttttggt gtttttttt ttttttttt tttttttttt taagatggag    23400
tctgtcgccc aggctagagt cttgttaccc agctggagtg tggtggcgca atcttggctc    23460
actgcagcct gtccctcccg ggtgcaggca tttctcctgc ctcagcctcc tgagggactg    23520
ggattacaga tgcccaccac gacacccggc tagttttgt attttattta gagacggggt    23580
ttcaccatgt tgttagccag gctagtctcg aactcctgac ctcaagcgat ccgcctgcct    23640
tcatctccca aagtgctggg attacaggtg ttagccaccg cgcccagccc cggaaagttt    23700
aattaactga tcagagtgac actaccagcc aggcagaaag gggacaagac tccaggtctg    23760
tgactctcag gacagtgctc cttccacagg gatccagatt gcctcatccc acaaacatgt    23820
ttgctgagca ccagctattt gctgggccag tgaattcgga tcattcctgg ccttcatgga    23880
gctaggcagt ctgaagggga agactgactt agggggaaatt tgattataaa gtgtcacagg    23940
tgtgggacag acagacagat gtgggccttg gaagcattg aggaggggag gtggtgttac    24000
agctggttct agaagatgag tgggtaagag ctaagatagg aactttgttc cagccagagg    24060
acaaagaacc ctgggaggtg agagcaagtg caagcaggaa cattcaggcc tgatcttgat    24120
ggcccagcct gagagaaagc aggagagagg gcagggtggg atcggagaga gggcagggtg    24180
```

```
ggatcagaga ggccttgagt gccactccac cctgaggcgc cctttgcctt taattatgct    24240
ggttcccact ggcatttgcg ggaaggactc agagcttcag aatagcgtac catcaccaca    24300
gttagggaag gttcttccca tccttgtctc ctgagctgca taaactgtgt cacactgggt    24360
cttagaataa aaattccatg agggcaggaa ttttaggctg ttaaaccagt tcttggcaca    24420
tagtagacat tcagtaaata tttgcaagat gaataaaagg cagtattttc ccaagatatc    24480
atgaggtcct tcaagatttt tacttgttca ttcccgtctt cataatgaac tgtcctgctt    24540
cctaccaggt cttcaggaac cagctttgca gcaggagccg tgcgtctttc catgcctggt    24600
gccatgaaac aggcagggcc aagcgtgcct ccctttttt tttttttaa acagagtct       24660 cagtcttttg cccaggctgg agtacggtgg cacaagctca gctgactgca acctccacct    24720
cccagactca agtgattctc gtgccttagc ctcctgagta gctggaatta caggtgtgca    24780
ccaccacacc cagctaattt tgtatttta gtagagatgg ggtttcacca tgttggccag     24840
gctggtctcg aattcctggc ctcaagtgat ccacccacct ctgtctccca aagcgctggg    24900
attacaggtg taagccacta cgcccagccc tagagtgcct tcctttctgt caatctttat    24960
tgttttattt ttattttgag acagggtctc acaccatcac ccaggctgga gtgcagtggc    25020
acagtcacgg ctcactgcag ccttgacctc ctgggctcag gtgatcctcc cacttcagcc    25080
ttctgagtag ctaggacgat aggtgcctgc ccccacaccc ggctaattgt tttgttttt     25140 ttgtagagtc agggtttcac tgtgttgccc gggctggtct tgttctctgg gactcaagcg    25200
atctgtccac ctcagcttcc caaagtgctg ggattatagg catgagccat cgcacttggc    25260
ctattgtttt attttcatta caaaagtaat tcgtgcttct ggtaacagat ctttaagaaa    25320
tacagccata tataaatcaa aaagttgcag tcactatatc atttgaatgt ttttgaatca    25380
ggtaacagaa aacttaacct cagtagcctg aataatatgg aaatgtgtta tttttaatgc    25440
tgacaacacc gtgaggtagg tgccctcgca gtcctcattt ttctttggaa gcaaaagagg    25500
ctcagcgagg tgaagagcct tgccccgggg ccagtcttgg cactcgaatt agattttagc    25560
actgcttcca aggcccacgc tctgtcccct aattctggtg ccttcacttt gattttggct    25620
tccttagccc agagtaaact gccagcccct ctcactctcc ccctcctcct tcctgtctgc    25680
agctccagaa agcagtgggg cctgagatca ccaagacaga cctggtccct gccttccaga    25740
acctgatgaa agactgtgag gccgaggtga gggccgcagc ctcccacaag gtcaaaggtt    25800
ggtgctggca gccggaacac agcaagtggg gtgggtatcc aaggggctgg aggtggaact    25860
agcacatcag gtctcacttc cctttgcctc cctctccctg cccacagagt tctgtgaaaa    25920
cctctcagct gactgtcggg agaatgtgat catgtcccag atcttgccct gcatcaaggt    25980
aacagagagt ttgatgggag gaaccaagtg gatccgagcc tgccaaaaag aggggctgga    26040
gacaaggctt tggggatagt cagctgcaaa ctaggttccc agccctctgg gaccaggcag    26100
ctcttgggtt tcaagcagtt aggggtcctg actgcagctt gaggctgacc ttaaaggtgg    26160
aagtactttc tagaacctca gatgtcactg agtcctgtca ttcacagggt tttgggggttg   26220 gagtgggggc tgctgagagc aggggtcatt gaactcttaa gtaggtggta ctcataagga    26280
atagtgattt cccctgtacc ctaagccatc ccctgctcta tgaatgagag gggcagaagc    26340
aggttattgt ctcttaggag ttggcatctg cttagccact tgctgctgca ggggttgcac    26400 tgaccccctgt gcctgcctct tctctctccc aggagctggt gtccgatgcc aaccaacatg   26460
tcaagtctgc cctggcctca gtcatcatgg gtctctctcc catcttgggc aaagacaaca    26520
```

```
ccatcgagca cctcttgccc ctcttcctgg ctcagctgaa ggatgaggta agggcaccag    26580
gatctcagct ctgggtttgt ggaggggaca ggcgggtctt cctagattgc tagggtttac    26640
ctagattgac caggaatctg ctgatatctc aacagacatc cagatctttg ctgagttgca    26700
tgtttgtggg catagctgtg tgttcatgcg ttcattcctc caggcactct tcatgaggcc    26760
tttcctggac atggaggata tgaaaaatag aaatttaaag ttttttattta tggccaggcg    26820
cggtggctca cgcctgtaat cccagcactt tgggaggctg aggcgggtgg atcacctgag    26880
gtcaggagtt cgagaccagc ctggccaaca tgatgaaacc tcgtgtctgc taaaaatgca    26940
aaaattagcc aggcatggtg gcgagtgcct gtaatctcag ctactcgggc agctaaggca    27000
ggagtatcac ttgaactcag gaggcagagg ttgcaatgag ccaagattgc accactgcac    27060
tccagcctgg acaacagagc aagactctgt ctcaaaaaaa aaattattta tttatgtttt    27120
gagatagggt cttgctctat tgcccacact gcagtgcagt gatgtgatca tggtctactg    27180
cagcctccac cttccaggct caagtgatcc tcccaccta gcctcccaag tagctgggac    27240
tacaggcaag agccaccaca tctagataat tttaaaaaac attttccata gagacaagat    27300
attatgttgc ccaggttggt cttgaactcc tgatctcaag cagtccttttt gccttggcct    27360
ccaaggcct gggattatag gcgtgagccg ctgcccccag cctagaataa gagttttgat    27420
ccccaaaagc cttcagagac tggcagtgga gagagacagg cagtcccatg atgccattaa    27480
ggtgttacag gtgctgttaa ggatgagttc atgtttttta ggggtttaggc taaggtgctc    27540
taatatagac cccagaatac attctggctt aaattcggtg gtggattttt tttctctctc    27600
tcataacagt ctaggacgag attcctcaca tgtgcttgca ccccatacac ccattggcca    27660
ggagggtcac gtgaccacac ccagcagttc aggttgcctg tattacaaag gatgagaggc    27720
ggtgctgggt gatgactgga gagatcatca gggtgaccac tggggaagga gtttggactt    27780
gactgtgggc aagcggaaga gccagaatag agttggtgtt agaaggcacc ctgaggctta    27840
tgtgaaggaa ggattgaagt gaggtggcca gcagcagtgt aggcagacca aaccggaggc    27900
tgtgggagtc tggaaggctg aggctagact aagtggtatg tagagatgag gctgcattga    27960
tacgaagga ttcaagattg ttcaggaggc agaagggacc acgtggtggt ttttgccttg    28020
gtggtgaaaa actgggcaga tggtgcaatt gtgtgctggt gtgtgacatc tttcccaaaa    28080
gatgggaagt gtgtgaggct tcccaaaagc ctcagtcttt cttcccccatc cccttctttc    28140
tttttttatac acaggcgccc acacagtctg ctagaaagtt ggaggaaata ctgtaacaga    28200
aagtactgca tcacatttca gtcctccatg cccctaaaag ttacgttatt caattctgtt    28260
acagtggagt aatctcttag ccccagaatt acagtgaatt ttttaataca ttgaaaagag    28320
tgcgctattt ttaatatttt tttgttcttt ttgttttttcc ctattagtgg gtgattaact    28380
gtactggttt taatcagtta attacgtcag ttgctaaaag tctgaatctt cattagtgtt    28440
catgacaaat tttatgactt aagtaattta tctgagttat gcttcacatg cacatagttt    28500
ttataatttt atagatatta atacaattta tatttgttttt tgatgcttta atgggcataa    28560
tttggcaggt gagagcccct caagttgtct gctatgtcat ttcacacctc tccagcgttt    28620
tgggatcat tttgcctctg gcatgaggga aggatccagg ctcagcccag tttgaaggca    28680
agcccatacg tgctgcaagt gcgctaggac tggagcattt tttgctccag tttcaccttc    28740
agcaagcgct atatggtaat cgtgtgctgg cagccagcct gtctcagggc agcttctctt    28800
agaagaaaag aaccagcatg gttttcttgg tgtgaggaat tcatctgact tatatttgag    28860
atttccattt tagatttata aactttatat tttacatttt gactctcacc agaatttata    28920
```

```
aacttgtcta aatgaaaaag gctacctttt tactggtgca ccaaaaataa gtcttttaa    28980
atgggtgagg tatagtctct gagccttctc ttctcatgca catgttcagc agcttgaggc    29040
tcacacagca agggctggag ctgggcaagg gccagtccta tcctcggaat gtgcagggtt    29100
tcaacagccc aagcctgcca ggcttgttca cttggttatt gattcatttc agtgctcctt    29160
tatttattta ttttttttaga ctaaaatagt tttaataagg aaatagtttt cttccttccc    29220
ttctcccatg ttgtggattg atacccagaa aggaacccct tgttagcaagc agcggagcta    29280
ggattagaag aatcatgtct gcctgttttt tccagggtgc tgtattttcc tactgtgatt    29340
cttaaagtct tttcaaaatg gataaacatt tcttgtgata ctattgtaag gtttaaaaat    29400
ctgcttaagt tagtgatcca tgctgcttgc tttttgtgtg ccgttaatgt gttcccagaa    29460
cggggagctg ggcttggaca ggagtagtcc ctcgggagat gtccataaaa gttgatgcag    29520
ctgagctctt tccatcctgt cctgggttgc tgtgtgcatt gcattctctc agaatccttc    29580
tttcctctcc tcagtgccct gaggtacggc tgaacatcat ctctaacctg gactgtgtga    29640
acgaggtgat tggcatccgg cagctgtccc agtccctgct ccctgccatt gtggagctgg    29700
ctgaggacgc caagtggcgg gtgcggctgg ccatcattga gtacatgccc ctcctggctg    29760
gacagctggt gagtgaggag gcctgggggc caggcagtgc tgcctcaggg gaggtgcagt    29820
atgtccaggg ctgtgatggg gaaacggggc tttgaaggct tagtggaggc tgtgacaact    29880
gcctggggag tcgaaggaag ggacccagga aatagggcct taaagatgc attggattca    29940
ataagagaga ggagggaaag gagcacctca gacaaagttg agaagtgtcc ggtctttcta    30000
gggtgggtgt aggttccatg ggatgtggct agcagctccc cctgtttgct ctcctggaac    30060
gcttaccttg gaacccttgg tttctcctgt agggagtgga gttctttgat gagaaactta    30120
actccttgtg catggcctgg cttgtggatc atggtgagta ccttcacagg agcagcaaga    30180
ggagatggga gctccagaaa ggcaggatgg attggctggg gctgtggcgg gcagtggagg    30240
aggctagagt cactccccac gccgctggat gctcgtatgg accagctcgc atgcttgtta    30300
gagtcctaga gaagtgttga gtgggaggag gacgaaacag atcacccagg ggttgcctgg    30360
tatagtggag agccagaggg ccactgagca gccagaccag ggttttgaat cctgcccttg    30420
gggctgtcag atctaaaaca agtcacctgc tgtcttttgaa tgagccccac actcattctt    30480
tgaaacttct tattctggtg ccttgggggcc attatgagaa tggctcattg tttacactaa    30540
gagaggtaaa aaataaaagg taatatttat ctctgtgaag ccctgtttga agtaataagt    30600
gccacataat ttaggcaaat cacttcttag agccttagtt tgcccatctg taaaatgaag    30660
ccagtagtgg aacctacctc ttggagtggt tgaaaagata ctgtataaaa aaaaacagtt    30720
actagatata gcacatagta agtccttttt tctctctttg gctcacatgc agcctggcac    30780
ctaggggctg cttttgtaagc catggtgagt gtgacctaca ttttgcccac atcagttctt    30840
cacctccaaa tccctgtctc tctcaccctc acccttctgc agtatatgcc atccgcgagg    30900
cagccaccag caacctgaag aagctagtgg aaaagtttgg gaaggagtgg gcccatgcca    30960
caatcatccc caaggtcttg gccatgtccg gagaccccaa ctacctgcac cgcatgacta    31020
cgctcttctg catcaatgtg agccttccac ctgcctgctg gcccatccct agggaactgg    31080
agcgcgtggg agaggaggga tgctagaggg ttccccaagg gagacacctg gcttgggaat    31140
ggagacatgg agtgcatctt ctatccagag atgagtcctt ggggaactgc aggcaagggg    31200
gtggggctcc cagggtcagg gtcataggggc ctctgggact ggggacttgg atggtgaggg    31260
```

```
acccagggcc tgggagactt gacctgttgg agcagcgatc tcaagcttta tgagcacccc   31320
tctccttccc tgagaaatgt gtgtctctat ctgtggtgcg ttgggtgagt gtatgggctc   31380
taggtcagac ctagttttaa attctggtac tgccatatat tagctatgga ccttggatag   31440
ttacctaacc gatgctttgg tcttctcatt tgtaaataat tcatactgta aagaattcat   31500
actggtaatc acagcctggt gagcgtgaag attaatcagg ttatacacgc acagggctta   31560
gaacagttat gctacaggta ggaagtgctc ctgtctattt gcttttccta cgattataat   31620
tatctcatgt actacttatt tatgtgtaaa ccatacacag ggctagaaag gaagggattt   31680
aaaaataaat ataactaagt gttctgatca tttcttccca cgccactctc tggagagcat   31740
tgctttaagg agggatccta gggcttggta attaaggtcg atctccagaa taattaaggg   31800
aagcctgagg acagagaaac tgggacatgg tgttaggatg gtgttagtgg agttgggaga   31860
ttcactccac taactgagtc acccgtattg ctcagcctct gtggggcctg atgatcacca   31920
gagtggcctg gtcagaggca gcaggaaatg agagttagcc aggagctttg catactcacc   31980
cctgccactc actggccccc aggtgctgtc tgaggtctgt gggcaggaca tcaccaccaa   32040
gcacatgcta cccacggttc tgcgcatggc tggggacccg gttgccaatg tccgcttcaa   32100
tgtggccaag tctctgcaga agatagggcc catcctggac aacaggtgag gtctggatac   32160
tcccccacac actggcaggg gcttcttgtg ggcaccttaa tctttgacct ttgaaggtag   32220
agcccagggt cagaggcctg gcagcgctcc ttgcttgctg tgtgaccttg gctcccttcc   32280
cttctcaagg tgtgtttttct caactgtaaa atgaacatca cagcatgaaa tagaaagagg   32340
gggtgatggg ttggcagtcc tgtatactag caacaagtca ttagaaaatg aaatcacctt   32400
atgttttata tgtaagtatg tgtataattt ataattgcac caaaaatatc aaatagccag   32460
gaataaattc aatgaaagat gtgtatgtaa cacctctaat gtaaactgta aaacactaat   32520
gtgagaaatt aaagcagacc tgaccaaggt gggcggatca gttgaggtca ggagttcacg   32580
accagcctgg ccaacatggc gaaaccccgt ctctagtaaa aatacaaaaa attagccggt   32640
gcggtagcac tcacctgtaa tcctagctat ttgggaggct gaaggcaaga gaattgcttg   32700
aatccaggag gtggaggttg cagtgagctg agatcatgcc actgcactcc agcctgggcg   32760
atagagcgag actgtctcaa aaaaaattaa agcagaccta cataatattc acggatggga   32820
cagttccctg aactcatctt tagattcagt ataagcccaa taatcttaac aggttcttta   32880
gtggaaaatt gacacttcta atgaacaaag ttgtctgatt tacactacca gagacgaaga   32940
cttatgacac cacaataatt aaaatagatg tgaacacaag catatttaaa tcgcccaata   33000
gaatggaatc aagggtacag aaacagtccc acatgtgttt aacagtaggc atctctgcag   33060
ttcagtggag aaatgtatgt ttttttaaaaa acatagctga gtcaatttga tatccattta   33120
ggaataaaag aaggctcgcc tcaatgcata aacaaattaa tttgagatga cagaccagaa   33180
ccagaaagat tttaaaaata aaggacctag aagaaaatgt aggaaaatat cttcttgagt   33240
tagcgtaggc acagatttgt taaacagcaa accagaggaa gtgatgggta agttgacctt   33300
ctgtaaaatg taacgctgtt tctcaaagaa cagcattttg agagtaaaat gcaagccact   33360
gactggagga agatgtttta atatatgttt ctgagaaagg actcatccac aatacctgtc   33420
tacaaatcag gcaagacaag aaagagatgg ggaaaaagac ttgaataggc acttgaaaaa   33480
ggatctccaa atagccagta agcatatgac aagggtgttc agcatcatta gccttcagga   33540
aaatgcaaat taaatctcag tgacatatga ctacacgcct cccagaacag ccaacattaa   33600
aaaagactca gtggtgcaaa tggtgaagac atagaagagc tggaactctc atccattgca   33660
```

-continued

```
cgtggggctg tacatttagg gtttgatcac tctgaaaacg ggagtggatc tggagtggaa    33720
tttggtgaag cttgttatac aaacagcctg tgaaacagcc cttccactcc tgggtctcta    33780
tccaggagaa atgagtgctg tttctgtcag aagaatgttc atggtagctt tattcatagt    33840
agccgtaaaa atggaaacaa cctccatgtc tgtccacagt agagtagata aattttagtt    33900
cattcaaaca gtggaaaact attcagcagt gacgaaacaa atgcctgcta taagcagcaa    33960
caggtgactc tcacagatac catgttgagt gaggagccaa atcaagaaa acacaccatt     34020 tatgtcaagt tcagaaacag gcagaatgaa ggaatcgaga tgatggaagt aagaatagtg    34080
gttatttggg gagaacaggg aactgtcaac tgaaagtgtg ggacccacaa ctgcagattt    34140
ctctttctgt ctgttccagg acacaacctc agctttagtt tctctccgaa gtcccctcc    34200 gttttccaaa acaattgact cttggtgcag gcggatttcc ctgggcccca tagatgagag    34260
tggatgcctc ctctgggctc ctggaggacc aggaacttcc ccttggggcc acttaccact    34320 ccctcttac gtaccagttt ggtctcttcc tcctggcccg ggtgcctcat ggcagaaatc     34380
aagagtgatt tagctctgta ttcactccta atacattgta ggcctcagtg aatatgtgtg    34440
aaatcaatga aagatacca tttgctgggc ctcagagact tgggggttct gagattctgt    34500
tccactttcc cagcctgctc tgatctccct gtttggggcc ccagtccttg tttatcatac    34560
ttctgacctt taagtaattg gttggttggt tggttttttg cagtttgttt ggttttcctt    34620
tgaggcagaa tctcgctctg tcgcccagac tggagtacag tggtgcgatc tcggctcact    34680
gcaacctctg cctcctgggt tcaggcagtt cttgtgcctc agcctttcaa gtagctggga    34740
ttacaagtgt gcaccaccat gcttggctaa ttttttgtact ttgagtagag atgggggttt    34800
tcccatgttg tccaggctgg tcttgaactc ctggcctcaa gtggtctgcc caccttggcg    34860
tcccaaagtg ctaggattac aggcttgagc ccccgtgctc ggccttgagt ttaccttttt    34920
tttttttttt ttttttttga gacggagttt cgctcttgtt gcccaggctg gagtgcaatg    34980
atgcaatctt ggctcaccac aacctccgcc tcccaggttc agcaattct cctgcctcag     35040 cctcccaagt agctgggatc acaggcgtgc accaccacgc cctgctaatt ttgtgttttt    35100
agtagggaca gggtttctcc atgttggttt ggccaggctg gtctcaaact cccaacctca    35160
gatgatccac ccaccttggc ctcccaaaat gctgggatta cagatgtgag ccaccacgtc    35220
cggcctgatt ttacttttaa ttgactcata attttatata tttatggggg tatagtagtg    35280
tttcaataat gtgtgcaaat gtgtaatgat caaattagga taattagcat atctatcacc    35340
ttaaatgttt actgtttctt tgtgatgaga acattcaaaa tcttctctta tagctgtttt    35400
gaaatatgca aaatgttatt attaactatg gtcacccgcc tgtgcagtga tcagagattt    35460
ctaattcctg tgtgtgccct ggattcttga gactcctccc accttgggtt tggtgtatcc    35520
gtgtctgtgt acactctctt gcccaagagc cctgtgccca cctgttgccc cagtccatcc    35580
tggctcaccc tctctctccc tgtctccttt cgctttccag cacctgcag agtgaagtca    35640 agcccatcct agagaagctg acccaggacc aggatgtgga cgtcaaatac tttgcccagg    35700
aggctctgac tggtaagacc tagaaagcac ggagccctag caggagggtg gactttgagg    35760
acaggcactg ggcctgtggg cagcagcttc tgggagggg aggtaccttg gcattgtggg     35820
cagagagagg gctctggttc tgattcttgc ctgttcctgt tttcctagtt ctgtctctcg    35880
cctga                                                               35885
```

<210> SEQ ID NO 5

<211> LENGTH: 1770
<212> TYPE: DNA
<213> ORGANISM: Homo sapiens

<400> SEQUENCE: 5

```
atggcggcgg ccgacggcga cgactcgctg tacccccatcg cggtgctcat agacgaactc    60
cgcaatgagg acgttcagct tcgcctcaac agcatcaaga agctgtccac catcgccttg   120
gcccttgggg ttgaaaggac ccgaagtgag cttctgcctt tccttacaga taccatctat   180
gatgaagatg aggtcctcct ggccctggca gaacagctgg gaaccttcac taccctggtg   240
ggaggcccag agtacgtgca ctgcctgctg ccaccgctgg agtcgctggc cacagtggag   300
gagacagtgg tgcgggacaa ggcagtggag tccttacggg ccatctcaca cgagcactcg   360
ccctctgacc tggaggcgca ctttgtgccg ctagtgaagc ggctggcggg cggcgactgg   420
ttcacctccc gcacctcggc ctgcggcctc ttctccgtct gctaccccccg agtgtccagt   480
gctgtgaagg cggaacttcg acagtacttc cggaacctgt gctcagatga cacccccatg   540
gtgcggcggg ccgcagcctc caagctgggg gagtttgcca aggtgctgga gctggacaac   600
gtcaagagtg agatcatccc catgttctcc aacctggcct ctgacgagca ggactcggtg   660
cggctgctgg cggtggaggc gtgcgtgaac atcgcccagc ttctgcccca ggaggatctg   720
gaggccctgg tgatgcccac tctgcgccag gccgctgaag acaagtcctg gcgcgtccgc   780
tacatggtgg ctgacaagtt cacagagctc cagaaagcag tggggcctga gatcaccaag   840
acagacctgg tccctgcctt ccagaacctg atgaaagact gtgaggccga ggtgagggcc   900
gcagcctccc acaaggtcaa agagttctgt gaaaacctct cagctgactg tcgggagaat   960
gtgatcatgt cccagatctt gccctgcatc aaggagctgg tgtccgatgc aaccaacat  1020
gtcaagtctg ccctggcctc agtcatcatg ggtctctctc ccatcttggg caaagacaac  1080
accatcgagc acctcttgcc cctcttcctg gctcagctga aggatgagtg ccctgaggta  1140
cggctgaaca tcatctctaa cctggactgt gtgaacgagg tgattggcat ccggcagctg  1200
tcccagtccc tgctccctgc cattgtggag ctggctgagg acgccaagtg gcgggtgcgg  1260
ctggccatca ttgagtacat gccccctcctg gctggacagc tgggagtgga gttctttgat  1320
gagaaactta actccttgtg catggcctgg cttgtggatc atgtatatgc catccgcgag  1380
gcagccacca gcaacctgaa gaagctagtg aaaagtttg ggaaggagtg ggcccatgcc  1440
acaatcatcc ccaaggtctt ggccatgtcc ggagacccca actacctgca ccgcatgact  1500
acgtctcttct gcatcaatgt gctgtctgag gtctgtgggc aggacatcac caccaagcac  1560
atgctaccca cggttctgcg catggctggg gacccggttg ccaatgtccg cttcaatgtg  1620
gccaagtctc tgcagaagat agggcccatc ctggacaaca gcaccttgca gagtgaagtc  1680
aagcccatcc tagagaagct gacccaggac caggatgtgg acgtcaaata ctttgcccag  1740
gaggctctga ctgttctgtc tctcgcctga                                    1770
```

<210> SEQ ID NO 6
<211> LENGTH: 589
<212> TYPE: PRT
<213> ORGANISM: Homo sapiens

<400> SEQUENCE: 6

```
Met Ala Ala Ala Asp Gly Asp Asp Ser Leu Tyr Pro Ile Ala Val Leu
  1               5                  10                  15

Ile Asp Glu Leu Arg Asn Glu Asp Val Gln Leu Arg Leu Asn Ser Ile
             20                  25                  30
```

```
Lys Lys Leu Ser Thr Ile Ala Leu Ala Leu Gly Val Glu Arg Thr Arg
        35                  40                  45

Ser Glu Leu Leu Pro Phe Leu Thr Asp Thr Ile Tyr Asp Glu Asp Glu
    50                  55                  60

Val Leu Ala Leu Ala Glu Gln Leu Gly Thr Phe Thr Thr Leu Val
65              70                  75                  80

Gly Gly Pro Glu Tyr Val His Cys Leu Leu Pro Pro Leu Glu Ser Leu
                85                  90                  95

Ala Thr Val Glu Glu Thr Val Val Arg Asp Lys Ala Val Glu Ser Leu
                100                 105                 110

Arg Ala Ile Ser His Glu His Ser Pro Ser Asp Leu Glu Ala His Phe
                115                 120                 125

Val Pro Leu Val Lys Arg Leu Ala Gly Gly Asp Trp Phe Thr Ser Arg
    130                 135                 140

Thr Ser Ala Cys Gly Leu Phe Ser Val Cys Tyr Pro Arg Val Ser Ser
145                 150                 155                 160

Ala Val Lys Ala Glu Leu Arg Gln Tyr Phe Arg Asn Leu Cys Ser Asp
                165                 170                 175

Asp Thr Pro Met Val Arg Arg Ala Ala Ser Lys Leu Gly Glu Phe
                180                 185                 190

Ala Lys Val Leu Glu Leu Asp Asn Val Lys Ser Glu Ile Ile Pro Met
            195                 200                 205

Phe Ser Asn Leu Ala Ser Asp Glu Gln Asp Ser Val Arg Leu Leu Ala
        210                 215                 220

Val Glu Ala Cys Val Asn Ile Ala Gln Leu Leu Pro Gln Glu Asp Leu
225                 230                 235                 240

Glu Ala Leu Val Met Pro Thr Leu Arg Gln Ala Ala Glu Asp Lys Ser
                245                 250                 255

Trp Arg Val Arg Tyr Met Val Ala Asp Lys Phe Thr Glu Leu Gln Lys
                260                 265                 270

Ala Val Gly Pro Glu Ile Thr Lys Thr Asp Leu Val Pro Ala Phe Gln
            275                 280                 285

Asn Leu Met Lys Asp Cys Glu Ala Glu Val Arg Ala Ala Ala Ser His
        290                 295                 300

Lys Val Lys Glu Phe Cys Glu Asn Leu Ser Ala Asp Cys Arg Glu Asn
305                 310                 315                 320

Val Ile Met Ser Gln Ile Leu Pro Cys Ile Lys Glu Leu Val Ser Asp
                325                 330                 335

Ala Asn Gln His Val Lys Ser Ala Leu Ala Ser Val Ile Met Gly Leu
            340                 345                 350

Ser Pro Ile Leu Gly Lys Asp Asn Thr Ile Glu His Leu Leu Pro Leu
        355                 360                 365

Phe Leu Ala Gln Leu Lys Asp Glu Cys Pro Glu Val Arg Leu Asn Ile
    370                 375                 380

Ile Ser Asn Leu Asp Cys Val Asn Glu Val Ile Gly Ile Arg Gln Leu
385                 390                 395                 400

Ser Gln Ser Leu Leu Pro Ala Ile Val Glu Leu Ala Glu Asp Ala Lys
                405                 410                 415

Trp Arg Val Arg Leu Ala Ile Ile Glu Tyr Met Pro Leu Leu Ala Gly
            420                 425                 430

Gln Leu Gly Val Glu Phe Phe Asp Glu Lys Leu Asn Ser Leu Cys Met
        435                 440                 445
```

```
Ala Trp Leu Val Asp His Val Tyr Ala Ile Arg Glu Ala Ala Thr Ser
    450                 455                 460

Asn Leu Lys Lys Leu Val Glu Lys Phe Gly Lys Glu Trp Ala His Ala
465                 470                 475                 480

Thr Ile Ile Pro Lys Val Leu Ala Met Ser Gly Asp Pro Asn Tyr Leu
                485                 490                 495

His Arg Met Thr Thr Leu Phe Cys Ile Asn Val Leu Ser Glu Val Cys
            500                 505                 510

Gly Gln Asp Ile Thr Thr Lys His Met Leu Pro Thr Val Leu Arg Met
            515                 520                 525

Ala Gly Asp Pro Val Ala Asn Val Arg Phe Asn Val Ala Lys Ser Leu
    530                 535                 540

Gln Lys Ile Gly Pro Ile Leu Asp Asn Ser Thr Leu Gln Ser Glu Val
545                 550                 555                 560

Lys Pro Ile Leu Glu Lys Leu Thr Gln Asp Gln Asp Val Asp Val Lys
                565                 570                 575

Tyr Phe Ala Gln Glu Ala Leu Thr Val Leu Ser Leu Ala
            580                 585
```

<210> SEQ ID NO 7
<211> LENGTH: 26
<212> TYPE: DNA
<213> ORGANISM: Homo sapiens

<400> SEQUENCE: 7
tgatggggcg catgtcctat gagcca                                    26

<210> SEQ ID NO 8
<211> LENGTH: 10
<212> TYPE: DNA
<213> ORGANISM: Homo sapiens

<400> SEQUENCE: 8
cgtcgtcttc                                                      10

<210> SEQ ID NO 9
<211> LENGTH: 11
<212> TYPE: DNA
<213> ORGANISM: Homo sapiens

<400> SEQUENCE: 9
cagcccagta t                                                    11

<210> SEQ ID NO 10
<211> LENGTH: 10
<212> TYPE: DNA
<213> ORGANISM: Homo sapiens

<400> SEQUENCE: 10
cggccaccca                                                      10

<210> SEQ ID NO 11
<211> LENGTH: 26
<212> TYPE: DNA
<213> ORGANISM: Homo sapiens

<400> SEQUENCE: 11
tgatggggcg catgtcctat gagcca                                    26

<210> SEQ ID NO 12

```
<211> LENGTH: 20
<212> TYPE: DNA
<213> ORGANISM: Homo sapiens

<400> SEQUENCE: 12
cccgttcgag ttcttcaggt                                                  20

<210> SEQ ID NO 13
<211> LENGTH: 18
<212> TYPE: DNA
<213> ORGANISM: Homo sapiens

<400> SEQUENCE: 13
gggaaaggag ctgcagga                                                    18

<210> SEQ ID NO 14
<211> LENGTH: 20
<212> TYPE: DNA
<213> ORGANISM: Homo sapiens

<400> SEQUENCE: 14
cagcagaact ctcacgacca                                                  20

<210> SEQ ID NO 15
<211> LENGTH: 20
<212> TYPE: DNA
<213> ORGANISM: Homo sapiens

<400> SEQUENCE: 15
gagaagagcc agacaatggc                                                  20

<210> SEQ ID NO 16
<211> LENGTH: 21
<212> TYPE: DNA
<213> ORGANISM: Homo sapiens

<400> SEQUENCE: 16
ttggaagcca aggatacatt c                                                21

<210> SEQ ID NO 17
<211> LENGTH: 21
<212> TYPE: DNA
<213> ORGANISM: Homo sapiens

<400> SEQUENCE: 17
accctgggcc tcctaagtat g                                                21

<210> SEQ ID NO 18
<211> LENGTH: 22
<212> TYPE: DNA
<213> ORGANISM: Homo sapiens

<400> SEQUENCE: 18
tgcacgttag agaaccactc tg                                               22

<210> SEQ ID NO 19
<211> LENGTH: 22
<212> TYPE: DNA
<213> ORGANISM: Homo sapiens

<400> SEQUENCE: 19
cagtcccata acccttcac ag                                                22
```

-continued

```
<210> SEQ ID NO 20
<211> LENGTH: 21
<212> TYPE: DNA
<213> ORGANISM: Homo sapiens

<400> SEQUENCE: 20
gaaactatgc aggcatgagc c                                              21

<210> SEQ ID NO 21
<211> LENGTH: 21
<212> TYPE: DNA
<213> ORGANISM: Homo sapiens

<400> SEQUENCE: 21
ttggctggat ctctttgtgt g                                              21

<210> SEQ ID NO 22
<211> LENGTH: 21
<212> TYPE: DNA
<213> ORGANISM: Homo sapiens

<400> SEQUENCE: 22
tcccaggata aggatggaga g                                              21

<210> SEQ ID NO 23
<211> LENGTH: 23
<212> TYPE: DNA
<213> ORGANISM: Homo sapiens

<400> SEQUENCE: 23
ttgaatgaca ttgtttggtg ttc                                            23

<210> SEQ ID NO 24
<211> LENGTH: 19
<212> TYPE: DNA
<213> ORGANISM: Homo sapiens

<400> SEQUENCE: 24
atcatctctg ggctggctg                                                 19

<210> SEQ ID NO 25
<211> LENGTH: 21
<212> TYPE: DNA
<213> ORGANISM: Homo sapiens

<400> SEQUENCE: 25
ggctgggatc ttgtcactct c                                              21

<210> SEQ ID NO 26
<211> LENGTH: 24
<212> TYPE: DNA
<213> ORGANISM: Homo sapiens

<400> SEQUENCE: 26
caagagactt ctgagaccct tagc                                           24

<210> SEQ ID NO 27
<211> LENGTH: 21
<212> TYPE: DNA
<213> ORGANISM: Homo sapiens

<400> SEQUENCE: 27
atccttggca tatcctgttg g                                              21
```

```
<210> SEQ ID NO 28
<211> LENGTH: 21
<212> TYPE: DNA
<213> ORGANISM: Homo sapiens

<400> SEQUENCE: 28
aacaaaggac acgcaggagt c                                              21

<210> SEQ ID NO 29
<211> LENGTH: 21
<212> TYPE: DNA
<213> ORGANISM: Homo sapiens

<400> SEQUENCE: 29
ggctgaagat aagtgcatgg g                                              21

<210> SEQ ID NO 30
<211> LENGTH: 20
<212> TYPE: DNA
<213> ORGANISM: Homo sapiens

<400> SEQUENCE: 30
gaactctgaa gagggcctgg                                                20

<210> SEQ ID NO 31
<211> LENGTH: 22
<212> TYPE: DNA
<213> ORGANISM: Homo sapiens

<400> SEQUENCE: 31
cagagtgagg taagcatgac cc                                             22

<210> SEQ ID NO 32
<211> LENGTH: 21
<212> TYPE: DNA
<213> ORGANISM: Homo sapiens

<400> SEQUENCE: 32
gtgagtaaag cctggtctcg g                                              21

<210> SEQ ID NO 33
<211> LENGTH: 21
<212> TYPE: DNA
<213> ORGANISM: Homo sapiens

<400> SEQUENCE: 33
ggaagaaaga gtggtggttg c                                              21

<210> SEQ ID NO 34
<211> LENGTH: 21
<212> TYPE: DNA
<213> ORGANISM: Homo sapiens

<400> SEQUENCE: 34
ggagatgtac agcgtgccat a                                              21

<210> SEQ ID NO 35
<211> LENGTH: 21
<212> TYPE: DNA
<213> ORGANISM: Homo sapiens

<400> SEQUENCE: 35
gctatgtgcg aggcaggtac t                                              21
```

```
<210> SEQ ID NO 36
<211> LENGTH: 20
<212> TYPE: DNA
<213> ORGANISM: Homo sapiens

<400> SEQUENCE: 36
attgcatggc aatgaaggag                                                    20

<210> SEQ ID NO 37
<211> LENGTH: 22
<212> TYPE: DNA
<213> ORGANISM: Homo sapiens

<400> SEQUENCE: 37
tggctaaaga tgagacattc cc                                                 22

<210> SEQ ID NO 38
<211> LENGTH: 21
<212> TYPE: DNA
<213> ORGANISM: Homo sapiens

<400> SEQUENCE: 38
gtcttgctct cgaagtgggt c                                                  21

<210> SEQ ID NO 39
<211> LENGTH: 21
<212> TYPE: DNA
<213> ORGANISM: Homo sapiens

<400> SEQUENCE: 39
ggcttcgaat ggtattggac a                                                  21

<210> SEQ ID NO 40
<211> LENGTH: 21
<212> TYPE: DNA
<213> ORGANISM: Homo sapiens

<400> SEQUENCE: 40
ggcgagtgta accaaggtgt t                                                  21

<210> SEQ ID NO 41
<211> LENGTH: 22
<212> TYPE: DNA
<213> ORGANISM: Homo sapiens

<400> SEQUENCE: 41
gctaagagtt cagaggccat ca                                                 22

<210> SEQ ID NO 42
<211> LENGTH: 20
<212> TYPE: DNA
<213> ORGANISM: Homo sapiens

<400> SEQUENCE: 42
ccttggttac actcgccaac                                                    20

<210> SEQ ID NO 43
<211> LENGTH: 21
<212> TYPE: DNA
<213> ORGANISM: Homo sapiens

<400> SEQUENCE: 43
```

```
gaggtggaag gaggagagag a                                              21

<210> SEQ ID NO 44
<211> LENGTH: 24
<212> TYPE: DNA
<213> ORGANISM: Homo sapiens

<400> SEQUENCE: 44
tcagttgcct gaagagaaac ataa                                           24

<210> SEQ ID NO 45
<211> LENGTH: 21
<212> TYPE: DNA
<213> ORGANISM: Homo sapiens

<400> SEQUENCE: 45
agtggttgcc accttgttac c                                              21

<210> SEQ ID NO 46
<211> LENGTH: 21
<212> TYPE: DNA
<213> ORGANISM: Homo sapiens

<400> SEQUENCE: 46
tggattaaga agcaatgccc t                                              21

<210> SEQ ID NO 47
<211> LENGTH: 21
<212> TYPE: DNA
<213> ORGANISM: Homo sapiens

<400> SEQUENCE: 47
atgcatggca ttagcaaaga c                                              21

<210> SEQ ID NO 48
<211> LENGTH: 23
<212> TYPE: DNA
<213> ORGANISM: Homo sapiens

<400> SEQUENCE: 48
ttgaaaccca aggtacattt cag                                            23

<210> SEQ ID NO 49
<211> LENGTH: 21
<212> TYPE: DNA
<213> ORGANISM: Homo sapiens

<400> SEQUENCE: 49
tctgctttgg gacaaccata c                                              21

<210> SEQ ID NO 50
<211> LENGTH: 20
<212> TYPE: DNA
<213> ORGANISM: Homo sapiens

<400> SEQUENCE: 50
gcctccgtga ggctacatta                                                20

<210> SEQ ID NO 51
<211> LENGTH: 24
<212> TYPE: DNA
<213> ORGANISM: Homo sapiens

<400> SEQUENCE: 51
```

```
aaatctacag agttccctgt ttgc                                          24

<210> SEQ ID NO 52
<211> LENGTH: 25
<212> TYPE: DNA
<213> ORGANISM: Homo sapiens

<400> SEQUENCE: 52
tgaatacttg ttgaaatttc tccct                                         25

<210> SEQ ID NO 53
<211> LENGTH: 21
<212> TYPE: DNA
<213> ORGANISM: Homo sapiens

<400> SEQUENCE: 53
cggagatttg gatgttctcc t                                             21

<210> SEQ ID NO 54
<211> LENGTH: 21
<212> TYPE: DNA
<213> ORGANISM: Homo sapiens

<400> SEQUENCE: 54
caaactccga cttcgtgatc c                                             21

<210> SEQ ID NO 55
<211> LENGTH: 22
<212> TYPE: DNA
<213> ORGANISM: Homo sapiens

<400> SEQUENCE: 55
ttggttgatc tttgtcttcg tg                                            22

<210> SEQ ID NO 56
<211> LENGTH: 21
<212> TYPE: DNA
<213> ORGANISM: Homo sapiens

<400> SEQUENCE: 56
tgaattttcc ttttggggaa g                                             21

<210> SEQ ID NO 57
<211> LENGTH: 21
<212> TYPE: DNA
<213> ORGANISM: Homo sapiens

<400> SEQUENCE: 57
atgaatgaag gcaagctagg g                                             21

<210> SEQ ID NO 58
<211> LENGTH: 21
<212> TYPE: DNA
<213> ORGANISM: Homo sapiens

<400> SEQUENCE: 58
tgctgagatc agccaaattc a                                             21

<210> SEQ ID NO 59
<211> LENGTH: 27
<212> TYPE: DNA
<213> ORGANISM: Homo sapiens
```

```
<400> SEQUENCE: 59
aaagctagta atgtaagaag tttggga                                          27

<210> SEQ ID NO 60
<211> LENGTH: 23
<212> TYPE: DNA
<213> ORGANISM: Homo sapiens

<400> SEQUENCE: 60
atagactaat agtaatatag tgt                                              23

<210> SEQ ID NO 61
<211> LENGTH: 22
<212> TYPE: DNA
<213> ORGANISM: Homo sapiens

<400> SEQUENCE: 61
cgggagtttg acattgttct ga                                               22

<210> SEQ ID NO 62
<211> LENGTH: 20
<212> TYPE: DNA
<213> ORGANISM: Homo sapiens

<400> SEQUENCE: 62
ggccaccttc tatgttccaa                                                  20

<210> SEQ ID NO 63
<211> LENGTH: 23
<212> TYPE: DNA
<213> ORGANISM: Homo sapiens

<400> SEQUENCE: 63
tttgagggta ggagaatgag aga                                              23

<210> SEQ ID NO 64
<211> LENGTH: 26
<212> TYPE: DNA
<213> ORGANISM: Homo sapiens

<400> SEQUENCE: 64
tctgttacca taggataaga aatgga                                           26

<210> SEQ ID NO 65
<211> LENGTH: 18
<212> TYPE: DNA
<213> ORGANISM: Homo sapiens

<400> SEQUENCE: 65
catgtgatgg cgtgatcc                                                    18

<210> SEQ ID NO 66
<211> LENGTH: 22
<212> TYPE: DNA
<213> ORGANISM: Homo sapiens

<400> SEQUENCE: 66
ggaaaggcag taaaggtcat gc                                               22

<210> SEQ ID NO 67
<211> LENGTH: 21
<212> TYPE: DNA
<213> ORGANISM: Homo sapiens
```

<400> SEQUENCE: 67
taaatggaaa cttgcaccct g                                              21

<210> SEQ ID NO 68
<211> LENGTH: 21
<212> TYPE: DNA
<213> ORGANISM: Homo sapiens

<400> SEQUENCE: 68
tacccaggct ggtttcaatt c                                              21

<210> SEQ ID NO 69
<211> LENGTH: 23
<212> TYPE: DNA
<213> ORGANISM: Homo sapiens

<400> SEQUENCE: 69
gacatttgag caaagacctg aag                                            23

<210> SEQ ID NO 70
<211> LENGTH: 21
<212> TYPE: DNA
<213> ORGANISM: Homo sapiens

<400> SEQUENCE: 70
ataagagacg cacgctgatt g                                              21

<210> SEQ ID NO 71
<211> LENGTH: 20
<212> TYPE: DNA
<213> ORGANISM: Homo sapiens

<400> SEQUENCE: 71
gctgactggg ttgagagctg                                                20

<210> SEQ ID NO 72
<211> LENGTH: 21
<212> TYPE: DNA
<213> ORGANISM: Homo sapiens

<400> SEQUENCE: 72
gtccatgtgt tctgagcttg g                                              21

<210> SEQ ID NO 73
<211> LENGTH: 21
<212> TYPE: DNA
<213> ORGANISM: Homo sapiens

<400> SEQUENCE: 73
aaggtcggga tgggtaatag g                                              21

<210> SEQ ID NO 74
<211> LENGTH: 20
<212> TYPE: DNA
<213> ORGANISM: Homo sapiens

<400> SEQUENCE: 74
tgctgagctc tgggattctc                                                20

<210> SEQ ID NO 75
<211> LENGTH: 20
<212> TYPE: DNA

```
<213> ORGANISM: Homo sapiens

<400> SEQUENCE: 75
ggttcctgcc catgaaagag                                                    20

<210> SEQ ID NO 76
<211> LENGTH: 20
<212> TYPE: DNA
<213> ORGANISM: Homo sapiens

<400> SEQUENCE: 76
tttagcactg cttccaaggc                                                    20

<210> SEQ ID NO 77
<211> LENGTH: 21
<212> TYPE: DNA
<213> ORGANISM: Homo sapiens

<400> SEQUENCE: 77
ctcccacaag gtcaaaggtt g                                                  21

<210> SEQ ID NO 78
<211> LENGTH: 21
<212> TYPE: DNA
<213> ORGANISM: Homo sapiens

<400> SEQUENCE: 78
tcagcagatt cctggtcaat c                                                  21

<210> SEQ ID NO 79
<211> LENGTH: 20
<212> TYPE: DNA
<213> ORGANISM: Homo sapiens

<400> SEQUENCE: 79
ccactaagcc ttcaaagccc                                                    20

<210> SEQ ID NO 80
<211> LENGTH: 21
<212> TYPE: DNA
<213> ORGANISM: Homo sapiens

<400> SEQUENCE: 80
gtgtccggtc tttctagggt g                                                  21

<210> SEQ ID NO 81
<211> LENGTH: 20
<212> TYPE: DNA
<213> ORGANISM: Homo sapiens

<400> SEQUENCE: 81
gaaccctcta gcatccctcc                                                    20

<210> SEQ ID NO 82
<211> LENGTH: 21
<212> TYPE: DNA
<213> ORGANISM: Homo sapiens

<400> SEQUENCE: 82
tgagtcaccc gtattgctca g                                                  21

<210> SEQ ID NO 83
<211> LENGTH: 20
```

```
<212> TYPE: DNA
<213> ORGANISM: Homo sapiens

<400> SEQUENCE: 83
acaatgccaa ggtacctccc                                              20

<210> SEQ ID NO 84
<211> LENGTH: 21
<212> TYPE: DNA
<213> ORGANISM: Homo sapiens

<400> SEQUENCE: 84
tggacagtga gacatcttcc c                                            21

<210> SEQ ID NO 85
<211> LENGTH: 20
<212> TYPE: DNA
<213> ORGANISM: Homo sapiens

<400> SEQUENCE: 85
gcagaaagcg gagagtcaca                                              20

<210> SEQ ID NO 86
<211> LENGTH: 18
<212> TYPE: DNA
<213> ORGANISM: Homo sapiens

<400> SEQUENCE: 86
acctctcggg gagctcag                                                18

<210> SEQ ID NO 87
<211> LENGTH: 20
<212> TYPE: DNA
<213> ORGANISM: Homo sapiens

<400> SEQUENCE: 87
cccactcagc tgtgtacctg                                              20

<210> SEQ ID NO 88
<211> LENGTH: 20
<212> TYPE: DNA
<213> ORGANISM: Homo sapiens

<400> SEQUENCE: 88
accctcaacc aactgctcac                                              20

<210> SEQ ID NO 89
<211> LENGTH: 22
<212> TYPE: DNA
<213> ORGANISM: Homo sapiens

<400> SEQUENCE: 89
aggttggtct cattgctctt tc                                           22

<210> SEQ ID NO 90
<211> LENGTH: 21
<212> TYPE: DNA
<213> ORGANISM: Homo sapiens

<400> SEQUENCE: 90
atatcttacc tgcggtggag g                                            21

<210> SEQ ID NO 91
```

```
<211> LENGTH: 21
<212> TYPE: DNA
<213> ORGANISM: Homo sapiens

<400> SEQUENCE: 91
acaaccagca aagtcctcac c                                              21

<210> SEQ ID NO 92
<211> LENGTH: 19
<212> TYPE: DNA
<213> ORGANISM: Homo sapiens

<400> SEQUENCE: 92
ctgggcaggg agacagaac                                                 19

<210> SEQ ID NO 93
<211> LENGTH: 24
<212> TYPE: DNA
<213> ORGANISM: Homo sapiens

<400> SEQUENCE: 93
aaagaacgtg tgtgatgtat ttgc                                           24

<210> SEQ ID NO 94
<211> LENGTH: 21
<212> TYPE: DNA
<213> ORGANISM: Homo sapiens

<400> SEQUENCE: 94
ttcatggtca aacagctctc c                                              21

<210> SEQ ID NO 95
<211> LENGTH: 21
<212> TYPE: DNA
<213> ORGANISM: Homo sapiens

<400> SEQUENCE: 95
ggacagccct tctctcacaa g                                              21

<210> SEQ ID NO 96
<211> LENGTH: 23
<212> TYPE: DNA
<213> ORGANISM: Homo sapiens

<400> SEQUENCE: 96
ggtccagaag catctcaata atc                                            23

<210> SEQ ID NO 97
<211> LENGTH: 21
<212> TYPE: DNA
<213> ORGANISM: Homo sapiens

<400> SEQUENCE: 97
cacagcacta tttggctcca g                                              21

<210> SEQ ID NO 98
<211> LENGTH: 21
<212> TYPE: DNA
<213> ORGANISM: Homo sapiens

<400> SEQUENCE: 98
gccaacaatt ctgcaggtaa g                                              21
```

```
<210> SEQ ID NO 99
<211> LENGTH: 21
<212> TYPE: DNA
<213> ORGANISM: Homo sapiens

<400> SEQUENCE: 99
catggtacca catgaagcca g                                              21

<210> SEQ ID NO 100
<211> LENGTH: 22
<212> TYPE: DNA
<213> ORGANISM: Homo sapiens

<400> SEQUENCE: 100
gaataccttt cagcctgatg gg                                             22

<210> SEQ ID NO 101
<211> LENGTH: 21
<212> TYPE: DNA
<213> ORGANISM: Homo sapiens

<400> SEQUENCE: 101
ggccttagga agaactttcc c                                              21

<210> SEQ ID NO 102
<211> LENGTH: 21
<212> TYPE: DNA
<213> ORGANISM: Homo sapiens

<400> SEQUENCE: 102
caagaaccct gagccattct c                                              21

<210> SEQ ID NO 103
<211> LENGTH: 21
<212> TYPE: DNA
<213> ORGANISM: Homo sapiens

<400> SEQUENCE: 103
aattggagag gcagattgag c                                              21

<210> SEQ ID NO 104
<211> LENGTH: 21
<212> TYPE: DNA
<213> ORGANISM: Homo sapiens

<400> SEQUENCE: 104
ccttgggtgg agaactgatt g                                              21

<210> SEQ ID NO 105
<211> LENGTH: 21
<212> TYPE: DNA
<213> ORGANISM: Homo sapiens

<400> SEQUENCE: 105
attgaggacg tggctcttca g                                              21

<210> SEQ ID NO 106
<211> LENGTH: 21
<212> TYPE: DNA
<213> ORGANISM: Homo sapiens

<400> SEQUENCE: 106
ccaaactgga atggaaattg g                                              21
```

```
<210> SEQ ID NO 107
<211> LENGTH: 19
<212> TYPE: DNA
<213> ORGANISM: Homo sapiens

<400> SEQUENCE: 107
tcggttcacg ccatgatag                                                19

<210> SEQ ID NO 108
<211> LENGTH: 19
<212> TYPE: DNA
<213> ORGANISM: Homo sapiens

<400> SEQUENCE: 108
gctcagcaag gcaccatgt                                                19

<210> SEQ ID NO 109
<211> LENGTH: 21
<212> TYPE: DNA
<213> ORGANISM: Homo sapiens

<400> SEQUENCE: 109
cctccatcta actaccagcc c                                             21

<210> SEQ ID NO 110
<211> LENGTH: 21
<212> TYPE: DNA
<213> ORGANISM: Homo sapiens

<400> SEQUENCE: 110
agacagaaac tgccttccac c                                             21

<210> SEQ ID NO 111
<211> LENGTH: 21
<212> TYPE: DNA
<213> ORGANISM: Homo sapiens

<400> SEQUENCE: 111
ggagaacctt tgggaaagga g                                             21

<210> SEQ ID NO 112
<211> LENGTH: 18
<212> TYPE: DNA
<213> ORGANISM: Homo sapiens

<400> SEQUENCE: 112
caggcaagga caagccag                                                 18

<210> SEQ ID NO 113
<211> LENGTH: 22
<212> TYPE: DNA
<213> ORGANISM: Homo sapiens

<400> SEQUENCE: 113
gctaagagtt cagaggccat ca                                            22

<210> SEQ ID NO 114
<211> LENGTH: 19
<212> TYPE: DNA
<213> ORGANISM: Homo sapiens

<400> SEQUENCE: 114
ccgcatcatg tccacacta                                                19
```

```
<210> SEQ ID NO 115
<211> LENGTH: 22
<212> TYPE: DNA
<213> ORGANISM: Homo sapiens

<400> SEQUENCE: 115
cagccgtgat tcgtacagag ta                                              22

<210> SEQ ID NO 116
<211> LENGTH: 20
<212> TYPE: DNA
<213> ORGANISM: Homo sapiens

<400> SEQUENCE: 116
ctcagtgacc gaaagaaccc                                                 20

<210> SEQ ID NO 117
<211> LENGTH: 21
<212> TYPE: DNA
<213> ORGANISM: Homo sapiens

<400> SEQUENCE: 117
taacagtctg catggagcag g                                               21

<210> SEQ ID NO 118
<211> LENGTH: 22
<212> TYPE: DNA
<213> ORGANISM: Homo sapiens

<400> SEQUENCE: 118
gaacaaacca ggattctagc cc                                              22

<210> SEQ ID NO 119
<211> LENGTH: 27
<212> TYPE: DNA
<213> ORGANISM: Homo sapiens

<400> SEQUENCE: 119
tggtgtagtg gaaactagga attacat                                         27

<210> SEQ ID NO 120
<211> LENGTH: 21
<212> TYPE: DNA
<213> ORGANISM: Homo sapiens

<400> SEQUENCE: 120
cgtcatcttt ggagcaggaa c                                               21

<210> SEQ ID NO 121
<211> LENGTH: 21
<212> TYPE: DNA
<213> ORGANISM: Homo sapiens

<400> SEQUENCE: 121
tcttaagcgt cgatggagga g                                               21

<210> SEQ ID NO 122
<211> LENGTH: 27
<212> TYPE: DNA
<213> ORGANISM: Homo sapiens

<400> SEQUENCE: 122
```
caacagttaa gctttatggt tatttgc        27

<210> SEQ ID NO 123
<211> LENGTH: 21
<212> TYPE: DNA
<213> ORGANISM: Homo sapiens

<400> SEQUENCE: 123
gcaatttaga gcaaaggcag c        21

<210> SEQ ID NO 124
<211> LENGTH: 21
<212> TYPE: DNA
<213> ORGANISM: Homo sapiens

<400> SEQUENCE: 124
tcagtataag cagtccctgc c        21

<210> SEQ ID NO 125
<211> LENGTH: 18
<212> TYPE: DNA
<213> ORGANISM: Homo sapiens

<400> SEQUENCE: 125
gcagagcctg cagtgagc        18

<210> SEQ ID NO 126
<211> LENGTH: 22
<212> TYPE: DNA
<213> ORGANISM: Homo sapiens

<400> SEQUENCE: 126
tgattgatct tgtgcttcaa cg        22

<210> SEQ ID NO 127
<211> LENGTH: 21
<212> TYPE: DNA
<213> ORGANISM: Homo sapiens

<400> SEQUENCE: 127
ttagtggatg aaggcagcaa c        21

<210> SEQ ID NO 128
<211> LENGTH: 21
<212> TYPE: DNA
<213> ORGANISM: Homo sapiens

<400> SEQUENCE: 128
atgaaccaaa gcaagcatga g        21

<210> SEQ ID NO 129
<211> LENGTH: 23
<212> TYPE: DNA
<213> ORGANISM: Homo sapiens

<400> SEQUENCE: 129
gagagaaggt ttgactgcca taa        23

<210> SEQ ID NO 130
<211> LENGTH: 22
<212> TYPE: DNA
<213> ORGANISM: Homo sapiens

<400> SEQUENCE: 130

-continued gatttgctga accctattgg tg                                            22

<210> SEQ ID NO 131
<211> LENGTH: 25
<212> TYPE: DNA
<213> ORGANISM: Homo sapiens

<400> SEQUENCE: 131
tcagcagtta ctattctgtg actgg                                         25

<210> SEQ ID NO 132
<211> LENGTH: 23
<212> TYPE: DNA
<213> ORGANISM: Homo sapiens

<400> SEQUENCE: 132
gggaaagata gttgtgaatg agc                                           23

<210> SEQ ID NO 133
<211> LENGTH: 21
<212> TYPE: DNA
<213> ORGANISM: Homo sapiens

<400> SEQUENCE: 133
aaggaagttg tatggatcta g                                             21

<210> SEQ ID NO 134
<211> LENGTH: 19
<212> TYPE: DNA
<213> ORGANISM: Homo sapiens

<400> SEQUENCE: 134
cggccatgca gaaactgac                                                19

<210> SEQ ID NO 135
<211> LENGTH: 21
<212> TYPE: DNA
<213> ORGANISM: Homo sapiens

<400> SEQUENCE: 135
caagaagcat aggcgtgtgt c                                             21

<210> SEQ ID NO 136
<211> LENGTH: 21
<212> TYPE: DNA
<213> ORGANISM: Homo sapiens

<400> SEQUENCE: 136
tctgagtgtt gctgctctgt g                                             21

<210> SEQ ID NO 137
<211> LENGTH: 24
<212> TYPE: DNA
<213> ORGANISM: Homo sapiens

<400> SEQUENCE: 137
gctaaattca tgcatcataa gctc                                          24

<210> SEQ ID NO 138
<211> LENGTH: 22
<212> TYPE: DNA
<213> ORGANISM: Homo sapiens

```
<400> SEQUENCE: 138
ggtgacactc cagaggcagt ag                                    22

<210> SEQ ID NO 139
<211> LENGTH: 23
<212> TYPE: DNA
<213> ORGANISM: Homo sapiens

<400> SEQUENCE: 139
gaggaataca caaacaccga cag                                   23

<210> SEQ ID NO 140
<211> LENGTH: 21
<212> TYPE: DNA
<213> ORGANISM: Homo sapiens

<400> SEQUENCE: 140
aaacaaatgg cacacgttct c                                     21

<210> SEQ ID NO 141
<211> LENGTH: 21
<212> TYPE: DNA
<213> ORGANISM: Homo sapiens

<400> SEQUENCE: 141
tggtgaaaga cgatggacaa g                                     21

<210> SEQ ID NO 142
<211> LENGTH: 21
<212> TYPE: DNA
<213> ORGANISM: Homo sapiens

<400> SEQUENCE: 142
tggattgtgc aattcctatg c                                     21

<210> SEQ ID NO 143
<211> LENGTH: 21
<212> TYPE: DNA
<213> ORGANISM: Homo sapiens

<400> SEQUENCE: 143
accaaagaaa cgcgagctta g                                     21

<210> SEQ ID NO 144
<211> LENGTH: 21
<212> TYPE: DNA
<213> ORGANISM: Homo sapiens

<400> SEQUENCE: 144
tccctttcac catctgtctc c                                     21

<210> SEQ ID NO 145
<211> LENGTH: 21
<212> TYPE: DNA
<213> ORGANISM: Homo sapiens

<400> SEQUENCE: 145
tgttggatta aagcggatgt c                                     21

<210> SEQ ID NO 146
<211> LENGTH: 21
<212> TYPE: DNA
```

```
<400> SEQUENCE: 146
tgggagtgga gagagttcag g                                                    21

<210> SEQ ID NO 147
<211> LENGTH: 21
<212> TYPE: DNA
<213> ORGANISM: Homo sapiens

<400> SEQUENCE: 147
aactgcagag tctgtgcttg c                                                    21

<210> SEQ ID NO 148
<211> LENGTH: 21
<212> TYPE: DNA
<213> ORGANISM: Homo sapiens

<400> SEQUENCE: 148
gatcttattg ctcaaacgcc c                                                    21

<210> SEQ ID NO 149
<211> LENGTH: 21
<212> TYPE: DNA
<213> ORGANISM: Homo sapiens

<400> SEQUENCE: 149
tgatgtgcta gttccacctc c                                                    21

<210> SEQ ID NO 150
<211> LENGTH: 21
<212> TYPE: DNA
<213> ORGANISM: Homo sapiens

<400> SEQUENCE: 150
aactgcttga aacccaagag c                                                    21

<210> SEQ ID NO 151
<211> LENGTH: 21
<212> TYPE: DNA
<213> ORGANISM: Homo sapiens

<400> SEQUENCE: 151
gggcagaagc aggttattgt c                                                    21

<210> SEQ ID NO 152
<211> LENGTH: 21
<212> TYPE: DNA
<213> ORGANISM: Homo sapiens

<400> SEQUENCE: 152
agctctttcc atcctgtcct g                                                    21

<210> SEQ ID NO 153
<211> LENGTH: 21
<212> TYPE: DNA
<213> ORGANISM: Homo sapiens

<400> SEQUENCE: 153
gatctgtttc gtcctcctcc c                                                    21

<210> SEQ ID NO 154
<211> LENGTH: 21
<212> TYPE: DNA
```

```
<213> ORGANISM: Homo sapiens

<400> SEQUENCE: 154
taagccatgg tgagtgtgac c                                              21

<210> SEQ ID NO 155
<211> LENGTH: 21
<212> TYPE: DNA
<213> ORGANISM: Homo sapiens

<400> SEQUENCE: 155
ctgaccctgg gctctacctt c                                              21

<210> SEQ ID NO 156
<211> LENGTH: 21
<212> TYPE: DNA
<213> ORGANISM: Homo sapiens

<400> SEQUENCE: 156
cttgagactc ctcccacctt g                                              21

<210> SEQ ID NO 157
<211> LENGTH: 21
<212> TYPE: DNA
<213> ORGANISM: Homo sapiens

<400> SEQUENCE: 157
ctagcaggag ggtggacttt g                                              21

<210> SEQ ID NO 158
<211> LENGTH: 17
<212> TYPE: DNA
<213> ORGANISM: Artificial Sequence
<220> FEATURE:
<223> OTHER INFORMATION: universal sequencing primer

<400> SEQUENCE: 158
gtaaaacgac ggccagt                                                   17
```

ARID1A AND PPP2R1A MUTATIONS IN CANCER

This application is a national stage application of PCT/US2011/050487 filed on September 6, 2011, which claims the benefit of Ser. No. 61/379,875 filed on Sep. 3, 2010, which is incorporated herein by reference in its entirety.

This invention was made with government support under OC0400600 awarded by the U.S. Department of Defense and CA121113, CA57345, CA62924, CA129080, CA134292, CA103937, and CA103938 awarded by the National Institutes of Health. The government has certain rights in the invention.

This application incorporates by reference the contents of a 200 kb text file created on Apr. 19, 2013 and named "13819933sequencelisting.txt," which is the sequence listing for this application.

Each reference cited in this disclosure is incorporated herein by reference in its entirety.

BRIEF DESCRIPTION OF THE FIGURES

FIG. 1A, ARID1A mutation; FIG. 1B, ARID1A mutation; FIG. 1C, PPP2R1A mutation; FIG. 1D, PPP2R1A mutation. Arrows indicate the position of the mutation.

FIG. 2A, gastric cancer; FIG. 2B, colon cancer; FIG. 2C, breast cancer; FIG. 2D, pancreatic cancer. Arrows indicate the position of the mutation.

DETAILED DESCRIPTION

Figure 1:
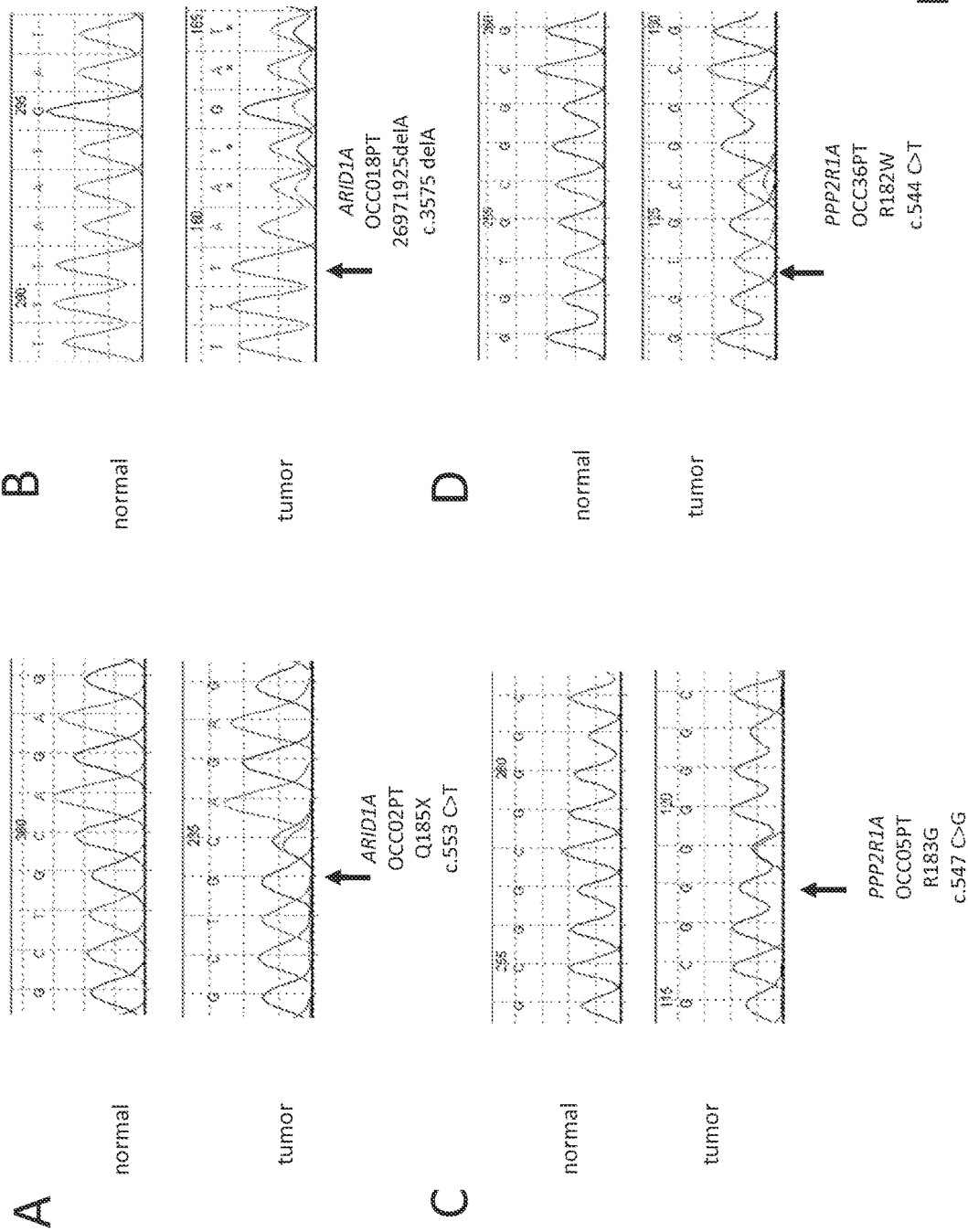
FIGS. 1A-D. Sequence chromatograms of examples of somatic ARID1A and PPP2R1A mutations.
Figure 2A:
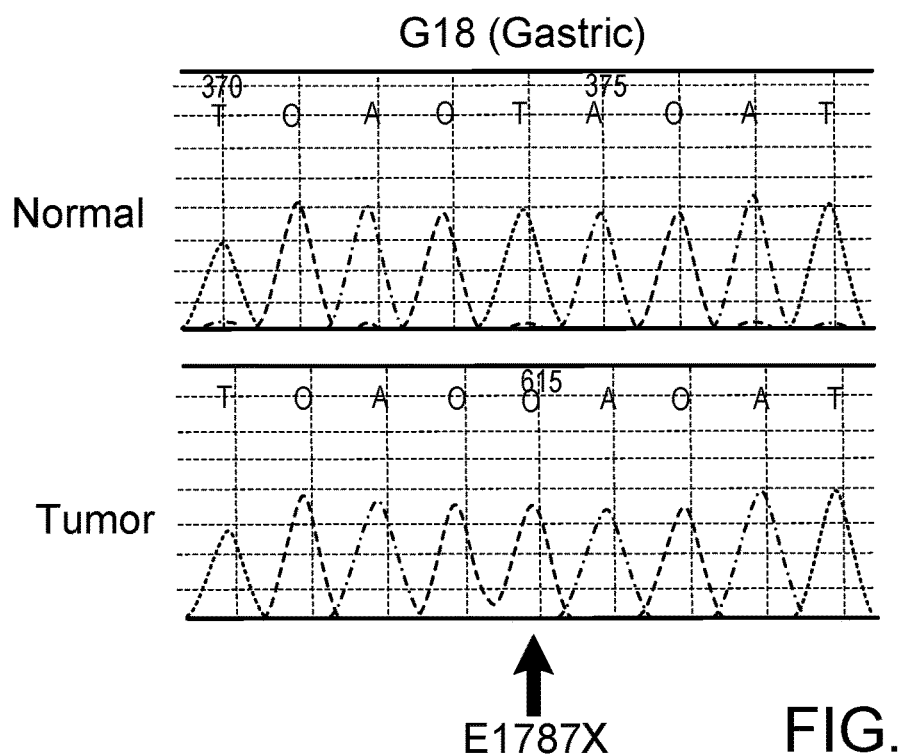
FIGS. 2A-D. Sequence chromatograms of examples of truncating mutations in ARID1A.
Figure 2B:
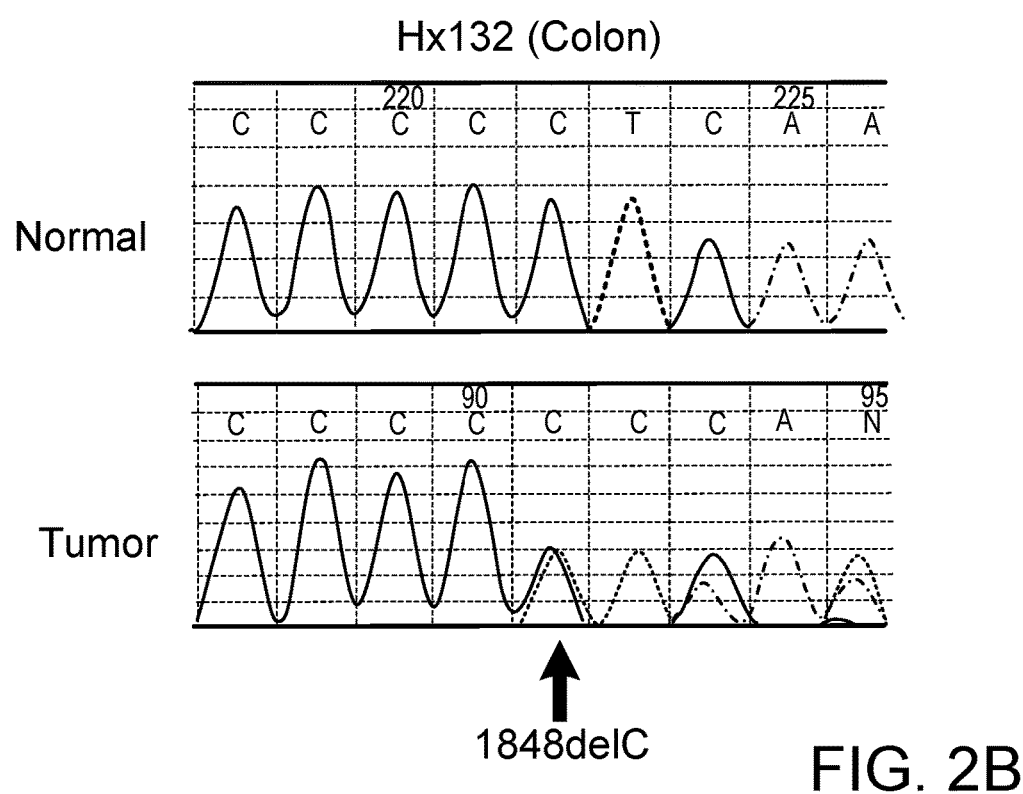
Figure 2C:
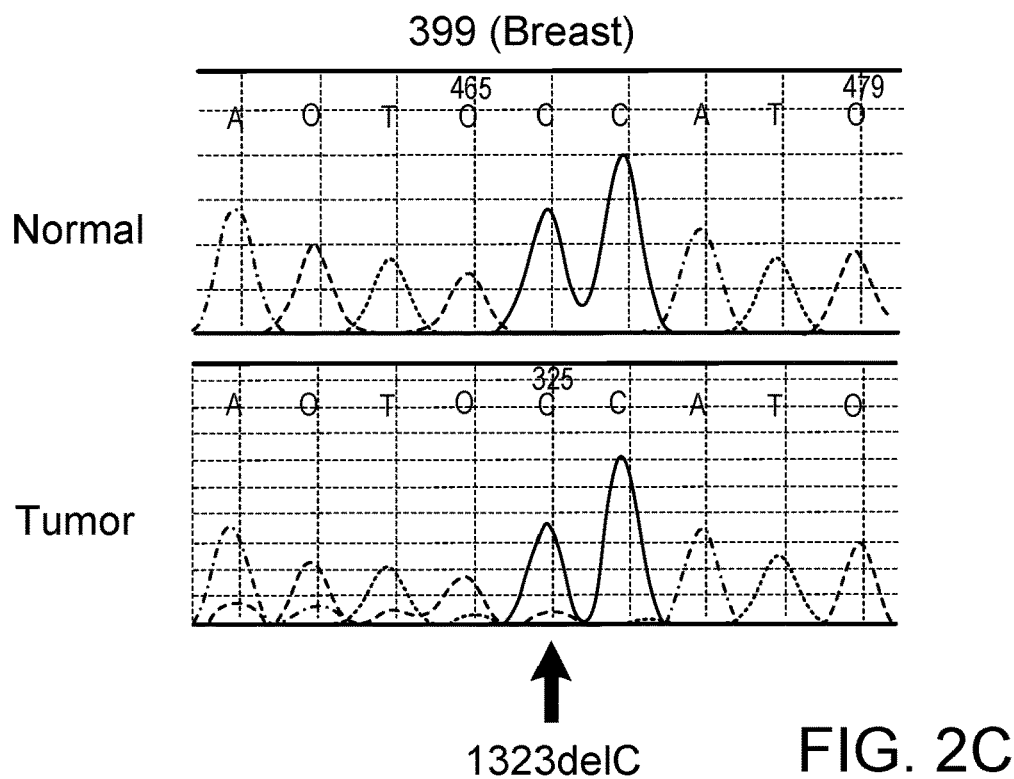
Figure 2D:
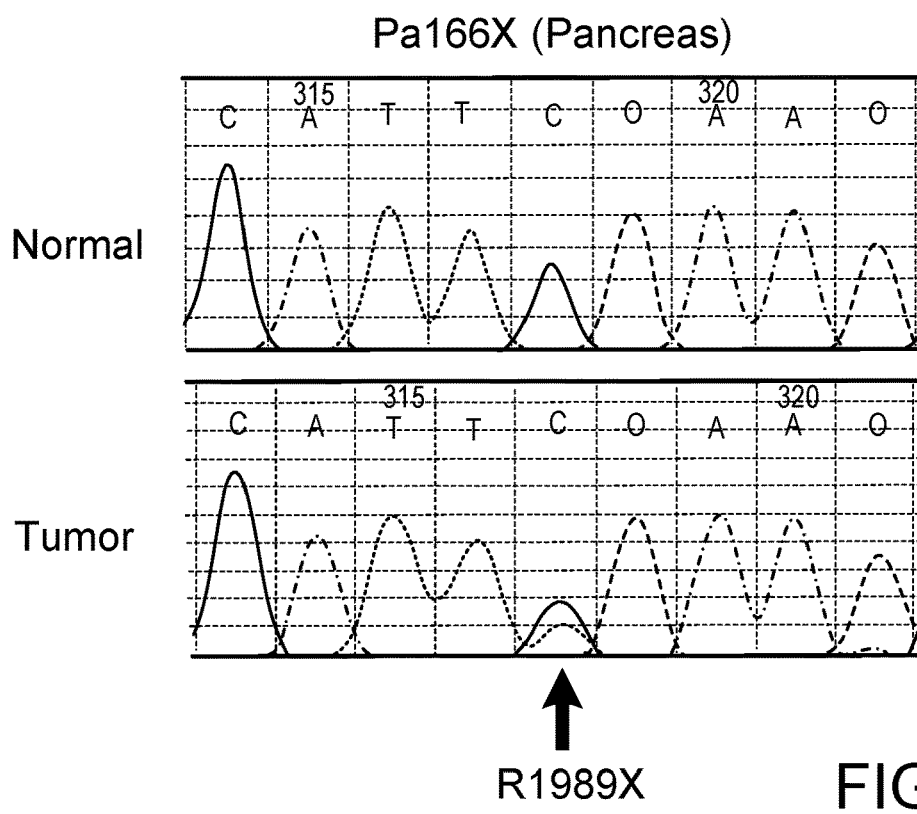

This disclosure identifies mutations in two genes: ARID1A (AT-rich interactive domain-containing protein 1A) and PPP2R1A (protein-phosphatase 2, regulatory subunit 1, alpha). This disclosure also provides methods which are useful for detecting cancer, diagnosing cancer, contributing to a diagnosis of cancer, or confirming a diagnosis of cancer, particularly ovarian clear cell carcinoma (OCCC), breast cancer, colon cancer, gastric cancer, lung cancer, medulloblastoma, pancreatic cancer, and prostate cancer. In some embodiments, nucleic acid is obtained from cells of an individual and tested to determine whether either or both of ARID1A and PPP2R1A. ARID1A mutations can be, for example, an insertion, a duplication, a missense mutation, or a deletion. PPP2R1A mutations typically are missense mutations. Examples of these mutations are provided below. Mutations in ARID1A and PPP2R1A typically are somatic mutations, but this disclosure also encompasses corresponding germline mutations.

Cancer cells which can be detected include, but are not limited to, cells from acute lymphoblastic leukemia, acute myeloid leukemia, adrenocortical carcinoma, AIDS-related lymphoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, breast cancer, breast sarcoma, bronchial cancer, bronchioalveolar carcinoma, Burkitt lymphoma, cervical cancer, chronic lymphocytic leukemia, chronic myelogenous leukemia, colon cancer, colorectal cancer, craniopharyngioma, cutaneous T-cell lymphoma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gallbladder cancer, gastric cancer, gastrointestinal carcinoid tumor, gastrointestinal stromal tumor, gestational trophoblastic tumor, gestational trophoblastic tumor, glioma, hairy cell leukemia, head and neck cancer, heart cancer, hepatocellular cancer, Hilar cholangiocarcinoma, Hodgkin's lymphoma, hypopharyngeal cancer, intraocular melanoma, islet cell tumor, Kaposi sarcoma, Langerhans cell histiocytosis, large-cell undifferentiated lung carcinoma, laryngeal cancer, lip cancer, lung adenocarcinoma, lymphoma, macroglobulinemia, malignant fibrous histiocytoma, medulloblastoma, medulloepithelioma, melanoma, Merkel cell carcinoma, mesothelioma, endocrine neoplasia, multiple myeloma, mycosis fungoides, myelodysplasia, myelodysplastic/myeloproliferative neoplasms, myeloproliferative disorders, nasal cavity cancer, nasopharyngeal cancer, neuroblastoma, non-Hodgkin's lymphoma, oral cancer, oropharyngeal cancer, osteosarcoma, ovarian clear cell carcinoma, ovarian epithelial cancer, ovarian germ cell tumor, pancreatic cancer, papillomatosis, paranasal sinus cancer, parathyroid cancer, penile cancer, pharyngeal cancer, pineal parenchymal tumor, pineoblastoma, pituitary tumor, plasma cell neoplasm, plasma cell neoplasm, pleuropulmonary blastoma, primary central nervous system lymphoma, prostate cancer, rectal cancer, renal cell cancer, respiratory tract cancer with chromosome 15 changes, retinoblastoma, rhabdomyosarcoma, salivary gland cancer, Sézary syndrome, small cell lung cancer, small intestine cancer, soft tissue sarcoma, squamous cell carcinoma, squamous non-small cell lung cancer, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, Waldenström macroglobulinemia, and Wilms tumor.

In some embodiments, mutations detected are in ARID1A and cancer cells which can be detected include, but are not limited to, cells from adrenocortical carcinoma, AIDS-related lymphoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, breast cancer, breast sarcoma, bronchial cancer, bronchioalveolar carcinoma. Burkitt lymphoma, cervical cancer, colon cancer, colorectal cancer, craniopharyngioma, cutaneous T-cell lymphoma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gallbladder cancer, gastric cancer, gastrointestinal carcinoid tumor, gastrointestinal stromal tumor, gestational trophoblastic tumor, gestational trophoblastic tumor, glioma, head and neck cancer, heart cancer, hepatocellular cancer. Hilar cholangiocarcinoma, Hodgkin's lymphoma, hypopharyngeal cancer, intraocular melanoma, islet cell tumor, Kaposi sarcoma, Langerhans cell histiocytosis, large-cell undifferentiated lung carcinoma, laryngeal cancer, lip cancer, lung adenocarcinoma, lymphoma, macroglobulinemia, malignant fibrous histiocytoma, medulloblastoma, medulloepithelioma, melanoma, Merkel cell carcinoma, mesothelioma, endocrine neoplasia, multiple myeloma, mycosis fungoides, myelodysplasia, myelodysplastic/myeloproliferative neoplasms, myeloproliferative disorders, nasal cavity cancer, nasopharyngeal cancer, neuroblastoma, non-Hodgkin's lymphoma, oral cancer, oropharyngeal cancer, osteosarcoma, ovarian clear cell carcinoma, ovarian epithelial cancer, ovarian germ cell tumor, pancreatic cancer, papillomatosis, paranasal sinus cancer, parathyroid cancer, penile cancer, pharyngeal cancer, pineal parenchymal tumor, pineoblastoma, pituitary tumor, plasma cell neoplasm, plasma cell neoplasm, pleuropulmonary blastoma, primary central nervous system lymphoma, prostate cancer, rectal cancer, renal cell cancer, respiratory tract cancer with chromosome 15 changes, retinoblastoma, rhabdomyosarcoma, salivary gland cancer, Sézary syndrome, small cell lung cancer, small intestine cancer, soft tissue sarcoma, squamous cell carcinoma, squamous non-small cell lung cancer, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, Waldenström macroglobulinemia, and Wilms tumor.

In some embodiments, mutations detected are in ARID1A and cancer cells which can be detected include, but are not limited to, cells from adrenocortical carcinoma, AIDS-related lymphoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, bronchial cancer, bronchioalveolar carcinoma, Burkitt lymphoma, cervical cancer, colon cancer, colorectal cancer, craniopharyngioma, cutaneous T-cell lymphoma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gallbladder cancer, gastric cancer, gastrointestinal carcinoid tumor, gastrointestinal stromal tumor, gestational trophoblastic tumor, gestational trophoblastic tumor, glioma, head and neck cancer, heart cancer, hepatocellular cancer, Hilar cholangiocarcinoma, Hodgkin's lymphoma, hypopharyngeal cancer, intraocular melanoma, islet cell tumor, Kaposi sarcoma, Langerhans cell histiocytosis, laryngeal cancer, lip cancer, lymphoma, macroglobulinemia, malignant fibrous histiocytoma, medulloblastoma, medulloepithelioma, melanoma, Merkel cell carcinoma, mesothelioma, endocrine neoplasia, multiple myeloma, mycosis fungoides, myelodysplasia, myelodysplastic/myeloproliferative neoplasms, myeloproliferative disorders, nasal cavity cancer, nasopharyngeal cancer, neuroblastoma, non-Hodgkin's lymphoma, oral cancer, oropharyngeal cancer, osteosarcoma, ovarian clear cell carcinoma, ovarian epithelial cancer, ovarian germ cell tumor, papillomatosis, paranasal sinus cancer, parathyroid cancer, penile cancer, pharyngeal cancer, pineal parenchymal tumor, pineoblastoma, pituitary tumor, plasma cell neoplasm, plasma cell neoplasm, pleuropulmonary blastoma, primary central nervous system lymphoma, prostate cancer, rectal cancer, renal cell cancer, respiratory tract cancer with chromosome 15 changes, retinoblastoma, rhabdomyosarcoma, salivary gland cancer, Sézary syndrome, small intestine cancer, soft tissue sarcoma, squamous cell carcinoma, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, Waldenström macroglobulinemia, and Wilms tumor.

In some embodiments, mutations detected are in ARID1A and cancer cells which can be detected include, but are not limited to, cells from adrenocortical carcinoma, AIDS-related lymphoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, bronchial cancer, bronchioalveolar carcinoma, Burkitt lymphoma, cervical cancer, colon cancer, colorectal cancer, craniopharyngioma, cutaneous T-cell lymphoma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gallbladder cancer, gastric cancer, gastrointestinal carcinoid tumor, gastrointestinal stromal tumor, gestational trophoblastic tumor, gestational trophoblastic tumor, glioma, head and neck cancer, heart cancer, hepatocellular cancer, Hilar cholangiocarcinoma, Hodgkin's lymphoma, hypopharyngeal cancer, intraocular melanoma, islet cell tumor, Kaposi sarcoma, Langerhans cell histiocytosis, laryngeal cancer, lip cancer, lymphoma, macroglobulinemia, malignant fibrous histiocytoma, medulloepithelioma, melanoma, Merkel cell carcinoma, mesothelioma, endocrine neoplasia, multiple myeloma, mycosis fungoides, myelodysplasia, myelodysplastic/myeloproliferative neoplasms, myeloproliferative disorders, nasal cavity cancer, nasopharyngeal cancer, neuroblastoma, non-Hodgkin's lymphoma, oral cancer, oropharyngeal cancer, osteosarcoma, ovarian clear cell carcinoma, ovarian epithelial cancer, ovarian germ cell tumor, papillomatosis, paranasal sinus cancer, parathyroid cancer, penile cancer, pharyngeal cancer, pineal parenchymal tumor, pineoblastoma, pituitary tumor, plasma cell neoplasm, plasma cell neoplasm, pleuropulmonary blastoma, primary central nervous system lymphoma, prostate cancer, rectal cancer, renal cell cancer, respiratory tract cancer with chromosome 15 changes, retinoblastoma, rhabdomyosarcoma, salivary gland cancer, Sézary syndrome, small intestine cancer, soft tissue sarcoma, squamous cell carcinoma, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, Waldenström macroglobulinemia, and Wilms tumor.

In some embodiments, mutations detected are in PPP2R1A and cancer cells which can be detected include, but are not limited to, cells from acute lymphoblastic leukemia, acute myeloid leukemia, adrenocortical carcinoma, AIDS-related lymphoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, bronchial cancer, bronchioalveolar carcinoma, Burkitt lymphoma, cervical cancer, chronic lymphocytic leukemia, chronic myelogenous leukemia, colon cancer, colorectal cancer, craniopharyngioma, cutaneous T-cell lymphoma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gallbladder cancer, gastric cancer, gastrointestinal carcinoid tumor, gastrointestinal stromal tumor, gestational trophoblastic tumor, gestational trophoblastic tumor, glioma, hairy cell leukemia, head and neck cancer, heart cancer, hepatocellular cancer, Hilar cholangiocarcinoma, Hodgkin's lymphoma, hypopharyngeal cancer, islet cell tumor, Kaposi sarcoma, Langerhans cell histiocytosis, laryngeal cancer, lip cancer, macroglobulinemia, malignant fibrous histiocytoma, medulloblastoma, medulloepithelioma, Merkel cell carcinoma, mesothelioma, endocrine neoplasia, multiple myeloma, mycosis fungoides, myelodysplasia, myelodysplastic/myeloproliferative neoplasms, myeloproliferative disorders, nasal cavity cancer, nasopharyngeal cancer, neuroblastoma, non-Hodgkin's lymphoma, oral cancer, oropharyngeal cancer, osteosarcoma, ovarian clear cell carcinoma, ovarian epithelial cancer, ovarian germ cell tumor, pancreatic cancer, papillomatosis, paranasal sinus cancer, parathyroid cancer, penile cancer, pharyngeal cancer, pineal parenchymal tumor, pineoblastoma, pituitary tumor, plasma cell neoplasm, plasma cell neoplasm, pleuropulmonary blastoma, primary central nervous system lymphoma, prostate cancer, rectal cancer, renal cell cancer, respiratory tract cancer with chromosome 15 changes, retinoblastoma, rhabdomyosarcoma, salivary gland cancer, Sézary syndrome, small intestine cancer, soft tissue sarcoma, squamous cell carcinoma, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, Waldenström macroglobulinemia, and Wilms tumor.

In some embodiments nucleic acids are tested to determine whether ARID1A and/or PPP2R1A comprises a mutation. In some embodiments, ARID1A and/or PPP2R1A proteins are tested to determine whether the protein comprises a structural alteration, such as an amino acid substitution or a truncation or deletion of a portion of the protein.

The disclosed methods are useful for individuals whether suspected or not of having cancer or a predisposition to cancer. The individual tested may be healthy and free of family history, may have a family history of cancer, may have a tentative diagnosis of cancer, or may be suspected of having cancer based on a symptom or condition or a previous diagnostic test.

The described methods also are useful for, e.g.:
 i. detecting OCCC, breast cancer, colon cancer, gastric cancer, lung cancer, medulloblastoma, pancreatic cancer, or prostate cancer;
 ii. diagnosing OCCC, breast cancer, colon cancer, gastric cancer, lung cancer, medulloblastoma, pancreatic cancer, or prostate cancer;
 iii. contributing to a diagnosis of OCCC, breast cancer, colon cancer, gastric cancer, lung cancer, medulloblastoma, pancreatic cancer, or prostate cancer,
 iv. confirming a diagnosis of OCCC, breast cancer, colon cancer, gastric cancer, lung cancer, medulloblastoma, pancreatic cancer, or prostate cancer;
 v. identifying appropriate treatments for OCCC, breast cancer, colon cancer, gastric cancer, lung cancer, medulloblastoma, pancreatic cancer, or prostate cancer;
 vi. monitoring treatment of OCCC, breast cancer, colon cancer, gastric cancer, lung cancer, medulloblastoma, pancreatic cancer, or prostate cancer; and
 vii. evaluating a treatment protocol for OCCC, breast cancer, colon cancer, gastric cancer, lung cancer, medulloblastoma, pancreatic cancer, or prostate cancer, including assessing efficacy of established or experimental therapies.

OCCC

The described methods are useful for detecting OCCC, diagnosing OCCC, contributing to a diagnosis of OCCC, or confirming a diagnosis of OCCC. Among ovarian cancers, OCCC is one of the most aggressive types because, unlike the more common high grade-serous type, it is refractory to standard platinum-based chemotherapy. Previous morphological and molecular studies have indicated that OCCC develops in a stepwise fashion from a common disease progenitor state, endometriosis, and proceeds through atypical endometriosis to frank malignancy (2-6). Activating mutations in PIK3CA (7) and genomic amplification of chr20q13.2 (8) are the most common molecular genetic alterations so far identified in OCCC.

In some embodiments, therefore, the cancer is OCCC. In some embodiments, ARID1A mutations useful for detecting OCCC include mutations listed in Tables 1, S3, and S5, wherein nucleotides are numbered by reference to SEQ ID NO:2.

In some embodiments, ARID1A mutations useful for detecting OCCC are 3854_3855insA; 553C>T; 903_904dupGT; 3659_3684delTGATGGGGCGCATGTCCTATGAGCCA (SEQ ID NO:7); 585C>A; 3391delC; 4001_4002dupGCA; 6828_6829delTG; 1455_1466insCCTAC; 4926_4927insTGCC; 4011_4012delTT; 4635G>A; 5202T>A; 486_492delCGCCGCC; 3575delA; 3223delG; 6718dupG; 898_899insCGTC; 6710_6711insT; 1663C>T; 782_791delCGTCGTCTTC (SEQ ID NO:8); 3634_3644delCAGCCCAGTAT (SEQ ID NO:9); 1873C>T; 2122C>T; 1804G>T; 6702delT; 1341T>G; 3442delC; 883dupC; 2868delC; 1881delT; 2179_2188delCGGCCACCCA (SEQ ID NO:10); 608dupA; 1626_1627delGC; 3994C>T; 6791C>G; 6625delC; 289G>T; 1650dupC; and 2272delC, wherein nucleotides are numbered by reference to SEQ ID NO:2.

In some embodiments, ARID1A mutations useful for detecting OCCC are 3854_3855insA; 553C>T; 903_904dupGT; 3659_3684delTGATGGGGCGCATGTCCTATGAGCCA (SEQ ID NO:7); 585C>A; 3391delC; 4001_4002dupGCA; 6828_6829delTG; 1455_1466insCCTAC; 4926_4927insTGCC; 4011_4012delTT; 4635G>A; 5202T>A; 486_492delCGCCGCC; 3575delA; 3223delG; 6718dupG; 898_899insCGTC; 6710_6711insT; 1663C>T; 782_791delCGTCGTCTTC (SEQ ID NO:8); 3634_3644delCAGCCCAGTAT (SEQ ID NO:9); 1873C>T; 2122C>T; 1804G>T; 6702delT; 1341T>G; 3442delC; 883dupC; 2868delC; 1881delT; and 2179_2188delCGGCCACCCA (SEQ ID NO:10), wherein nucleotides are numbered by reference to SEQ ID NO:2.

In some embodiments PPP2R12A mutations useful for detecting OCCC include mutations listed in Tables 1 and S5, wherein nucleotides are numbered by reference to SEQ ID NO:5.

In some embodiments PPP2R12A mutations useful for detecting OCCC are 547C>G, 547C>T, 547C>T, and 548G>A, wherein nucleotides are numbered by reference to SEQ ID NO:5.

In some embodiments PPP2R12A mutations useful for detecting OCCC are 547C>G, 547C>T, and 547C>T, wherein nucleotides are numbered by reference to SEQ ID NO:5.

Breast Cancer

In some embodiments the cancer is breast cancer. In some embodiments ARID1A mutations useful for detecting breast cancer include those listed in Table 2, wherein nucleotides are numbered by reference to SEQ ID NO:2.

In some embodiments ARID1A mutations useful for detecting breast cancer are 1323delC, 6259G>A, 5719A>T, and 2830C>T, wherein nucleotides are numbered by reference to SEQ ID NO:2.

Colon Cancer

In some embodiments the cancer is colon cancer. In some embodiments ARID1A mutations useful for detecting colon cancer include those listed in Table 2, wherein nucleotides are numbered by reference to SEQ ID NO:2.

In some embodiments ARID1A mutations useful for detecting colon cancer are 1014delG, 4689delC, 3281delA, 3344delC, 5548delG, 4354delC, 5548delG, 5548delG, 5548dupG, 1848delC, 2944_2946delAAC, 1657C>T, 6228C>A, 5838_5844dupACAGAGC, 5834_5835insAG-CACAG, and 2467_2468dupTA, wherein nucleotides are numbered by reference to SEQ ID NO:2.

Gastric Cancer

In some embodiments the cancer is gastric cancer. In some embodiments ARID1A mutations useful for detecting gastric cancer include those listed in Table 2, wherein nucleotides are numbered by reference to SEQ ID NO:2.

In some embodiments ARID1A mutations useful for detecting gastric cancer are 879dupC, 827delG, 4743_4744delCA, 5548delG, 4972C>T, 5359G>T, 5548delG, 4524T>A, 5548delG, 6420delC, 2357dupG, 854delG, 969_975delGGGCGCC, wherein nucleotides are numbered by reference to SEQ ID NO:2.

Lung Cancer

In some embodiments the cancer is lung cancer. In some embodiments ARID1A mutations useful for detecting lung cancer include those listed in Table 2, wherein nucleotides are numbered by reference to SEQ ID NO:2.

In some embodiments ARID1A mutations useful for detecting lung cancer are 2834delG and 6403_6408delAT-TCTG, wherein nucleotides are numbered by reference to SEQ ID NO:2.

Brain Cancer

In some embodiments the cancer is brain cancer (e.g., medulloblastoma, grade I (anaplastic) astrocytoma, grade II astrocytoma, grade III astrocytoma, grade IV astrocytoma, atypical teratoid/rhabdoid tumor of the central nervous system, neuroblastoma).

In some embodiments ARID1A mutations useful for detecting brain cancer, particularly medulloblastoma, include those listed in Table 2, wherein nucleotides are numbered by reference to SEQ ID NO:2.

In some embodiments ARID1A mutations useful for detecting brain cancer, particularly medulloblastoma, are 1015delG, 4893_4894InsC, and 5012delG, wherein nucleotides are numbered by reference to SEQ ID NO:2.

In some embodiments ARID1A mutations useful for detecting medulloblastoma are 4893_4894InsC and 5012delG, wherein nucleotides are numbered by reference to SEQ ID NO:2.

Pancreatic Cancer

In some embodiments the cancer is pancreatic cancer. In some embodiments ARID1A mutations useful for detecting pancreatic cancer include those listed in Table 2, wherein nucleotides are numbered by reference to SEQ ID NO:2.

In some embodiments ARID1A mutations useful for detecting pancreatic cancer are 3826C>T, 5947_5948delTG, IVS10+1G>A, 1945_1946insT, 2296dupC, 5965C>T, 5965C>T, 6287C>G, 1585C>T, 5548dupG, and 2402delG, wherein nucleotides are numbered by reference to SEQ ID NO:2.

In some embodiments ARID1A mutations useful for detecting pancreatic cancer are IVS10+1G>A, 1945_1946insT, 2296dupC, 5965C>T, 5965C>T, 6287C>G, 1585C>T, 5548dupG, and 2402delG, wherein nucleotides are numbered by reference to SEQ ID NO:2.

Prostate Cancer

In some embodiments the cancer is prostate cancer. In some embodiments ARID1A mutations useful for detecting prostate cancer include those listed in Table 2, wherein nucleotides are numbered by reference to SEQ ID NO:2.

In some embodiments ARID1A mutations useful for detecting prostate cancer are 3977delC, 5548dupG, and 3999_410delGCA, wherein nucleotides are numbered by reference to SEQ ID NO:2.

Individuals to be Tested

Individuals to be tested include those suspected of having a cancer, as well as individuals who have no apparent signs of cancer. Individuals to be tested can be asymptomatic or may have one or more symptoms of a cancer.

In some embodiments the individual has a symptom of ovarian cancer, including OCCC, such as an accumulation of ascites fluid, and/or a predisposing condition such as endometriosis.

In some embodiments the individual has a symptom of breast cancer, such as a breast lump or thickening, bloody discharge from the nipple, change in size or shape of a breast, changes to the skin over the breast (such as dimpling), inverted nipple, peeling, scaling or flaking of the nipple or breast skin; and redness or pitting of the skin over the breast.

In some embodiments the individual has a symptom of colon cancer, such as a change in bowel habits, including diarrhea or constipation, a change in stool consistency, rectal bleeding, and persistent abdominal discomfort, such as cramps, gas, or pain.

In some embodiments the individual has a symptom of gastric cancer, including abdominal fullness or pain, dark stools, difficulty swallowing, excessive belching, general decline in health, loss of appetite, nausea and vomiting, premature abdominal fullness after meals, vomiting blood, weakness or fatigue, and unintentional weight loss.

In some embodiments the individual has a symptom of lung cancer, including persistent cough, coughing up blood, shortness of breath, wheezing, chest pain, loss of appetite, and unintended weight loss.

In some embodiments the individual has a symptom of brain cancer, including headache; seizure; confusion or other changes in mental function; change in alertness (including sleepiness, unconsciousness, and coma); changes in sensory functions (hearing, taste, smell); difficulty swallowing, writing, walking, or reading; dizziness or vertigo; asymmetric pupils; uncontrollable movements; tremors; muscle weakness; numbness or tingling; personality, mood, behavioral, or emotional changes; and problems with eyesight, including decreased vision, double vision, or total loss of vision.

In some embodiments the individual has a symptom of pancreatic cancer, including pain or discomfort in the upper part of the belly or abdomen, loss of appetite and weight loss, jaundice, dark urine, clay-colored stools, fatigue, weakness, nausea, and vomiting.

In some embodiments the individual has a symptom of prostate cancer, such as delayed or slowed start of urinary stream; dribbling or leakage of urine, most often after urinating; slow urinary stream; straining when urinating, or not being able to empty out all of the urine; or blood in the urine or semen.

In some embodiments the described methods can be used to monitor an individual who has one or more risk factors for developing a cancer. One can readily identify individuals with an increased risk or family history of cancer, such as OCCC, breast cancer, colon cancer, gastric cancer, lung cancer, brain cancer (e.g., medulloblastoma), pancreatic cancer, and prostate cancer. Typically, inquiries are made about an individual's family history of the cancer. If two or more first-degree relatives (sibling-sibling or parent-child) or second-degree relatives (uncle/aunt-cousin, grandparent-grandchild, etc.) in a family have been diagnosed with the cancer, then individuals in the family can be identified as having a family history of the cancer and/or as having an increased risk of developing the cancer.

Other recognized indices of elevated risk of various cancers can be determined by standard clinical tests or medical history. For example, in some embodiments, an individual has a predisposing condition such as *Helicobacter pylori* infection, history of an adenomatous gastric polyp larger than 2 centimeters, history of chronic atrophic gastritis, history of pernicious anemia, or smoking, intestinal polyps, a history of smoking, exposure to second-hand smoke, high levels of air pollution, high levels of arsenic in drinking water, exposure to radon gas or asbestos, radiation therapy (e.g., to the lungs or brain), an inherited condition with an increased risk of brain tumors, such as neurofibromatosis, Von Hippel-Lindau syndrome, Li-Fraumeni syndrome, and Turcot syndrome, obesity, age, sex, exposure to agent orange or cadmium, alcohol abuse, and high fat diet.

Methods of Detecting Mutations

Methods of detecting mutations in PPP2R1A or ARID1A are useful for a variety of purposes, including, but not limited to, detecting cancer, diagnosing cancer, contributing to a diagnosis of cancer, confirming a diagnosis of cancer, identifying appropriate treatments for cancer, monitoring treatment of cancer, and evaluating treatment protocols for cancer, including ovarian clear cell carcinoma, breast cancer, colon cancer, gastric cancer, lung cancer, medulloblastoma, pancreatic cancer, and prostate cancer.

A biological sample, i.e., tissue or fluid, can be tested for a mutation in PPP2R1A or ARID1A or for diminished expression from ARID1A or for overexpression from PPP2R1A. In non-tumor samples, a detected mutation is likely to be a germline mutation. The biological sample can be obtained by any suitable means, including biopsy, surgery, and aspiration of an appropriate fluid. Biological samples which can be tested include without limitation suspected cancerous tissues, stool, sputum, and biological fluids such as tears, saliva, blood, plasma, serum, urine, ascites, and bronchioalveolar lavage. Cells which can be tested include, but are not limited to, neurons, glia, skin, blood cells, bone cells, colorectal cells, heart cells, lung cells, stomach cells, smooth muscle cells, striated muscle cells, thymus cells, thyroid cells, ovarian cells, uterine cells, kidney cells, and breast cells.

Obtaining Cells

Cells to be tested can be obtained from individuals using methods well known in the art. For example, in some embodiments ovarian cells are obtained by biopsy (e.g., Papanicolaou or "Pap" smear). In other embodiments, ovarian cells are obtained from a fluid sample. For example, a sample of ascites fluid can be obtained using needle aspiration. Culdocentesis can be used to obtain fluid from the space surrounding the ovaries. Paracentesis can be used to remove fluid from the abdominal cavity.

Cells can be obtained from patients suspected of having breast cancer using procedures such as fine needle aspiration (FNA), core biopsy (e.g., ultrasound-guided core biopsy and stereotactic biopsy), open excisional biopsy, and sentinel node biopsy.

Cells can be obtained from patients suspected of having colon cancer by biopsy during colonoscopy, flexible sigmoidoscopy, or surgery.

Cells can be obtained from patients suspected of having gastric cancer by biopsy during endoscopy.

Cells can be obtained from patients suspected of having lung cancer by taking a biopsy during bronchoscopy or by needle biopsy.

Cells can be obtained from patients suspected of having brain cancer by biopsy during surgery or from a sample of cerebrospinal fluid.

Cells can be obtained from patients suspected of having pancreatic cancer using FNA or brush biopsy.

Cells can be obtained from patients suspected of having prostate cancer by transrectal, transurethral, or transperineal biopsy.

Reference Sequences

The reference genomic DNA sequence for ARID1A is provided in SEQ ID NO:1. The reference cDNA (coding) sequence for ARID1A is provided in SEQ ID NO:2. The reference amino acid sequence of ARID1A protein is provided in SEQ ID NO:3.

The reference genomic DNA sequence for PPP2R1A is provided in SEQ ID NO:4. The reference cDNA (coding) sequence for PPP2R1A is provided in SEQ ID NO:5. The reference amino acid sequence of PPP2R1A protein is provided in SEQ ID NO:6.

Nucleic Acids

Isolated nucleic acids (e.g., DNA) comprising a portion of an PPP2R1A or ARID1A gene sequence comprising one of the mutations identified in Tables 1, S3, S5, and 2 can be used as primers or probes for mutation detection. The isolated nucleic acids may have 17, 18, 19, 20, 21, 25 or 30 to about 100, 200, 300, 400 or 500 consecutive nucleotides of ARID1A genomic DNA or cDNA, spanning and/or containing one of the mutations identified in Tables 1, S3, S5, and 2. For example, isolated nucleic acids may have from 18, 19, 20 or 21 to about 100, 200, 300 400 or 500 nucleotides comprising at least 18, 19, 20 or 21 consecutive nucleotides spanning nucleotides 3659-3684, 3854-3855, 553, 903-904, 585, or 3391 numbered according to ARID1A cDNA (SEQ ID NO:2) or nucleotide 547 numbered according to PPP2R1A cDNA (SEQ ID NO:5). Pairs of primers can be used to amplify portions of PPP2R1A or ARID1A that comprise the disclosed mutations.

Mutations in PPP2R1A and ARID1A include deletions, insertions, duplications, substitutions (missense or nonsense mutations), etc. Such mutations, alterations, and defects can be detected inter alia by comparing to a wild type in another (non-tumor) tissue of an individual or by comparing to reference sequences, for example in databases or as provided in this disclosure. Mutations that are found in all tissues of an individual are genomic mutations, whereas those that occur only in tumor tissue are somatic mutations. Examples of PPP2R1A and ARID1A mutations include those in Table 1 and Table S3. Other examples of PPP2R1A and ARID1A mutations include those in Table S5. Other examples of ARID1A mutations include those in Table 2.

In various embodiments, mutations in the PPP2R1A and ARID1A genes, alterations in PPP2R1A and ARID1A gene expression, or structural alterations in PPP2R1A and ARID1A proteins can be analyzed in a patient sample by any suitable technique known in the art which is sufficiently sensitive. Non-limiting examples are described below.

Techniques involving genomic DNA, mRNA, or cDNA can be used. In a nucleic acid-based detection method, genomic DNA is first obtained (using any standard technique) from ovarian cells of an individual to be tested. If appropriate, cDNA can be prepared or mRNA can be obtained. In some embodiments, nucleic acids can be amplified by any known nucleic acid amplification technique such as PCR, to a sufficient quantity and purity, and further analyzed to detect mutations. For example, genomic DNA can be isolated from a sample, and all exonic sequences and the intron/exon junction regions including the regions required for exon/intron splicing can be amplified into one or more amplicons, and further analyzed for the presence or absence of mutations.

Nucleotide sequencing methods can be used to detect the presence or absence of mutations. Various sequencing techniques are generally known and widely used in the art including the Sanger method and Gilbert chemical method. Pyrosequencing monitors DNA synthesis in real time using a luminometric detection system. Pyrosequencing has been shown to be effective in analyzing genetic polymorphisms such as single-nucleotide polymorphisms and thus can also be used. See Nordstrom et al., *Biotechnol. Appl. Biochem.* 31(2):107-112 (2000); Ahmadian et al., *Anal. Biochem.*, 280:103-110 (2000). The obtained sequence is then compared to a wild-type reference sequence such as the reference sequences identified in Table S3 and provided in this disclosure.

Mutation scanning in a target gene can also be carried out using denaturing high pressure liquid chromatography (dH-PLC). Specifically, the target gene is first amplified by PCR into different amplicons, and each amplicon is analyzed by dHPLC to detect the presence or absence of heterozygosity in each amplicon. The heterozygous amplicons thus identified are further sequenced to detect mutations. See, e.g., Cao et al., *Breast Cancer Res Treat.*, 114(3):457-62 (2009).

High resolution melting analysis can also be used in the disclosed methods. Like dHPLC. PCR amplification is used to produce amplicons from the target gene, and each amplicon is analyzed by high resolution melting analysis to detect the presence or absence of heterozygosity in each amplicon. The heterozygous amplicons thus identified are further sequenced to detect mutations. See, e.g., Jiménez et al., *Clin Biochem.*, 42(15):1572-6 (2009).

Restriction fragment length polymorphism (RFLP) and amplified fragment length polymorphism (AFLP) methods may also be useful techniques. In particular, if a mutation in the target nucleic acid region results in the elimination or creation of a restriction enzyme recognition site, then digestion of the target DNA with that particular restriction enzyme will generate an altered restriction fragment length pattern. Thus, a detected RFLP or AFLP will indicate the presence of a mutation.

Another useful approach is the single-stranded conformation polymorphism assay (SSCA), which is based on the altered mobility of a single-stranded target DNA spanning the mutations of interest. A single nucleotide change in the target sequence can result in different intramolecular base pairing pattern, and thus different secondary structure of the single-stranded DNA, which can be detected in a non-denaturing gel. See Orita et al., *Proc. Natl. Acad. Sci. USA*, 86:2776-2770 (1989). Denaturing gel-based techniques such as clamped denaturing gel electrophoresis (CDGE) and denaturing gradient gel electrophoresis (DGGE) detect differences in migration rates of mutant sequences as compared to wild-type sequences in denaturing gel. See Miller et al., *Biotechniques.* 5:1016-24 (1999); Sheffield et al., *Am. J. Hum, Genet.,* 49:699-706 (1991); Wartell et al., *Nucleic Acids Res.,* 18:2699-2705 (1990); and Sheffield et al., *Proc. Natl. Acad. Sci. USA,* 86:232-236 (1989). In addition, the double-strand conformation analysis (DSCA) can also be useful. See Arguello et al., *Nat. Genet.* 18:192-194 (1998).

The presence or absence of a mutation at a particular locus in a genomic region of an individual can also be detected using the amplification refractory mutation system (ARMS) technique. See e.g., European Patent No. 0,332,435; Newton et al., *Nucleic Acids Res.,* 17:2503-2515 (1989); Fox et al., *Br. J. Cancer,* 77:1267-1274 (1998); Robertson et al., *Eur. Respir. J.,* 12:477-482 (1998). In the ARMS method, a primer is synthesized matching the nucleotide sequence immediately 5' upstream from the locus being tested except that the 3'-end nucleotide which corresponds to the nucleotide at the locus is a predetermined nucleotide. For example, the 3'-end nucleotide can be the same as that in the mutated locus. The primer can be of any suitable length so long as it hybridizes to the target DNA under stringent conditions only when its 3'-end nucleotide matches the nucleotide at the locus being tested. Preferably the primer has at least 12 nucleotides, more preferably from about 18 to 50 nucleotides. If the individual tested has a mutation at the locus and the nucleotide therein matches the 3'-end nucleotide of the primer, then the primer can be further extended upon hybridizing to the target DNA template, and the primer can initiate a PCR amplification reaction in conjunction with another suitable PCR primer. In contrast, if the nucleotide at the locus is of wild type, then primer extension cannot be achieved. Various forms of ARMS techniques can be used. See e.g., Gibson et al., *Clin. Chem.* 43:1336-1341 (1997).

Similar to the ARMS technique is the mini sequencing or single nucleotide primer extension method, which is based on the incorporation of a single nucleotide. An oligonucleotide primer matching the nucleotide sequence immediately 5' to the locus being tested is hybridized to the target DNA or mRNA in the presence of labeled dideoxyribonucleotides. A labeled nucleotide is incorporated or linked to the primer only when the dideoxyribonucleotides matches the nucleotide at the variant locus being detected. Thus, the identity of the nucleotide at the variant locus can be revealed based on the detection label attached to the incorporated dideoxyribonucleotides. See Syvanen et al., *Genomics,* 8:684-692 (1990); Shumaker et al., *Hum. Mutat.,* 7:346-354 (1996); Chen et al., *Genome Res.,* 10:549-547 (2000).

Another set of useful techniques are oligonucleotide ligation assays (OLA) in which differentiation between a wild-type locus and a mutation is based on the ability of two oligonucleotides to anneal adjacent to each other on the target DNA molecule allowing the two oligonucleotides joined together by a DNA ligase. See Landergren et al., *Science,* 241:1077-1080 (1988); Chen et al, *Genome Res.,* 8:549-556 (1998); Iannone et al., *Cytometry,* 39:131-140 (2000). Thus, for example, to detect a single-nucleotide mutation at a particular locus in a genomic region, two oligonucleotides can be synthesized, one having the genomic sequence just 5' upstream from the locus with its 3' end nucleotide being identical to the nucleotide in the variant locus, the other having a nucleotide sequence matching the genomic sequence immediately 3' downstream from the variant locus. The oligonucleotides can be labeled for the purpose of detection. Upon hybridizing to the target nucleic acid under a stringent condition, the two oligonucleotides are subject to ligation in the presence of a suitable ligase. The ligation of the two oligonucleotides would indicate that the target DNA has a mutation at the locus being detected.

Detection of mutations can also be accomplished by a variety of hybridization-based approaches. For example, allele-specific oligonucleotides are useful. See Conner et al., *Proc. Natl. Acad. Sci. USA,* 80:278-282 (1983), Saiki et al, *Proc. Natl. Acad. Sci. USA,* 86:6230-6234 (1989). Oligonucleotide probes (allele-specific) hybridizing specifically to an allele having a particular mutation at a particular locus but not to other alleles can be designed by methods known in the art. The probes can have a length of, e.g., from 10 to about 50 nucleotide bases. The target DNA and the oligonucleotide probe can be contacted with each other under conditions sufficiently stringent such that the mutations can be distinguished from the alternative variant/allele at the same locus based on the presence or absence of hybridization. The probe can be labeled to provide detection signals. Alternatively, an allele-specific oligonucleotide probe can be used as a PCR amplification primer in an "allele-specific PCR" and the presence or absence of a PCR product of the expected length would indicate the presence or absence of a particular mutation.

Other useful hybridization-based techniques allow two single-stranded nucleic acids annealed together even in the presence of mismatch due to nucleotide substitution, insertion or deletion. The mismatch can then be detected using various techniques. For example, the annealed duplexes can be subjected to electrophoresis. A mismatched duplex can be detected based on an electrophoretic mobility that is different from that of a perfectly matched duplex. See Cariello, *Human Genetics,* 42:726 (1988). Alternatively, in a RNase protection assay, a RNA probe can be prepared spanning the mutations site to be detected and having a detection marker. See Giunta et al., *Diagn. Mol. Path.,* 5:265-270 (1996); Finkelstein et al., *Genomics.* 7:167-172 (1990); Kinzler et al., *Science* 251:1366-1370 (1991). The RNA probe can be hybridized to the target DNA or mRNA forming a heteroduplex that is then subject to the ribonuclease RNase A digestion. RNase A digests the RNA probe in the heteroduplex only at the site of mismatch. The digestion can be determined on a denaturing electrophoresis gel based on size variations. In addition, mismatches can also be detected by chemical cleavage methods known in the art. See e.g., Roberts et al., *Nucleic Acids Res.,* 25:3377-3378 (1997).

A great variety of improvements and variations have been developed in the art on the basis of the above-described basic techniques, and can all be useful in detecting mutations. For example, the "sunrise probes" or "molecular beacons" utilize the fluorescence resonance energy transfer (FRET) property and give rise to high sensitivity. See Wolf et al., *Proc. Nat. Acad. Sci. USA,* 85:8790-8794 (1988). Typically, a probe spanning the nucleotide locus to be detected is designed into a hairpin-shaped structure and labeled with a quenching fluorophore at one end and a reporter fluorophore at the other end. In its natural state, the fluorescence from the reporter fluorophore is quenched by the quenching fluorophore due to the proximity of one fluorophore to the other. Upon hybridization of the probe to the target DNA, the 5' end is separated apart from the 3'-end and thus fluorescence signal is regenerated. See Nazarenko et al., *Nucleic Acids Res.,* 25:2516-2521 (1997); Rychlik et al., *Nucleic Acids Res.,* 17:8543-8551 (1989); Sharkey et al., *Bio/Technology* 12:506-509 (1994); Tyagi et al., *Nat. Biotechnol.,* 14:303-308 (1996); Tyagi et al., *Nat. Biotechnol.,* 16:49-53 (1998). A homo-tag assisted non-dimer system (HANDS) can be used in combination with the molecular beacon methods to suppress primer-dimer accumulation. See Brownie et al., *Nucleic Acids Res.,* 25:3235-3241 (1997).

A dye-labeled oligonucleotide ligation assay, which is a FRET-based method that combines the OLA assay and PCR, can be used. See Chen et al., *Genome Res.* 8:549-556 (1998). TaqMan is another FRET-based method for detecting mutations. A TaqMan probe can be an oligonucleotide designed to have the nucleotide sequence of the human nucleic acid spanning the variant locus of interest and to differentially hybridize with different alleles. The two ends of the probe are labeled with a quenching fluorophore and a reporter fluorophore, respectively. The TaqMan probe is incorporated into a PCR reaction for the amplification of a target nucleic acid region containing the locus of interest using Taq polymerase. Because Taq polymerase exhibits 5'-3' exonuclease activity but has no 3'-5' exonuclease activity, if the TaqMan probe is annealed to the target DNA template, the 5'-end of the TaqMan probe will be degraded by Taq polymerase during the PCR reaction thus separating the reporting fluorophore from the quenching fluorophore and releasing fluorescence signals. See Holland et al., *Proc. Natl. Acad. Sci. USA,* 88:7276-7280 (1991); Kalinina et al., *Nucleic Acids Res.,* 25:1999-2004 (1997); Whitcombe et al., *Clin. Chem.,* 44:918-923 (1998).

Chemiluminescence-based techniques can be used. For example, an oligonucleotide probe can be designed to hybridize to either the wild-type or a variant locus but not both. The probe is labeled with a highly chemiluminescent acridinium ester. Hydrolysis of the acridinium ester destroys chemiluminescence. The hybridization of the probe to the target DNA prevents the hydrolysis of the acridinium ester. Therefore, the presence or absence of a particular mutation in the target DNA is determined by measuring chemiluminescence changes. See Nelson et al., *Nucleic Acids Res.,* 24:4998-5003 (1996).

The detection of mutations can also be based on the "base excision sequence scanning" (BESS) technique. The BESS method is a PCR-based mutation scanning method. BESS T-Scan and BESS G-Tracker are generated which are analogous to T and G ladders of dideoxy sequencing. Mutations are detected by comparing the sequence of normal and mutant DNA. See, e.g., Hawkins et al., *Electrophoresis,* 20:1171-1176 (1999).

Mass spectrometry can be used. See Graber et al., *Curr. Opin. Biotechnol.,* 9:14-18 (1998). For example, in the primer oligo base extension (PROBE™) method, a target nucleic acid is immobilized to a solid-phase support. A primer is annealed to the target immediately 5' upstream from the locus to be analyzed. Primer extension is carried out in the presence of a selected mixture of deoxyribonucleotides and dideoxyribonucleotides. The resulting mixture of newly extended primers is then analyzed by MALDI-TOF. See e.g., Monforte et al., *Nat. Med.,* 3:360-362 (1997).

Microchip or microarray technologies are also applicable to the disclosed methods as will be apparent to a skilled artisan in view of this disclosure. For example, isolated genomic DNA can be prepared and hybridized to a DNA microchip having probes designed based on the target gene sequence.

As is apparent from the above survey of the suitable detection techniques, it may or may not be necessary to amplify the target nucleic acid, i.e., the genomic region of interest, or the corresponding cDNA or mRNA to increase the number of target molecules, depending on the detection techniques used. For example, most PCR-based techniques combine the amplification of a portion of the target and the detection of the mutations. PCR amplification is well known in the art and is disclosed in U.S. Pat. Nos. 4,683,195 and 4,800.159. For non-PCR-based detection techniques, if necessary, the amplification can be achieved by, e.g., in vivo plasmid multiplication, or by purifying the target DNA from a large amount of tissue or cell samples. See generally, Sambrook et al., *Molecular Cloning: A Laboratory Manual,* $2^{nd}$ ed., Cold Spring Harbor Laboratory, Cold Spring Harbor, N.Y., 1989. However, even with scarce samples, many sensitive techniques have been developed in which small genetic variations such as single-nucleotide substitutions can be detected without having to amplify the target DNA in the sample. For example, techniques have been developed that amplify the signal as opposed to the target DNA by, e.g., employing branched DNA or dendrimers that can hybridize to the target DNA. The branched or dendrimer DNAs provide multiple hybridization sites for hybridization probes to attach thereto thus amplifying the detection signals. See Detmer et al., *J. Clin. Microbiol.* 34:901-907 (1996); Collins et al., *Nucleic Acids Res.,* 25:2979-2984 (1997); Horn et al., *Nucleic Acids Res.,* 25:4835-4841 (1997); Horn et al., *Nucleic Acids Res.,* 25:4842-4849 (1997); Nilsen et al., *J. Theor. Biol.,* 187:273-284 (1997).

In yet another technique for detecting mutations, the INVADER®assay utilizes a novel linear signal amplification technology that improves upon the long turnaround times required of the typical PCR DNA sequenced-based analysis. See Cooksey et al., *Antimicrobial Agents and Chemotherapy* 44:1296-1301 (2000). This assay is based on cleavage of a unique secondary structure formed between two overlapping oligonucleotides that hybridize to the target sequence of interest to form a "flap." Each "flap" then generates thousands of signals per hour. Thus, the results of this technique can be easily read, and the methods do not require exponential amplification of the DNA target. The INVADER®system utilizes two short DNA probes, which are hybridized to a DNA target. The structure formed by the hybridization event is recognized by a special cleavase enzyme that cuts one of the probes to release a short DNA "flap." Each released "flap" then binds to a fluorescently-labeled probe to form another cleavage structure. When the cleavase enzyme cuts the labeled probe, the probe emits a detectable fluorescence signal. See e.g. Lyamichev et al., *Nat. Biotechnol.,* 17:292-296 (1999).

The rolling circle method is another method that avoids exponential amplification. Lizardi et al., *Nature Genetics,* 19:225-232 (1998). For example, SNIPER™, a commercial embodiment of this method, is a sensitive, high-throughput SNP scoring system designed for the accurate fluorescent detection of specific variants. For each mutation, two linear, allele-specific probes are designed. The two allele-specific probes are identical with the exception of the 3'-base, which is varied to complement the variant site. In the first stage of the assay, target DNA is denatured and then hybridized with a pair of single, allele-specific, open-circle oligonucleotide probes. When the 3'-base exactly complements the target DNA, ligation of the probe will preferentially occur. Subsequent detection of the circularized oligonucleotide probes is by rolling circle amplification, whereupon the amplified probe products are detected by fluorescence. See Clark and Pickering, *Life Science News* 6, 2000, *Amersham Pharmacia Biotech* (2000).

Techniques that avoid amplification all together include, e.g., surface-enhanced resonance Raman scattering (SERRS), fluorescence correlation spectroscopy, and single-molecule electrophoresis. In SERRS, a chromophore-nucleic acid conjugate is absorbed onto colloidal silver and is irradiated with laser light at a resonant frequency of the chromophore. See Graham et al., *Anal. Chem.,* 69:4703-4707 (1997). The fluorescence correlation spectroscopy is based on the spatio-temporal correlations among fluctuating light signals and trapping single molecules in an electric field. See Eigen et al., *Proc. Natl. Acad. Sci. USA,* 91:5740-5747 (1994). In single-molecule electrophoresis, the electrophoretic velocity of a fluorescently tagged nucleic acid is determined by measuring the time required for the molecule to travel a predetermined distance between two laser beams. See Castro et al., *Anal. Chem.* 67:3181-3186 (1995).

In addition, the allele-specific oligonucleotides (ASO) can also be used in in situ hybridization using tissues or cells as samples. The oligonucleotide probes which can hybridize differentially with the wild-type gene sequence or the gene sequence harboring a mutation may be labeled with radioactive isotopes, fluorescence, or other detectable markers. In situ hybridization techniques are well known in the art and their adaptation to the disclosed methods for detecting the presence or absence of a mutation in a genomic region of a particular individual should be apparent to a skilled artisan in view of this disclosure.

Proteins

Protein-based detection techniques may also prove to be useful, especially when the mutations causes amino acid substitutions or deletions or insertions or frameshift that affect the protein primary, secondary or tertiary structure. To detect the amino acid variations, protein sequencing techniques may be used. Alternatively, the recently developed HPLC-microscopy tandem mass spectrometry technique can be used for determining the amino acid sequence variations. See Gatlin et al., *Anal. Chem.,* 72:757-763 (2000).

Other useful protein-based detection techniques include immunoaffinity assays based on antibodies selectively immunoreactive with mutant proteins or specifically with wild-type proteins. Antibodies can be used to immunoprecipitate specific proteins from solution samples or to immunoblot proteins separated by, e.g., polyacrylamide gels. Immunocytochemical methods can also be used in detecting specific protein in tissues or cells. Other well-known antibody-based techniques can also be used including, e.g., enzyme-linked immunosorbent assay (ELISA), radioimmunoassay (RIA), immunoradiometric assays (IRMA) and immunoenzymatic assays (IEMA), including sandwich assays using monoclonal or polyclonal antibodies. See e.g., U.S. Pat. Nos. 4,376,110 and 4,486,530.

Antibodies (or fragments thereof) can be employed histologically—e.g., IHC, immunofluorescence or immuno-electron microscopy—for in situ detection of peptides encoded by nucleic acids of interest. In situ detection can be accomplished by removing a histological specimen from a patient, and applying thereto a labeled antibody. The antibody (or its fragment) is preferably applied by overlaying the labeled antibody (or fragment) onto a biological sample. Through the use of such a procedure, it is possible to determine not only the presence and amount of the expression product of a target gene, but also its distribution in the examined tissue. A skilled artisan will readily perceive that any of a wide variety of histological methods (e.g., staining procedures) can be modified to achieve such in situ detection.

U.S. Pat. No. 5,965,377 discloses an antibody-based method for determining the presence of mutated protein in cells expressing the protein, wherein the normal protein contains amino-terminus and carboxy-terminus regions and wherein the mutated protein is typically a foreshortened protein from which carboxy-terminus regions are missing. This method can be adapted to detect truncation mutations in PPP2R1A or ARID1A proteins. Specifically, an antibody reactive with the N-terminus of the target protein and an antibody reactive with the C-terminus of the target protein are used to react with a cell sample, and the ratio between the reactivity with the C-terminus and N-terminus can be obtained. If the reactivity with the C-terminus is about zero or no greater than about half of the reactivity with the N-terminus in the sample, it would indicate the presence of a truncation mutation in the gene. The antibody reactivity can be measured by any suitable immunoassays, e.g., immunohistochemistry (IHC) and ELISA.

The antibody based methods described above can also be used to determine generally the expression level of PPP2R1A and ARID1A, as will be apparent to skilled artisan.

For purposes of detecting a reduced level of gene expression, either mRNA or protein level in a sample from a patient can be determined by conventional methods known in the art. Protein expression level in a sample can be determined using an immunoassay described above. For mRNA level, typically hybridization of DNA probes or primers is utilized. For example, for mRNA expression level, qRT-PCT can be used. mRNA can be isolated from a particular sample, and the target gene mRNA, and preferably in addition, a reference gene mRNA (typically a housekeeping gene), are amplified by qRT-PCR, and the relative amount of the target gene mRNA is determined, which is compared to a predetermined reference standard level (e.g., an average level determined in a plurality of normal samples). Alternatively, digital PCR is also useful.

Additionally, gene expression levels can also be detected indirectly by determining the methylation status of the target gene. If the target gene is methylated at a greater extent than normal, then the target gene expression is usually reduced. Methods for determining gene methylation status are well known in the art.

Additional Diagnostic Tests

In some embodiments one or more other diagnostic tests can follow a disclosed method. In some embodiments one or more other diagnostic tests can be performed in conjunction with a disclosed method.

Diagnostic tests for OCCC include imaging studies (e.g., ultrasound, CT scan, endoscopic ultrasound), blood tests (e.g., CA125 testing), microscopic examination of cells obtained from fluid (e.g., ascites fluid, fluid from the space surrounding the ovaries, or fluid from the abdominal cavity) and biopsies (e.g., percutaneous needle biopsy or Papanicolaou smear).

Diagnostic tests for breast cancer include mammograms, ultrasound, MRI, CAT scans, PET scans, and biopsies.

Diagnostic tests for colon cancer include colonoscopies (including high-definition colonoscopy and virtual colonoscopy) and biopsies.

Diagnostic tests for gastric cancer include esophagogastroduodenoscopy (EGD), biopsy, and imaging studies (e.g., upper GI series).

Diagnostic tests for lung cancer include chest x-ray, sputum cytology test, CT scan, MRI, PET scan, bronchoscopy combined with biopsy, pleural biopsy, CT-scan-directed needle biopsy, mediastinoscopy with biopsy, and open lung biopsy.

Diagnostic tests for brain cancer include CT scans, EEGs, examination of cerebral spinal fluid, MRIs, and biopsy.

Diagnostic tests for pancreatic cancer include CT scan, MRI, endoscopic retrograde cholangiopancreatography (ERCP), endoscopic ultrasound, and pancreatic biopsy.

Diagnostic tests for prostate cancer include PSA testing and biopsy.

Use of Test Results

The result of the tests described herein can be recorded in a tangible medium, such as such as paper or a computer readable medium (for example, a diskette, CD-ROM, ROM, or fixed disk, memory drive, a solid state memory device, or an optical storage device). Results can be displayed on a computer screen or the screen of a hand-held device such as a smartphone.

In some embodiments, following a test as described above, a diagnosis of cancer is provided to the patient and/or to a medical professional, such as the patient's doctor. The diagnosis can be provided orally, in writing, or via electronic media.

In some embodiments, a course of treatment is recommended to the patient. "Treatment" as used in this context includes surgery and chemotherapy as well as surveillance for the cancer via biopsy or imaging techniques or by assessing levels of diagnostic markers such as prostate specific antigen (prostate cancer), MUC1 (multiple myeloma), carcinoembryonic antigen (CEA; colon cancer), and CA125 (ovarian cancer). Administration of a therapy to a patient in treatment does not require any particular effect or cure. In some embodiments, appropriate treatments for OCCC, breast cancer, colon cancer, gastric cancer, lung cancer, medulloblastoma, pancreatic cancer, or prostate cancer are identified. In some embodiments, treatments for OCCC, breast cancer, colon cancer, gastric cancer, lung cancer, medulloblastoma, pancreatic cancer, or prostate cancer are modified.

Cancer tissues can be categorized on the basis of which, if any, PPP2R1A and/or ARID1A mutation(s) they contain. Somatic mutations are identified on the basis of a difference between an affected tissue and a normal tissue of the same individual. Categorization of the tissue can be used for stratifying patients for clinical trials, for analyzing data from clinical trials, for correlating with prognostic data (such as recurrence, metastasis, and life expectancy), as well as for selecting an appropriate course of treatment for a cancer patient. Categorization can be correlated with efficacy of a therapeutic agent to enable prescription of drugs for individuals with higher probability of successful treatment. The categorization can be used in conjunction with other data, for example, histopathological data, to identify a cancer. Somatic mutation analysis can be used in any tissue or body sample to diagnose cancer. Presence of a mutant PPP2R1A and/or ARID1A protein or PPP2R1A and/or ARID1A coding sequence in a tissue or body sample indicates the presence of cancer cells, either in the sample itself, or in a tissue which drains into the sample. Thus, for example, detection of PPP2R1A and/or ARID1A mutations in a fecal sample reflects the presence of colorectal cancer cells in the individual from whom the sample was taken. Detection of PPP2R1A and/or ARID1A mutations in a sample of ovarian cells reflects the presence of ovarian cancer in the individual from whom the sample was taken.

Kits

This disclosure also provides kits for use in the disclosed methods. The kits may include a carrier for the various components of the kits. The carrier can be a container or support, in the form of, e.g., bag, box, tube, rack, and is optionally compartmentalized. The kit also includes various components useful in detecting mutations, or determining gene expression (mRNA and protein) levels, using the above-discussed detection techniques. For example, the detection kit may include one or more oligonucleotides useful as primers for amplifying all or a portion of the PPP2R1A and ARID1A genomic or cDNA. The detection kit may also include one or more oligonucleotide probes for hybridization to the PPP2R1A and ARID1A genomic or cDNA or mRNA. Optionally the oligonucleotides are affixed to a solid support, e.g., incorporated in a microchip or microarray included in the kit.

In some embodiments, a detection kit contains one or more antibodies selectively immunoreactive with PPP2R1A and ARID1A protein, for example antibodies selectively immunoreactive with the N-terminus of PPP2R1A and ARID1A protein, and/or antibodies selectively immunoreactive with the C-terminus of PPP2R1A and ARID1A protein.

Various other components useful in the detection techniques can also be included in a detection kit. Examples of such components include, but are not limited to, Taq polymerase, deoxyribonucleotides, dideoxyribonucleotides other primers suitable for the amplification of a target DNA sequence, RNase A, mutS protein, and the like. A detection kit can include instructions on using the kit for the various embodiments described above.

Therapeutic Methods

This disclosure also provides methods of inhibiting growth of cancer cells. In some embodiments a polynucleotide encoding ARID1A is administered to cancer cells, such as ovarian cancer cells. The cells can be in culture or can be in vivo, such as in an animal cancer model or a human. The polynucleotide can be administered by intratumoral injection.

Screening Methods

Test compounds can be tested to determine whether they have a differential effect in a tumor comprising a mutation in ARID1A or PPP2R1A. In some embodiments the effect of a test compound on a tumor cell is compared with the effect of the test compound on a cell that does not comprise the mutation (either a non-tumor cell or a tumor cell that does not comprise a mutation in ARID1A or PPP2R1A. The results can be recorded as described above. The differential effect can be, for example, inhibition of tumor cell growth, inhibition of tumor cell proliferation, stimulation of apoptosis, or inhibition of tumor growth. The tested cells can be in vitro or can be in an animal cancer model.

Unless otherwise defined, all technical and scientific terms used herein have the same meaning as commonly understood by one of ordinary skill in the art to which this disclosure pertains. Although methods and materials similar or equivalent to those described herein can be used in the practice of the disclosed methods, suitable methods and materials are described below. In case of conflict, the present specification, including definitions, will control. In addition, the materials, methods, and examples are illustrative only and not intended to be limiting.

REFERENCES

1. Cho & Ie, Annu Rev Pathol 4, 287 (2009).
2. Erzen et al., Gynecol Oncol 83, 100 (2001).
3. Fukunaga et al., Histopathology 30, 249 1997.
4. Marquez et al., Clin Cancer Res 11, 6116 (2005).
5. Sato et al., Cancer Res 60, 7052 (2000).
6. Veras et al., Am J Surg Pathol 33, 844 (2009).
7. Kuo et al., Am J Pathol 174, 1597 (2009).
8. Kuo et al., Clin Cancer Res 16, 1997 2010.
9. Jones et al., Science 330:228-31 (2010), supporting material on Science Online.
10. Greenman et al., Nature 446, 153 (2007).
11. Sjöblom et al., Science 314, 268-74 (2006).
12. Wood et al., Science 318, 1108-13 (2007).
13. Jones et al., Science 321, 1801-06 (2010).
14. Parsons et al. Science 321, 1807-12 (2010).
15. Vogelstein, K. W. Kinzler, Nat Med 10, 789 (2004).
16. Calin et al., Oncogene 19, 1191 (2000).
17. Tang et al., Dev Cell 10, 575 (2006).
18. Wu et al., Cell 136, 200-06 (2009).
19. Weissamn & Knudsen, Cancer Res 69, 8223-30 (2009).
20. Nagl et al., Embo J 26, 752 (2007).
21. Luo et al., Proc Natl Acad Sci USA 105, 20380 (2010).
22. Huang et al., Genes Chromosomes Cancer 46, 745-50 (2007).
23. Van Raamsdonk et al., Nature 457, 599 (2009).
24. Dalgliesh et al., Nature 463, 360-63 (2010).
25. Eshleman et al., Oncogene 12:1425-32 (1996).
26. Jones et al., Science 330:228-31 (2010).
27. Kern, Cancer Biol Ther. 1:189-94 (2002).
28. Markowitz et al., Science. 268:1336-38 (1994).
29. Medina et al., Hum Mutat 29:617-22 (2010).
30. Meyerson et al., Nat Rev Genet 11:685-96 (2010).
31. Parsons et al., Science 331:435-59 (2011).
32. Rampino et al. Science 275:967-69 (1997).
33. Varela et al., Nature 469:539-42 (2011).
34. Wang et al., Biochem J 383:319-25 (2004).
35. Wiegand et al., N Engl J Med 363:1532-43 (2010).
36. Yan et al., N Engl. J. Med. 360: 765-73 (2009).
37. Morin et al., Nature. doi: 10.1038/nature10351 (2011).
38. 1000 Genomes Project Consortium, Nature 457: 1061-73 (2010).

EXAMPLE 1

Identification of Mutations

To comprehensively explore the genetic basis of OCCC tumors, we determined the sequences of the ~18,000 protein-encoding genes listed in the RefSeq database in tumors from eight patients (Table S1). Because these tumors are composed of a mixture of neoplastic and non-neoplastic stromal cells, we purified the neoplastic cells using epithelial cell target antibodies attached to magnetic beads (Epi-CAM, Dynal) (see the Examples, below). Staining of the cells bound to the beads revealed that >90% of them were OCCC cells. This procedure thereby maximized the sensitivity of the sequencing analyses by eliminating most of the contaminating normal cells and therefore, the normal genomes from the sample. DNA from the purified cells, as well as from normal cells obtained from the blood or uninvolved tissues of the same patients, were used to generate libraries suitable for massively parallel sequencing by synthesis (see the Examples, below). Following capture of the coding sequences of the targeted genes with a SureSelect Enrichment System, the DNA was sequenced using an Illumina GAIIx platform. The average coverage of each base in the targeted regions was 84 fold and 92.7% of these bases were represented in at least 10 reads (Tables S2A-S2D).

Using stringent criteria for analysis of these data (see the Examples, below) we identified 268 somatic mutations in 253 genes among the eight tumors. The range of mutations per tumor was 13 to 125 alterations. The tumor with 125 mutations (OCC06PT) was from a patient with recurrent disease that had previously been treated with chemotherapy. Excluding OCC06PT, there was an average of 20 mutations per tumor (Tables S2A-S2D and S3). The mutation spectrum was enriched for C to T transitions at 5'-CG base pairs, similar to those of other tumors whose exomes have been sequenced (10-14). Only four genes were mutated in more than one of the eight tumors studied: PIK3CA, KRAS, PPP2R1A (protein phosphatase 2, regulatory subunit A, alpha) and ARID1A (AT-rich interactive domain-containing protein 1A). The mutations in each of these four genes, and their somatic nature, were confirmed by Sanger sequencing of the DNA from the tumor and normal tissues of the corresponding patients (examples in FIG. 1). The sequences of these four genes were then determined in the tumor and normal tissues of an additional 34 OCCC cases using PCR amplification and Sanger sequencing with the primers listed in Table S4. In total, PIK3CA, KRAS, PPP2R1A, and ARID1A mutations were identified in 40%, 4.7%, 7.1%, and 57% of the 42 tumors, respectively (Table 1).

We extended the analysis of these four genes in seven OCCC cell lines that were derived from tumors independent of those described above. In these seven cell lines we identified nine ARID1A mutations in five cell lines, three with PPP2R1A mutations, one with a KRAS mutation and four with PIK3CA, mutations (Table S5).

The nature of the somatic mutations in tumors can often be used to classify them as oncogenes or tumor suppressor genes (15). In particular, all bona fide oncogenes are mutated recurrently (that is, at the same codon, or clustered in few codons, in different tumors), and the mutations are nearly always missense. In contrast, all bona fide tumor suppressor genes are mutated at a variety of positions throughout the coding region of the gene and the mutations often truncate the encoded protein through production of a stop codon by a base substitution, an out-of-frame insertion or deletion ("indel") or a splice site mutation. Moreover, tumor suppressor gene mutations generally affect both alleles while mutations in oncogenes commonly affect only one allele.

The nature of the mutations we discovered in OCCCs could thereby be used to gain insights into their likely function. PIK3CA and KRAS are well-studied oncogenes, and the 19 mutations identified in OCCC were heterozygous and clustered; fourteen of the 17 mutations in PIK3CA were at codons 381, 542 to 546, or 1047, while both mutations in KRAS were at codon 12 (Table 1). The three mutations in PPP2R1A were similarly heterozygous and clustered, suggesting it functions, when mutated, as an oncogene (Table 1). In contrast, the 32 mutations in ARID1A were distributed throughout the coding region and all were predicted to truncate the protein through a base substitution resulting in a stop codon (9 mutations), or an out-of-frame insertion or deletions (23 mutations) (Table 1). In 10 of the 24 tumors with ARID1A mutations, both ARID1A alleles were affected through either a mutation in one allele and loss of heterozygosity of the other allele, or through two mutations which were presumably biallelic. Thus. ARID1A apparently functions as a tumor suppressor gene in OCCC, and the mutations likely inactivate the gene product.

The phosphatase PP2A is a trimer composed of a common heteromeric core enzyme composed of the PPP2CA catalytic subunit and the PPP2R1A regulatory subunit acting as a scaffold to coordinate the assembly of the catalytic subunit with a variety of other regulatory subunits. Somatic mutations in PPP2R1A are not listed in the Cancer Gene Census of the COSMIC database, although a few alterations in this gene have been previously reported (16). Functional studies have shown that PP2A is involved in the control of cell growth and division. Specifically, this protein is required for proper chromosome segregation through its interactions with Bub1 and Sgo1 (17). The two arginine residues that were somatically mutated in OCCC are highly conserved and reside within one of the HEAT domains of PPP2R1A that are involved in binding regulatory subunits.

The protein encoded by ARID1A, as its name implies, can bind to AT-rich DNA sequences and is a component of the ATP-dependent chromatin modeling complex SWI/SNF. The SWI/SNF chromatin-remodeling complex allows DNA to become accessible to repair enzymes and transcription factors, thereby influencing the epigenetic regulation of a number of genes, including genes that may play a role in cancer (18, 19). ARID1A is one of the two mutually exclusive ARID1 subunits of the SWI/SNF complex and is thought to provide specificity to this complex (18). Functional studies have implicated ARID1A in the anti-proliferative properties of the complex (20). No mutations of ARID1A are listed in the Cancer Gene Census of the COSMIC database, but chromosomal translocations that involve this gene have been identified in a breast and a lung cancer (21). Knock-down of ARID1A has been shown to make a leukemia cancer cell line resistant to Fas-mediated apoptosis (22).

The results of this study emphasize two themes in modern cancer genetics. The first is that specific tumor types are characterized by mutations in "communal cancer genes" like KRAS and PIK3CA but also by "restricted cancer genes" like PPP2R1A and ARID1A. The communal cancer genes are involved in a variety of cancers and have been extensively studied. Restricted cancer genes have been shown to play a role in specific types of leukemias and sarcomas, mainly through translocations (e.g., ABL in CML, and EWS fused to an ETS family member in Ewing's sarcoma). With the advent of whole exome sequencing, we are beginning to see similar specificity with respect to point mutations (e.g., IDH1 in gliomas (14) and GNAQ in uveal melanomas (23)). The second theme is that mutations of chromatin-modifying genes are characteristic of certain tumor types. Recent examples include the JARID1C gene in renal cell cancers (24) and now ARID1A. Epigenetic changes in cancer cells are of great interest as they are thought to open new avenues of therapeutic intervention. Genetic inactivation of ARID1A is likely to lead to epigenetic changes in cancer cells through modifications of chromatin proteins.

EXAMPLE 2

Immunoaffinity Isolation of Ovarian Clear Cell Carcinoma Cells

Because the sensitivity of mutation detection in tumor tissues can be affected by the purity of the tumor DNA analyzed, we affinity purified tumor cells using Epi-CAM antibody coated beads from 26 freshly collected ovarian clear cell carcinoma samples. Briefly, tumors were minced to small fragments (1 mm×1 mm×1 mm) and digested with collagenase I (1 mg/ml in RPMI1640 supplemented with 10% FBS) at 37° C. for 40 min. The cells were washed and incubated with 300-500 ml of Epi-CAM conjugated Dynal® (cat no: 162-03, Invitrogen) beads for 30 minutes at 2-8° C. Tumor cells that bound to the beads were separated from non-tumor cell population by a magnet and repeated sorting. Tumor cells ($\sim 2 \times 10^6$-$10^7$ cells) were then collected and their genomic DNA purified using a Qiagen DNA purification kit.

EXAMPLE 3

Preparation of Illumina Genomic DNA Library

DNA samples were obtained from patients after informed consent as described (1, 2). Genomic DNA libraries were prepared following Illumina's (Illumina, San Diego, Calif.) suggested protocol with the following modifications. (1) 3 micrograms (μg) of genomic DNA from tumor or normal cells in 100 microliters (μl) of TE was fragmented in a Covaris sonicator (Covaris, Woburn, Mass.) to a size of 100-500 bp. DNA was purified with a PCR purification kit (Cat #28104, Qiagen, Valencia, Calif.) and eluted in 35 μl of elution buffer included in the kit. (2) Purified, fragmented DNA was mixed with 40 μl of $H_2O$, 10 μl of 10×T4 ligase buffer with 10 mM ATP, 4 μl of 10 mM dNTP, 5 μl of T4

DNA polymerase, 1 μl of Klenow Polymerase, and 5 μl of T4 polynucleotide Kinase. All reagents used for this step and those described below were from New England Biolabs (NEB, Ipswich, Mass.) unless otherwise specified. The 100 μl end-repair mixture was incubated at 20° C. for 30 min, purified by a PCR purification kit (Cat #28104, Qiagen) and eluted with 32 μl of elution buffer (EB). (3) To A-tail, all 32 μl of end-repaired DNA was mixed with 5 μl of 10× Buffer (NEB buffer 2), 10 μl of 1 mM dATP and 3 μl of Klenow (exo-). The 50 μl mixture was incubated at 37° C. for 30 min before DNA was purified with a MinElute PCR purification kit (Cat #28004, Qiagen). Purified DNA was eluted with 12.5 μl of 70° C. EB and obtained with 10 μl of EB. (4) For adaptor ligation, 10 μl of A-tailed DNA was mixed with 10 μl of PE-adaptor (Illumina), 25 μl of 2× Rapid ligase buffer and 5 μl of Rapid Ligase. The ligation mixture was incubated at room temperature (RT) or 20° C. for 15 min. (5) To purify adaptor-ligated DNA, 50 μl of ligation mixture from step (4) was mixed with 200 μl of NT buffer from NucleoSpin Extract II kit (cat#636972, Clontech, Mountain View, Calif.) and loaded into NucleoSpin column. The column was centrifuged at 14000 g in a desktop centrifuge for 1 min, washed once with 600 μl of wash buffer (NT3 from Clontech), and centrifuged again for 2 min to dry completely. DNA was eluted in 50 μl elution buffer included in the kit. (6) To obtain an amplified library, ten PCRs of 25 μl each were set up, each including 12 μl of $H_2O$, 5 μl of 5× Phusion HF buffer, 0.5 μl of a dNTP mix containing 10 mM of each dNTP, 1.25 μl of DMSO, 0.5 μl of Illumina PE primer #1, 0.5 μl of Illumina PE primer #2, 0.25 μl of Hotstart Phusion polymerase, and 5 μl of the DNA from step (5). The PCR program used was: 98° C. 1 minute; 6 cycles of 98° C. for 20 seconds, 65° C. for 30 seconds, 72° C. for 30 seconds; and 72° C. for 5 min. To purify the PCR product, 250 μl PCR mixture (from the ten PCR reactions) was mixed with 500 μl NT buffer from a NucleoSpin Extract II kit and purified as described in step (5). Library DNA was eluted with 70° C. elution buffer and the DNA concentration was estimated by absorption at 260 nm.

EXAMPLE 4

Exome and Targeted Subgenomic DNA Capture

Human exome capture was performed following a protocol from Agilent's SureSelect Paired-End Version 2.0 Human Exome Kit (Agilent, Santa Clara, Calif.) with the following modifications. (1) A hybridization mixture was prepared containing 25 μl of SureSelect Hyb #1, 1 μl of SureSelect Hyb #2, 10 μl of SureSelect Hyb #3, and 13 μl of SureSelect Hyb #4. (2) 3.4 μl (0.5 μg) of the PE-library DNA described above, 2.5 μl of SureSelect Block #1, 2.5 μl of SureSelect Block #2 and 0.6 μl of Block #3; was loaded into one well in a 384-well Diamond PCR plate (cat#AB-1111, Thermo-Scientific, Lafayette, Colo.), sealed with microAmp clear adhesive film (cat#4306311; ABI, Carlsbad, Calif.) and placed in GeneAmp PCR system 9700 thermocycler (Life Sciences Inc., Carlsbad Calif.) for 5 minutes at 95° C., then held at 65° C. (with the heated lid on). (3) 25-30 μl of hybridization buffer from step (1) was heated for at least 5 minutes at 65° C. in another sealed plate with heated lid on. (4) 5 μl of SureSelect Oligo Capture Library, 1 μl of nuclease-free water, and 1 μl of diluted RNase Block (prepared by diluting RNase Block 1:1 with nuclease-free water) were mixed and heated at 65° C. for 2 minutes in another sealed 384-well plate. (5) While keeping all reactions at 65° C., 13 μl of Hybridization Buffer from Step (3) was added to the 7 μl of the SureSelect Capture Library Mix from Step (4) and then the entire contents (9 μl) of the library from Step (2). The mixture was slowly pipetted up and down 8 to 10 times. (6) The 384-well plate was sealed tightly and the hybridization mixture was incubated for 24 hours at 65° C. with a heated lid.

After hybridization, five steps were performed to recover and amplify captured DNA library: (1) Magnetic beads for recovering captured DNA: 50 μl of Dynal M-280 Streptavidin magnetic beads (Cat #112-05D, Invitrogen) was placed in a 1.5 ml microfuge tube and vigorously resuspended on a vortex mixer. Beads were washed three times by adding 200 μl SureSelect Binding buffer, mixed on a vortex for five seconds, then removing and discarding supernatant after placing the tubes in a Dynal magnetic separator. After the third wash, beads were resuspended in 200 μl of SureSelect Binding buffer. (2) To bind captured DNA, the entire hybridization mixture described above (29 μl) was transferred directly from the thermocycler to the bead solution and mixed gently; the hybridization mix/bead solution was rotated for 30 minutes at room temperature. (3) To wash the beads, the supernatant was removed from beads after applying a Dynal magnetic separator and the beads was resuspended in 500 μl SureSelect Wash Buffer #1 by mixing on vortex mixer for 5 seconds and incubated for 15 minutes at room temperature. Wash Buffer#1 was then removed from beads after magnetic separation. The beads were further washed three times, each with 500 μl pre-warmed SureSelect Wash Buffer #2 after incubation at 65° C. for 10 minutes. After the final wash, SureSelect Wash Buffer #2 was completely removed. (4) To elute captured DNA, the beads were suspended in 50 μl SureSelect Elution Buffer, vortex-mixed and incubated for 10 minutes at room temperature. The supernatant was removed after magnetic separation, collected in a new 1.5 ml microcentrifuge tube, and mixed with 50 μl of SureSelect Neutralization Buffer. DNA was purified with a Qiagen MinElute column and eluted in 17 μl of 70° C. EB to obtain 15 μl of captured DNA library. (5) The captured DNA library was amplified in the following way: 15 PCR reactions each containing 9.5 μl of $H_2O$, 3 μl of 5× Phusion HF buffer, 0.3 μl of 10 mM dNTP, 0.75 μl of DMSO, 0.15 μl of Illumina PE primer #1, 0.15 μl of Illumina PE primer #2, 0.15 μl of Hotstart Phusion polymerase, and 1 μl of captured exome library were set up. The PCR program used was: 98° C. for 30 seconds; 14 cycles of 98° C. for 10 seconds, 65° C. for 30 seconds, 72° C. for 30 seconds; and 72° C. for 5 min. To purify PCR products, 225 μl PCR mixture (from 15 PCR reactions) was mixed with 450 μl NT buffer from NucleoSpin Extract II kit and purified as described above. The final library DNA was eluted with 30 μl of 70° C. elution buffer and DNA concentration was estimated by OD260 measurement.

EXAMPLE 5

Somatic Mutation Identification by Illumina GAIIx Sequencing and Sanger Sequencing All captured DNA libraries were sequenced with Illumina GAIIx Genome Analyzer, yielding 75 base pairs from the final library fragments. All sequencing reads were analyzed and aligned to human genome hg18 with the Eland algorithm of CASAVA 1.6 software (Illumina). A mismatched base was identified as a mutation only when (i) it was identified by more than four distinct tags; (ii) the number of distinct tags containing a particular mismatched base was at least 20% of the total distinct tags; and (iii) it was not present in >0.5% of the tags in the matched normal sample.

All somatic mutations identified by the first round of exome sequencing were subjected to conventional Sanger sequencing. PCR amplification and sequencing were performed following protocols described previously (3) using the primers listed in Table S4. SNP search databases included ncbi.nlm.nih.gov/projects/SNP/ and /browser.1000genomes.org/index.html.

EXAMPLE 6

Evaluation of Genes in Additional Tumors and Matched Normal Controls

For the ARID1A, PPP2R1A, PIK3CA, and KRAS genes, the coding region was sequenced in a series of additional ovarian clear cell carcinomas and matched controls. PCR and Sanger sequencing were performed as described above using the primers listed in Table S4.

EXAMPLE 7

Occurrence of Somatic Mutations in ARI1A in Other Tumor Types

The protein encoded by ARID1A is a key component of the highly conserved SWI-SNF chromatin remodeling complex that uses ATP-dependent helicase activities to allow access of transcriptional activators and repressors to DNA (Wang et al, 2004). The protein therefore appears to be involved in regulating processes including DNA repair, differentiation and development (Weissman et al, 2009). Functional studies by Nagl et al (2007) have demonstrated that the SWI-SNF complex suppresses proliferation. The ARID1A encoded protein, BAF250a, is one of two mutually exclusive ARID1 subunits. BAF250a has a DNA-binding domain that specifically binds to AT-rich DNA sequences and is thought to confer specificity to the complex (Wu et al, 2009).

Passenger mutations are best defined as those which do not confer a selective growth advantage to the cells in which they occur, while driver mutations are those which do confer a growth advantage. It is often difficult to distinguish driver mutations from passenger mutations when the mutations occur at low frequency. One of the best examples of this challenge is provided by IDH1 mutations. A single mutation of IDH1, R132H, was discovered in a whole exomic screen of 11 colorectal cancers (CRCs) (Sjoblom et al, 2006). This mutation was not identified in more than 200 additional colorectal cancer samples and was presumed to be a passenger mutation. However, frequent IDH1 mutations at the identical residue were found when brain tumors, such as lower grade astrocytomas and oligodendrogliomas were evaluated (Parsons et al, 2008; Yan et al, 2009). Thus the IDH1 mutation in that original CRC in retrospect was undoubtedly a driver.

This example illustrates that once a genetic alteration is identified as a driver in one tumor type, infrequent mutations of the same type in the same gene in other tumors can be more reliably interpreted. Given that it is now known that ARID1A is a bona fide tumor suppressor gene in OCCC, we applied this principle to the evaluation of ARID1A mutations in other tumor types. As described below, we studied more than 700 different neoplasms of seven different types using Sanger sequencing to determine the contribution of ARID1A alterations to tumorigenesis in general.

Samples

A total of 763 neoplasms subdivided into 119 pancreas (2 mutations among 24 samples were previously reported (Jones et al, 2008), 114 breast (0 mutations among 11 samples previously studied (Wood et al, 2007), 36 lung, 104 gastric, 34 glioblastoma (0 mutations among 22 samples previously studied) (Parsons et al, 2008), 125 medulloblastoma (1 mutation among 110 samples was previously reported) (Parsons et al, 2011), 119 colon, 23 prostate and 89 leukemias were obtained according to appropriate IRB protocols. Tumor DNA was extracted as previously described (Sjoblom et al, 2006). Of the 763 neoplasms, 103 were cell lines and the remainder were primary tumors or xenografts. As we considered only truncating mutations as drivers, and because truncating mutations of ARID1A have never been observed in the human germline (Jones et al, 2010; Wiegand et al, 2010; dbSNP (http:/www.ncbi.nlm.nih.gov/projects/SNP); 1000 Genomes Consortium, 2010), we considered any truncating mutation to be somatic in origin. The somatic nature of the truncating mutations was confirmed in 100% of the cases in which matched normal DNA was available (n=17).

Amplification

The coding regions of ARID1A (CCDS285.1; NM_006015.4; OMIM603024) were amplified by the polymerase chain reaction in 5 µl reactions containing 1×PCR Buffer (67 mM Tris-HCl, pH 8.8, 6.7 mM $MgCl_2$, 16.6 mM $NH_4SO_4$, 10 mM 2-mercaptoethanol), 1 mM dNTPs (Invitrogen, San Diego, Calif.), 1 µM forward and 1 µM reverse primers, 6% DMSO, 2 mM ATP, 0.25 U Platinum Taq (Invitrogen, San Diego, Calif.) and 3 ng DNA. The 34 pairs of primer sequences used were reported in Jones et al, 2010. PCR cycling conditions were as follows: 94° C. for 2 min; three cycles of 94° C. for 15 s, 64° C. for 30 s, 70° C. for 30 s; three cycles of 94° C. for 15 s, 61° C. for 30 s, 70° C. for 30 s; three cycles of 94° C. for 15 s, 58° C. for 30 s, 70° C. for 30 s; and 41 cycles of 94° C. for 15 s, 57° C. for 30 s, 70° C. for 30 s, followed by 70° C. for 5 min.

Sequencing

Sequencing was carried out as described in Sjoblom et al. In brief, PCR products were purified using AMPure (Agencourt Biosciences, Beverly, Mass.) and sequencing was carried out with Big Dye Terminator Kit v.3.1 (Applied Biosystems, Foster City, Calif.). One PCR primer of each pair was tagged with an M13F sequence (5'-GTAAAAC-GACGGCCAGT; SEQ ID NO:158) to allow Sanger sequencing with this universal primer. Sequencing reactions were purified using the CleanSEQ kit (Agencourt Biosciences, Beverly, Mass.) and run on ABI PRISM 3730 machines (Applied Biosystems, Foster City, Calif.). Mutation surveyor software (SoftGenetics, State College, Pa.) was used to visually analyze sequencing traces for mutations and all potential variants were confirmed by an independent PCR and sequencing reaction.

Microsatellite Instability Testing

Microsatellite instability was detected using the MSI Analysis System (Promega, Madison, Wis.), which contains 5 mononucleotide repeats (BAT-25, BAT-26, NR-21, NR-24 and MONO-27) and 2 pentanucleotide repeat loci, per manufacturer's instructions. Following amplification, the fluorescent PCR products were sized on an Applied Biosystems 3130 capillary electrophoresis instrument (Invitrogen, Calsbad, Calif.). Tumor samples were designated as: MSI-high if two or more mononucleotides varied in length compared to the germline DNA, MSI-low if only one locus varied, and microsatellite stable (MSS) if there was no variation compared to the germline. Pentanucleotide loci confirmed identity in all cases where normal DNA was available. For samples lacking normal DNA, tumor microsatellite length was interpreted relative to population length of these generally monomorphic alleles.

Results

Somatic mutations were identified in 43 of the 763 neoplasms studied (6%) (Table 2). Eight neoplasms contained two or three (1 case) different mutations, presumably on different alleles, so the total number of mutations was fifty-two. A relatively high frequency of mutations was observed in neoplasms of the colon (10%; 12/119), stomach (10%; 10/104), and pancreas (8%; 10/119). Though only a small number of prostate tumors was available for study, we identified 2 carcinomas with mutations among the 23 studied. Mutations were observed in three of 125 (2%) medulloblastomas, in four of 114 (4%) breast cancers, and in two of 36 (6%) lung carcinomas (Table 2; FIG. 2). No mutations were observed among 34 glioblastomas or 89 leukemias tested.

As expected for inactivating mutations of a tumor suppressor gene, the mutations were distributed throughout the gene and included nonsense variants, out of frame and in-frame small insertions and deletions, as well as a small number (three) of missense changes. Mutations were most commonly observed in a 7 base G tract around position g.chr1:26978524 (c.5548) where there were six single base pair deletions and three duplications among gastric, colon, prostate and pancreas carcinomas. This G tract is the longest mononucleotide repeat in the coding region and the probability of slippage at mononucleotide repeats clearly increases with run length (Markowitz et al, 1995; Eshleman et al, 1996). Thirty-eight of the 43 samples with somatic mutations were available for microsatellite instability (MSI) testing. Twelve tumors (6 colon, 5 gastric and 1 prostate) were shown to be MSI high, and all carried mutations at mononucleotide tracts in the ARID1A gene (Table 2). It is therefore possible that ARID1A, like TGFβRII or BAX, is associated with microsatellite instability and that the homopolymeric repeat frameshifts may result from defects in mismatch repair (Markowitz et al, 1995; Rampino et al 1997). Though the interpretation of mutations in mismatch repair deficient tumors is challenging (Kern, 2002), the fact that ~40% of the colorectal cancers with ARID1A mutations did not have MSI leaves little doubt that ARID1A plays a role in this tumor type.

The identification of mutations in ARID1A in several different types of cancer indicates that this gene has a wider role in human tumorigenesis than previously appreciated. In addition, ARID1A appears to be frequently mutated in gastrointestinal tumors displaying high levels of microsatellite instability. Mutations in other members of the SWI-SNF chromatin remodeling complex have also been reported. For example, truncating mutations in SMARCA4/BRG1 were identified in three pancreatic cancers, in a medulloblastoma, and in several lung cancers (Jones et al, 2008; Parsons et al, 2011; Medina et al, 2008). More recently, 41% of renal cancers have been shown to have truncating mutations in the SWI-SNF chromatin remodeling complex gene, PBRM1 (Varela et al, 2011). In addition, a pattern of somatic mutation of genes involved more generally in chromatin remodeling is starting to appear. MLL3 appears to be involved in a small number of colon and pancreatic cancers and medulloblastomas (Wood et al. 2007; Jones et al, 2009; Parsons et al, 2011); MLL2 is mutated in 14% of medulloblastomas and a large fraction of non-Hodgkin's lymphomas (Parsons et al, 2011; Morin et al, 2011) and JARID1C is genetically altered in a small proportion of kidney cancers (Dalgliesh et al, 2010). These data collectively link genetic alterations to epigenetic changes and pave the way for a better understanding of both.

ADDITIONAL REFERENCES

S1. M. D. Fallin et al., Am J Hum Genet 73, 601 (2003).
S2. M. D. Fallin et al., Am J Hum Genet 77, 918 (2005).
S3. T. Sjoblom et al., Science 314, 268 (2006).

TABLE 1

Mutations in ARID1A, KRAS, PIK3CA and PPP2R1A in Ovarian Clear Cell Carcinomas

| Sample | Gene | Transcript Accession | Nucleotide (genomic)* | Nucleotide (cDNA) | Amino acid (protein) | Mutation type |
|---|---|---|---|---|---|---|
| OCC01PT | ARID1A | CCDS285.1 | g.chr1: 26972561_26972562insA | c.3854_3855insA | fs | Indel |
| OCC02PT | ARID1A | CCDS285.1 | g.chr1: 26896034C > T | c.553C > T | p.Q185X | Nonsense |
| OCC02PT | ARID1A | CCDS285.1 | g.chr1: 26978879-26978880dupGT | c.903_904dupGT | fs | Indel |
| OCC03PT | ARID1A | CCDS285.1 | g.chr1: 26972009_26972034del TGATGGGGCGCATGTCCTATGAGCCA (hom) (SEQ ID NO: 7) | c.3659_3684del TGATGGGGCGCATGTCC TATGAGCCA (SEQ ID NO: 7) | fs | Indel |
| OCC07PT | ARID1A | CCDS285.1 | g.chr1: 26896066C > A | c.585C > A | p.Y195X | Nonsense |
| OCC08PT | ARID1A | CCDS285.1 | g.chr1: 26970389delC | c.3391delC | fs | Indel |
| OCC10PT | ARID1A | CCDS285.1 | g.chr1: 26972790_26972792dupGCA (hom) | c.4001_4002dupGCA (hom) | fs | Indel |
| OCC10PT | ARID1A | CCDS285.1 | g.chr1: 26979804_26979805delTG (hom) | c.6828_6829delTG(hom) | fs | Indel |
| OCC11PT | ARID1A | CCDS285.1 | g.chr1: 26930334_26930335insCCTAC | c.1455_1466insCCTAC | fs | Indel |
| OCC13PT | ARID1A | CCDS285.1 | g.chr1: 26974233_26974234insTGGC | c.4926_4927insTGGC | fs | Indel |
| OCC14PT | ARID1A | CCDS285.1 | g.chr1: 26972886_26972887_delTT (hom) | c.4011_4012delTT (hom) | fs | Indel |
| OCC15PT | ARID1A | CCDS285.1 | g.chr1: 26973940G > A | c.4635G > A | p.W1545X | Nonsense |

TABLE 1-continued

Mutations in ARID1A, KRAS, PIK3CA and PPP2R1A in Ovarian Clear Cell Carcinomas

| Sample | Gene | Transcript Accession | Nucleotide (genomic)* | Nucleotide (cDNA) | Amino acid (protein) | Mutation type |
|---|---|---|---|---|---|---|
| OCC15PT | ARID1A | CCDS285.1 | g.chr1: 26978178T > A | c.5202T > A | p.Y1734X | Nonsense |
| OCC16PT | ARID1A | CCDS285.1 | g.chr1: 26895967_26895973delCGCCGCC (hom) | c.486_492delCGCCGCC (hom) | fs | Indel |
| OCC18PT | ARID1A | CCDS285.1 | g.chr1: 26971925delA | c.3575delA | fs | Indel |
| OCC20PT | ARID1A | CCDS285.1 | g.chr1: 26970221delG | c.3223delG | fs | Indel |
| OCC22PT | ARID1A | CCDS285.1 | g.chr1: 26979694dupG | c.6718dupG | fs | Indel |
| OCC23PT | ARID1A | CCDS285.1 | g.chr1: 26896379_2689637980_insCGTC | c.898_899insCGTC | fs | Indel |
| OCC23PT | ARID1A | CCDS285.1 | g.chr1: 26979686_26979687insT | c.6710_6711insT | fs | Indel |
| OCC24PT | ARID1A | CCDS285.1 | g.chr1: 26930542C > T | c.1663C > T | p.Q555X | Nonsense |
| OCC27PT | ARID1A | CCDS285.1 | g.chr1: 26896263_26896272delCGTCGTCTTC (SEQ ID NO: 8) | c.782_791delCGTCGTCTTC (SEQ ID NO: 8) | fs | Indel |
| OCC27PT | ARID1A | CCDS285.1 | g.chr1.: 26971984_26971994delCAGCCCAGAT (SEQ ID NO: 9) | c.3634_3644delCAGCCCAGTATfs (SEQ ID NO: 9) | | Indel |
| OCC30PT | ARID1A | CCDS285.1 | g.chr1: 26931823C > T | c.1873C > T | p.Q625X | Nonsense |
| OCC32PT | ARID1A | CCDS285.1 | g.chr1: 26960135C > T | c.2122C > T | p.Q708X | Nonsense |
| OCC34PT | ARID1A | CCDS285.1 | g.chr1: 26931754G > T | c.1804G > T | p.E602X | Nonsense |
| OCC34PT | ARID1A | CCDS285.1 | g.chr1: 26979678delT | c.6702delT | fs | Indel |
| OCC36PT | ARID1A | CCDS285.1 | g.chr1: 26928932T > G | c.1341T > G | p.Y447X | Nonsense |
| OCC36PT | ARID1A | CCDS285.1 | g.chr1: 26971613delC | c.3442delC | fs | Indel |
| OCC39PT | ARID1A | CCDS285.1 | g.chr1: 26896364dupC | c.883dupC | fs | Indel |
| OCC39PT | ARID1A | CCDS285.1 | g.chr1: 26965434delC | c.2868delC | fs | Indel |
| OCC41PT | ARID1A | CCDS285.1 | g.chr1: 26931831delT | c.1881delT | fs | Indel |
| OCC42PT | ARID1A | CCDS285.1 | g.chr1: 26960479_26960488delCGGCCACCCA (SEQ ID NO: 10) | c.2179_2188delCGGCCACCCA (SEQ ID NO: 10) | fs | Indel |
| OCC04PT | KRAS | CCDS8703.1 | g.chr12: 25289551C > T | c.35G > A | p.G12D | Missense |
| OCC05PT | KRAS | CCDS8703.1 | g.chr12: 25289551C > G | c.35G > C | p.G12A | Missense |
| OCC01PT | PIK3CA | CCDS43171.1 | g.chr3: 180418788C > A | c.1636C > A | p.Q546K | Missense |
| OCC02PT | PIK3CA | CCDS43171.1 | g.chr3: 180418776G > A | c.1624G > A | p.E542K | Missense |
| OCC06PT | PIK3CA | CCDS43171.1 | g.chr3: 180418785G > A | c.1633G > A | p.E545K | Missense |
| OCC08PT | PIK3CA | CCDS43171.1 | g.chr3: 180418785G > A | c.1633G > A | p.E545K | Missense |
| OCC09PT | PIK3CA | CCDS43171.1 | g.chr3: 180434779A > T | c.3140A > T | p.H1047L | Missense |
| OCC10PT | PIK3CA | CCDS43171.1 | g.chr3: 180434779A > G | c.3140A > G | p.H1047R | Missense |
| OCC11PT | PIK3CA | CCDS43171.1 | g.chr3: 180418777A > T | c.1625A > T | p.E542V | Missense |
| OCC13PT | PIK3CA | CCDS43171.1 | g.chr3: 180434779A > G | c.3140A > G | p.H1047R | Missense |
| OCC15PT | PIK3CA | CCDS43171.1 | g.chr3: 180410152C > G | c.1221C > G | p.C407W | Missense |
| OCC20PT | PIK3CA | CCDS43171.1 | g.chr3: 180434779A > G | c.3140A > G | p.H1047R | Missense |
| OCC22PT | PIK3CA | CCDS43171.1 | g.chr3: 180434779A > G | c.3140A > G | p.H1047R | Missense |
| OCC23PT | PIK3CA | CCDS43171.1 | g.chr3: 180399648_180399649insCCTCAA | c.341_342insCCTCAA | fs | Indel |

TABLE 1-continued

Mutations in ARID1A, KRAS, PIK3CA and PPP2R1A in Ovarian Clear Cell Carcinomas

| Sample | Gene | Transcript Accession | Nucleotide (genomic)* | Nucleotide (cDNA) | Amino acid (protein) | Mutation type |
|---|---|---|---|---|---|---|
| OCC27PT | PIK3CA | CCDS43171.1 g.chr3: 180399638A > G | c.331A > G | p.K111E | Missense |
| OCC30PT | PIK3CA | CCDS43171.1 g.chr3: 180434779A > G | c.3140A > G | p.H1047R | Missense |
| OCC35PT | PIK3CA | CCDS43171.1 g.chr3: 180418776G > A | c.1624G > A | p.E542K | Missense |
| OCC36PT | PIK3CA | CCDS43171.1 g.chr3: 180418785G > A | c.1633G > A | p.E545K | Missense |
| OCC42PT | PIK3CA | CCDS43171.1 g.chr3: 180434779A > G | c.3140A > G | p.H1047R | Missense |
| OCC05PT | PPP2R1A | CCDS12849.1 g.chr19: 57407794C > G | c.547C > G | p.R183G | Missense |
| OCC07PT | PPP2R1A | CCDS12849.1 g.chr19: 57407794C > T | c.547C > T | p.R183W | Missense |
| OCC36PT | PPP2R1A | CCDS12849.1 g.chr19: 57407791C > T | c.544C > T | p.R182W | Missense |

*Coordinates refer to the human reference genome hg18 release (NCBI 36.1, March 2006).

TABLE S1

Characteristics of ovarian clear cell carcinoma samples

| Sample | Patient age (years) | Tissue derivation | Stage | Sample type | Screen* | ARID1A Mutation | PPP2R1A Mutation | PIK3CA Mutation | KRAS Mutation |
|---|---|---|---|---|---|---|---|---|---|
| OCC01PT | 39 | Primary tumor | IV | immunopurified | Discovery | | | | |
| OCC02PT | 47 | Primary tumor | IIIC | Immunopurified | Discovery | Y | N | Y | N |
| OCC03PT | 58 | Primary tumor | IC | Immunopurified | Discovery | Y | N | Y | N |
| OCC04PT | 32 | Primary tumor | IV | Immunopurified | Discovery | Y | N | N | N |
| OCC05PT | 55 | Primary tumor | IC | Immunopurified | Discovery | N | N | N | Y |
| OCC06PT | 46 | Recurrent tumor$ | na** | Immunopurified | Discovery | N | Y | N | Y |
| OCC07PT | 52 | Primary tumor | IIIC | Immunopurified | Discovery | N | N | Y | N |
| OCC08PT | 53 | Primary tumor | IC | Immunopurified | Discovery | Y | Y | N | N |
| OCC09PT | 38 | Primary tumor | IC | immunopurified | Validation | Y | N | Y | N |
| OCC10PT | 47 | Primary tumor | IA | Immunopurified | Validation | N | N | Y | N |
| OCC11PT | 53 | Primary tumor | IIIC | Immunopurified | Validation | Y | N | Y | N |
| OCC12PT | 56 | Primary tumor | IV | Bulk tumor, >80% tumor cells | Validation | Y | N | Y | N |
| OCC13PT | 49 | Recurrent tumor | na | Immunopurified | Validation | N | N | N | N |
| OCC14PT | 46 | Primary tumor | IIIC | Immunopurified | Validation | Y | N | Y | N |
| OCC15PT | 54 | Primary tumor | IIIC | Immunopurified | Validation | Y | N | N | N |
| OCC16PT | 82 | Primary tumor | IIB | Immunopurified | Validation | Y | N | Y | N |
| OCC17PT | 56 | Primary tumor | IA | Bulk tumor, >80% tumor cells | Validation | Y | N | N | N |
| OCC18PT | 63 | Primary tumor | IA | Bulk tumor, >80% tumor cells | Validation | N | N | N | N |
| OCC19PT | 45 | Primary tumor | IC | Bulk tumor, >80% tumor cells | Validation | Y | N | N | N |
| OCC20PT | 62 | Primary tumor | IC | Immunopurified | Validation | N | N | N | N |
| OCC21PT | 63 | Primary tumor | IC | Bulk tumor, >80% tumor cells | Validation | Y | N | Y | N |
| OCC22PT | 38 | Primary tumor | IC | Bulk tumor, >70% tumor cells | Validation | N | N | N | N |
| OCC23PT | 40 | Primary tumor | IC | Bulk tumor, >70% tumor cells | Validation | Y | N | Y | N |
| OCC24PT | 50 | Primary tumor | IC | Bulk tumor, >70% tumor cells | Validation | Y | N | Y | N |
| OCC25PT | 52 | Primary tumor | IC | Bulk tumor, >70% tumor cells | Validation | Y | N | N | N |
| OCC26PT | 47 | Primary tumor | IC | Bulk tumor, >70% tumor cells | Validation | N | N | N | N |
| OCC27PT | 51 | Primary tumor | IIIC | Bulk tumor, >70% tumor cells | Validation | N | N | N | N |
| OCC28PT | 62 | Primary tumor | IC | Bulk tumor, >70% tumor cells | Validation | Y | N | Y | N |
| OCC29PT | 60 | Primary tumor | IV | Immunopurified | Validation | N | N | N | N |
| OCC30PT | 53 | Primary tumor | IC | Immunopurified | Validation | N | N | N | N |
| OCC31PT | 52 | Primary tumor | IC | Immunopurified | Validation | Y | N | Y | N |
| OCC32PT | 42 | Primary tumor | IC | Immunopurified | Validation | N | N | N | N |

TABLE S1-continued

Characteristics of ovarian clear cell carcinoma samples

| Sample | Patient age (years) | Tissue derivation | Stage | Sample type | Screen* | ARID1A Mutation | PPP2R1A Mutation | PIK3CA Mutation | KRAS Mutation |
|---|---|---|---|---|---|---|---|---|---|
| OCC33PT | 55 | Primary tumor | IIIC | Immunopurified | Validation | Y | N | N | N |
| OCC34PT | 47 | Recurrent tumor | na | Immunopurified | Validation | N | N | N | N |
| OCC35PT | 46 | Primary tumor | IC | Immunopurified | Validation | Y | N | N | N |
| OCC36PT | 37 | Primary tumor | IC | Immunopurified | Validation | N | N | Y | N |
| OCC37PT | 57 | Primary tumor | IC | immunopurified | Validation | Y | Y | Y | N |
| OCC38PT | 53 | Primary tumor | IC | Immunopurified | Validation | N | N | N | N |
| OCC39PT | 70 | Primary tumor | IIA | Bulk tumor, >70% tumor cells | Validation | N | N | N | N |
| OCC40PT | 47 | Primary tumor | IC | Bulk tumor, >70% tumor cells | Validation | Y | N | N | N |
| OCC41PT | 57 | Primary tumor | IC | Bulk tumor, >70% tumor cells | Validation | N | N | N | N |
| OCC42PT | 51 | Primary tumor | IIIC | Bulk tumor, >70% lumor cells | Validation | Y | N | N | N |

*Discovery: the eight samples used to capture and sequence all the ~18,000 genes.
Validation: additional samples used to determine the sequence of PIK3CA, KRAS, PPP21R1A, and ARID1A by Sanger sequencing.
$Sample from patient with recurrent tumor previously treated with 3 cycles of cisplatin and cyclophosphamide.
**na indicates not available.

TABLE S2A

|  | Average | OCC01 Normal | OCC01 Tumor | OCC02 Normal | OCC02 Tumor |
|---|---|---|---|---|---|
| Bases in target region | 37,806,033 | 37,806,033 | 37,806,033 | 37,806,033 | 37,806,033 |
| Bases sequenced (after quality filtering) | 6,511,999,219 | 5,869,322,400 | 6,039,432,975 | 7,743,998,175 | 5,887,057,800 |
| Bases mapped to genome | 5,061,811,983 | 4,697,337,900 | 4,752,944,850 | 6,092,898,975 | 4,526,013,900 |
| Bases mapped to targeted region | 3,181,949,119 | 2,951,410,606 | 2,905,106,291 | 3,938,277,117 | 2,787,699,744 |
| Average # of reads per targeted base | 84 | 78.1 | 76.8 | 104.2 | 73.7 |
| Targeted bases with at least 10 reads (%) | 92.7% | 93.5% | 91.7% | 94.5% | 91.7% |
| Known SNPs identified in targeted region | 20,037 | 19,703 | 19,519 | 19,800 | 19,504 |
| Somatic mutations identified in targeted region | 20 (excluding OCC06) | 20 | | 19 | |

TABLE S2B

|  | Average | OCC03 Normal | OCC03 Tumor | OCC04 Normal | OCC04 Tumor |
|---|---|---|---|---|---|
| Bases in target region | 37,806,033 | 37,806,033 | 37,806,033 | 37,806,033 | 37,806,033 |
| Bases sequenced (after quality filtering) | 6,511,999,219 | 4,927,758,075 | 5,350,539,525 | 5,481,781,050 | 4,796,809,725 |
| Bases mapped to genome | 5,061,811,983 | 3,560,079,675 | 4,074,495,075 | 4,294,296,450 | 3,835,246,875 |
| Bases mapped to targeted region | 3,181,949,119 | 2,372,688,851 | 2,347,615,071 | 2,789,190,234 | 2,415,146,056 |
| Average # of reads per targeted base | 84 | 62.8 | 62.1 | 73.8 | 63.9 |
| Targeted bases with at least 10 reads (%) | 92.7% | 89.6% | 89.4% | 93.1% | 90.7% |
| Known SNPs identified in targeted region | 20,037 | 19,551 | 18,998 | 19,524 | 19,266 |
| Somatic mutations identified in targeted region | 20 (excluding OCC06) | 23 | | 13 | |

TABLE S2C

|  | Average | OCC05 Normal | OCC05 Tumor | OCC06 Normal | OCC06 Tumor |
|---|---|---|---|---|---|
| Bases in target region | 37,806,033 | 37,806,033 | 37,806,033 | 37,806,033 | 37,806,033 |
| Bases sequenced (after quality filtering) | 6,511,999,219 | 8,072,903,325 | 6,098,389,650 | 8,784,608,625 | 10,792,972,200 |
| Bases mapped to genome | 5,061,811,983 | 6,609,351,825 | 4,836,418,575 | 7,064,921,250 | 7,611,497,100 |
| Bases mapped to targeted region | 3,181,949,119 | 4,205,386,181 | 2,944,517,632 | 4,405,093,249 | 4,716,682,489 |
| Average # of reads per targeted base | 84 | 111.2 | 77.9 | 116.5 | 124.8 |
| Targeted bases with at least 10 reads (%) | 92.7% | 94.0% | 92.8% | 95.1% | 93.5% |

TABLE S2C-continued

|  | Average | OCC05 | | OCC06 | |
| --- | --- | --- | --- | --- | --- |
|  |  | Normal | Tumor | Normal | Tumor |
| Known SNPs identified in targeted region | 20,037 | 21,391 | 21,240 | 18,907 | 18,632 |
| Somatic mutations identified in targeted region | 20 (excluding OCC06) | | 24 | | 125 |

TABLE S2D

|  | Average | OCC07 | | OCC08 | |
| --- | --- | --- | --- | --- | --- |
|  |  | Normal | Tumor | Normal | Tumor |
| Bases in target region | 37,806,033 | 37,806,033 | 37,806,033 | 37,806,033 | 37,806,033 |
| Bases sequenced (after quality filtering) | 6,511,999,219 | 5,876,999,250 | 7,251,704,925 | 5,324,268,750 | 5,893,441,050 |
| Bases mapped to genome | 5,061,811,983 | 4,593,099,375 | 5,707,748,925 | 4,159,913,325 | 4,572,727,650 |
| Bases mapped to targeted region | 3,181,949,119 | 2,984,229,243 | 3,581,297,932 | 2,652,614,272 | 2,914,230,935 |
| Average # of reads per targeted base | 84 | 78.9 | 94.7 | 70.2 | 77.1 |
| Targeted bases with at least 10 reads (%) | 92.7% | 93.0% | 93.6% | 93.1% | 93.7% |
| Known SNPs identified in targeted region | 20,037 | 22,946 | 18,765 | 24,318 | 18,523 |
| Somatic mutations identified in targeted region | 20 (excluding OCC06) | | 20 | | 24 |

TABLE S3

Mutations identified in the discovery screen

| Sample | Gene | Transcript Accession | Nucleotide (genomic)* | Nucleotide (cDNA) | Amino acid (protein) | Mutation type |
| --- | --- | --- | --- | --- | --- | --- |
| OCC06PT | ABCC10 | CCDS4896.1 | g.chr6: 43523575T > G | c.3797T > G | p.F1266C | Missense |
| OCC06PT | ABCD4 | CCDS9828.1 | g.chr14: 73823213C > T | c.1696G > A | p.G566S | Missense |
| OCC06PT | ACADVL | CCDS11090.1 | g.chr17: 7067740G > C | c.1236G > C | p.Q412H | Missense |
| OCC04PT | ADAM7 | CCDS6045.1 | g.chr8: 24414262G > A | c.2072G > A | p.R691H | Missense |
| OCC08PT | ADNP2 | CCDS32853.1 | g.chr18: 75994633C > T | c.346C > T | p.Q116X | Nonsense |
| OCC06PT | AFF4 | CCDS4164.1 | g.chr5: 132260486G > C | c.1.735C > G | p.R579G | Missense |
| OCC01PT | AICDA | CCDS41747.1 | g.chr12: 8648681G > A | c.532C > T | p.R178C | Missense |
| OCC08PT | AMPD1 | CCDS876.1 | g.chr1: 115017346delT | c.2154delA | fs | Indel |
| OCC06PT | ANKDD1A | CCDS10197.2 | g.chr15: 63021732C > G | c.883C > G | p.L295V | Missense |
| OCC02PT | ARHGAP5 | CCDS32062.1 | g.chr14: 31631490G > A | c.1864G > A | p.E622K | Missense |
| OCC01PT | ARID1A | CCDS285.1 | g.chr1: 26972561_26972562insA | c.3854_3855insA | fs | Indel |
| OCC02PT | ARID1A | CCDS285.1 | g.chr1: 26896034C > T | c.553C > T | p.Q185X | Nonsense |
| OCC02PT | ARID1A | CCDS285.1 | g.chr1: 26978879_26978880dupGT | c.903_904dupGT | fs | Indel |
| OCC03PT | ARID1A | CCDS285.1 | g.chr1: 2697200926972034delTGATGGGGCGCATGTCCTATGAGCCA (hom) (SEQ. ID NO: 11) | c.3659_3684delTGATGGGGCGCATGTCCTATGAGCCA (SEQ ID NO: 11) | fs | Indel |
| OCC07PT | ARID1A | CCDS285.1 | g.chr1: 26896066C > A | c.585C > A | p.Y195X | Nonsense |
| OCC08PT | ARID1A | CCDS285.1 | g.chr1: 26970389delC | c.3391delC | fs | Indel |
| OCC02PT | ARID1B | CCDS5251.1 | g.chr6: 157570517dupC | c.6500dupC | fs | Indel |
| OCC06PT | ARPC2 | CCDS2410.1 | g.chr2: 218822398G > A | c.743G > A | p.R248Q | Missense |
| OCC06PT | ASB2 | CCDS9915.1 | g.chr14: 93487138C > G | c.696G > C | p.Q232H | Missense |
| OCC02PT | ATP4A | CCDS12467.1 | g.chr19: 40737917C > T | c.2317G > A | p.V773M | Missense |
| OCC06PT | ATP6V0C | CCDS10470.1 | g.chr16: 2509574G > A | c.295G > A | p.V99M | Missense |

TABLE S3-continued

Mutations identified in the discovery screen

| Sample | Gene | Transcript Accession | Nucleotide (genomic)* | Nucleotide (cDNA) | Amino acid (protein) | Mutation type |
|---|---|---|---|---|---|---|
| OCC06PT | B3GALTL | CCDS9341.1 | g.chr13: 30687235C > T | c.118C > T | p.Q40X | Nonsense |
| OCC07PT | B4GALNT3 | CCDS8504.1 | g.chr12: 537114_537118delCAACA | c.2460_2464delCAACA | fs | Indel |
| OCC06PT | BCL11A | CCDS1862.1 | g.chr2: 60542953C > G | c.598G > C | p.E200Q | Missense |
| OCC06PT | BMF | CCDS10052.1 | g.chr15: 38185428delG | c.154delC | fs | Indel |
| OCC06PT | BZW2 | CCDS5362.1 | g.chr7: 16704324C > G | c.1096C > G | p.L366V | Missense |
| OCC06PT | C10orf90 | CCDS31310.1 | g.chr10: 128183143G > A | c.616C > T | p.R206W | Missense |
| OCC08PT | C10orf91 | CCDS7668.1 | g.chr10: 134111295C > G | c.178C > G | p.Q60E | Missense |
| OCC03PT | C13orf35 | CCDS9526.1 | g.chr13: 112381800G > T | c.106G > T | p.D36Y | Missense |
| OCC06PT | C14orf43 | CCDS9819.1 | g.chr14: 73255795G > C | c.3100C > G | p.Q1034E | Missense |
| OCC06PT | C16orf70 | CCDS10828.1 | g.chr16: 65731955C > T | c.836C > T | p.S279L | Missense |
| OCC06PT | C17orf61 | CCDS11102.1 | g.chr17: 7247227G > C | c.224C > G | p.T75R | Missense |
| OCC06PT | C1orf168 | CCDS30729.1 | g.chr1: 56989372C > G | c.1320G > C | p.M440I | Missense |
| OCC06PT | C2CD3 | CCDS31636.1 | g.chr11: 73481254C > G | c.3372G > C | p.Q1124H | Missense |
| OCC01PT | C2orf16 | CCDS42666.1 | g.chr2: 27654243G > A | c.1300G > A | p.V434I | Missense |
| OCC06PT | CC2D18 | CCDS30714.1 | g.chr1: 525931470 > G | c.2310G > C | p.K770N | Missense |
| OCC06PT | CCT2 | CCDS8991.1 | g.chr12: 68267579G > T | c.172G > T | p.D58Y | Missense |
| OCC06PT | CCT8L1 | ENST00000021776 | g.chr7: 151774819C > A | c.1325C > A | p.A442D | Missense |
| OCC06PT | CD97 | CCDS32929.1 | g.chr19: 14374516G > T | c.1291G > T | p.E431X | Nonsense |
| OCC06PT | CDH11 | CCDS10803.1 | g.chr16: 63584411G > A | c.551C > T | p.S184L | Missense |
| OCC06PT | CDK19 | CCDS5085.1 | g.chr6: 111243029C > T | c.4G > A | p.D2N | Missense |
| OCC05PT | CELF5 | CCDS12106.1 | g.chr19: 3233451C > T | c.994C > T | p.P332S | Missense |
| OCC03PT | CELSR3 | CCDS2775.1 | g.chr3: 48660374G > A | c.7033C > T | p.R2345C | Missense |
| OCC03PT | CHD4 | CCDS8552.1 | g.chr12: 6567814T > C | c.3376A > G | p.T1126A | Missense |
| OCC06PT | CHD5 | CCDS57.1 | g.chr1: 6110824C > G | c.3772G > C | p.D1258H | Missense |
| OCC06PT | CLCN1 | CCDS5881.1 | g.chr7: 142746776G > C | c.1522G > C | p.D508H | Missense |
| OCC08PT | CLEC4C | CCDS8583.1 | g.chr12: 7785340T > C | c.179A > G | p.E60G | Missense |
| OCC04PT | COL22A1 | CCDS6376.1 | g.chr8: 139761041C > A | IVS39 + 1G > T | Splice site | Splice site |
| OCC04PT | CRMP1 | CCDS33950.1 | g.chr4: 5881160G > A | c.1760C > T | p.A587V | Missense |
| OCC06PT | CSMD2 | CCDS380.1 | g.chr1: 33844067A > G | c.6332T > C | p.L2111P | Missense |
| OCC03PT | CSMD3 | CCDS6315.1 | g.chr8: 113718308G > A | c.3629C > I | p.S1210L | Missense |
| OCC03PT | CSNK1D | CCDS11805.1 | g.chr17 77802635T > C | c.794A > G | p.D265G | Missense |
| OCC06PT | CYP1A1 | CCDS10268.1 | g.chr15: 72800116C > G | c.1306G > C | p.D436H | Missense |
| OCC03PT | CYP4F22 | CCDS12331.1 | g.chr19: 15509730G > A | c.597G > A | p.M199I | Missense |
| OCC05PT | DCAF12L1 | CCDS14610.1 | g.chrX: 125513117T > A | c.1156A > T | p.R386X | Nonsense |
| OCC06PT | DDHD1 | CCDS9714.1 | g.chr14: 52610215C > G | c.1390G > C | p.D464H | Missense |
| OCC07PT | DDX53 | CCDS35214.1 | g.chrX: 22929339G > A | c.1244G > A | p.R415H | Missense |

TABLE S3-continued

Mutations identified in the discovery screen

| Sample | Gene | Transcript Accession | Nucleotide (genomic)* | Nucleotide (cDNA) | Amino acid (protein) | Mutation type |
|---|---|---|---|---|---|---|
| OCC02PT | DIS3L2 | CCDS42834.1 | g.chr2: 232811498G > A | c.1216G > A | p.V406M | Missense |
| OCC05PT | DMRT81 | CCDS581.1 | g.chr1: 53697826G > A | c.112G > A | p.E38K | Missense |
| OCC03PT | DNAH8 | CCDS4838.1 | g.chr6: 38971909G > A | c.8219G > A | p.R2740H | Missense |
| OCC05PT | DNAJC13 | CCDS33857.1 | g.chr3: 133703893C > T | c.4607C > T | p.T1536I | Missense |
| OCC06PT | DNAJC14 | CCDS8894.1 | g.chr12: 54507891G > C | c.819C > G | p.I273M | Missense |
| OCC03PT | DPP8 | CCDS10207.1 | g.chr15: 63526323G > C | c.2649C > G | p.Y883X | Nonsense |
| OCC06PT | DSC2 | CCDS11892.1 | g.chr18: 26903091G > T | c.2275C > A | p.Q759K | Missense |
| OCC03PT | DYRK1A | CCDS42925.1 | g.chr21: 37799751C > T | c.1535C > T | p.S512L | Missense |
| OCC06PT | EIF5B | CCDS42721.1 | g.chr2: 99347175G > A | c.1147G > A | p.E383K | Missense |
| OCC06PT | ELP2 | CCDS11918.1 | g.chr18: 31976873C > G | c.742C > G | p.Q248E | Missense |
| OCC05PT | EML3 | CCDS8023.2 | g.chr11: 62129695_62129698delGGTC | c.del1906-1909delGACC | fs | Indel |
| OCC08PT | EPHA1 | CCDS5884.1 | g.chr7: 142801.541G > C | c.2370C > G | p.I790M | Missense |
| OCC05PT | ETV6 | CCDS8643.1 | g.chr12: 11796732C > T | c.115C > T | p.R39X | Nonsense |
| OCC06PT | EXOC3L2 | CCDS12657.1 | g.chr19: 50426910G > C | c.41C > G | p.S14C | Missense |
| OCC02PT | FAM13C | CCDS7255.1 | g.chr10: 60699701G > A | c.767C > T | p.S256L | Missense |
| OCC06PT | FAM40A | CCDS30798.1 | g.chr1: 110387874G > A | c.1159G > A | p.D387N | Missense |
| OCC01PT | FAM71B | CCDS4335.1 | g.chr5: 156522716T > C | c.1138A > G | p.I380V | Missense |
| OCC01PT | FAT4 | CCDS3732.2 | g.chr4: 126631378A > G | c.13780A > G | p.I4594V | Missense |
| OCC06PT | F8XO34 | CCDS32086.1 | g.chr14: 54887408G > T | c.547G > T | p.G183C | Missense |
| OCC06PT | FILIP1 | CCDS4984.1 | g.chr6: 76081298G > C | c.970C > G | p.Q324E | Missense |
| OCC06PT | FLG2 | CCDS30861.1 | g.chr1: 150590126C > A | c.6760G > T | p.G2254C | Missense |
| OCC03PT | FNDC38 | CCDS3217.1 | g.chr3: 173578891C > T | c.3146C > T | p.T1049I | Missense |
| OCC06PT | FOLH1 | CCDS7946.1 | g.chr11: 49154047C > T | c.959G > A | p.R320K | Missense |
| OCC06PT | GADD45A | CCDS640.1 | g.chr1: 67925936_67925937delCA | c.389_390delCA | fs | Indel |
| OCC02PT | GAL3ST3 | CCDS8128.1 | g.chr11: 65567327C > T | c.523G > A | p.V175I | Missense |
| OCC03PT | GALNT8 | CCDS8533.1 | g.chr12: 4724019G > A | c.752G > A | p.R251Q | Missense |
| OCC02PT | GARNL3 | CCDS6869.1 | g.chr9: 129159326G > A | c.1889G > A | p.C630Y | Missense |
| OCC01PT | GATA3 | CCDS31143.1 | g.chr10: 8155905G > T | c.1248G > T | p.M416I | Missense |
| OCC06PT | GBA2 | CCDS6589.1 | g.chr9: 35730929T > G | c.919A > C | p.N307H | Missense |
| OCC06PT | GCN1L1 | CCDS41847.1 | g.chr12: 119063135C > T | c.5905G > A | p.E1969K | Missense |
| OCC06PT | GFI1B | CCDS6957.1 | g.chr9: 134856217G > A | c.952G > A | p.D318N | Missense |
| OCC02PT | GIMAP8 | CCDS34777.1 | g.chr7: 149805569G > A | c.1766G > A | p.R589H | Missense |
| OCC06PT | GOPC | CCDS5117.1 | g.chr6: 118006855T > G | c.351A > C | p.K117N | Missense |
| OCC06PT | GPR22 | CCDS5744.1 | g.chr7: 106903043G > C | c.1302G > C | p.X434Y | Missense |
| OCC08PT | GPR3 | CCDS303.1 | g.chr1: 27593530C > A | c.641C > A | p.A214D | Missense |
| OCC06PT | GPRIN3 | CCDS34030.1 | g.chr4: 90389594C > G | c.691G > C | p.E231Q | Missense |
| OCC01PT | GPT | CCDS6430.1 | g.chr8: 145702267G > A | c.901G > A | p.A301T | Missense |

TABLE S3-continued

Mutations identified in the discovery screen

| Sample | Gene | Transcript Accession | Nucleotide (genomic)* | Nucleotide (cDNA) | Amino acid (protein) | Mutation type |
|---|---|---|---|---|---|---|
| OCC01PT | GRN | CCDS11483.1 | g.chr17: 39782410G > A | c.229G > A | p.V77I | Missense |
| OCC06PT | H3F3B | CCDS11729.1 | g.chr17: 71286367G > C | c.315C > G | p.F105L | Missense |
| OCC05PT | HAO2 | CCDS901.1 | g.chr1: 119729197A > T | c.559A > T | p.K187X | Nonsense |
| OCC06PT | HDAC2 | CCDS43493.1 | g.chr6: 114384509C > G | c.607G > C | p.E203Q | Missense |
| OCC06PT | HEATR4 | CCDS9815.1 | g.chr14: 73059203A > C | c.266T > G | p.V89G | Missense |
| OCC07PT | HECTD1 | CCDS41939.1 | g.chr14: 30645942de A | c.6887delA | fs | Indel |
| OCC06PT | HIBADH | CCDS5414.1 | g.chr7: 27655756G > C | c.113C > G | p.S38X | Nonsense |
| OCC06PT | HIST1H4B | CCDS4572.1 | g.chr6: 26135340C > A | c.120G > T | p.R40S | Missense |
| OCC06PT | HIST1H4B | CCDS4572.1 | g.chr6: 26135341C > A | c.119G > T | p.R40M | Missense |
| OCC08PT | HSP90B1 | CCDS9094.1 | g.chr12: 102851919G > A | c.467G > A | p.R156K | Missense |
| OCC05PT | HSPA14 | CCDS7103.1 | g.chr10: 14937857A > C | c.902A > C | p.E301A | Missense |
| OCC05PT | IGSF10 | CCDS3160.1 | g.chr3: 152647246delC | c.3213delG | fs | Indel |
| OCC01PT | IL1RAP | CCDS3298.1 | g.chr3: 191804683A > T | c.137A > T | p.K46M | Missense |
| OCC06PT | ITGA1 | CCDS3955.1 | g.chr5: 52269009C > T | c.2986C > T | p.P996S | Missense |
| OCC06PT | ITGB2 | CCDS13716.1 | g.chr21: 45136197C > T | c.1367G > A | p.R456H | Missense |
| OCC06PT | KCNT2 | CCDS1384.1 | g.chr1: 194843995C > A | c.68G > T | p.G23V | Missense |
| OCC03PT | KCNV2 | CCDS6447.1 | g.chr9: 2707998G > A | c.259G > A | p.E87K | Missense |
| OCC06PT | KCTD3 | CCDS1515.1 | g.chr1: 213818978G > A | c.410G > A | p.R137H | Missense |
| OCC01PT | KIAA0247 | CCDS9796.1 | g.chr14: 69195186dupT | IVS1 + 2dupT | Splice site | Splice site |
| OCC06PT | KIAA0649 | CCDS6988.1 | g.chr9: 137516929A > C | c.752A > C | p.K251T | Missense |
| OCC07PT | KIAA1109 | CCDS43267.1 | g.chr4: 123387357C > T | c.5254C > T | p.H1752Y | Missense |
| OCC05PT | KIAA1539 | CCDS6578.1 | g.chr9: 35097703_35097704delAA | c.568_569delTT | fs | Indel |
| OCC06PT | KIAA1715 | CCDS33332.1 | g.chr2: 176520535C > G | c.625G > C | p.E209Q | Missense |
| OCC01PT | KLHL28 | CCDS9680.1 | g.chr14: 44484193C > T | c.689G > A | p.S230N | Missense |
| OCC04PT | KRAS | CCDS8703.1 | g.chr12: 2528955lC > T | c.35G > A | p.G12D | Missense |
| OCC05PT | KRAS | CCDS8703.1 | g.chr12: 2528955lC > G | c.35G > C | p.G12A | Missense |
| OCC01PT | LAMA5 | CCDS33502.1 | g.chr20: 60332924C > A | c.5611G > T | p.D1871Y | Missense |
| OCC07PT | LECT1 | CCDS9437.1 | g.chr13: 52175897C > T | c.839G > A | p.G280E | Missense |
| OCC06PT | LGALS4 | CCDS12521.1 | g.chr19: 43984294C > A | c.922G > T | p.D308Y | Missense |
| OCC06PT | LIFR | CCDS3927.1 | g.chr5: 38566445_38566452dupCTCATTCT | c.55_62dupAGAATGT | fs | Indel |
| OCC05PT | LRP1B | CCDS2182.1 | g.chr2: 141175367G > A | c.6320C > T | p.S2107F | Missense |
| OCC05PT | LRP1B | CCDS2182.1 | g.chr2: 141175868A > T | c.6319T > A | p.S2107T | Missense |
| OCC06PT | LRRC7 | CCDS645.1 | g.chr1: 70277630G > A | c.3421G > A | p.D1141N | Missense |
| OCC08PT | LRRK2 | CCDS31774.1 | g.chr12: 38995283G > A | c.4741G > A | p.V1581I | Missense |
| OCC06PT | MARCH6 | CCDS34135.1 | g.chr5: 10447235G > A | c.808G > A | p.E270K | Missense |
| OCC03PT | MARK1 | CCDS31029.2 | g.chr1: 218892093G > A | c.1714G > A | p.G572S | Missense |

TABLE S3-continued

Mutations identified in the discovery screen

| Sample | Gene | Transcript Accession | Nucleotide (genomic)* | Nucleotide (cDNA) | Amino acid (protein) | Mutation type |
|---|---|---|---|---|---|---|
| OCC03PT | MARK3 | CCDS41993.1 | g.chr14: 103039093C > T | c.1966C > T | p.R656C | Missense |
| OCC08PT | MAS1 | CCDS5272.1 | g.chr6: 160248330C > T | c.353C > T | p.T118M | Missense |
| OCC02PT | MCF2L2 | CCDS3243.1 | g.chr3: 184408211C > T | c.2591G > A | p.R864Q | Missense |
| OCC06PT | MDGA2 | CCDS41948.1 | g.chr14: 46413127C > A | c.1570G > T | p.G524C | Missense |
| OCC06PT | MED13L | CCDS9177.1 | g.chr12: 115159803G > T | c.163C > A | p.P55T | Missense |
| OCC08PT | MFSD5 | CCDS8851.1 | g.chr12: 51933584C > G | c.698C > G | p.S233X | Nonsense |
| OCC06PT | MLL3 | CCDS5931.1 | g.chr7: 151509027G > T | c.6851C > A | p.S2284X | Nonsense |
| OCC06PT | MLL3 | CCDS5931.1 | g.chr7: 151522533G > A | c.4432C > T | p.Q1478X | Nonsense |
| OCC05PT | MRI1 | CCDS32923.1 | g.chr19: 13740712A > G | c.799A > G | p.I267V | Missense |
| OCC06PT | MTO1 | CCDS4979.1 | g.chr6: 74246564C > T | c.1123C > T | p.Q375X | Nonsense |
| OCC06PT | MYH11 | CCDS10565.1 | g.chr16: 15777493C > T | c.832G > A | p.E278K | Missense |
| OCC03PT | MYO16 | CCDS32008.1 | g.chr13: 108502685C > A | c.2843C > A | p.S948X | Nonsense |
| OCC04PT | MYO1G | CCDS34629.1 | g.chr7: 44971978G > A | c.2164C > T | p.R722W | Missense |
| OCC06PT | MYO3B | CCDS42773.1 | g.chr2 170764100_170764101delAA | c.139_140delAA | fs | Indel |
| OCC01PT | MYO58 | CCDS42436.1 | g.chr18: 45660823G > A | c.3046C > T | p.R1016X | Nonsense |
| OCC06PT | MYST3 | CCDS6124.1 | g.chr8: 41919512C > G | c.2392G > C | p.E798Q | Missense |
| OCC07PT | NDRG2 | CCDS9565.1 | g.chr14: 20558829A > G | c.422T > C | p.I141T | Missense |
| OCC06PT | NDUFAF4 | CCDS5037.1 | g.chr6: 97445894C > T | c.335G > A | p.G112D | Missense |
| OCC06PT | NFKBIL2 | CCDS34968.1 | g.chr8: 145630246C > T | c.2833G > A | p.D945N | Missense |
| OCC06PT | NFKBIL2 | CCDS34968.1 | g.chr8: 145630291C > T | c.2788G > A | p.E930K | Missense |
| OCC06PT | NGRN | CCDS32329.1 | g.chr15: 88615882G > C | c.734G > C | p.R245T | Missense |
| OCC06PT | NIPBL | CCDS3920.1 | g.chr5: 37007894C > A | c.862C > A | p.P288T | Missense |
| OCC04PT | NLGN4X | CCDS14126.1 | g.chrX: 5837139C > A | c.767G > T | p.G256V | Missense |
| OCC06PT | NLRP3 | CCDS1632.1 | g.chr1: 245654152C > T | c.784C > T | p.R262X | Nonsense |
| OCC06PT | NOS1 | CCDS41842.1 | g.chr12: 116142349C > T | c.4084G > A | p.D1362N | Missense |
| OCC06PT | NR1I2 | CCDS2995.1 | g.chr3: 121014470G > A | c.884G > A | p.S295N | Missense |
| OCC02PT | NR2F2 | CCDS10375.1 | g.chr15: 94681704T > C | c.1094T > C | p.L365P | Missense |
| OCC03PT | NR6A1 | CCDS35137.1 | g.chr9: 126326955C > G | c.1220G > C | p.S407T | Missense |
| OCC08PT | NUP98 | CCDS7746.1 | g.chr11: 3671072G > C | c.4277C > G | p.S1426C | Missense |
| OCC02PT | OR4D1 | CCDS42365.1 | g.chr17: 53587855dupT | c.342dupT | fs | Indel |
| OCC05PT | OR51I2 | CCDS31383.1 | g.chr11: 5431563G > A | c.269G > A | p.R90H | Missense |
| OCC05PT | OR52I3 | CCDS31370.1 | g.chr11: 5024450C > T | c.119C > T | p.A40V | Missense |
| OCC06PT | OR5D16 | CCDS31512.1 | g.chr11: 55363314C > T | c.511C > T | p.H171Y | Missense |
| OCC05PT | OR6C75 | CCDS31820.1 | g.chr12: 54045519C > T | c.358C > T | p.R120C | Missense |
| OCC05PT | OXCT1 | CCDS3937.1 | g.chr5: 41843189C > A | IVS8 + 1G > T | Splice site | Splice site |
| OCC06PT | PALMD | CCDS758.1 | g.chr1: 99927932G > A | c.1528G > A | p.E510K | Missense |

TABLE S3-continued

Mutations identified in the discovery screen

| Sample | Gene | Transcript Accession | Nucleotide (genomic)* | Nucleotide (cDNA) | Amino acid (protein) | Mutation type |
|---|---|---|---|---|---|---|
| OCC07PT | PAPSS1 | CCDS3676.1 | g.chr4: 108794150G > A | c.1183C > T | p.Q395X | Nonsense |
| OCC04PT | PCDH10 | CCDS34063.1 | g.chr4: 134303647A > C | c.2863A > C | p.M955L | Missense |
| OCC06PT | PCDH17 | CCDS31986.1 | g.chr13: 57105042G > C | c.361G > C | p.E121Q | Missense |
| OCC04PT | PCDHA3 | CCDS34248.1 | g.chr5: 140162411C > T | c.1445C > T | p.A482V | Missense |
| OCC07PT | PCDHA7 | CCDS34252.1 | g.chr5: 140195657G > A | c.1505G > A | p.R502H | Missense |
| OCC07PT | PCDHA8 | CCDS34253.1 | g.chr5: 140202604C > T | c.1514C > T | p.S505L | Missense |
| OCC06PT | PCDHB7 | CCDS4249.1 | g.chr5: 140534794C > T | c.2194C > T | p.R732X | Nonsense |
| OCC01PT | PDE4DIP | CCDS30824.1 | g.chr1: 143590779C > T | c.4028G > A | p.R1343Q | Missense |
| OCC06PT | PDE9A | CCDS13690.1 | g.chr21: 43058674G > C | IVS15 + 1G > C | Splice site | Splice site |
| OCC05PT | PDZD7 | CCDS31269.1 | g.chr10: 102773205A > G | c.520T > C | p.F174L | Missense |
| OCC06PT | PEPD | CCDS42544.1 | g.chr19: 38594443G > A | c.793C > T | p.R265X | Nonsense |
| OCC02PT | PFKM | CCDS8760.1 | g.chr12: 46817867C > T | c.1033C > T | p.R345C | Missense |
| OCC05PT | PGM1 | CCDS625.1 | g.chr1: 63886821C > T | c.1190C > T | p.A397V | Missense |
| OCC06PT | PHF3 | CCDS4966.1 | g.chr6: 64480931G > C | c.5488G > C | p.G1830R | Missense |
| OCC06PT | PHLPP2 | CCDS32479.1 | g.chr16: 70270185C > T | c.1242G > A | p.M414I | Missense |
| OCC06PT | PIAS2 | CCDS32824.1 | g.chr18: 42649287G > T | c.1672C > A | p.P558T | Missense |
| OCC01PT | PIK3CA | CCDS43171.1 | g.chr3: 180418788C > A | c.1636C > A | p.Q546K | Missense |
| OCC02PT | PIK3CA | CCDS43171.1 | g.chr3: 180418776G > A | c.1624G > A | p.E542K | Missense |
| OCC06PT | PIK3CA | CCDS43171.1 | g.chr3: 180418785G > A | c.1633G > A | p.E545K | Missense |
| OCC08PT | PIK3CA | CCDS43171.1 | g.chr3: 180418785G > A | c.1633G > A | p.E545K | Missense |
| OCC06PT | PKD1L1 | CCDS34633.1 | g.chr7: 47835604G > A | c.6679C > T | p.R2227C | Missense |
| OCC06PT | PLD5 | CCDS1621.1 | g.chr1: 240343918T > G | c.691A > C | p.S231R | Missense |
| OCC08PT | PLEKHA6 | CCDS1444.1 | g.chr1: 202484579G > A | c.1817C > T | p.A606V | Missense |
| OCC06PT | PLIN2 | CCDS6490.1 | g.chr9: 19116246G > T | c.92C > A | p.S31X | Nonsense |
| OCC06PT | PLS1 | CCDS3125.1 | g.chr3: 143885798G > T | c.759G > T | p.L253F | Missense |
| OCC07PT | PMFBP1 | CCDS32483.1 | g.chr16: 70727871T > G | c.1180A > C | p.K394Q | Missense |
| OCC06PT | PMM1 | CCDS14020.1 | g.chr22: 40315716C > G | c.40G > C | p.V14L | Missense |
| OCC07PT | POLRMT | CCDS12036.1 | g.chr19: 572222C > G | c.2476G > C | p.E826Q | Missense |
| OCC08PT | PPL | CCDS10526.1 | g.chr16: 4875813C > G | c.2844G > C | p.E948D | Missense |
| OCC06PT | PPP1R12C | CCDS12916.1 | g.chr19: 60315966C > T | c.331G > A | p.D111N | Missense |
| OCC05PT | PPP2R1A | CCDS12849.1 | g.chr19: 57407794C > G | c.547C > G | p.R183G | Missense |
| OCC07PT | PPP2R1A | CCDS12849.1 | g.chr19: 57407794C > T | c.547C > T | p.R183W | Missense |
| OCC07PT | PTPRM | CCDS11840.1 | g.chr18: 7945226C > G | c.946C > G | p.R316G | Missense |
| OCC06PT | R3HDM2 | CCDS8937.1 | g.chr12: 55935044G > C | c.1693C > G | p.Q565E | Missense |
| OCC06PT | RAB8B | CCDS10183.1 | g.chr15: 61328957G > A | c.246G > A | p.M82I | Missense |
| OCC04PT | RAI2 | CCDS14183.1 | g.chrX: 17729307G > A | c.745C > T | p.P249S | Missense |
| OCC06PT | RCBTB1 | CCDS9418.1 | g.chr13: 49006380A > C | c.1475G | p.F492C | Missense |

TABLE S3-continued

Mutations identified in the discovery screen

| Sample | Gene | Transcript Accession | Nucleotide (genomic)* | Nucleotide (cDNA) | Amino acid (protein) | Mutation type |
|---|---|---|---|---|---|---|
| OCC06PT | RETSAT | CCDS1972.1 | g.chr2: 85431542C > G | c.469G > C | p.V157L | Missense |
| OCC06PT | REV3L | CCDS5091.2 | g.chr6: 111759634C > G | c.7972G > C | p.D2658H | Missense |
| OCC08PT | RHBDD3 | CCDS13850.1 | g.chr22: 27986387G > A | c.911C > T | p.S304L | Missense |
| OCC06PT | RIPK2 | CCDS6247.1 | g.chr8: 90871585G > A | c.1423G > A | p.E475K | Missense |
| OCC06PT | ROPN1L | CCDS3879.1 | g.chr5: 10518033G > C | c.667G > C | p.E223Q | Missense |
| OCC06PT | RPAP2 | CCDS740.1 | g.chr1: 92561809G > T | c.744G > T | p.M248I | Missense |
| OCC07PT | RRAS | CCDS12774.1 | g.chr19: 54830555C > T | c.545G > A | p.V216I | Missense |
| OCC03PT | SAGE1 | CCDS14652.1 | g.chrX: 134818022C > A | c.1258C > A | p.A423D | Missense |
| OCC03PT | SALL3 | CCDS12013.1 | g.chr18: 74853558C > T | c.579C > T | p.R227C | Missense |
| OCC06PT | SEL1L2 | CCDS42852.1 | g.chr20: 13798815G > C | c.1138C > G | p.L380V | Missense |
| OCC06PT | SENP7 | CCDS2941.2 | g.chr3: 102539043G > A | c.2480C > T | p.S827L | Missense |
| OCC01PT | SERPINB3 | CCDS11986.1 | g.chr18: 59457541G > T | c.626C > A | p.S209Y | Missense |
| OCC04PT | SFRP1 | CCDS34886.1 | g.chr8: 41285481G > C | c.355C > G | p.P119A | Missense |
| OCC06PT | SLC12A2 | CCDS4144.1 | g.chr5: 127531402G > C | c.2667G > C | p.K889N | Missense |
| OCC03PT | SLC12A7 | CCDS34129.1 | g.chr5: 1129308C > T | c.1792G > A | p.V598M | Missense |
| OCC01PT | SLC18A3 | CCDS7231.1 | g.chr10: 50490297G > A | c.1505G > A | p.R502H | Missense |
| OCC07PT | SLC30A1 | CCDS1499.1 | g.chr1: 209818351C > A | c.227G > T | p.R76L | Missense |
| OCC06PT | SLC38A6 | CCDS9751.1 | g.chr14: 60519109G > A | c.236G > A | p.S79N | Missense |
| OCC02PT | SLC4A3 | CCDS2446.1 | g.chr2: 220212528G > T | c.3185G > T | p.G1062V | Missense |
| OCC02PT | SLITRK2 | CCDS14680.1 | g.chrX: 144712029G > A | c.394G > A | p.G132S | Missense |
| OCC07PT | SMAD3 | CCDS10222.1 | g.chr15: 65269917A > G | c.1267A > G | p.S423G | Missense |
| OCC06PT | SMARCA4 | CCDS12253.1 | g.chr19: 10999550C > G | c.3306C > G | p.F1102L | Missense |
| OCC04PT | SOCS3 | CCDS11756.1 | g.chr17: 73866491C > A | c.281G > T | p.R94L | Missense |
| OCC06PT | SOLH | CCDS10410.1 | g.chr16: 539033delC | c.1491delC | fs | Indel |
| OCC07PT | SON | CCDS13629.1 | g.chr21: 33848740G > T | c.5333G > T | p.R1778I | Missense |
| OCC04PT | SPACA3 | CCDS11275.1 | g.chr17: 28348073G > A | c.443G > A | p.R148Q | Missense |
| OCC06PT | SPARCL1 | CCDS3622.1 | g.chr4: 88622650C > A | c.1618G > T | p.E540X | Nonsense |
| OCC08PT | SPATA5L1 | CCDS10123.1 | g.chr15: 43489979G > T | c.1393G > T | p.E465X | Nonsense |
| OCC05PT | SPOP | CCDS11551.1 | g.chr17: 45054368C > T | c.139G > A | p.E47K | Missense |
| OCC06PT | SPTBN1 | CCDS33198.1 | g.chr2: 54727813C > G | c.4908C > G | p.I1636M | Missense |
| OCC06PT | ST6GAL2 | CCDS2073.1 | g.chr2: 106825995G > A | c.871C > T | p.R291C | Missense |
| OCC06PT | STAG3 | CCDS34703.1 | g.chr7: 99637885G > A | c.2549G > A | p.G850E | Missense |
| OCC06PT | TAF1 | CCDS14412.1 | g.chrX: 70559765C > T | c.4586C > T | p.S1529F | Missense |
| OCC06PT | TAF1 | CCDS14412.1 | g.chrX: 70559773C > G | c.4594C > G | p.L1532V | Missense |
| OCC06PT | TANK | CCDS2215.1 | g.chr2: 161769509G > C | c.286G > C | p.D96H | Missense |
| OCC06PT | TCERG1 | CCDS4282.1 | g.chr5: 145843332delA | c.2060delA | fs | Indel |
| OCC05PT | TCN1 | CCDS7978.1 | g.chr11: 59377272C > G | c.1220G > C | p.G407A | Missense |
| OCC06PT | TCP11L2 | CCDS9104.1 | g.chr12: 105239560G > A | c.581G > A | p.R194Q | Missense |

TABLE S3-continued

Mutations identified in the discovery screen

| Sample | Gene | Transcript Accession | Nucleotide (genomic)* | Nucleotide (cDNA) | Amino acid (protein) | Mutation type |
|---|---|---|---|---|---|---|
| OCC05PT | TENC1 | CCDS8842.1 | g.chr12: 51734479G > C | c.539G > C | p.R180P | Missense |
| OCC06PT | TFAP2A | CCDS4510.1 | g.chr6: 10518385G > C | c.215C > G | p.P72R | Missense |
| OCC01PT | THBS1 | CCDS32194.1 | g.chr15: 37666969C > T | c.1250C > T | p.S417L | Missense |
| OCC06PT | THBS2 | CCDS34574.1 | g.chr6: 169371666C > G | c.2185G > C | p.E729Q | Missense |
| OCC08PT | TKTL2 | CCDS3805.1 | g.chr4: 164613564G > A | c.773C > T | p.A258V | Missense |
| OCC01PT | TNNT3 | CCDS7727.1 | g.chr11: 1912711C > T | c.667C > T | p.R223C | Missense |
| OCC03PT | TOP1 | CCDS13312.1 | g.chr20: 39174872C > T | c.1345C > T | p.R449W | Missense |
| OCC04PT | TP53 | CCDS11118.1 | g.chr17: 7518978C > A | c.596G > T | p.G199V | Missense |
| OCC07PT | TPO | CCDS1643.1 | g.chr2: 1478811C > T | c.2050C > T | p.R684C | Missense |
| OCC08PT | TRIM7 | CCDS4462.1 | g.chr5: 180555122G > A | c.1186C > T | p.R396W | Missense |
| OCC03PT | TRPV6 | CCDSS874.1 | g.chr7: 142282824C > T | c.1241G > A | p.R414H | Missense |
| OCC06PT | TSHZ2 | CCDS33490.1 | g.chr20: 51304068G > A | c.664G > A | p.A222T | Missense |
| OCC07PT | TXLNB | CCDS34545.1 | g.chr6: 139651330C > T | c.400G > A | p.E134K | Missense |
| OCC03PT | UBE3A | CCDS32177.1 | g.chr1S: 23167713T > C | c.641A > G | p.D214G | Missense |
| OCC01PT | UHRF1BP1L | CCDS31882.1 | g.chr12: 98990653G > T | c.1477C > A | p.L493I | Missense |
| OCC06PT | UTRN | CCDS34547.1 | g.chr6: 144837577C > T | c.3325C > T | p.L1109F | Missense |
| OCC06PT | VPS33B | CCDS10369.1 | g.chr1S: 89362068C > G | c.148G > C | p.D50H | Missense |
| OCC02PT | WAR52 | CCDS900.1 | g.chr1: 119377335G > A | c.805C > T | p.R269C | Missense |
| OCC02PT | YEATS2 | CCDS43175.1 | g.chr3: 184959448G > C | IVS12 + 1G > C | Splice site | Splice site |
| OCC08PT | ZHX3 | CCDS13315.1 | g.chr20: 39265364C > G | c.1607G > C | p.R536T | Missense |
| OCC08PT | ZNF223 | CCDS12635.1 | g.chr19: 49262723C > T | c.902C > T | p.S301L | Missense |
| OCC08PT | ZNF318 | CCDS4895.2 | g.chr6: 43414988C > A | c.4726G > T | p.G1576C | Missense |
| OCC06PT | ZNF454 | CCDS4441.1 | g.chr5: 178324711C > T | c.700C > T | p.H234Y | Missense |
| OCC06PT | ZNF7 | CCDS6435.1 | g.chr8: 146038269C > T | c.973C > T | p.Q325X | Nonsense |
| OCC0SPT | ZP4 | CCDS1615.1 | g.chr1: 236117373G > C | c.665C > G | p.A222G | Missense |
| OCC06PT | ZSCAN1 | CCDS12969.1 | g.chr19: 63257154G > A | c.1150G > A | p.V384I | Missense |
| OCC08PT | ZZEF1 | CCDS11043.1 | g.chr17: 3882226A > C | c.6835T > G | p.F2279V | Missense |

*All coordinates refer to the human reference genome hg18 release (NCBI 36.1, March 2006).

TABLE S4

Primers used for PCR amplification and sequencing

| Gene Symbol | Transcript IDs | Coding Exon No. | Genomic Region of Interest* | M13 PCR primer sequence† | SEQ ID NO: |
|---|---|---|---|---|---|
| ARID1A | ENST00000324856 | 1 | chr1: 26895478-26895713 | CCCGTTCGAGTTCTTCAGGT | 12 |
| ARID1A | ENST00000324856 | 1 | chr1: 26895714-26896145 | GGGAAAGGAGCTGCAGGA | 13 |
| ARID1A | ENST00000324856 | 1 | chr1: 26896146-26896381 | CAGCAGAACTCTCACGACCA | 14 |
| ARID1A | ENST00000324856 | 1 | chr1: 26896382-26896622 | GAGAAGAGCCAGACAATGGC | 15 |
| ARID1A | ENST00000324856 | 2 | chr1: 26928725-26928945 | TTGGAAGCCAAGGATACATTC | 16 |
| ARID1A | ENST00000324856 | 3 | chr1: 26930226-26930491 | ACCCTGGGCCTCCTAAGTATG | 17 |
| ARID1A | ENST00000324856 | 3 | chr1: 26930492-26930686 | TGCACGTTAGAGAACCACTCTG | 18 |

TABLE S4-continued

Primers used for PCR amplification and sequencing

| Gene | Transcript | Exon | Location | Primer sequence | SEQ ID NO: |
|---|---|---|---|---|---|
| ARID1A | ENST00000324856 | 4 | chr1: 26931750-26931874 | CAGTCCCATAACCCTTTCACAG | 19 |
| ARID1A | ENST00000324856 | 5 | chr1: 26959930-26960178 | GAAACTATGCAGGCATGAGCC | 20 |
| ARID1A | ENST00000324856 | 6 | chr1: 26960458-26960555 | TTGGCTGGATCTCTTTGTGTG | 21 |
| ARID1A | ENST00000324856 | 7 | chr1: 26961226-26961401 | TCCCAGGATAAGGATGAGAG | 22 |
| ARID1A | ENST00000324856 | 8 | chr1: 26962047-26962367 | TTGAATGACATTGTTTGGTGTTC | 23 |
| ARID1A | ENST00000324856 | 9 | chr1: 26965295-26965448 | ATCATCTCTGGGCTGGCTG | 24 |
| ARID1A | ENST00000324856 | 10 | chr1: 26965531-26965648 | GGCTGGGATCTTGTCACTCTC | 25 |
| ARID1A | ENST00000324856 | 11 | chr1: 26966864-26967081 | CAAGAGACTTCTGAGACCCTTAGC | 26 |
| ARID1A | ENST00000324856 | 12 | chr1: 26970193-26970408 | ATCCTTGGCATATCCTGTTGG | 27 |
| ARID1A | ENST00000324856 | 13 | chr1: 26971574-26971714 | AACAAGGACACGCAGGAGTC | 28 |
| ARID1A | ENST00000324856 | 14 | chr1: 26971886-26972069 | GGCTGAAGATAAGTGCATGGG | 29 |
| ARID1A | ENST00000324856 | 15 | chr1: 26972420-26972578 | GAACTCTGAAGAGGGCCTGG | 30 |
| ARID1A | ENST00000324856 | 16 | chr1: 26972654-26972799 | CAGAGTGAGGTAAGCATGACCC | 31 |
| ARID1A | ENST00000324856 | 17 | chr1: 26972876-26972980 | GTGAGTAAAGCCIGGTCTCGG | 32 |
| ARID1A | ENST00000324856 | 18 | chr1: 26973403-26973673 | GGAAGAAAGAGIGGTGGTTGC | 33 |
| ARID1A | ENST00000324856 | 18 | chr1: 26973674-26973835 | GGAGATGTACAGCGTGCCATA | 34 |
| ARID1A | ENST00000324856 | 18 | chr1: 26973836-26974028 | GCTATGTGCGAGGCAGGTACT | 35 |
| ARID1A | ENST00000324856 | 18 | chr1: 26974029-26974302 | ATTGCATGGCAATGAAGGAG | 36 |
| ARID1A | ENST00000324856 | 19 | chr1: 26974651-26974789 | TGGCTAAAGATGAGACATTCCC | 37 |
| ARID1A | ENST00000324856 | 20 | chr1: 26978097-26978514 | GTCTTGCTCTCGAAGTGGGTC | 38 |
| ARID1A | ENST00000324856 | 20 | chr1: 26978515-26978778 | GGCTTCGAATGGTATTGGACA | 39 |
| ARID1A | ENST00000324856 | 20 | chr1: 26978779-26979042 | GGCGAGTGTAACCAAGGTGTT | 40 |
| ARID1A | ENST00000324856 | 20 | chr1: 26979043-26979306 | GCTAAGAGTTCAGAGGCCATCA | 41 |
| ARID1A | ENST00000324856 | 20 | chr1: 26979307-26979580 | CCTTGGTTACACTCGCCAAC | 42 |
| ARID1A | ENST00000324856 | 20 | chr1: 26979581-26979838 | GAGGTGGAAGGAGGAGAGAGA | 43 |
| KRAS | ENST00000311936 | 1 | chr12: 25253992-25254116 | TCAGTTGCCTGAAGAGAAACATAA | 44 |
| KRAS | ENST00000395977 | 1 | chr12: 25259638-25259765 | AGTGGTTGCCACCTTGTTACC | 45 |
| KRAS | ENST00000395977 | 2 | chr12: 25269811-25269978 | TGGATTAAGAAGCAATGCCCT | 46 |
| KRAS | ENST00000395977 | 3 | chr12: 25271431-25271617 | ATGCATGGCATTAGCAAAGAC | 47 |
| KRAS | ENST00000395977 | 4 | chr12: 25289471-25289589 | TTGAAACCCAAGGTACATTTCAG | 48 |
| PIK3CA | ENST00000263967 | 1 | chr3: 180399280-180399543 | TCTGCTTTGGGACAACCATAC | 49 |
| PIK3CA | ENST00000263967 | 1 | chr3: 180399544-180399663 | GCCTCCGTGAGGCTACATTA | 50 |
| PIK3CA | ENST00000263967 | 2 | chr3: 180400168-180400385 | AAATCTACAGAGTTCCCTGTTTGC | Si |
| PIK3CA | ENST00000263967 | 3 | chr3: 180401768-180402026 | TGAATACTTGTTGAAATTTCTCCCT | 52 |
| PIK3CA | ENST00000263967 | 4 | chr3: 180404022-180404275 | CGGAGATTTGGATGTTCTCCT | 53 |
| PIK3CA | ENST00000263967 | 5 | chr3: 180404981-180405074 | CAAACTCCGACTTCGTGATCC | 54 |
| PIK3CA | ENST00000263967 | 6 | chr3: 180410073-180410186 | TTGGTTGATCTTTGTCTTCGTG | 55 |
| PIK3CA | ENST00000263967 | 7 | chr3: 180410664-180410824 | TGAATTTTCCTTTTGGGGAAG | 56 |
| PIK3CA | ENST00000263967 | 8 | chr3: 180410909-180411051 | ATGAATGAAGGCAAGCTAGGG | 57 |
| PIK3CA | ENST00000263967 | 9 | chr3: 180418688-180418820 | TGCTGAGATCAGCCAAATTCA | 58 |
| PIK3CA | ENST00000263967 | 10 | chr3: 180419674-180419763 | AAAGCTAGTAATGTAAGAAGTTTGGGA | 59 |
| PIK3CA | ENST00000263967 | 11 | chr3: 180420049-180420221 | ATAGACTAATAGTAATATAGTGT | 60 |
| PIK3CA | ENST00000263967 | 12 | chr3: 180420427-180420538 | CGGGAGTTTGACATTGTTCTGA | 61 |
| PIK3CA | ENST00000263967 | 13 | chr3: 180421464-180421643 | GGCCACCTTCTATGTTCCAA | 62 |
| PIK3CA | ENST00000263967 | 14 | chr3: 180424559-180424673 | TTTGAGGGTAGGAGAATGAGAGA | 63 |
| PIKCA | ENST00000263967 | 15 | chr3: 180425178-180425307 | TCTGTTACCATAGGATAAGAAATGGA | 64 |
| PIK3CA | ENST00000263967 | 16 | chr3: 180426440-180426526 | CATGTGATGGCGTGATCC | 65 |
| PIK3CA | ENST00000263967 | 17 | chr3: 180429750-180429928 | GGAAAGGCAGTAAAGGTCATGC | 66 |
| PIK3CA | ENST00000263967 | 18 | chr3: 180430482-180430607 | TAAATGGAAACTTGCACCCTG | 67 |
| PIK3CA | ENST00000263967 | 19 | chr3: 180430703-180430862 | TACCCAGGCTGGTTTCAATTC | 68 |
| PIK3CA | ENST00000263967 | 20 | chr3: 180434572-180434850 | GACATTTGAGCAAAGACCTGAAG | 69 |
| PPP2R1A | ENST00000322088 | 1 | chr19: 57385158-57385243 | ATAAGAGCACGCTGGTCA | 70 |
| PPP2R1A | ENST00000322088 | 2 | chr19: 57397005-57397103 | GCTGACTGGGTTGAGAGCTG | 71 |
| PPP2R1A | ENST00000322088 | 3 | chr19: 57401024-57401132 | GTCCATGTGTTCTGAGCTTGG | 72 |
| PPP2R1A | ENST00000322088 | 4 | chr19: 57406321-57406561 | AAGGTCGGGATGGGTAATAGG | 73 |
| PPP2R1A | ENST00000322088 | 5 | chr19: 57407747-57407902 | TGCTGAGCTCTGGGATTCTC | 74 |
| PPP2R1A | ENST00000322088 | 6 | chr19: 57408016-57408179 | GGTTCCTGCCCATGAAAGAG | 75 |
| PPP2R1A | ENST00000322088 | 7 | chr19: 57410840-57410962 | TTTAGCACTGCTTCCAAGGC | 76 |
| PPP2R1A | ENST00000322088 | 8 | chr19: 57411065-57411143 | CTCCCACAAGGTCAAAGGTTG | 77 |
| PPP2R1A | ENST00000322088 | 9 | chr19: 57411590-57411732 | TCAGCAGATTCCTGGTCAATC | 78 |
| PPP2R1A | ENST00000322088 | 10 | chr19: 57414752-57414933 | CCACTAAGACCTTCAAAGCCC | 79 |
| PPP2R1A | ENST00000322088 | 11 | chr19: 57415250-57415318 | GTGTCCGGTCTTTCTAGGGTG | 80 |
| PPP2R1A | ENST00000322088 | 12 | chr19: 57416040-57416202 | GAACCCTCTAGCATCCCTCC | 81 |
| PPP2R1A | ENST00000322088 | 13 | chr19: 57417160-57417310 | TGAGTCACCCGTATTGCTCAG | 82 |
| PPP2R1A | ENST00000322088 | 14 | chr19: 57420778-57420877 | ACAATGCCAAGGTACCTCCC | 83 |
| PPP2R1A | ENST00000322088 | 15 | chr19: 57421026-57421050 | TGGACAGTGAGACATCTTCCC | 84 |

| Gene Symbol | PCR primer sequence | SEQ ID NO: |
|---|---|---|
| ARID1A | GCAGAAAGCGGAGAGTCACA | 85 |
| ARID1A | ACCTCTCGGGGAGCTCAG | 86 |
| ARID1A | CCCACTCAGCTGTGTACCTG | 87 |
| ARID1A | ACCCTCAACCAACTGCTCAC | 88 |
| ARID1A | AGGTTGGTCTCATTGCTCTTTC | 89 |
| ARID1A | ATATCTTACCTGCGGTGGAGG | 90 |
| ARID1A | ACAACCAGCAAAGTCCTCACC | 91 |
| ARID1A | CTGGGCAGGGAGACAGAAC | 92 |

TABLE S4-continued

Primers used for PCR amplification and sequencing

| Gene | Sequence | SEQ ID NO |
|---|---|---|
| ARID1A | AAAGAACGTGTGTGATGTATTTGC | 93 |
| ARID1A | TTCATGGTCAAACAGCTCTCC | 94 |
| ARID1A | GGACAGCCCTTCTCTCACAAG | 95 |
| ARID1A | GGTCCAGAAGCATCTCAATAATC | 96 |
| ARID1A | CACAGCACTATTTGGCTCCAG | 97 |
| ARID1A | GCCAACAATTCTGCAGGTAAG | 98 |
| ARID1A | CATGGTACCACATGAAGCCAG | 99 |
| ARID1A | GAATACCTTACAGCCTGATGGG | 100 |
| ARID1A | GGCCTTAGGAAGAACTTTCCC | 101 |
| ARID1A | CAAGAACCCTGAGCCATTCTC | 102 |
| ARID1A | AATTGGAGAGGCAGATTGAGC | 103 |
| ARID1A | CCTTGGGTGGAGAACTGATTG | 104 |
| ARID1A | ATTGAGGACGTGGCTCTTCAG | 105 |
| ARID1A | CCAAACTGGAATGGAAATTGG | 106 |
| ARID1A | TCGGTTCACGCCATGATAG | 107 |
| ARID1A | GCTCAGCAAGGCACCATGT | 108 |
| ARID1A | CCTCCATCTAACTACCAGCCC | 109 |
| ARID1A | AGACAGAAACTGCCTTCCACC | 110 |
| ARID1A | GGAGAACCTTTGGGAAAGGAG | 111 |
| ARID1A | CAGGCAAGGACAAGCCAG | 112 |
| ARID1A | GCTAAGAGTTCAGAGGCCATCA | 113 |
| ARID1A | CCGCATCATGTCCACACTA | 114 |
| ARID1A | CAGCCGTGATTCGTACAGAGTA | 115 |
| ARID1A | CTCAGTGACCGAAAGAACCC | 116 |
| KRAS | TAACAGTCTGCATGGAGCAGG | 117 |
| KRAS | GAACAAACCAGGATTCTAGCCC | 118 |
| KRAS | TGGTGTAGTGGAAACTAGGAATTACAT | 119 |
| KRAS | CGTCATCTTTGGAGCAGGAAC | 120 |
| KRAS | TCTTAAGCGTCGATGGAGGAG | 121 |
| PIK3CA | CAACAGTTAAGCTTTATGGTTATTTGC | 122 |
| PIK3CA | GCAATTTAGAGCAAAGGCAGC | 123 |
| PIK3CA | TCAGTATAAGCAGTCCCTGCC | 124 |
| PIK3CA | GCAGAGCCTGCAGTGAGC | 125 |
| PIK3CA | TGATTGATCTTGTGCTTCAACG | 126 |
| PIK3CA | TTAGTGGATGAAGGCAGCAAC | 127 |
| PIK3CA | ATGAACCAAAGCAAGCATGAG | 128 |
| PIK3CA | GAGAGAAGGTTTGACTGCCATAA | 129 |
| PIK3CA | GATTTGCTGAACCCTATTGGTG | 130 |
| PIK3CA | TCAGCAGTTACTATTCTGTGACTGG | 131 |
| PIK3CA | GGGAAAGATAGTTGTGAATGAGC | 132 |
| PIK3CA | AAGGAAGTTGTATGGATCTAG | 133 |
| PIK3CA | CGGCCATGCAGAAACTGAC | 134 |
| PIK3CA | CAAGAAGCATAGGCGTGTGTC | 135 |
| PIK3CA | TCTGAGTGTTGCTGCTCTGTG | 136 |
| PIKCA | GCTAAATTCATGCATCATAAGCTC | 137 |
| PIK3CA | GGTGACACTCCAGAGGCAGTAG | 138 |
| PIK3CA | GAGGAATACACAAACACCGACAG | 139 |
| PIK3CA | AAACAAATGGCACACGTTCTC | 140 |
| PIK3CA | TGGTGAAAGACGATGGACAAG | 141 |
| PIK3CA | TGGATTGTGCAATTCCTATGC | 142 |
| PPP2R1A | ACCAAAGAAACGCGAGCTTAG | 143 |
| PPP2R1A | TCCCTTTCACCATCTGTCTCC | 144 |
| PPP2R1A | TGTTGGATTAAAGCGGATGTC | 145 |
| PPP2R1A | TGGGAGTGGAGAGAGTTCAGG | 146 |
| PPP2R1A | AACTGCAGAGTCTGTGCTTGC | 147 |
| PPP2R1A | GATCTTATTGCTCAAACGCCC | 148 |
| PPP2R1A | TGATGTGCTAGTTCCACCTCC | 149 |
| PPP2R1A | AACTGCTTGAAACCCAAGAGC | 150 |
| PPP2R1A | GGGCAGAAGCAGGTTATTGTC | 151 |
| PPP2R1A | AGCTCTTTCCATCCTGTCCTG | 152 |
| PPP2R1A | GATCTGTTTCGTCCTCCTCCC | 153 |
| PPP2R1A | TAAGCCATGGTGAGTGTGACC | 154 |
| PPP2R1A | CTGACCCTGGGCTCTACCTTC | 155 |
| PPP2R1A | CTTGAGACTCCTCCCACCTTG | 156 |
| PPP2R1A | CTAGCAGGAGGGIGGACTTTG | 157 |

*Coordinates refer to the human reference genome hg18 release (NCBI 36.1, March 2006). *Coordinates refer to the human reference genome hg18 release (NCBI 36.1, March 2006).
†M13 denotes the universal sequencing primer 5'-GTAAAACGACGGCCAGT-3' (SEQ ID NO: 158).

TABLE S5

Mutations in ARID1A, KRAS, PIK3CA and PPP2R1A in Human Ovarian Clear Cell Carcinoma Cell lines

| Sample | Gene | Transcript Accession | Nucleotide (genomic)* | Nucleotide (cDNA) | Amino acid (protein) | Mutation type |
|---|---|---|---|---|---|---|
| OV207 | ARID1A | CCDS285.1 | g.chr1:26973940G>A | c.4635G>A | p.W1545X | Nonsense |
| OVISE | ARID1A | CCDS285.1 | g.chr1:26896089dupA | c.608dupA | fs | Indel |
| OVISE | ARID1A | CCDS285.1 | g.chr1:26930505_26930506delGC | c.1626_1627delGC | fs | Indel |
| OVMANA | ARID1A | CCDS285.1 | g.chr1:26972785C>T | c.3994C>T | p.Q1332X | Nonsense |
| OVMANA | ARID1A | CCDS285.1 | g.chr1:26979767C>G | c.6791C>G | p.S2264X | Nonsense |
| OVTOKO | ARID1A | CCDS285.1 | g.chr1:26979601het_delC | c.6625delC | fs | Indel |
| OVTOKO | ARID1A | CCDS285.1 | g.chr1:26895770G>T | c.289G>T | P.E97X | Nonsense |
| TOV 21G | ARID1A | CCDS285.1 | g.chr1:26930529dupC | c.1650dupC | fs | Indel |
| TOV 21G | ARID1A | CCDS285.1 | g.chr1:269611250delC | c.2272delC | fs | Indel |
| TOV 21G | KRAS | CCDS8703.1 | g.chr12:25289549C>A | c.38G>T | p.G13C | Missense |
| KK | P1K3CA | CCDS43171.1 | g.chr3:180418794A>C | c.1634A>C | P.E545A | Missense |
| OVCA429 | P1K3CA | CCDS43171.1 | g.chr3:180418793G>A | c.1633G>A | p.E545K | Missense |
| OVMANA | P1K3CA | CCDS43171.1 | g.chr3:180418794A>T | c.1634A>T | p.E545V | Missense |
| TOV 21G | P1K3CA | CCDS43171.1 | g.chr3:180434778C>CT | c.3139C>T | p.H1047Y | Missense |
| KK | PPP2R1A | CCDS12849.1 | g.chr19:57407795G>A | c.548G>A | p.R183Q | Missense |
| OVISE | PPP2R1A | CCDS12849.1 | g.chr19:57407794C>T | c.547C>T | p.R183W | Missense |
| OVTOKO | PPP2R1A | CCDS12849.1 | g.chr19:57407794C>G | c.547C>G | p.R183G | Missense |

*Coordinates refer to the human reference genome hg18 release (NCBI 36.1, March 2006).

TABLE 2

Mutations in the chromatin remodeling gene, ARID1A

| Sample | Tumor type | Nucleotide (genomic)# | Nucleotide (cDNA)$ | Amino acid (protein) | Mutation type | MSI Status |
|---|---|---|---|---|---|---|
| 399 | Breast | g.chr1:26928914delC | c.1323delC | fs | Indel | MSS |
| 3814 | Breast | g.chr1:26979235G>A | c.6259G>A | p.G2087R | Missense | MSS |
| 5887 | Breast | g.chr1:26978695A>T | c.5719A>T | p.I1907F | Missense | MSS |
| C-122 | Breast | g.chr1:26965396C>T | c.2830C>T | p.Q944X | Nonsense | MSS |
| Co001 | Colon | g.chr1:26896495delG | c.1014delG | fs | Indel | High MSI- |
| Co001 | Colon | g.chr1:26973994delC | c.4689delC | fs | Indel | High MSI- |
| Co014 | Colon | g.chr1:26970279delA | c.3281delA | fs | Indel | High MSI- |
| Co024 | Colon | g.chr1:26970342delC | c.3344delC | fs | Indel | High MSI- |
| Co024 | Colon | g.chr1:26978524delG | c.5548delG | fs | Indel | High MSI- |
| Co038 | Colon | g.chr1:26973659delC | c.4354delC | fs | Indel | High MSI- |
| Co038 | Colon | g.chr1:26978524delG | c.5548delG | fs | Indel | High MSI- |
| Co083 | Colon | g.chr1:26978524delG | c.5548delG | fs | Indel | High MSI- |
| Co097 | Colon | g.chr1:26978524dupG | c.5548dupG | fs | Indel | High |
| Hx132 | Colon | g.chr1:26931798delC | c.1848delC | fs | Indel | ND |
| Hx132 | Colon | g.chr1:26965600_26965602delAAC | c2944_2946delAAC | in-frame del | Indel | ND |
| Hx164 | Colon | g.chr1:26930536C>T | c.1657C>T | p.Q553X | Nonsense | MSS |
| Hx245 | Colon | g.chr1:26979204C>A | c.6228C>A | p.Y2076X | Nonsense | MSS |
| Hx290 | Colon | g.chr1:26978814_26978820dupACAGAGC (horn) | c.5838_5844dupACAGAGC | fs | Indel | MSS |
| Hx308 | Colon | g.chr1:26978810_26978811insAGCACAG | C.5834_5835insAGCACAG | fs | Indel | ND |
| Hx326 | Colon | g.chr1:26962098_26962099dupTA | c.2467_2468dupTA | fs | Indel | MSS |
| G07 | Gastric | g.chr1:26896360dupC | c.879dupC | fs | Indel | MSI-High |
| G08 | Gastric | g.chr1:26896308delG | c.827delG | fs | Indel | MSI-High |
| G13 | Gastric | g.chr1:26974048_26974049delCA | c.4743_4744delCA | fs | Indel | MSI-High |
| G13 | Gastric | g.chr1:26978524delG | e.5548delG | fs | Indel | MSI-High |
| G13 | Gastric | g.chr1:26974277C>T | c.4972C>T | p.R1658W | Missense | High |
| G18 | Gastric | g.chr1:26978335G>T | e.5359G>T | p.E1787X | Nonsense | MSS |
| G21 | Gastric | g.chr1:26978524delG | c.5548delG | fs | Indel | MSI-High |
| G24 | Gastric | g.chr1:26973829T>A | e.4524T>A | p.Y1508X | Nonsense | MSI-High |
| G61 | Gastric | g.chr1:26978524delG | c.5548delG | fs | Indel | ND |
| G61 | Gastric | g.chr1:26979396delC | c.6420delC | fs | Indel | ND |
| G84 | Gastric | g.chr1:26961335dupG | c.2357dupG | fs | Indel | MSS |
| G144 | Gastric | g.chr1:26896335delG | c.854delG | fs | Indel | MSS |
| G280 | Gastric | g.chr1:26896450_26896456dclO< K iC(iCC | c.969_975delGGGCGCC | fs | Indel | MSS |
| L11C | Lung | g.chr1:26965400delG | c.2834delG | fs | Indel | ND |
| L17C | Lung | g.chr1:26979379_26979384UelATTCTG | c.6403_6408delATTCTG | in-frame del | Indel | MSS |
| MH118PT* | Medulloblastoma | g.chr1:26896496delG | c.1015delG | fs | Indel | MSS |

TABLE 2-continued

Mutations in the chromatin remodeling gene, ARID1A

| Sample | Tumor type | Nucleotide (genomic)# | Nucleotide (cDNA)$ | Amino acid (protein) | Mutation type | MSI Status |
|---|---|---|---|---|---|---|
| MB155PT | Medulloblastoma | g.chr1:26974 i 98_26974199InsC | c.4893_48941nsC | fs | Indel | MSS |
| MB156PT | Medulloblastoma | g.chr1:26974673delG | e.5012delG | fs | Indel | MSS |
| Pa07C** | Pancreas | g.chr1:26972534C>T | c.3826C>T | p.R1276X | Nonsense | MSS |
| Pa37X** | Pancreas | g.chr1:26978923_26978924dclTG | c.5947_5948delTG | fs | Indel | MSS |
| Pa102C | Pancreas | g.chr1:26965645G>A | IVS10+1G>A | Splice site | Splice site | MSS |
| Pa144X | Pancreas | g.chr1:26959958_26959959insT | c.1945_1946insT | fs | Indel | MSS |
| Pa158X | Pancreas | g.chr1:26961274dupC | c.2296dupC | fs | Indel | MSS |
| Pa166X | Pancreas | g.chr1:26978941C>T | c.5965C>T | p.R1989X | Nonsense | MSS |
| Pa194X | Pancreas | g.chr1:26978941C>T | c.5965C>T | p.R1989X | Nonsense | MSS |
| Pa194X | Pancreas | g.chr1:26979263C>G | c.6287C>G | p.S2096X | Nonsense | MSS |
| Pa197X | Pancreas | g.chr1:26930464C>T | c.1585C>T | P.Q529X | Nonsense | MSS |
| Pa198X | Pancreas | g.chr1:26978524dupG | c.5548dupG | fs | Indel | MSS |
| Pa216X | Pancreas | g.chr1:26961380delG | c.2402delG | fs | Indel | MSS |
| SW32 | Prostate | g.chr1:26972768delC | c.3977delC | fs | Indel | ND |
| SW32 | Prostate | g.chr1:26978524dupG | c.5548dupG | fs | Indel | ND |
| Pr04PT | Prostate | g.chr1:26972790_26972792het_delGCA | c.3999_4101delGCA | in-frame del | Indel | MSI-High |

\* Mutation previously reported in Parsons et al. Science 2011 Jan. 28;331(6016):435-9:
\*\* Mutation previously reported in Jones et al., Science 2008 Sep. 26;321(5897): 1801-6;
Genomic co-ordinates refer to hg18;
$Reference sequence CCDS285.1;
MSI. microsatellite instability;
MSS. microsatellite stable;
ND, not determined

The invention claimed is:

1. A method, comprising:
   amplifying coding regions of ARID1A gene or cDNA in a biological sample of an individual, wherein the biological sample comprises ovarian cells;
   sequencing the amplified coding regions of ARID1A gene or cDNA;
   detecting a mutation, wherein the mutation is a frameshift or a stop codon in the gene or cDNA.

2. The method of claim 1, wherein the biological sample is selected from the group consisting of tissue, blood, serum, plasma, ascites, and urine.

3. The method of claim 1, wherein the individual is suspected of having ovarian cancer.

4. The method of claim 1, further comprising the step of obtaining the biological sample from the individual.

5. The method of claim 1, wherein the biological sample is obtained by a method selected from the group consisting of culdocentesis, paracentesis, and biopsy.

6. The method of claim 1 wherein the mutation is hemizgyous in the ovarian cells.

7. The method of claim 1 wherein the mutation is 3854_3855insA.

8. The method of claim 4, wherein the biological sample is obtained by a method selected from the group consisting of culdocentesis, paracentesis, and biopsy.

9. The method of claim 1, wherein the individual is suspected of having ovarian clear cell carcinoma (OCCC).

10. The method of claim 1, wherein the individual has endometriosis.

11. The method of claim 1, wherein the individual has abdominal swelling due to ascites.

12. The method of claim 1, wherein the mutation is a stop codon caused by a nonsense mutation.

13. The method of claim 1 wherein the mutation is a frameshift mutation caused by an insertion or a deletion.

14. The method of claim 1 wherein the mutation is selected from the group consisting of mutations:
   c.3854_3855insA; c.553C>T; c.903_904dupGT;
   c.3659_3684delTGATGGGGCGCATGTCCTATGAGCCA (SEQ ID NO:7), c.585C>A;
   c.3391delC; c.4001_4002dupGCA (hom); c.6828_6829delTG(hom); c.1455_1466insCCTAC;
   c.4926_4927insTGGC, c.4011_4012delTT (hom); c.4635G>A; c.5202T>A;
   486_492delCGCCGCC (hom); c.3575delA; 3223delG; 6718dupG; c.898_899insCGTC;
   c.6710_6711insT;1663C>T;
   c.782_791delCGTCGTCTTC (SEQ ID NO:8);

c.3634_3644delCAGCCCAGTAT (SEQ ID NO:9); c.1873C>T; c.2122C>T; 1804G>T; c.6702delT; c.1341T>G; c.3442delC; c.883dupC; c.2868delC; c.1881delT; and
c.2179_2188delCGGCCACCCA (SEQ ID NO:10) wherein the nucleotides are numbered by reference to SEQ ID NO: 2.

15. The method of claim 1 further comprising:
amplifying mononucleotide repeats in nucleic acids of a biological sample of the individual;
sizing the amplified mononucleotide repeats by electrophoresis.

16. A method, comprising:
testing and detecting in a biological sample of an individual a shortened ARIDIA protein, wherein the biological sample comprises proteins of ovarian cells of the individual which are contacted with an antibody reactive with the N-terminus of the ARID1A protein;
amplifying mononucleotide repeats in nucleic acids of a biological sample of the individual; and
sizing the amplified mononucleotide repeats by electrophoresis.

17. The method of claim 15 wherein the mononucleotide repeats are in an ARID1A gene.

18. The method of claim 16 wherein the mononucleotide repeats are in an ARID1A gene.

19. A method comprising:
amplifying mononucleotide repeats in an ARID1A gene in nucleic acids of a biological sample of an individual, wherein the biological sample comprises ovarian cells;
sizing the amplified mononucleotide repeats by electrophoresis.

* * * * *